(12) United States Patent
Zhu et al.

(10) Patent No.: US 8,889,673 B2
(45) Date of Patent: Nov. 18, 2014

(54) TRIAZOLOPYRIDINE JAK INHIBITOR COMPOUNDS AND METHODS

(75) Inventors: Bing-Yan Zhu, Palo Alto, CA (US); Michael Siu, Burlingame, CA (US); Steven R. Magnuson, Dublin, CA (US); Richard Pastor, San Francisco, CA (US); He Haiying, Shanghai (CN); Xiao Yisong, Shanghai (CN); Zheng Jifu, Shanghai (CN); Xu Xing, Chengdu (CN); Zhao Junping, Yan'an (CN); Wendy Liu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/529,946

(22) Filed: Jun. 21, 2012

(65) Prior Publication Data

US 2012/0264747 A1 Oct. 18, 2012

Related U.S. Application Data

(63) Continuation of application No. 12/488,406, filed on Jun. 19, 2009, now abandoned.

(60) Provisional application No. 61/074,510, filed on Jun. 20, 2008.

(51) Int. Cl.
| | |
|---|---|
| A61K 31/5377 | (2006.01) |
| A61K 31/454 | (2006.01) |
| A61K 31/497 | (2006.01) |
| A61K 31/4196 | (2006.01) |
| A61K 31/4439 | (2006.01) |
| A61K 31/496 | (2006.01) |
| C07D 211/00 | (2006.01) |
| C07D 413/02 | (2006.01) |
| C07D 403/02 | (2006.01) |
| C07D 249/08 | (2006.01) |
| C07D 401/02 | (2006.01) |
| C07D 471/04 | (2006.01) |

(52) U.S. Cl.
CPC .................................. C07D 471/04 (2013.01)
USPC ............. 514/233.2; 514/253.09; 514/254.06; 514/318; 514/322; 514/333; 514/338; 544/132; 544/364; 544/366; 546/194; 546/199; 546/256; 546/272.4

(58) Field of Classification Search
USPC ............ 514/233.2, 253.09, 254.06, 318, 322, 514/333, 338; 544/132, 364, 366; 546/194, 546/199, 256, 272.4, 119
See application file for complete search history.

(56) References Cited

U.S. PATENT DOCUMENTS

| | | | |
|---|---|---|---|
| 4,847,256 A | 7/1989 | Tseng et al. | |
| 6,355,653 B1 | 3/2002 | Trottmann et al. | |
| 6,514,989 B1 | 2/2003 | Nettekoven et al. | |
| 6,579,857 B1 * | 6/2003 | Lind et al. ...................... 514/46 |
| 6,693,116 B2 | 2/2004 | Nettekoven et al. | |
| 7,119,200 B2 | 10/2006 | Guzi et al. | |
| 7,161,003 B1 | 1/2007 | Guzi et al. | |
| 7,196,078 B2 | 3/2007 | Guzi et al. | |
| 7,306,631 B2 | 12/2007 | Glenn et al. | |
| 8,299,056 B2 * | 10/2012 | Bahmanyar et al. ..... 514/210.21 |
| 2004/0209878 A1 | 10/2004 | Guzi et al. | |
| 2004/0214817 A1 | 10/2004 | Pierce et al. | |
| 2005/0020639 A1 | 1/2005 | Smith et al. | |
| 2005/0288502 A1 | 12/2005 | Andersen et al. | |
| 2006/0089362 A1 | 4/2006 | Seno et al. | |
| 2006/0128725 A1 | 6/2006 | Guzi et al. | |
| 2006/0183761 A1 | 8/2006 | Ledeboer et al. | |
| 2006/0241134 A1 | 10/2006 | Buhr et al. | |
| 2007/0037824 A1 | 2/2007 | Guzi et al. | |
| 2007/0054906 A1 | 3/2007 | Guzi et al. | |
| 2007/0054925 A1 | 3/2007 | Guzi et al. | |
| 2007/0072881 A1 | 3/2007 | Guzi et al. | |
| 2007/0142402 A1 | 6/2007 | Ding et al. | |
| 2007/0225270 A1 | 9/2007 | Guzi et al. | |

(Continued)

FOREIGN PATENT DOCUMENTS

| | | |
|---|---|---|
| WO | 03/010167 | 2/2003 |
| WO | 03/031445 | 4/2003 |

(Continued)

OTHER PUBLICATIONS

Zips et al., "New anticancer agents: In Vitro and In Vivo Evailuation." In vivo, 19: 1-8 (2005).*

(Continued)

*Primary Examiner* — Samantha Shterengarts
(74) *Attorney, Agent, or Firm* — Tamara Kale; Genentech, Inc.

(57) ABSTRACT

A compound of Formula I, enantiomers, diasteriomers, tautomers or pharmaceutically acceptable salts thereof, wherein $R^1$, $R^2$, $R^3$, $R^4$ and $R^5$ are defined herein, are useful as JAK kinase inhibitors. A pharmaceutical composition that includes a compound of Formula I and a pharmaceutically acceptable carrier, adjuvant or vehicle, and methods of treating or lessening the severity of a disease or condition responsive to the inhibition of JAK kinase activity in a patient are disclosed.

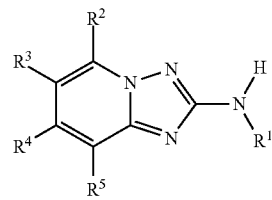

I

6 Claims, No Drawings

(56) References Cited

U.S. PATENT DOCUMENTS

| | | | |
|---|---|---|---|
| 2007/0270408 | A1 | 11/2007 | Andersen et al. |
| 2007/0281951 | A1 | 12/2007 | Guzi et al. |
| 2008/0014189 | A1 | 1/2008 | Pierce et al. |
| 2008/0050384 | A1 | 2/2008 | Guzi et al. |
| 2010/0035875 | A1 | 2/2010 | Zhu et al. |
| 2010/0048557 | A1 | 2/2010 | Zhu et al. |

FOREIGN PATENT DOCUMENTS

| | | | |
|---|---|---|---|
| WO | 2004/046120 | 6/2004 | |
| WO | 2005/054230 | 6/2005 | |
| WO | 2005/066156 | 7/2005 | |
| WO | 2006/038116 | 4/2006 | |
| WO | 2006/119542 | 11/2006 | |
| WO | 2006/133426 | 12/2006 | |
| WO | 2007/013673 | 2/2007 | |
| WO | 2007/027238 | 3/2007 | |
| WO | 2007/070872 | 6/2007 | |
| WO | 2007/095588 | 8/2007 | |
| WO | 2007/103760 | 9/2007 | |
| WO | 2007/147647 | 12/2007 | |
| WO | 2008/008539 | 1/2008 | |
| WO | 2008/025821 | 3/2008 | |
| WO | 2008/052734 | 5/2008 | |
| WO | 2009/017954 | 2/2009 | |
| WO | 2009/027283 | 3/2009 | |
| WO | 2009/047514 | 4/2009 | |
| WO | 2010/010184 | 1/2010 | |
| WO | 2010/010186 | 1/2010 | |
| WO | 2010/010188 | 1/2010 | |
| WO | 2010/010189 | 1/2010 | |
| WO | 141796 | 1/2010 | |
| WO | 2010/010186 | 12/2010 | |
| WO | 2010/141796 | 12/2010 | |
| WO | WO 2010/141796 * | 12/2010 | ........... C07D 471/04 |
| WO | 2013/085802 | 6/2013 | |

OTHER PUBLICATIONS (Notice of Allowance for U.S. Appl. No. 13/471,269 dated Oct. 7, 2013).

(Final Office Action of U.S. Appl. No. 12/488,406 dated Dec. 21, 2011).

(Final Office Action of U.S. Appl. No. 13/471,269 dated May 30, 2013).

(Genentech, Inc., IPER and Written Opinion for International Application No. PCT/US2009/048041 Sep. 3, 2009).

(Genentech, Inc., Reply to Office Action for U.S. Appl. No. 12/488,406 Oct. 10, 2011).

(Otton, A.L., Office Action for U.S. Appl. No. 12/488,406, USPTO, 16 pages Jun. 22, 2011).

(WIPO, IPER and Written Opinion for International Application No. PCT/US2009/048017 Sep. 9, 2009).

Chung, S.L., Office Action for U.S. Appl. No. 12/488,312, USPTO, 879 pages ( Jun. 8, 2011).

Dameshek, "Editorial: Some Speculations on the Myeloproliferative Syndromes" Blood 6(4):372-375 ( 1951).

Dymock et al., "Inhibitors of JAK2 and JAK3: an update on the patent literature 2010-2012" Expert Opin. Ther. Patents 23(4):449-501 ( 2013).

Genentech, Inc., Response to OA for U.S. Appl. No. 12/488,312, 34 pages ( Oct. 7, 2011).

Morgan et al., "A Role for JAK2 Mutations in Myeloproliferative Diseases" Annu Rev Med 59:213-222 ( 2008).

Nettekoven et al., "Synthetic Access to 2-Amido-5-aryl-8-methoxy-triazolopyridine and 2-Amido-5-morphonlino-8-methoxy-triazolopyridine Derivatives as Potential Inhibitors of the Adenosine Receptor Subtypes" Synthesis 11:1649-1652 (2003).

Norman, "Selective JAK1 inhibitor and selective Tyk2 inhibitor patents" Expert Opin. Ther. Patents 22(10):1233-1249 ( 2012).

Zips et al., "New Anticancer Agents: In Vitro and In Vivo Evaluation" in vivo 19:1-8 ( 2005).

* cited by examiner

TRIAZOLOPYRIDINE JAK INHIBITOR COMPOUNDS AND METHODS

FIELD OF THE INVENTION

Triazolopyridine compounds of Formula I, which are inhibitors of Janus kinases, for example JAK2 kinase, as well as compositions containing these compounds and methods of use including, but not limited to, in vitro, in situ and in vivo diagnosis or treatment of mammalian cells.

BACKGROUND OF INVENTION

Myeloproliferative disorders (MPD) originate in hematopoietic stem cells and primarily manifest in elevated counts of mostly normal cells of the myeloid lineage. A primary distinction between Philadelphia-chromosome positive (Ph+) and Philadelphia-chromosome negative (Ph−) can be made. Ph+ MPD results in chronic myelogenous leukemia and is driven by a bcr-abl fusion protein that drives hematopoietic cell proliferation. Ph− MPD can be further subclassified into three distinct disorders by related varieties, namely polycythemia vera (PV), essential thrombocythemia (ET) and idiopathic myelofibrosis (IMF). Dameshek, W., *Blood* 6(4): 372-375 (1951). Patients with PV suffer from high counts of red blood cells, whereas patients with ET have high levies of circulating platelets. If left untreated, both diseases can result in life-threatening thrombotic events. Patients with IMF experience fibrosis of the bone marrow with subsequent displacement of hematopoiesis into the spleen and liver. This primarily leads to splenomegaly, which is followed by anemia in later stages of the disease as hematopoiesis becomes nonproductive. These patients have a poor prognosis, although under certain conditions they can be cured by means of an allogeneic bone marrow transplant. There is no known cure for Ph− MPD diseases.

An activating mutation in the tyrosine kinase JAK2 is associated with PV, ET, IMF and other diseases. Virtually all patients with PV and about 50% patients with ET and IMF harbor this mutation. Morgan, K. J. and Gilliland, D. G., *Ann. Rev. Med.* 59:213-222 (2008). The mutation is an exchange from valine to phenylalanine at position 617 in the mature human JAK2 protein (V617F). Additional mutations in JAK2, commonly found in exon 12 and referred to as exon 12 mutations, also have an activating effect and can lead to MPD. Furthermore, a T875N mutation was associated with megakaryoblastic leukemia. Finally, JAK2 fusion proteins have been identified in acute leukemias.

The V617F mutation functions to activate JAK2, which leads to MPD. In non-mutated form, JAK2 is linked to cytokine receptors (i.e. EPO-R, TPO-R and others) and only gets activated if the receptor itself is activated by stimulation with the cognate cytokine ligand. Hematopoiesis as a whole is then regulated through the availability of ligands. For example, the cytokine erythropoietin (EPO) stimulates hematopoietic progenitor cells to give rise to red blood cells. A mutation that uncouples JAK2 activation from EPO, therefore, leads to elevated levels of red blood cells. By analogy, thrombopoietin (TPO) regulates platelet growth by binding to the TPO-R, which in turn also signals through JAK2. Thus, elevated levels of platelets can also result from aberrant JAK2 activation.

Compounds are needed that inhibit JAK2, which would be beneficial to patients with JAK2 driven myeloproliferative disorders, as well as, other diseases that are responsive to the inhibition of JAK2. Such diseases include both diseases in which JAK2 is activated by mutation or amplification, as well as, diseases in which JAK2 activation is a part of the oncogenic cascade. Numerous tumor cell lines and tumor samples have high levels of phospho-STAT3, which is a JAK2 target gene.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). JAK1 knockout mice die perinatally due to defects in LIF receptor signaling (Kisseleva et al., 2002, gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and Il-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

SUMMARY OF INVENTION

One embodiment includes a compound of Formula I:

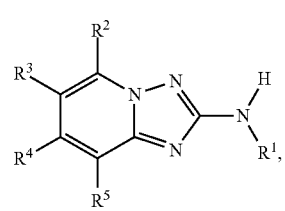

enantiomers, diasteriomers, tautomers or pharmaceutically acceptable salts thereof, wherein $R^1$, $R^2$, $R^3$, $R^4$ and $R^5$ are defined herein.

Another embodiment includes a pharmaceutical composition that includes a compound of Formula I and a pharmaceutically acceptable carrier, adjuvant or vehicle.

Another embodiment includes a method of treating or lessening the severity of a disease or condition responsive to the inhibition of one or more Janus kinase activity, selected from JAK1, JAK2, JAK3 and TYK2, in a patient. The method includes administering to the patient a therapeutically effective amount of a compound of Formula I.

Another embodiment includes a method of treating or lessening the severity of a disease or condition responsive to the inhibition of JAK2 kinase activity in a patient. The method includes administering to the patient a therapeutically effective amount of a compound of Formula I.

Another embodiment includes a kit for treating a disease or disorder responsive to the inhibition of a JAK kinase. The kit includes a first pharmaceutical composition comprising a compound of Formula I and instructions for use

DETAILED DESCRIPTION OF THE INVENTION

Reference will now be made in detail to certain embodiments, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. Examples of alkyl groups include $C_1$-$C_8$ hydrocarbon moieties such as methyl (Me, —$CH_3$), ethyl (Et, —$CH_2CH_3$), 1-propyl (n-Pr, n-propyl, —$CH_2CH_2CH_3$), 2-propyl (i-Pr, propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_{10}$ or $C_5$-$C_{10}$. In other examples, the cycloalkyl group, as a monocycle, is $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo [2.2.2]octane, and bicyclo[3.2.2]nonane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_9$. In another example, the aryl group is a $C_6$ aryl group. Aryl groups may be represented in the exemplary structures as "Ar". Aryl includes a bicyclic group comprising an aromatic ring with a fused non-aromatic or partially saturated ring. Example aryl groups include, but are not limited to, phenyl, naphthalenyl, anthracenyl, indenyl, indanyl, 1,2-dihydronapthalenyl, 1,2,3,4-tetrahydronapthyl, and the like.

"Halo" refers to F, Cl, Br or I.

"Heterocyclyl" refers to a saturated or a partially unsaturated (i.e., having one or more double and/or triple bonds within the ring) cyclic group in which at least one ring atom is a heteroatom independently selected from nitrogen, oxygen, phosphorus and sulfur, the remaining ring atoms being carbon. The heterocyclyl group may be optionally substituted with one or more substituents described below. In one embodiment, heterocyclyl includes monocycles or bicycles having 1 to 9 carbon ring members ($C_1$-$C_9$). In other examples, heterocyclyl includes monocycles or bicycles having $C_1$-$C_5$, $C_3$-$C_5$ or $C_4$-$C_5$. Examples of bicycle systems include, but are not limited to, [3,5], [4,5], [5,5], [3,6], [4,6], [5,6], or [6,6] systems. In another embodiment, heterocyclyl includes bridged ring systems having [2.2.1], [2.2.2], [3.2.2] and [4.1.0] arrangements, and having 1 to 3 heteroatoms selected from N, O, S and P. In another embodiment, heterocyclyl includes spiro groups having 1 to 3 heteroatoms selected from N, O, S and P. The heterocyclyl group may be a carbon-linked group or heteroatom-linked group. "Heterocyclyl" includes a heterocyclyl group fused to a cycloalkyl group.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3-azabicyclo[4.1.0]heptanyl and azabicyclo[2.2.2]hexanyl. Examples of a heterocyclyl group wherein a ring atom is substituted with oxo (=O) are pyrimidinonyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

The term "heteroaryl" refers to an aromatic carbocyclic radical in which at least one ring atom is a heteroatom independently selected from nitrogen, oxygen and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_5$-$C_{10}$. In one embodiment, exemplary heteroaryl groups include monocyclic aromatic 5-, 6- and 7-membered rings containing one or more heteroatoms independently selected from nitrogen, oxygen, and sulfur. In another embodiment, exemplary heteroaryl groups include fused ring systems of 8 to 20 atoms wherein at least one aromatic ring contains one or more heteroatoms independently selected from nitrogen, oxygen, and sulfur. "Heteroaryl" includes heteroaryl groups fused with an aryl, cycloalkyl or heterocyclyl group. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

In an embodiment, for Formula I, alkyl, alkenyl and alkynyl are optionally substituted by 1 to 5 substituents independently selected from by one or more $OR^a$, $NR^cR^d$, oxo and halo, and aryl, heterocyclyl, heteroaryl and cycloalkyl are optionally substituted by 1 to 5 substituents independently selected from $OR^a$, oxo, halo, $CF_3$, $NR^cR^d$, $C_1$-$C_4$ alkyl and $C(O)(C_1$-$C_4$ alkyl), wherein $R^a$, $R^c$ and $R^d$ are defined below for Formula I. In another embodiment, for Formula I, alkyl, alkenyl and alkynyl are optionally substituted by 1 to 3 substituents independently selected from by one or more $OR^a$, $NR^cR^d$, oxo and halo, and aryl, heterocyclyl, heteroaryl and cycloalkyl are optionally substituted by 1 to 3 substituents independently selected from $OR^a$, oxo, halo, $CF_3$, $NR^cR^d$, $C_1$-$C_4$ alkyl and $C(O)(C_1$-$C_4$ alkyl), wherein $R^a$, $R^c$ and $R^d$ are defined below for Formula I.

In an embodiment, for Formula I, alkyl, alkenyl and alkynyl are optionally substituted by 1 to 5 substituents independently selected from oxo and halo, and aryl is optionally substituted by 1 to 5 substituents independently selected from $OR^a$, halo, $CF_3$, $NR^cR^d$ and $C_1$-$C_4$ alkyl, wherein $R^a$, $R^c$ and $R^d$ are defined below for Formula I. In another embodiment, for Formula I, alkyl, alkenyl and alkynyl are optionally substituted by 1 to 3 substituents independently selected from oxo and halo, and aryl is optionally substituted by 1 to 3 substituents independently selected from $OR^a$, halo, $CF_3$, $NR^cR^d$ and $C_1$-$C_4$ alkyl, wherein $R^a$, $R^c$ and $R^d$ are defined below for Formula I.

In an embodiment, for Formula I, alkyl, aryl and cycloalkyl are optionally substituted by 1 to 5 substituents independently selected from $C_1$-$C_4$ alkyl, $(C_0$-$C_3$ alkyl)$OR^c$, oxo, halo, $NR^cR^d$ and $C_4$-$C_5$ heterocyclyl, wherein $R^c$ and $R^d$ are defined below for Formula I. In another embodiment, for Formula I, alkyl, aryl and cycloalkyl are optionally substituted by 1 to 3 substituents independently selected from $C_1$-$C_4$ alkyl, $(C_0$-$C_3$ alkyl)$OR^c$, oxo, halo, $NR^cR^d$ and $C_4$-$C_5$ heterocyclyl, wherein $R^c$ and $R^d$ are defined below for Formula I.

In an embodiment, for Formula I, alkyl, cycloalkyl and phenyl are optionally substituted by 1 to 5 substituents independently selected from halo, $CH_3$ OH, $NH_2$, $C(O)O(C_1$-$C_6$ alkyl) and $C(O)NH(C_1$-$C_6$ alkyl). In another embodiment, for Formula I, alkyl, cycloalkyl and phenyl are optionally substituted by 1 to 3 substituents independently selected from halo, $CH_3$ OH, $NH_2$, $C(O)O(C_1$-$C_6$ alkyl) and $C(O)NH(C_1$-$C_6$ alkyl).

"Treat" and "treatment" includes both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol- Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF inhibitors (e.g., ANGIOZYME®) and (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents; and (x) pharmaceutically acceptable salts, acids and derivatives of any of the above.

Humanized monoclonal antibodies with therapeutic potential as agents in combination with the Janus kinase inhibitors of the invention include: adalimumab, etanercept, infliximab, alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1\lambda$ antibody genetically modified to recognize interleukin-12 p40 protein.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as a compound of Formula I and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of a compound of Formula I. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of Formula I. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "compound of this invention," and "compounds of the present invention", and "compounds of Formula I", unless otherwise indicated, include compounds of Formula I and stereoisomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula I, wherein one or more hydrogen atoms are replaced deuterium or tritium, or one or more carbon atoms are replaced by a $^{13}C$- or $^{14}C$-enriched carbon are within the scope of this invention.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "JAK kinase," and "Janus kinase" refer to the JAK1, JAK2, JAK3 and TYK2 protein kinases.
Triazolopyridine JAK Inhibitor Compounds In one embodiment, a compound of Formula I, and pharmaceutical formulations thereof, are provided that are useful in the treatment of diseases, conditions and/or disorders responsive to the inhibition of JAK kinases.

Another embodiment includes compounds of Formula I:

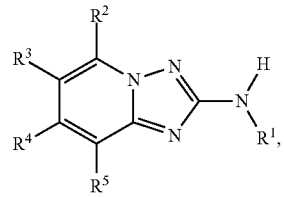

enantiomers, diasteriomers, tautomers or pharmaceutically acceptable salts thereof, wherein:

$R^1$ is H, $C(O)OR^a$, phenyl or $C_1$-$C_9$ heteroaryl, wherein said phenyl and heteroaryl are optionally substituted by 1 to 6 $R^6$;

$R^2$ is phenyl, $C_1$-$C_9$ heteroaryl or $C_1$-$C_9$ heterocyclyl, wherein the phenyl, heteroaryl and heterocyclyl are optionally substituted by 1 to 5 $R^7$;

$R^3$, $R^4$ and $R^5$ are independently H, $CH_3$, $CH_2CH_3$, $CF_3$, F or Cl, with the proviso that when $R^1$ is H, then $R^4$ is H, $CH_3$, $CH_2CH_3$, F or Cl;

$R^6$ is independently H, $C_1$-$C_6$ alkyl, $C_2$-$C_6$ alkenyl, $C_2$-$C_6$ alkynyl, $(C_0$-$C_6$ alkyl)$OR^a$, $(C_0$-$C_6$ alkyl)$NR^aR^b$, halo, CN, $S(O)_{1-2}R^a$, $S(O)_{1-2}NR^aR^b$, $NR^aS(O)_{1-2}R^b$, $NR^aC(O)R^b$, $NR^aC(O)OR^b$, $OC(O)NR^aR^b$, $CF_3$ $(C_0$-$C_5$ alkyl)$C_1$-$C_5$ heteroaryl, $(C_0$-$C_5$ alkyl)$C_1$-$C_5$ heterocyclyl, $(C_0$-$C_5$ alkyl)$C_3$-$C_6$ cycloalkyl, $(C_0$-$C_5$ alkyl)$C_6$-$C_9$ aryl, $C(O)OR^a$, $C(O)(C_0$-$C_5$ alkyl)$NR^aR^b$, $C(O)(C_0$-$C_5$ alkyl)($C_1$-$C_5$ heterocyclyl), $C(O)NR^a(C_0$-$C_5$ alkyl)($C_1$-$C_5$ heterocyclyl), $C(O)NR^a(C_0$-$C_5$ alkyl)($C_3$-$C_6$ cycloalkyl), $C(O)NR^a(C_0$-$C_5$ alkyl)($C_0$-$C_5$ heteroaryl), $C(O)NR^a(C_1$-$C_5$ alkyl)$NR^aR^b$, $C(O)NR^a(C_1$-$C_5$ alkyl)($C_6$ aryl), wherein said alkyl, alkenyl and alkynyl are optionally substituted by 1 to 5 substituents independently selected from $OR^a$, $NR^cR^d$, oxo, $S(O)_{1-2}R^a$, $S(O)_{1-2}NR^aR^b$, and halo, and said aryl, heterocyclyl, heteroaryl and cycloalkyl are optionally substituted by 1 to 5 substituents independently selected from $(C_0$-$C_5$ alkyl)$OR^a$, oxo, halo, $CF_3$, $(C_0$-$C_5$ alkyl)$NR^cR^d$, $C_1$-$C_4$ alkyl and $C(O)R^c$;

$R^7$ is independently H, $C_1$-$C_6$ alkyl, $C_2$-$C_6$ alkenyl, $C_2$-$C_6$ alkynyl, $(C_0$-$C_6$ alkyl)$OR^a$, $(C_0$-$C_6$ alkyl)$NR^aR^b$, $(C_0$-$C_6$ alkyl)$C_1$-$C_5$ heterocyclyl, $C(O)(C_0$-$C_6$ alkyl)$C_1$-$C_5$ heterocyclyl, $(C_0$-$C_6$ alkyl)($C_6$-$C_9$ aryl), halo, $CF_3$, $OCF_3$, $C(O)NR^a(C_0$-$C_6$ alkyl)$C_1$-$C_5$ heterocyclyl, $C(O)NR^aR^b$, $NR^aC(O)R^b$, $SO_2(C_1$-$C_6$ alkyl), $SO_2NR^aR^b$, $S(O)_{1-2}R^a$, $S(O)NR^aR^b$, $NR^aS(O)_{1-2}R^b$, CN, nitro, wherein said alkyl, alkenyl and alkynyl are optionally substituted by 1 to 5 substituents independently selected from oxo and halo, and said aryl and heterocyclyl are optionally substituted by 1 to 5 substituents independently selected from $OR^a$, halo, $CF_3$, $NR^cR^d$, oxo and $C_1$-$C_4$ alkyl;

$R^a$ and $R^b$ are independently H, $OR^c$, $C(O)O(C_1$-$C_6$ alkyl), $C_1$-$C_6$ alkyl, $C_6$ aryl or $C_3$-$C_6$ cycloalkyl, wherein said alkyl, aryl and cycloalkyl are optionally substituted by 1 to 5 substituents independently selected from $C_1$-$C_4$ alkyl, $(C_0$-$C_3$ alkyl)$OR^c$, oxo, halo, $NR^cR^d$ and $C_4$-$C_5$ heterocyclyl; or $R^a$ and $R^b$ together with the atom to which they are attached form a $C_1$-$C_5$ heterocyclyl, optionally substituted by oxo, halo or $C_1$-$C_3$ alkyl; and $R^c$ and $R^d$ are independently H, $C_1$-$C_3$ alkyl, $C_3$-$C_6$ cycloalkyl or phenyl, wherein said alkyl, cycloalkyl and phenyl are optionally substituted by 1 to 5 substituents independently selected from halo, $CH_3$ OH or $NH_2$, $C(O)O(C_1$-$C_6$ alkyl) and $C(O)NH(C_1$-$C_6$ alkyl).

Another embodiment includes compounds of Formula I:

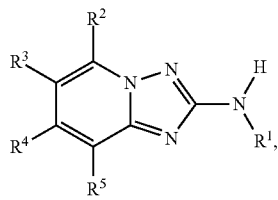

I enantiomers, diasteriomers, tautomers or pharmaceutically acceptable salts thereof, wherein:

In one embodiment, $R^1$ is H, C(O)O$R^a$, phenyl or $C_1$-$C_9$ heteroaryl, wherein said phenyl and heteroaryl are optionally substituted by 1 to 6 $R^6$;

$R^2$ is phenyl, $C_1$-$C_9$ heteroaryl or $C_1$-$C_9$ heterocyclyl, wherein the phenyl, heteroaryl and heterocyclyl are optionally substituted by 1 to 6 $R^7$;

$R^3$, $R^4$ and $R^5$ are independently H, $CH_3$, $CH_2CH_3$, $CF_3$, F or Cl, with the proviso that when $R^1$ is H, then $R^4$ is H, $CH_3$, $CH_2CH_3$, F or Cl;

$R^6$ is independently H, $C_1$-$C_6$ alkyl, $C_2$-$C_6$ alkenyl, $C_2$-$C_6$ alkynyl, ($C_0$-$C_6$ alkyl)O$R^a$, ($C_0$-$C_6$ alkyl)N$R^aR^b$, halo, CN, $C_1$-$C_5$ heteroaryl, $C_1$-$C_5$ heterocyclyl, $C_3$-$C_6$ cycloalkyl, $C_6$-$C_9$ aryl, C(O)O$R^a$, C(O)($C_0$-$C_5$ alkyl)N$R^aR^b$, C(O)($C_0$-$C_5$ alkyl)($C_1$-$C_5$ heterocyclyl), C(O)N$R^a$($C_0$-$C_5$ alkyl)($C_1$-$C_5$ heterocyclyl), C(O)N$R^a$($C_0$-$C_5$ alkyl)($C_3$-$C_6$ cycloalkyl), C(O)N$R^a$($C_0$-$C_5$ alkyl)($C_1$-$C_5$ heteroaryl), C(O)N$R^a$($C_1$-$C_5$ alkyl)N$R^aR^b$, C(O)N$R^a$($C_1$-$C_5$ alkyl)($C_6$ aryl), wherein said alkyl, alkenyl and alkynyl are optionally substituted by 1 to 5 substituents independently selected from O$R^a$, N$R^cR^d$, oxo and halo, and said aryl, heterocyclyl, heteroaryl and cycloalkyl are optionally substituted by 1 to 5 substituents independently selected from O$R^a$, oxo, halo, $CF_3$, N$R^cR^d$, $C_1$-$C_4$ alkyl and C(O)($C_1$-$C_4$ alkyl);

$R^7$ is independently H, $C_1$-$C_6$ alkyl, $C_2$-$C_6$ alkenyl, $C_2$-$C_6$ alkynyl, ($C_0$-$C_6$ alkyl)O$R^a$, ($C_0$-$C_6$ alkyl)N$R^aR^b$, ($C_0$-$C_6$ alkyl)($C_6$-$C_9$ aryl), halo, C(O)N$R^aR^b$, N$R^a$C(O)$R^b$, $SO_2$($C_1$-$C_6$ alkyl), $SO_2$N$R^aR^b$, CN, nitro, wherein said alkyl, alkenyl and alkynyl are optionally substituted by 1 to 5 substituents independently selected from oxo and halo, and said aryl is optionally substituted by 1 to 5 substituents independently selected from O$R^a$, halo, $CF_3$, N$R^cR^d$ and $C_1$-$C_4$ alkyl;

$R^a$ and $R^b$ are independently H, O$R^c$, C(O)O($C_1$-$C_6$ alkyl), $C_1$-$C_6$ alkyl, $C_6$ aryl or $C_3$-$C_6$ cycloalkyl, wherein said alkyl, aryl and cycloalkyl are optionally substituted by 1 to 5 substituents independently selected from $C_1$-$C_4$ alkyl, ($C_0$-$C_3$ alkyl)O$R^c$, oxo, halo, N$R^cR^d$ and $C_4$-$C_5$ heterocyclyl; or $R^a$ and $R^b$ together with the atom to which they are attached form a $C_1$-$C_5$ heterocyclyl; and $R^c$ and $R^d$ are independently H, $C_1$-$C_3$ alkyl, $C_3$-$C_6$ cycloalkyl or phenyl, wherein said alkyl, cycloalkyl and phenyl are optionally substituted by 1 to 5 substituents independently selected from halo, $CH_3$, OH, $NH_2$, C(O)O($C_1$-$C_6$ alkyl) and C(O)NH($C_1$-$C_6$ alkyl).

In one embodiment, $R^1$ is phenyl or $C_1$-$C_9$ heteroaryl, wherein said phenyl and heteroaryl are optionally substituted by 1 to 5 $R^6$.

In one embodiment, $R^1$ is phenyl optionally substituted by 1 to 5 $R^6$.

In one embodiment, $R^1$ is phenyl optionally substituted by 1 to 3 $R^6$.

In one embodiment, $R^1$ is phenyl optionally substituted by 2 $R^6$.

In one embodiment, $R^1$ is phenyl optionally substituted by 1 $R^6$.

In one embodiment, $R^1$ is phenyl optionally substituted by C(O)N$R^a$($C_0$-$C_5$ alkyl)($C_1$-$C_5$ heterocyclyl), wherein said heterocyclyl is optionally substituted by oxo, $C_1$-$C_3$-alkyl, C(O)($C_1$-$C_4$ alkyl) or fluoro. In one example of this embodiment, $R^a$ is H, $C_0$-$C_5$ alkyl is $C_0$-$C_3$ alkyl, and $C_1$-$C_5$ heterocyclyl is piperidinyl, piperizinyl or morpholinyl, optionally substituted by oxo, $C_1$-$C_3$-alkyl, C(O)($C_1$-$C_4$ alkyl) or fluoro. In another example of this embodiment, $R^a$ is H, $C_0$-$C_5$ alkyl is $C_0$ alkyl, and $C_1$-$C_5$ heterocyclyl is piperidinyl, optionally substituted by $CH_3$.

In one embodiment, $R^1$ is $C_1$-$C_9$ heteroaryl optionally substituted by 1 to 5 $R^6$.

In one embodiment, $C_1$-$C_9$ heteroaryl is pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl or furopyridinyl, each of which is optionally substituted by 1 to 5 $R^6$.

In one embodiment, $R^1$ is pyridinyl optionally substituted by 1 to 4 $R^6$.

In one embodiment, $R^1$ is pyridinyl optionally substituted by 2 $R^6$.

In one embodiment, $R^1$ is pyridinyl optionally substituted by 1 $R^6$.

In one embodiment, $R^1$ is phenyl or $C_1$-$C_5$ heteroaryl, optionally substituted by 1 to 3 $R^6$. In one example, $R^1$ is phenyl, pyrazolyl, oxazolyl, thiazolyl or pyridyl, optionally substituted by 1 to 3 $R^6$. In one example, In one example, $R^1$ is phenyl, pyrazolyl, oxazolyl, thiazolyl or pyridyl, optionally substituted by 1 to 3 $R^6$, wherein $R^6$ is independently $C_1$-$C_6$ alkyl, ($C_0$-$C_6$ alkyl)O$R^a$, ($C_0$-$C_6$ alkyl)N$R^aR^b$, halo, $CF_3$, C(O)O$R^a$, C(O)($C_0$-$C_5$ alkyl)N$R^aR^b$, C(O)($C_0$-$C_5$ alkyl)($C_1$-$C_5$ heterocyclyl), C(O)N$R^a$($C_0$-$C_5$ alkyl)($C_1$-$C_5$ heterocyclyl), C(O)N$R^a$($C_0$-$C_5$ alkyl)($C_3$-$C_6$ cycloalkyl), C(O)N$R^a$($C_0$-$C_5$ alkyl)($C_1$-$C_5$ heteroaryl), C(O)N$R^a$($C_1$-$C_5$ alkyl)N$R^aR^b$, C(O)N$R^a$($C_1$-$C_5$ alkyl)($C_6$ aryl), wherein said alkyl is optionally substituted by 1 to 5 substituents independently selected from O$R^a$, N$R^cR^d$, oxo and halo, and said aryl, heterocyclyl, heteroaryl and cycloalkyl are optionally substituted by 1 to 5 substituents independently selected from O$R^a$, oxo, halo, $CF_3$, N$R^cR^d$, $C_1$-$C_4$ alkyl, ($C_0$-$C_6$ alkyl)$C_1$-$C_5$ heterocyclyl and C(O)($C_1$-$C_4$ alkyl). In one example, $R^1$ is phenyl, pyrazolyl, oxazolyl, thiazolyl or pyridyl, optionally substituted by 1 $R^6$, wherein $R^6$ is independently C(O)O$R^a$, C(O)($C_0$-$C_5$ alkyl)N$R^aR^b$, C(O)($C_0$-$C_5$ alkyl)($C_1$-$C_5$ heterocyclyl), C(O)N$R^a$($C_0$-$C_5$ alkyl)($C_1$-$C_5$ heterocyclyl), C(O)N$R^a$($C_0$-$C_5$ alkyl)($C_3$-$C_6$ cycloalkyl), C(O)N$R^a$($C_0$-$C_5$ alkyl)($C_1$-$C_5$ heteroaryl), C(O)N$R^a$($C_1$-$C_5$ alkyl)N$R^aR^b$, C(O)N$R^a$($C_0$-$C_5$ alkyl)($C_6$ aryl), wherein said alkyl is optionally substituted by 1 to 5 substituents independently selected from O$R^a$, N$R^cR^d$, oxo and halo, and said aryl, heterocyclyl, heteroaryl and cycloalkyl are optionally substituted by 1 to 5 substituents independently selected from O$R^a$, oxo, halo, $CF_3$, N$R^cR^d$, $C_1$-$C_4$ alkyl, ($C_0$-$C_6$ alkyl)$C_1$-$C_5$ heterocyclyl and C(O)($C_1$-$C_4$ alkyl).

In one embodiment, $R^1$ is phenyl or pyridinyl, optionally substituted by 1 to 3 $R^6$, wherein $R^6$ is independently $C_1$-$C_3$ alkyl, ($C_0$-$C_6$ alkyl)O$R^a$, ($C_0$-$C_6$ alkyl)N$R^aR^b$, halo, $CF_3$, $S(O)_{1-2}R^a$, $S(O)_{1-2}NR^aR^b$, $NR^aS(O)_{1-2}R^b$, ($C_0$-$C_5$ alkyl)$C_1$-$C_5$ heterocyclyl or C(O)O$R^a$, wherein said alkyl is optionally substituted by 1 to 5 substituents independently selected from $OR^a$, $NR^cR^d$, oxo, $S(O)_{1-2}R^a$, $S(O)_{1-2}NR^aR^b$ and halo, and said heterocyclyl is optionally substituted by 1 to 3 substituents independently selected from $(C_0-C_5\ alkyl)OR^a$, oxo, halo, $CF_3$, $(C_0-C_5\ alkyl)NR^cR^d$, $C_1-C_4$ alkyl and $C(O)R^c$. In one example, $R^1$ is selected from the following:
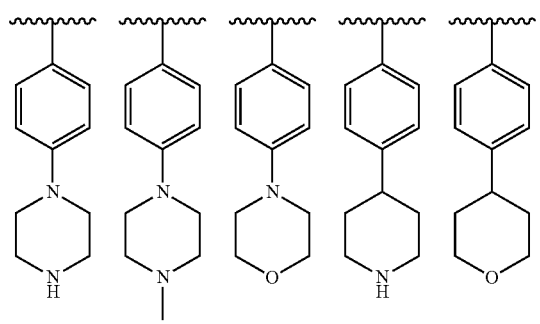
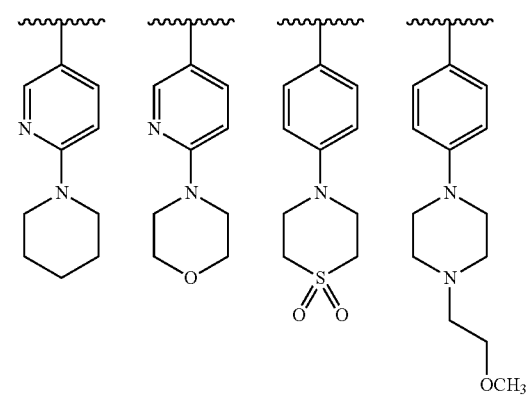
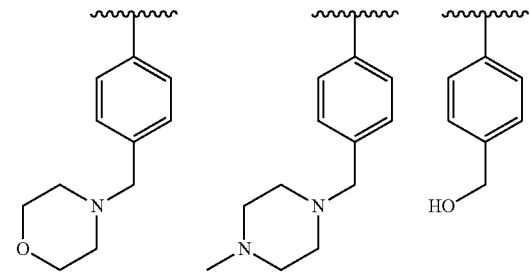
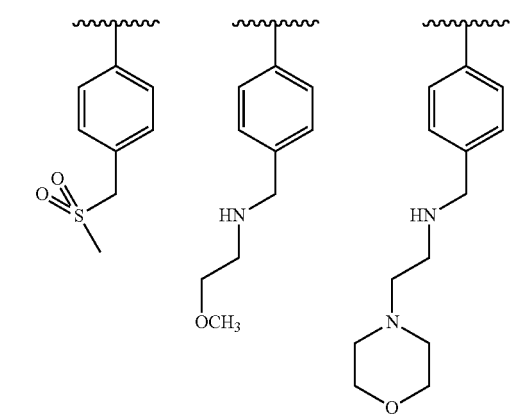
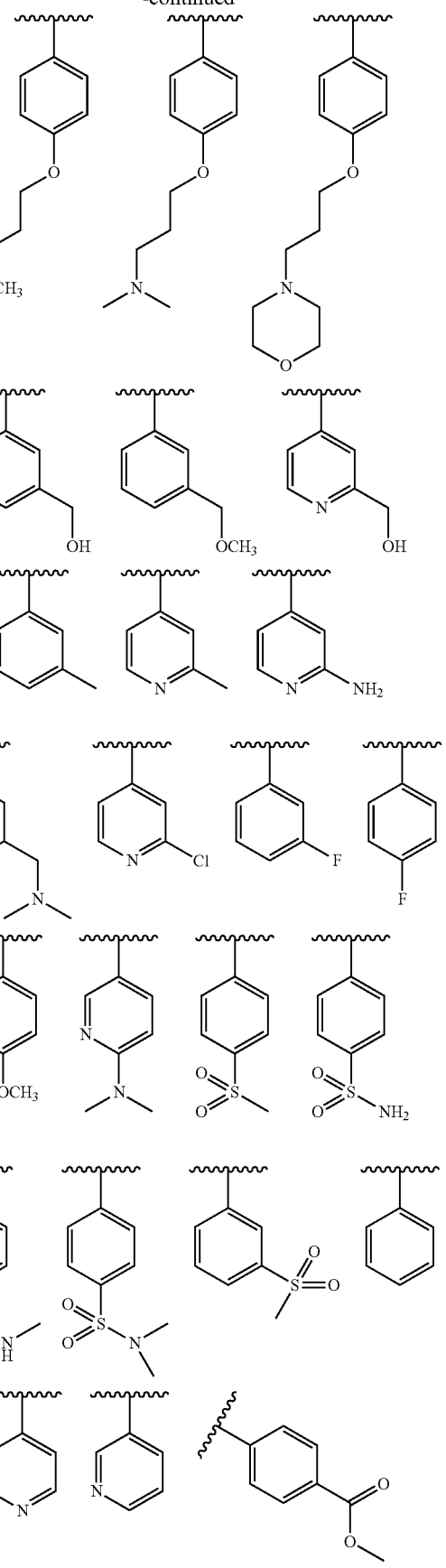

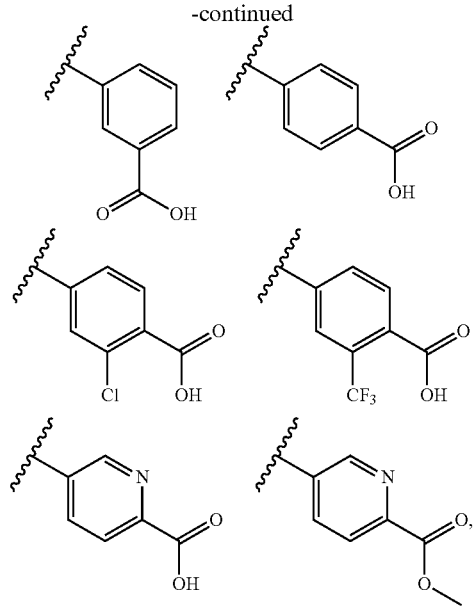

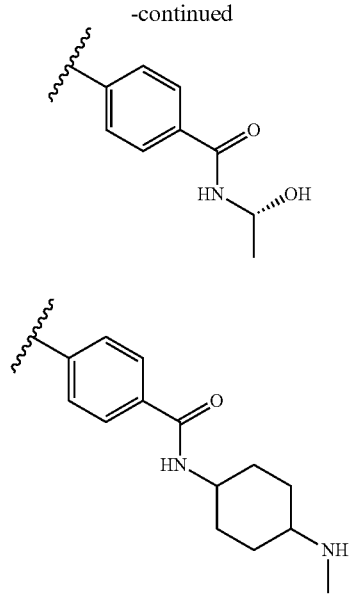

wherein the wavy line represents the point of attachment to Formula I.

In one embodiment, $R^1$ is phenyl or pyridinyl, optionally substituted by 1 $R^6$, wherein $R^6$ is independently $C(O)(C_0\text{-}C_5$ alkyl$)NR^aR^b$, $C(O)NR^a(C_0\text{-}C_5$ alkyl$)(C_1\text{-}C_5$ heterocyclyl), $C(O)NR^a(C_0\text{-}C_5$ alkyl$)(C_3\text{-}C_6$ cycloalkyl), $C(O)NR^a(C_0\text{-}C_5$ alkyl$)(C_1\text{-}C_5$ heteroaryl), $C(O)NR^a(C_1\text{-}C_5$ alkyl$)NR^aR^b$, $C(O)NR^a(C_0\text{-}C_5$ alkyl$)(C_6$ aryl), wherein said aryl, heterocyclyl, heteroaryl and cycloalkyl are optionally substituted by 1 to 5 substituents independently selected from $OR^a$, oxo, halo, $CF_3$, $NR^cR^d$, $C_1\text{-}C_4$ alkyl, $(C_0\text{-}C_6$ alkyl$)C_1\text{-}C_5$ heterocyclyl and $C(O)(C_1\text{-}C_4$ alkyl). In one example, $R^1$ is selected from the following:

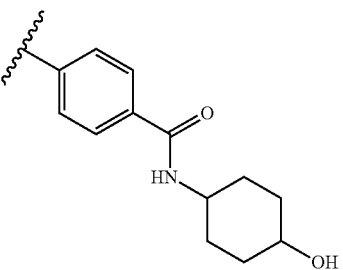

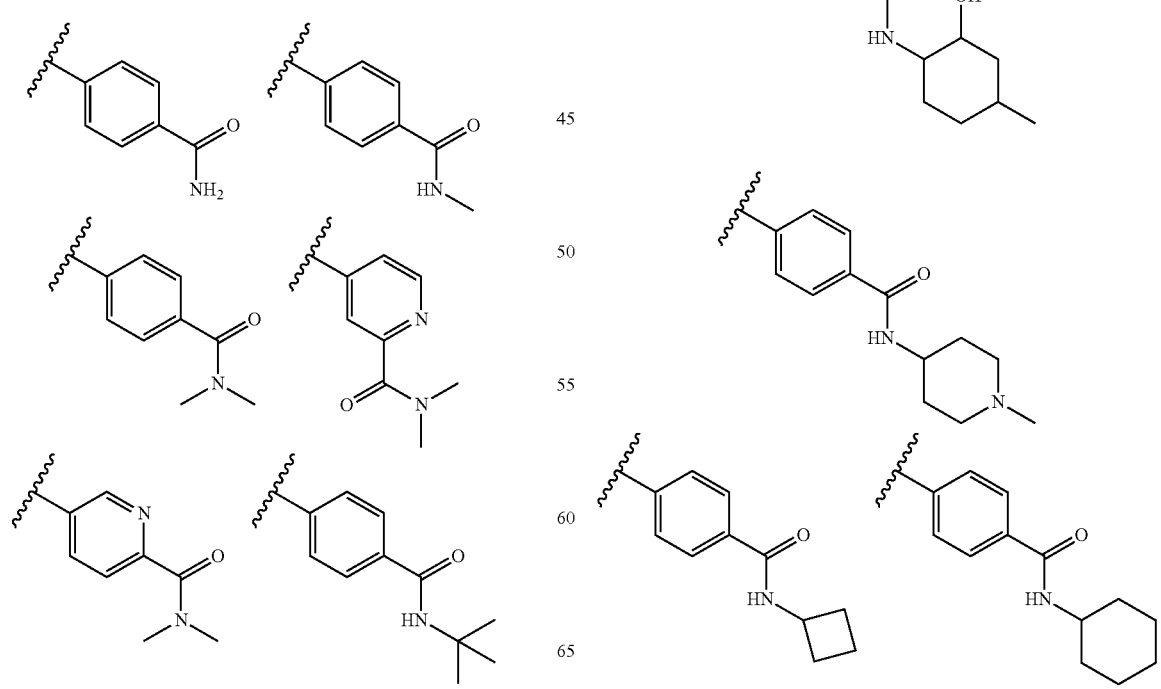

-continued
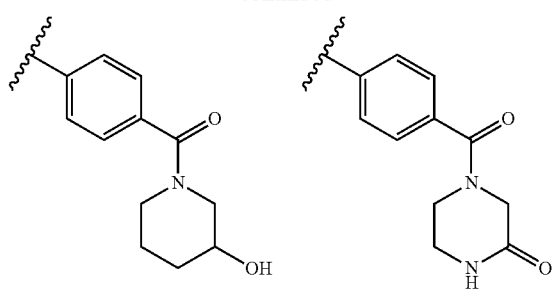
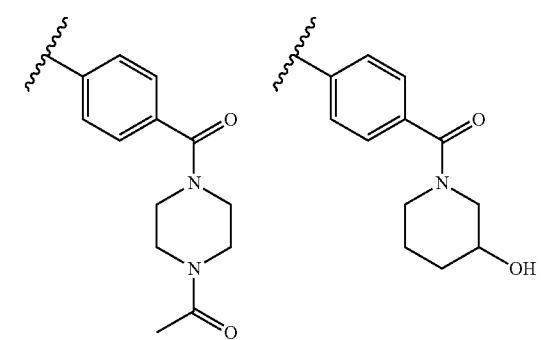
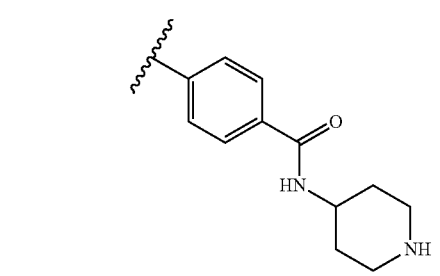
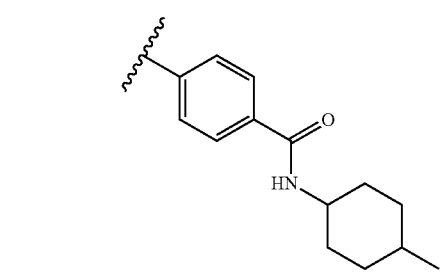
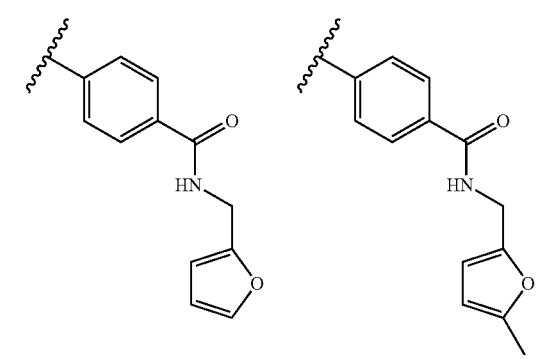
-continued
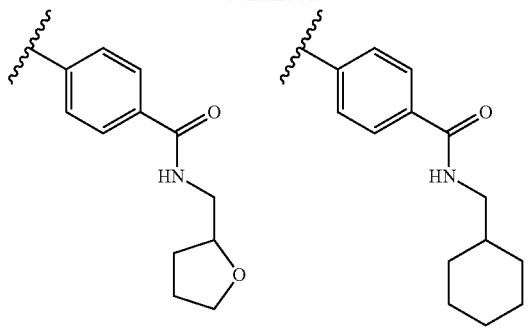
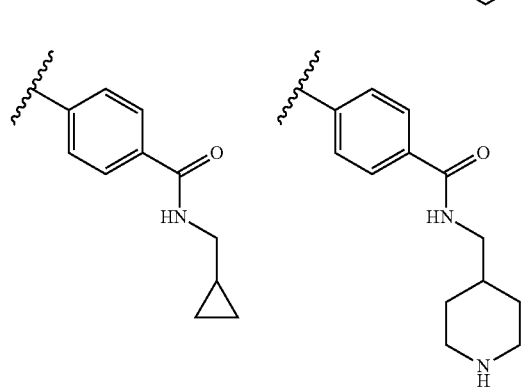
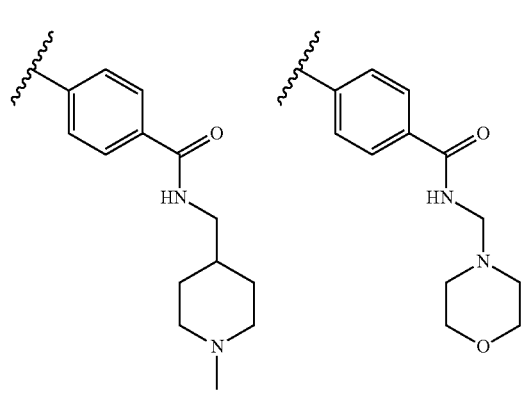
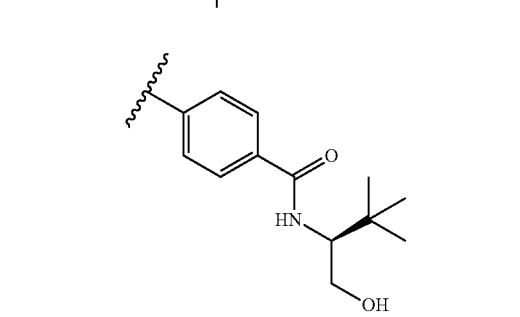
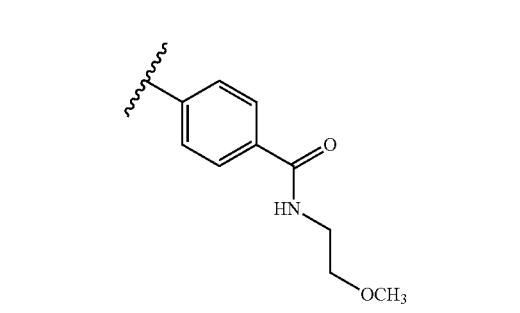

23
-continued
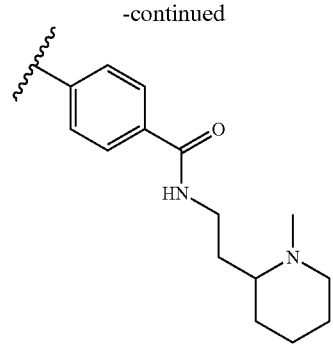
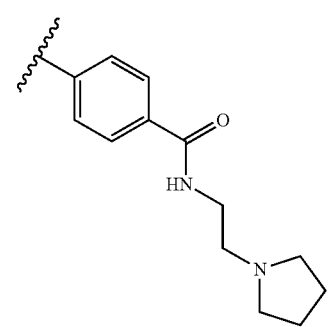
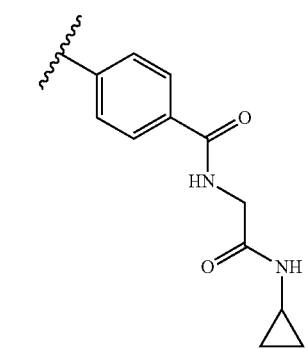
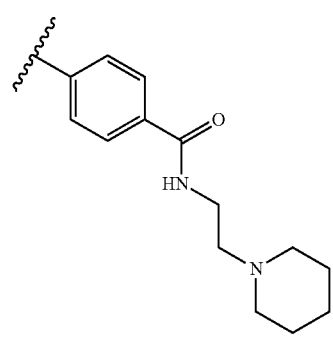
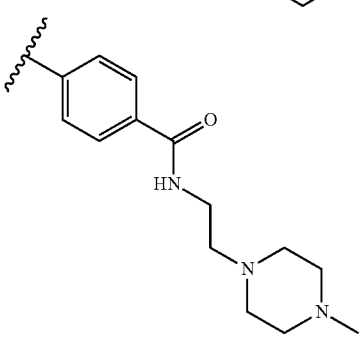
24
-continued
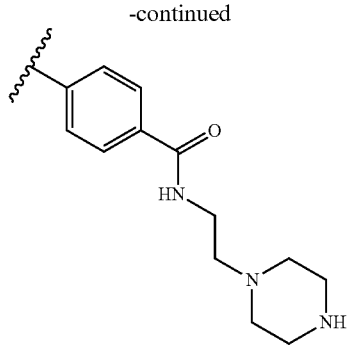
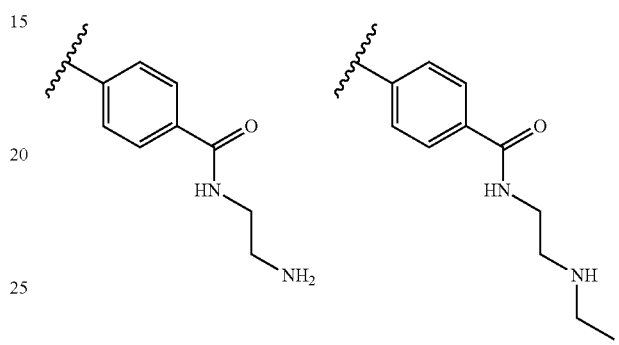
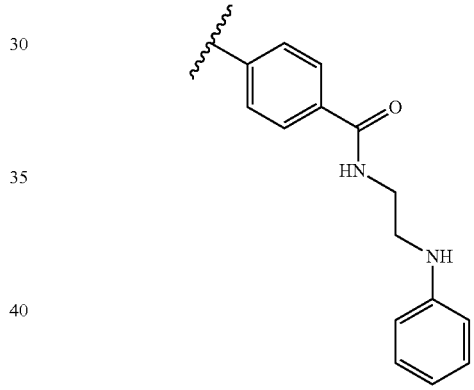
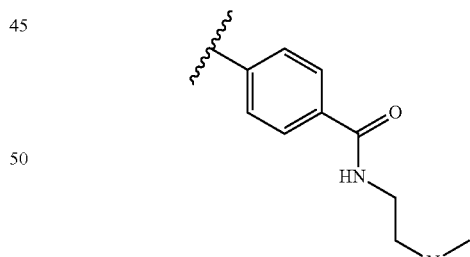
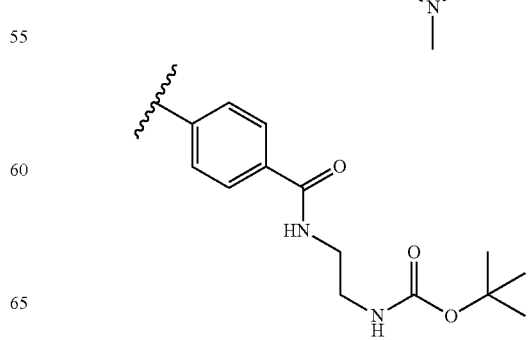

25
-continued
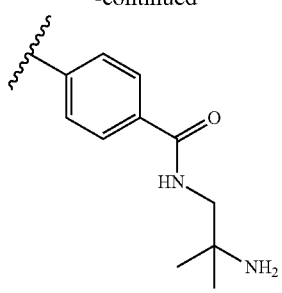
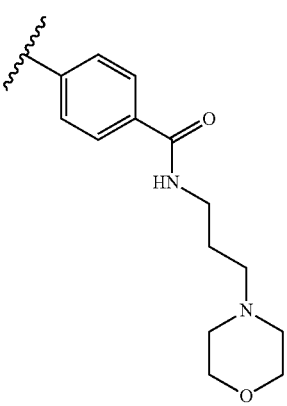
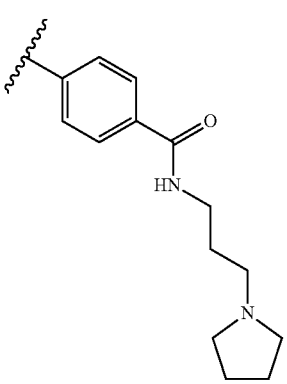
26
-continued
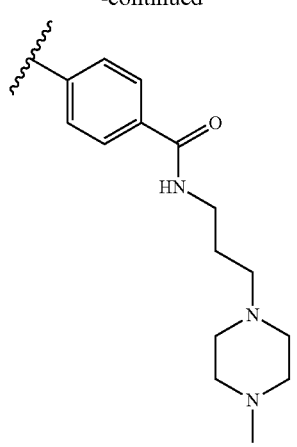
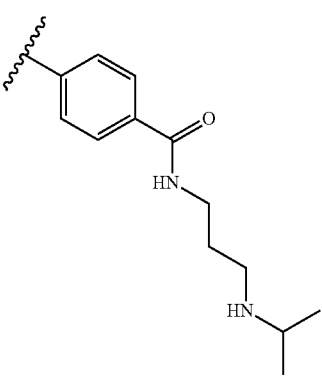
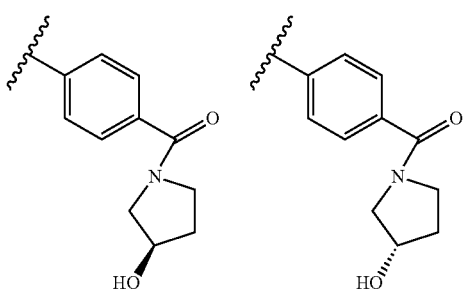

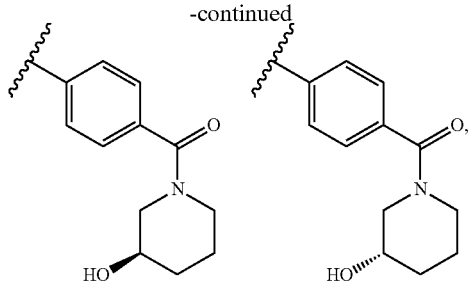

wherein the wavy line represents the point of attachment to Formula I.

In one embodiment, $R^1$ is $C_1$-$C_5$ heteroaryl, optionally substituted by 1 to 3 $R^6$. In one example, $R^1$ is pyrazolyl, oxazolyl or thiazolyl, optionally substituted by 1 or 2 $R^6$, wherein $R^6$ is $C_1$-$C_6$ alkyl or ($C_0$-$C_6$ alkyl)$C_1$-$C_5$ heterocyclyl, wherein said alkyl is optionally substituted by 1 to 5 substituents independently selected from $OR^a$, $NR^cR^d$, oxo and halo, and said heterocyclyl is optionally substituted by 1 to 5 substituents independently selected from $OR^a$, oxo, halo, $CF_3$, $NR^cR^d$, $C_1$-$C_4$ alkyl, ($C_0$-$C_6$ alkyl)$C_1$-$C_5$ heterocyclyl and $C(O)(C_1$-$C_4$ alkyl). In one example, said heterocyclyl is pyrrolidinyl, tetrahydrofuranyl, tetrahydropyranyl, piperidinyl, piperazinyl or morpholinyl. In one example, $R^1$ is selected from the following:

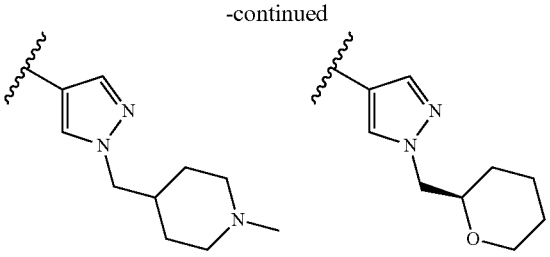

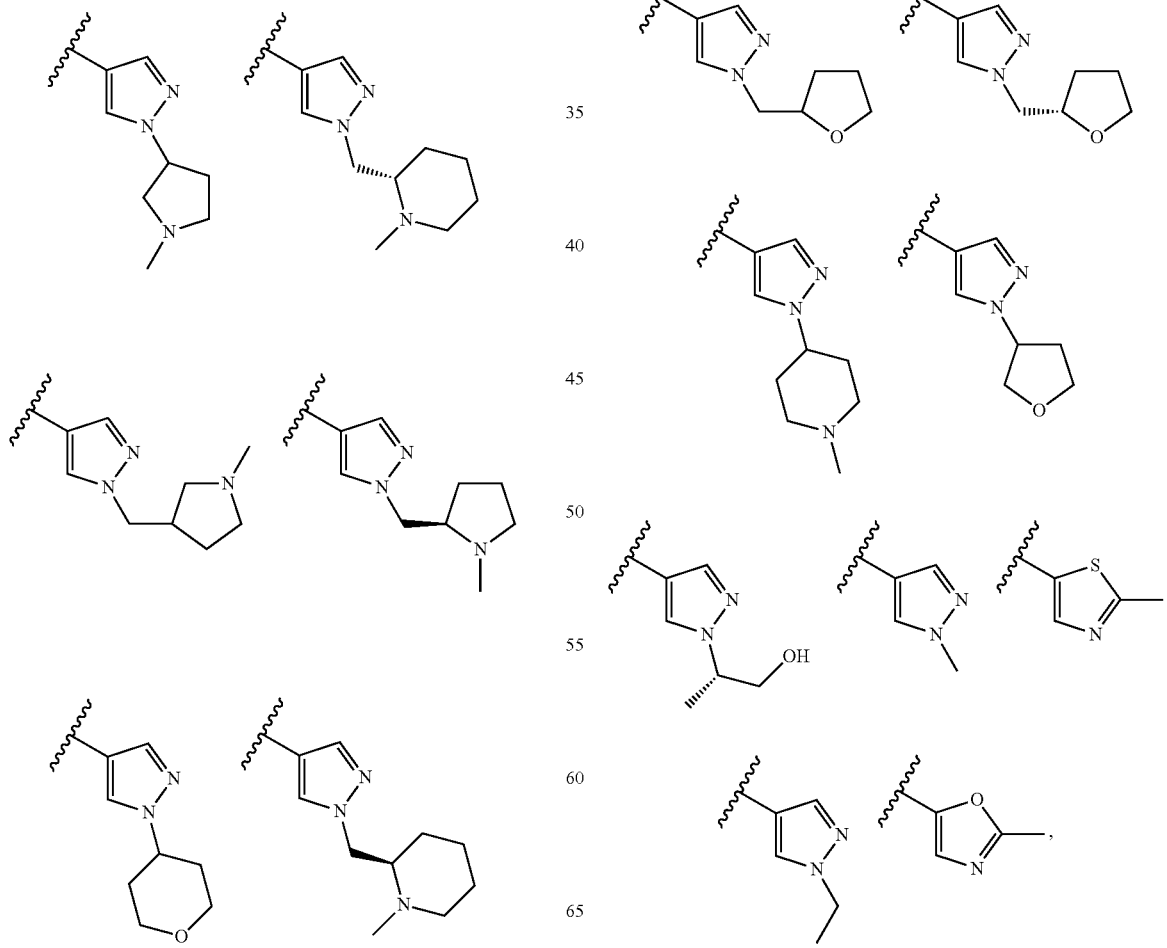

wherein the wavy line represents the point of attachment to Formula I.

In one embodiment, $R^6$ is independently $C_1$-$C_6$ alkyl, ($C_0$-$C_6$ alkyl)$OR^a$, ($C_0$-$C_6$ alkyl)$NR^aR^b$, halo, CN, $C_1$-$C_5$ heteroaryl, $C_4$-$C_5$ heterocyclyl, $C_3$-$C_6$ cycloalkyl, $C_6$ aryl, C(O)$OR^a$, C(O)($C_0$-$C_5$ alkyl)$NR^aR^b$, C(O)($C_0$-$C_5$ alkyl)($C_1$-$C_5$ heterocyclyl), C(O)$NR^a$($C_0$-$C_5$ alkyl)($C_1$-$C_5$ heterocyclyl), C(O)$NR^a$($C_0$-$C_5$ alkyl)($C_3$-$C_6$ cycloalkyl), C(O)$NR^a$($C_0$-$C_5$ alkyl)($C_1$-$C_5$ heteroaryl), C(O)$NR^a$($C_1$-$C_5$ alkyl)$NR^aR^b$, C(O)$NR^a$($C_1$-$C_5$ alkyl)($C_6$ aryl), wherein said alkyl is optionally substituted by 1 to 5 substituents independently selected from $OR^a$, $NR^cR^d$, oxo and halo, and said aryl, heterocyclyl, heteroaryl and cycloalkyl are optionally substituted by 1 to 5 substituents independently selected from $OR^a$, oxo, halo, $CF_3$, $NR^cR^d$, $C_1$-$C_4$ alkyl and C(O)($C_1$-$C_4$ alkyl).

In one embodiment, $R^6$ is $C_4$-$C_5$ heterocyclyl optionally substituted by 1 to 5 substituents independently selected from OH, oxo, halo, $CF_3$, $NR^cR^d$, $C_1$-$C_4$ alkyl and C(O)($C_1$-$C_4$ alkyl).

In one embodiment, heterocyclyl is pyrrolidinyl, tetrahydrofuranyl, tetrahydrothiophenyl, 1,1-dioxotetrahydrothiophenyl, piperidinyl, piperizinyl, tetrahydropyranyl, thianyl, morpholinyl, pyridizinyl or hexahydropyrimidinyl.

In one embodiment, heterocyclyl is piperidinyl, piperizinyl or morpholinyl.

In one embodiment, $R^6$ is ($C_0$-$C_6$ alkyl)$OR^a$ or ($C_0$-$C_6$ alkyl)$NR^aR^b$.

In one embodiment, $R^6$ is ($C_0$-$C_3$ alkyl)$OR^a$ or ($C_0$-$C_3$ alkyl)$NR^aR^b$.

In one embodiment, $R^6$ is halo.

In one embodiment, $R^6$ is F or Cl.

In one embodiment, $R^6$ is $S(O)_{1-2}NR^aR^b$. In one example, $R^6$ is $S(O)_2NH_2$.

In one embodiment, $R^6$ is $NR^aC(O)R^b$. In one example, $R^6$ is $NHCOCH_3$.

In one embodiment, $R^6$ is C(O)$NR^a$($C_0$-$C_5$ alkyl)($C_1$-$C_5$ heterocyclyl), C(O)$NR^a$($C_0$-$C_5$ alkyl)($C_3$-$C_6$ cycloalkyl), C(O)$NR^a$($C_0$-$C_5$ alkyl)($C_1$-$C_5$ heteroaryl), C(O)$NR^a$($C_1$-$C_5$ alkyl)$NR^aR^b$, C(O)$NR^a$($C_1$-$C_5$ alkyl)($C_6$ aryl), wherein said alkyl is optionally substituted by 1 to 5 substituents independently selected from $OR^a$, $NR^cR^d$, oxo and halo, and said aryl, heterocyclyl, heteroaryl and cycloalkyl are optionally substituted by 1 to 5 substituents independently selected from $OR^a$, oxo, halo, $CF_3$, $NR^cR^d$, $C_1$-$C_4$ alkyl and C(O)($C_1$-$C_4$ alkyl).

In one embodiment, $R^6$ is C(O)$OR^a$, C(O)($C_0$-$C_5$ alkyl)$NR^aR^b$ or C(O)($C_0$-$C_5$ alkyl)($C_1$-$C_5$ heterocyclyl), wherein said alkyl is optionally substituted by 1 to 5 substituents independently selected from $OR^a$, $NR^cR^d$, oxo and halo, and said aryl, heterocyclyl, heteroaryl and cycloalkyl are optionally substituted by 1 to 5 substituents independently selected from $OR^a$, oxo, halo, $CF_3$, $NR^cR^d$, $C_1$-$C_4$ alkyl and C(O)($C_1$-$C_4$ alkyl).

In one embodiment, $R^6$ is independently $C_1$-$C_6$ alkyl, ($C_0$-$C_6$ alkyl)$NR^aR^b$, ($C_0$-$C_6$ alkyl)$C_1$-$C_5$ heterocyclyl, ($C_0$-$C_6$ alkyl)$C_3$-$C_6$ cycloalkyl, or C(O)($C_0$-$C_5$ alkyl)($C_1$-$C_5$ heterocyclyl), wherein said alkyl is optionally substituted by 1 to 5 substituents independently selected from $OR^a$, $NR^cR^d$, oxo and halo, and said heterocyclyl and cycloalkyl are optionally substituted by 1 to 5 substituents independently selected from $OR^a$, oxo, halo, $CF_3$, $NR^cR^d$, $C_1$-$C_4$ alkyl, ($C_0$-$C_6$ alkyl)$C_1$-$C_5$ heterocyclyl and C(O)($C_1$-$C_4$ alkyl). In one example, $R^6$ is selected from the following:

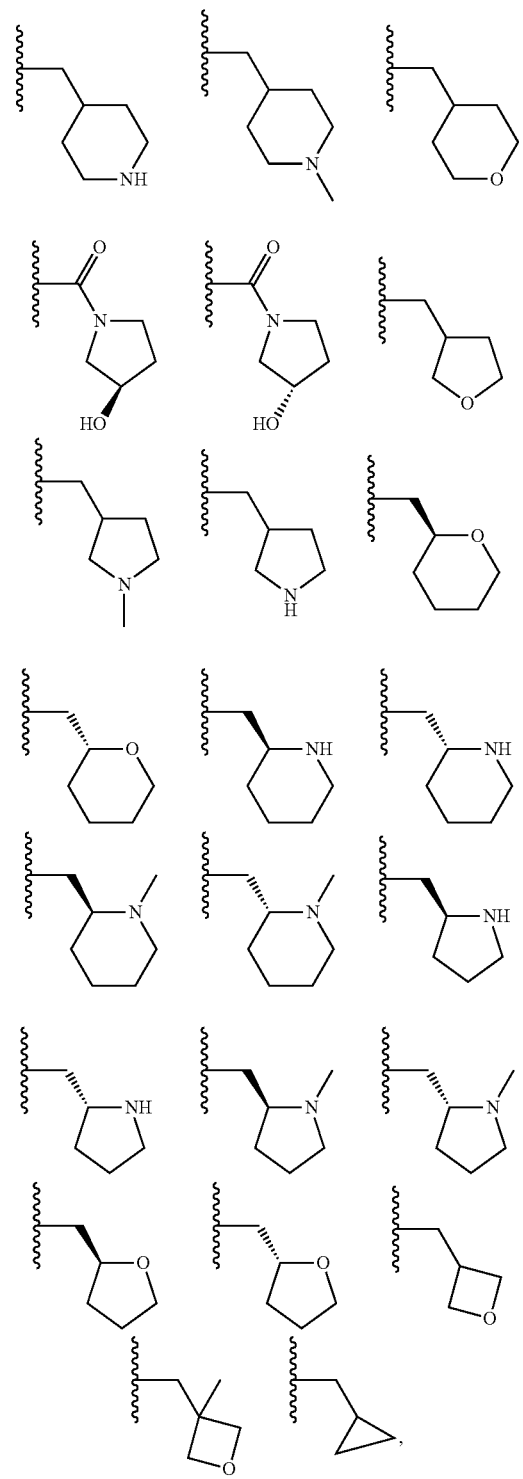

wherein the wavy line represents the point of attachment in Formula I.

In one embodiment, $R^6$ is ($C_0$-$C_6$ alkyl)$C_1$-$C_5$ heteroaryl, optionally substituted by 1 to 5 substituents independently selected from $OR^a$, halo, $CF_3$, $NR^cR^d$ and $C_1$-$C_4$ alkyl. In one example, $R^7$ is pyridinyl, optionally substituted by 1 to 5 substituents independently selected from $OR^a$, halo, $CF_3$, $NR^cR^d$ and $C_1$-$C_4$ alkyl.

In one embodiment, $R^6$ is selected from the following:

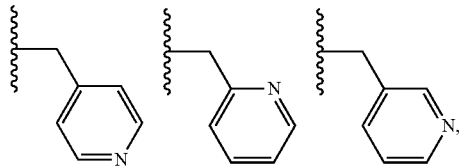

wherein the wavy line represents the point of attachment in Formula I.

In one embodiment, $R^1$ is H.

In one embodiment, $R^1$ is $C(O)OR^a$, wherein $R^a$ is independently H, $OR^c$, $C(O)O(C_1-C_6$ alkyl), $C_1-C_6$ alkyl, $C_6$ aryl or $C_3-C_6$ cycloalkyl, wherein said alkyl, aryl and cycloalkyl are optionally substituted by 1 to 5 substituents independently selected from $C_1-C_4$ alkyl, $(C_0-C_3$ alkyl)$OR^c$, oxo, halo, $NR^cR^d$ and $C_4-C_5$ heterocyclyl.

In one embodiment, $R^3$, $R^4$ and $R^5$ are independently H, $CH_3$, $CF_3$ or F, with the proviso that when $R^1$ is H, then $R^4$ is H, $CH_3$ or F.

In one embodiment, $R^3$, $R^4$ and $R^5$ are independently H or F.

In one embodiment, $R^3$, $R^4$ and $R^5$ are H.

In one embodiment, $R^3$ is $OCH_3$.

In one embodiment, $R^2$ is phenyl, $C_1-C_9$ heteroaryl or $C_3-C_5$ heterocyclyl, wherein the phenyl, heteroaryl and heterocyclyl are optionally substituted by 1 to 5 $R^7$.

In one embodiment, $R^2$ is phenyl optionally substituted by 1 to 5 $R^7$.

In one embodiment, $R^2$ is phenyl optionally substituted by 1 to 3 $R^7$.

In one embodiment, $R^2$ is phenyl optionally substituted by 2 $R^7$.

In one embodiment, $R^2$ is phenyl or pyridinyl, optionally substituted by 2 $R^7$, wherein $R^7$ is independently $C_1-C_6$ alkyl, $OCF_3$, $OCH_3$, $NH_2$, $NO_2$, $CH_2NH_2$, F, Cl, $C(O)NR^aR^b$, $NR^aC(O)R^b$, $SO_2(C_1-C_3$ alkyl), $SO_2NR^aR^b$, CN, $CF_3$, $OCF_3$, $C(O)R^a$, $C(O)OR^a$, $(C_0-C_6$ alkyl)$C_1-C_5$ heterocyclyl, $C(O)(C_0-C_6$ alkyl)$C_1-C_5$ heterocyclyl or $C(O)NR^a(C_0-C_6$ alkyl)$C_1-C_5$ heterocyclyl, wherein said heterocyclyl is optionally substituted by $C_1-C_4$ alkyl. In one example, $R^2$ is selected from:

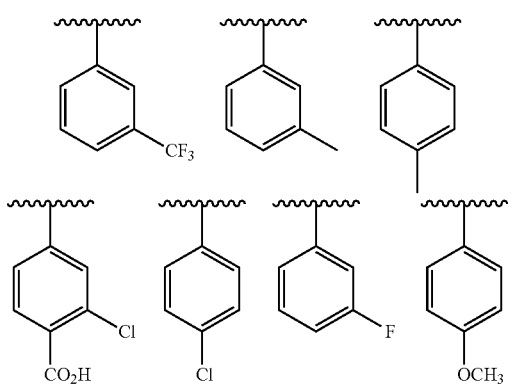

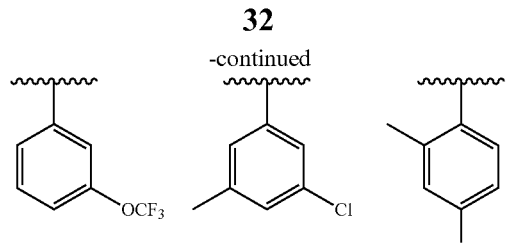

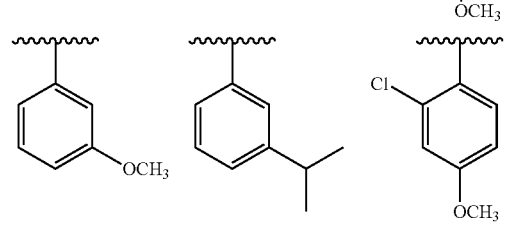

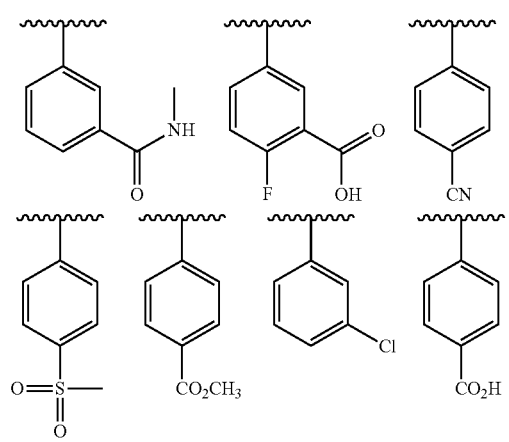

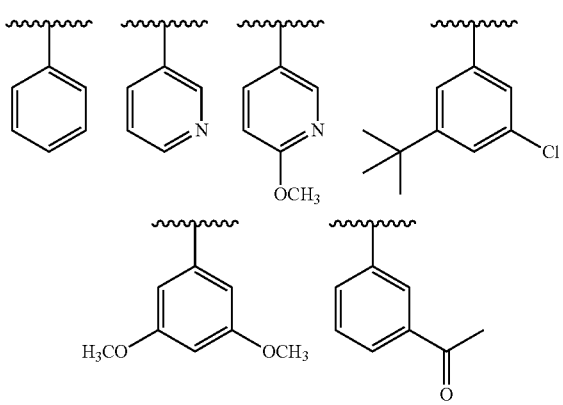

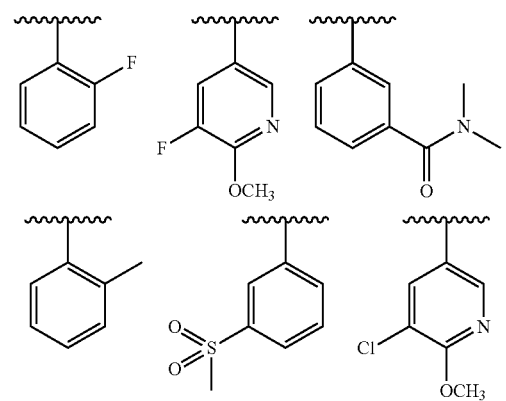

-continued
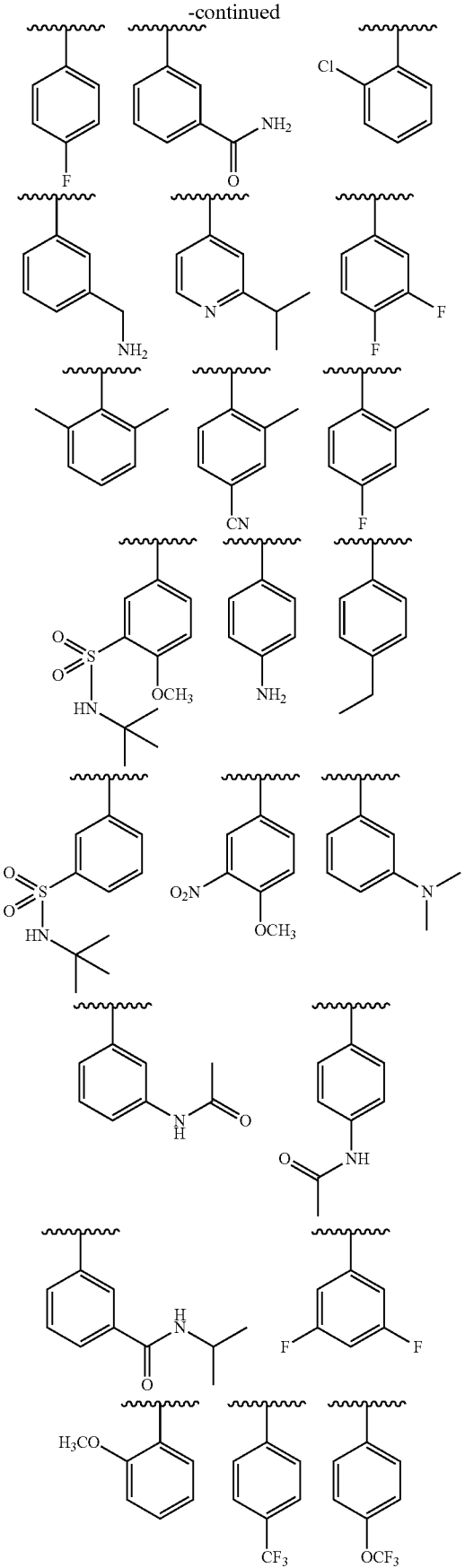
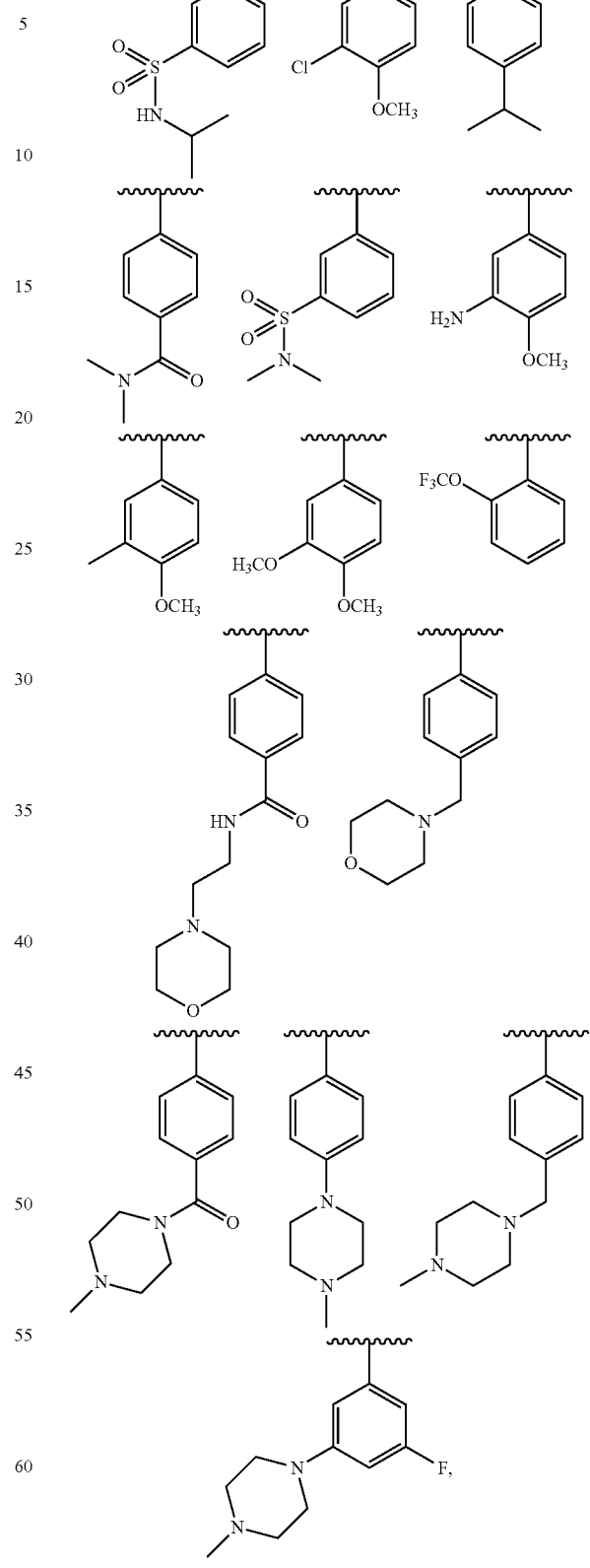
wherein the wavy line represents the point of attachment in Formula I.

In one embodiment, $R^2$ is pyrazolyl, optionally substituted by 1 or 2 $R^7$, wherein $R^7$ is independently $R^7$ is independently $C_1$-$C_6$ alkyl, ($C_0$-$C_6$ alkyl)$OR^a$, ($C_0$-$C_6$ alkyl)$NR^aR^b$, ($C_0$-$C_6$ alkyl)($C_6$-$C_9$ aryl), halo, ($C_0$-$C_6$ alkyl)$C_1$-$C_5$ heteroaryl, ($C_0$-$C_6$ alkyl)$C_1$-$C_5$ heterocyclyl or ($C_0$-$C_6$ alkyl)$C_3$-$C_6$ cycloalkyl, wherein said alkyl, is optionally substituted by 1 to 5 substituents independently selected from oxo, $NR^aR^b$, $OR^a$, and halo, and said aryl, heteroaryl, heterocyclyl and cycloalkyl are optionally substituted by 1 to 5 substituents independently selected from $OR^a$, halo, $CF_3$, $NR^cR^d$ and $C_1$-$C_4$ alkyl. In one example, $R^2$ is selected from

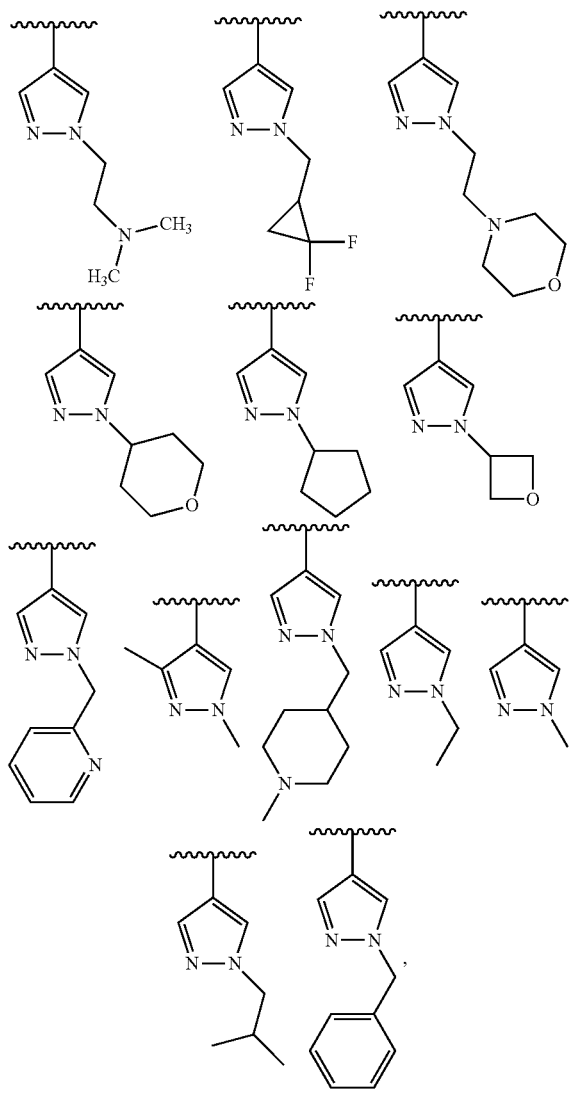

wherein the wavy line represents the point of attachment in Formula I.

In one embodiment, $R^2$ is phenyl optionally substituted by 1 $R^7$.

In one embodiment, $R^7$ is independently $C_1$-$C_6$ alkyl, ($C_0$-$C_6$ alkyl)$OR^a$, ($C_0$-$C_6$ alkyl)$NR^aR^b$, ($C_0$-$C_6$ alkyl)($C_6$-$C_9$ aryl), halo, $C(O)NR^aR^b$, $NR^aC(O)R^b$, $SO_2(C_1$-$C_6$ alkyl), $SO_2NR^aR^b$, CN, nitro, wherein said alkyl is optionally substituted by 1 to 5 substituents independently selected from oxo and halo, and said and said aryl is optionally substituted by 1 to 5 substituents independently selected from $OR^a$, halo, $CF_3$, $NR^cR^d$ and $C_1$-$C_4$ alkyl.

In one embodiment, $R^7$ is independently $C_1$-$C_4$ alkyl, ($C_0$-$C_6$ alkyl)$OR^a$, ($C_0$-$C_6$ alkyl)$NR^aR^b$, halo, $NR^aC(O)R^b$, $SO_2$($C_1$-$C_6$ alkyl), $SO_2NR^aR^b$, CN or nitro.

In one embodiment, $R^7$ is independently $C_3$-$C_6$ cycloalkyl.

In one embodiment, $R^7$ is independently $NH_2$, $OCH_3$, $CH_3$, $CH_2CH_3$, $CH(CH_3)_2$, $NO_2$, $OCF_3$, $S(O)_2N(CH_3)_2$, $S(O)_2NH(CH(CH_3)_2)$, $S(O)_2NH(C(CH_3)_3)$, CN, $CF_3$, F, Cl, NHC(O)$CH_3$ or $S(O)_2CH_3$, $C(O)N(CH_3)_2$, $CO_2H$, $S(O)CH_3$, cyclopentyl, 1-hydroxyethyl, 1-aminoethyl or $CH_2CF_3$.

In one embodiment, $R^2$ is $C_1$-$C_9$ heteroaryl optionally substituted by 1 to 5 $R^7$.

In one embodiment, $C_1$-$C_9$ heteroaryl is pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl or furopyridinyl, each of which is optionally substituted by 1 to 5 $R^7$.

In one embodiment, $R^2$ is pyridinyl or pyrazolyl optionally substituted by 1 to 5 $R^7$.

In one embodiment, $R^2$ is pyridinyl or pyrazolyl optionally substituted by 1 to 3 $R^7$.

In one embodiment, $R^2$ is pyridinyl or pyrazolyl optionally substituted by 1 $R^7$.

In one embodiment, $R^2$ is 1H-indazolyl.

In one embodiment, $R^7$ is independently $CH_3$, $CH_2$(phenyl), $CH_2CH(CH_3)_2$, or $CF_3$.

In one embodiment, $R^2$ is $C_3$-$C_5$ heterocyclyl optionally substituted by 1 to 5 $R^7$.

In one embodiment, $R^2$ is piperidinyl, morpholinyl or piperizinyl optionally substituted by 1 to 5 $R^7$.

In one embodiment, $R^2$ is piperidinyl, morpholinyl or piperizinyl optionally substituted by 1 to 3 $R^7$.

In one embodiment, $R^2$ is piperidinyl, morpholinyl or piperizinyl optionally substituted by 2 $R^7$.

In one embodiment, $R^2$ is piperidinyl, morpholinyl or piperizinyl optionally substituted by 1 $R^7$.

In one embodiment, $R^7$ is independently $CH_3$, $CH_2CH_3$, OH or $OCH_3$.

In one embodiment, $R^1$ is phenyl, optionally substituted by 1 to 5 $R^6$; and $R^2$ is phenyl, optionally substituted by 1 to 5 $R^7$.

In one embodiment, $R^1$ is phenyl, optionally substituted by 1 to 5 $R^6$; and $R^2$ is heterocyclyl, optionally substituted by 1 to 5 $R^7$.

In one embodiment, heterocyclyl is piperidinyl, morpholinyl or piperizinyl.

In one embodiment, $R^1$ is pyridyl, optionally substituted by 1 to 4 $R^6$; and $R^2$ is phenyl, optionally substituted by 1 to 5 $R^7$.

In one embodiment, $R^1$ is pyridyl, optionally substituted by 1 to 4 $R^6$; and $R^2$ is heterocyclyl, optionally substituted by 1 to 5 $R^7$.

In one embodiment, heterocyclyl is piperidinyl, morpholinyl or piperizinyl.

In one embodiment, $R^1$ is phenyl, optionally substituted by 1 to 5 $R^6$; and $R^2$ is pyridyl, optionally substituted by 1 to 4 $R^7$.

In one embodiment, $R^1$ is pyridyl, optionally substituted by 1 to 4 $R^6$; and $R^2$ is pyridyl, optionally substituted by 1 to 4 $R^7$.

In one embodiment, $R^1$ is phenyl or pyridinyl, optionally substituted by 1 to 3 $R^6$, wherein $R^6$ is independently $C_1$-$C_3$ alkyl, halo, $CF_3$ or $C(O)OR^a$; and $R^2$ is phenyl or pyridinyl, optionally substituted by 2 $R^7$, wherein $R^7$ is independently $C_1$-$C_6$ alkyl, $OCF_3$, $OCH_3$, $NH_2$, $CH_2NH_2$, F, Cl, C(O)N-$R^aR^b$, $NR^aC(O)R^b$, $SO_2$($C_1$-$C_3$ alkyl), $SO_2NR^aR^b$, CN, $CF_3$, $OCF_3$, $C(O)R^a$, $C(O)OR^a$.
Another embodiment includes a compound selected from:
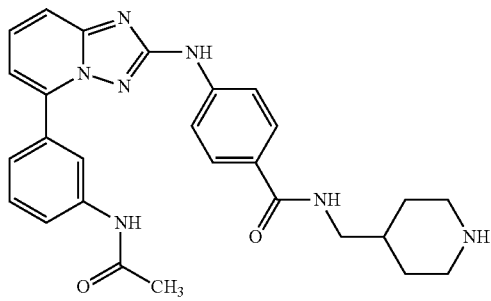
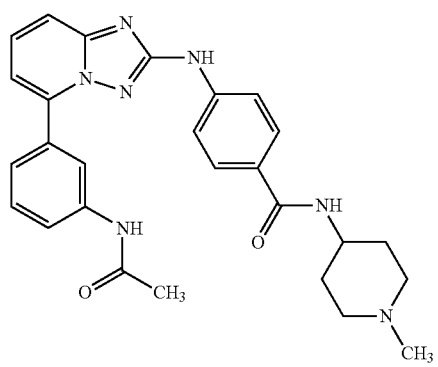
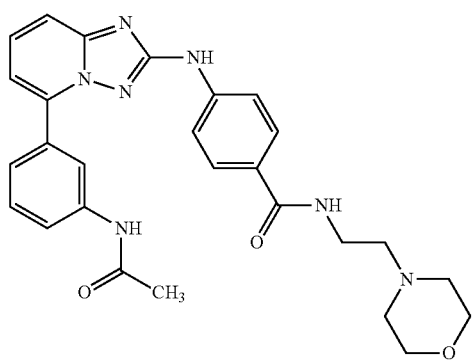
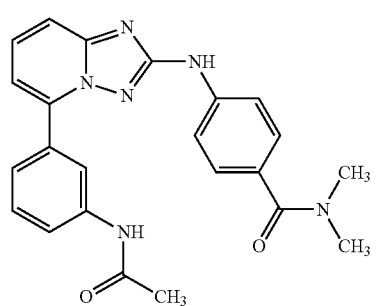
-continued
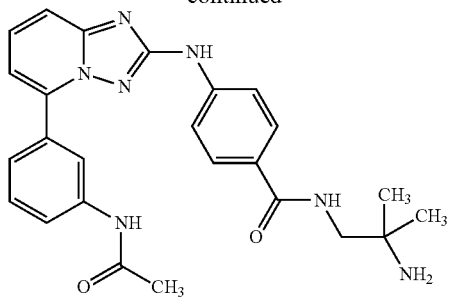
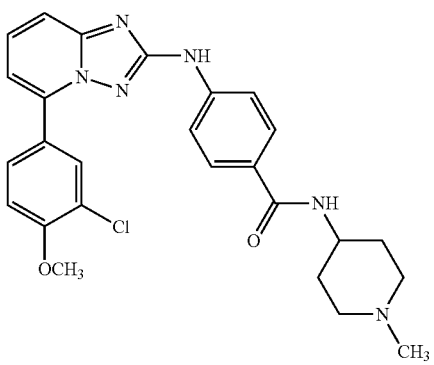
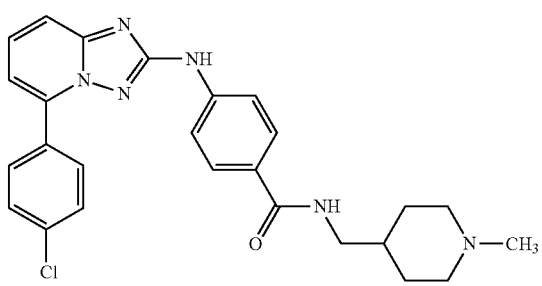
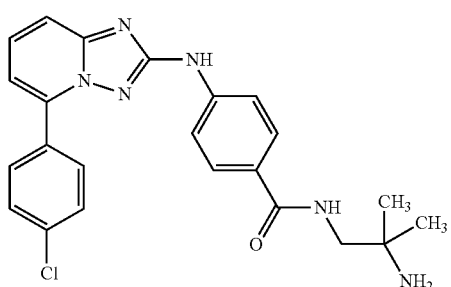
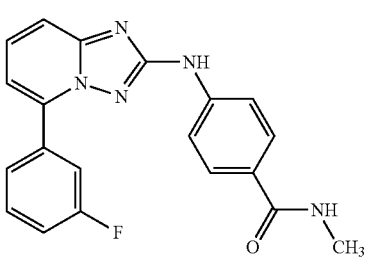

39
-continued
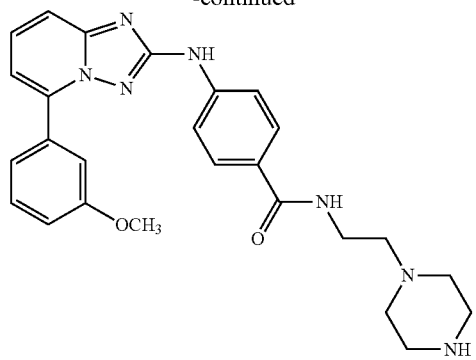
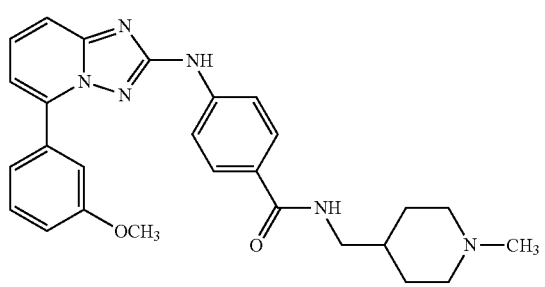
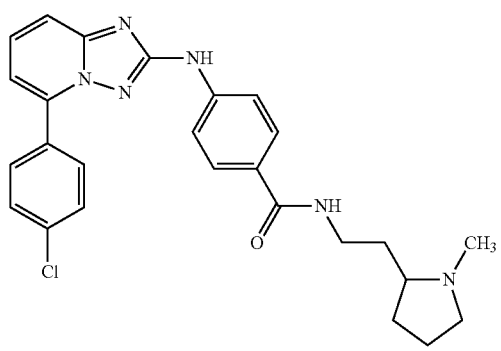
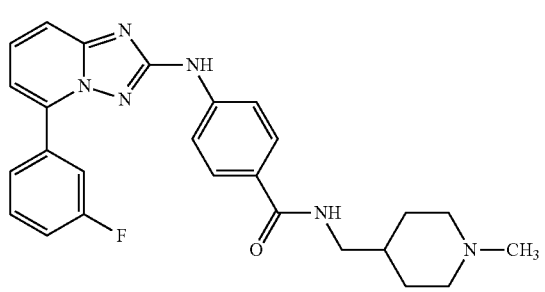
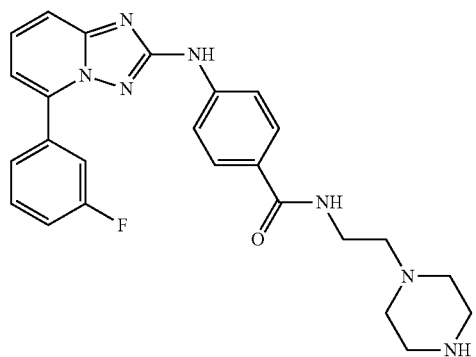
40
-continued
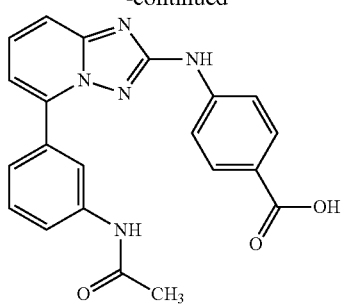
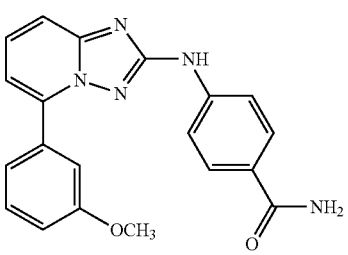
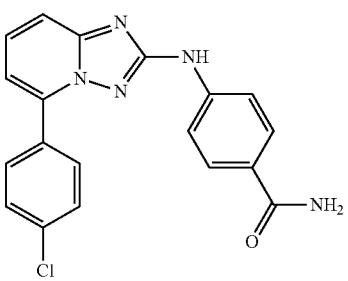
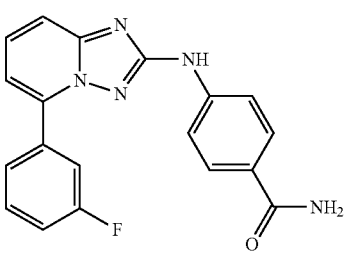
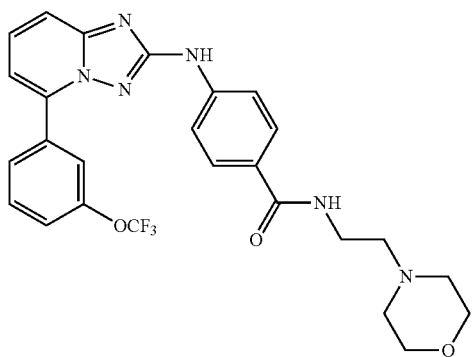

41
-continued
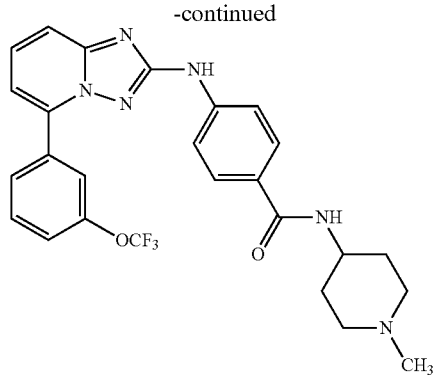
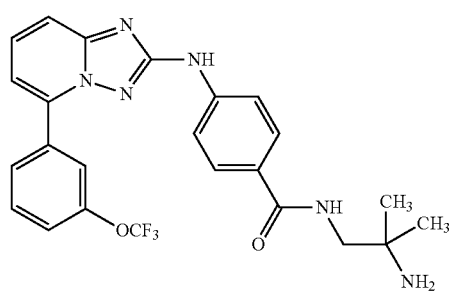
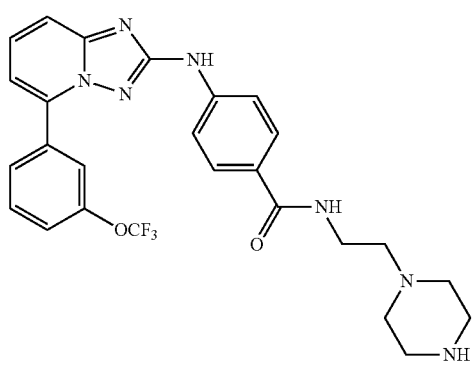
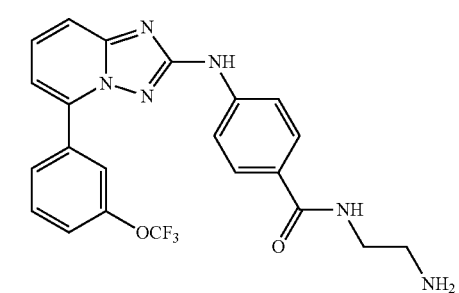
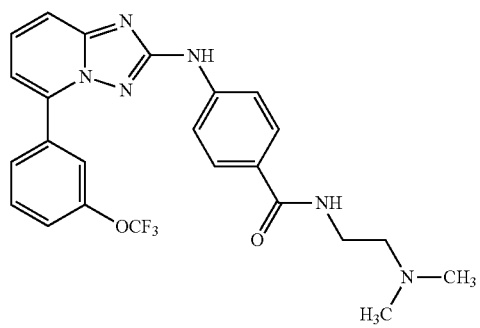
42
-continued
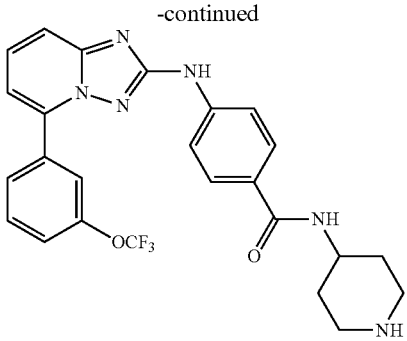
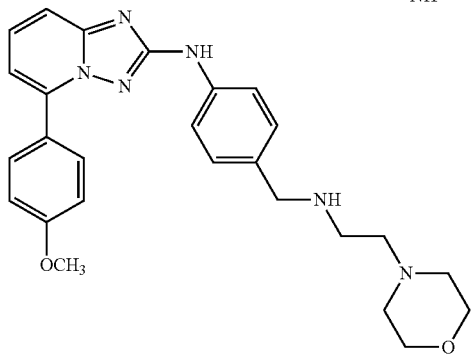
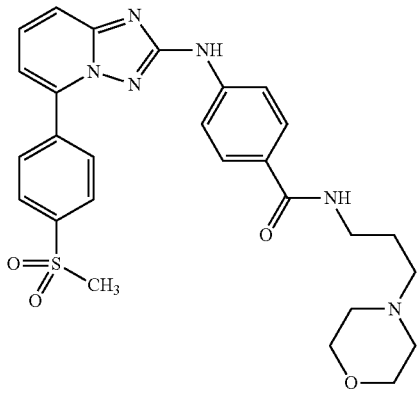
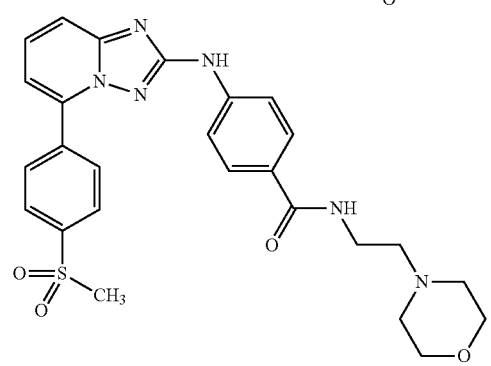
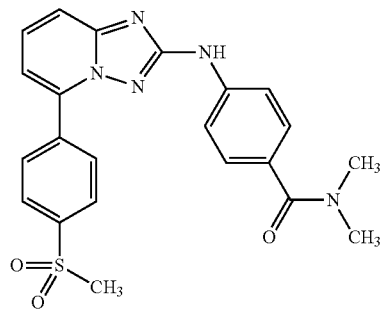

43
-continued
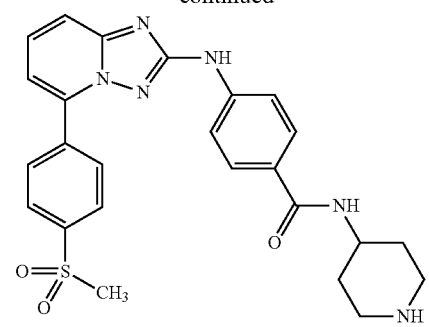
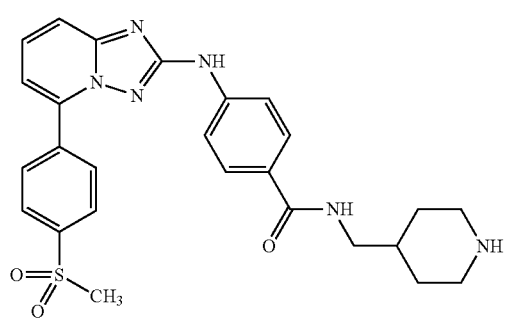
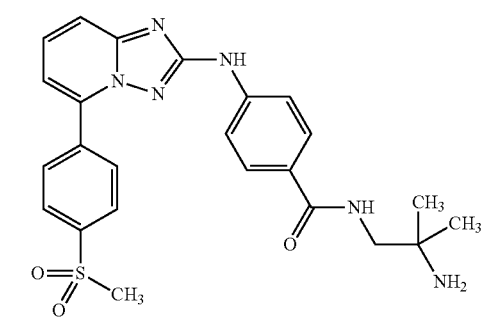
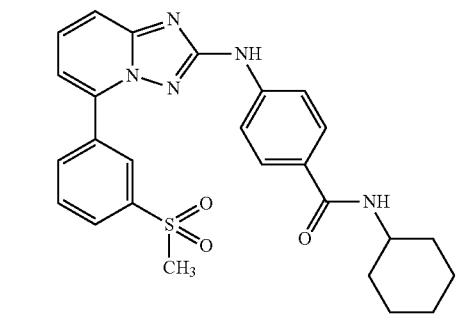
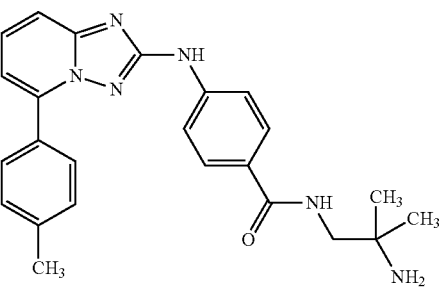
44
-continued
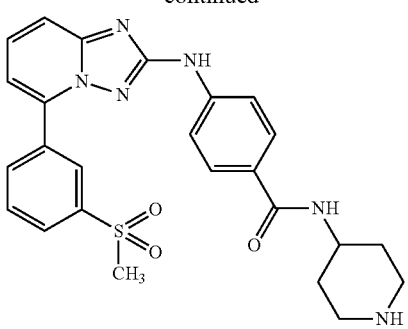
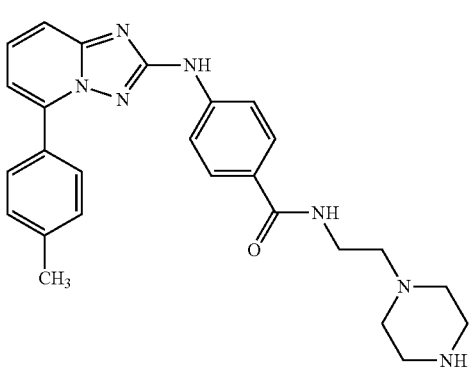
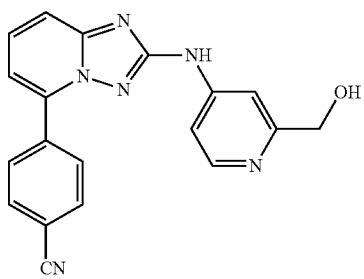
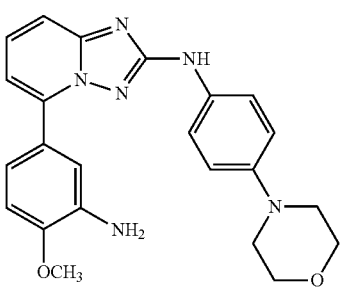
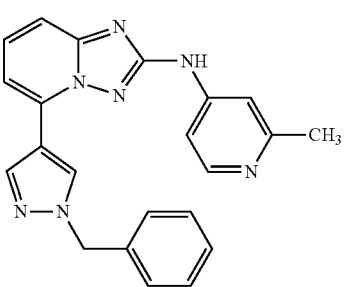

-continued
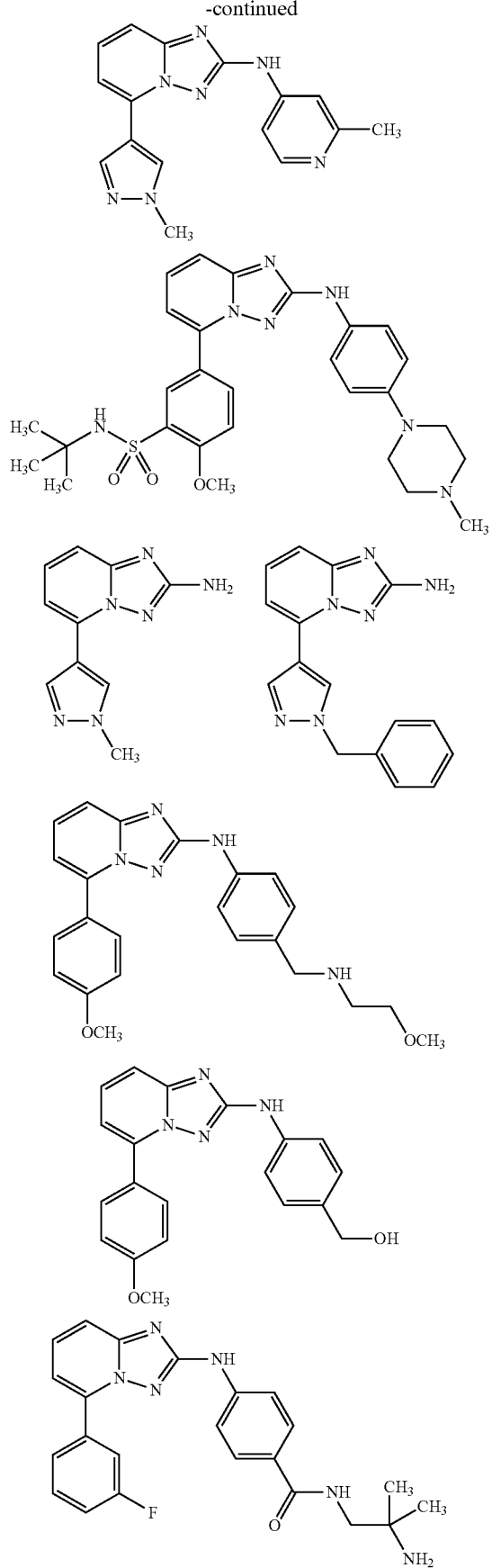
-continued
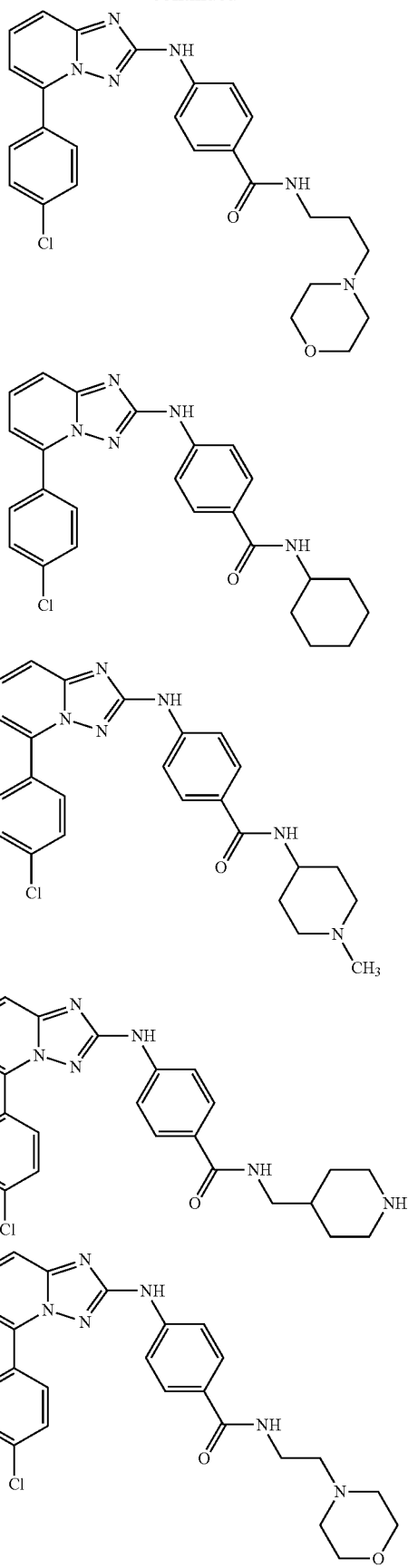

-continued
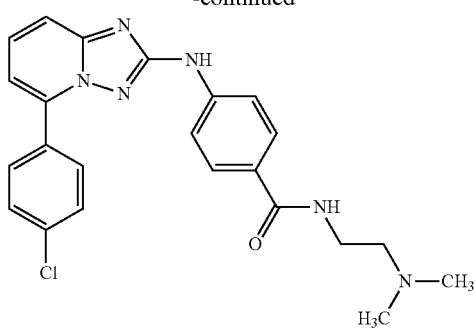
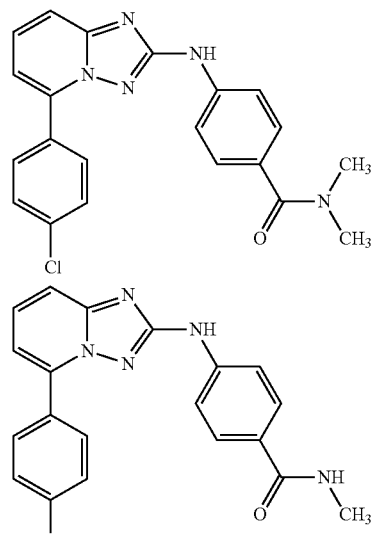
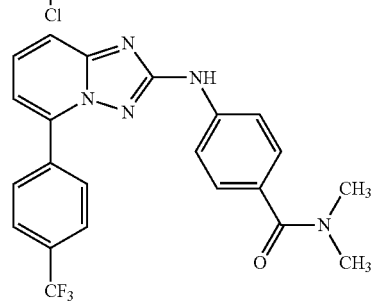
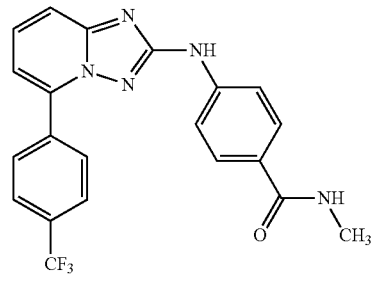
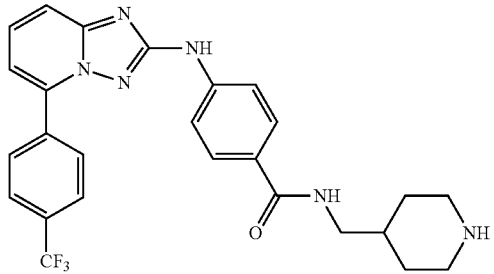
-continued
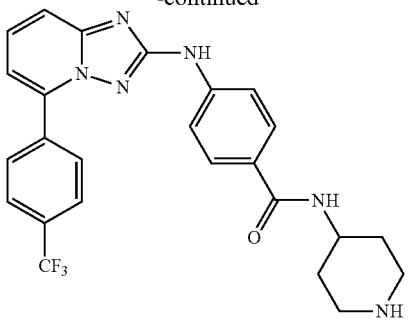
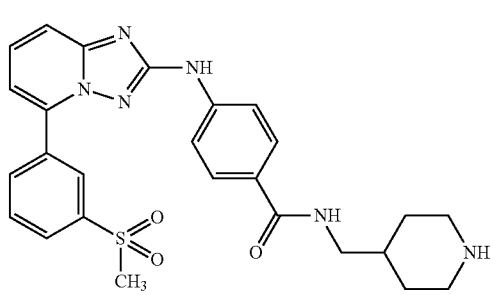
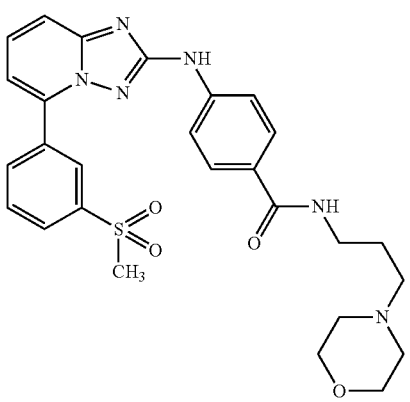
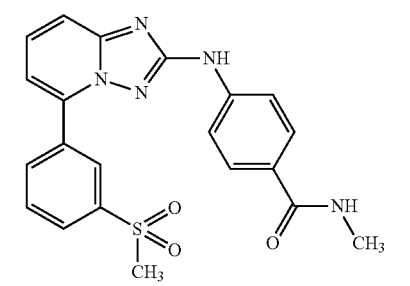
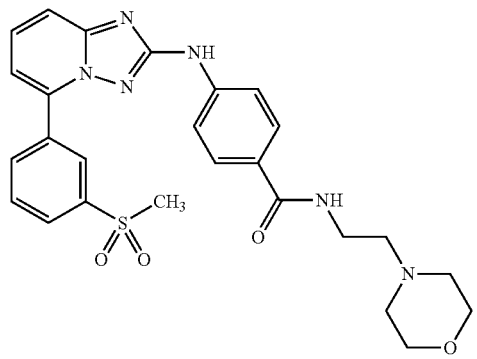

49
-continued
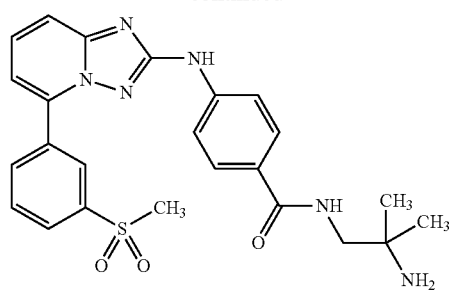
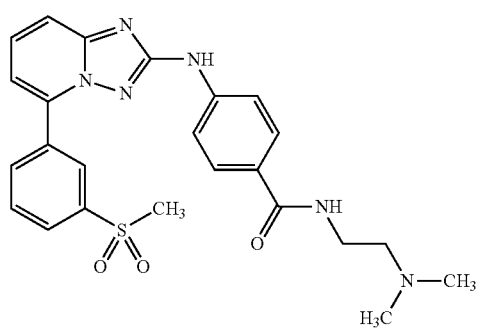
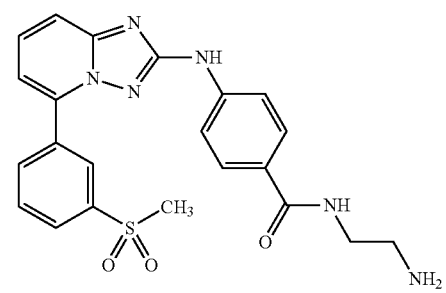
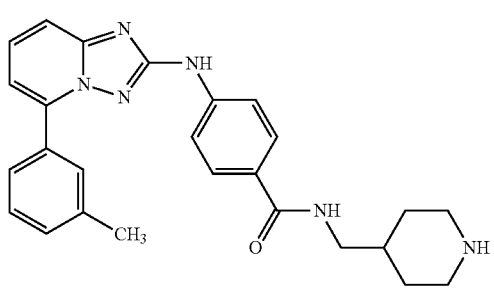
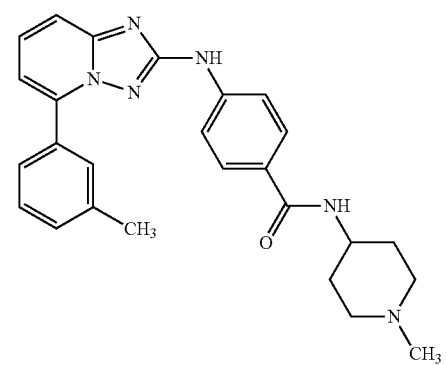
50
-continued
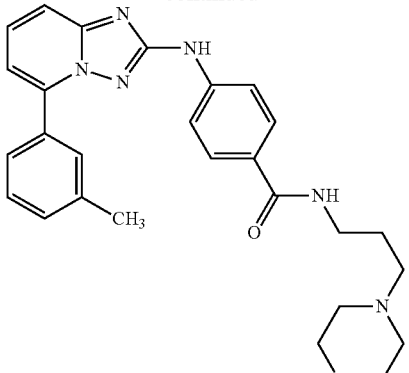
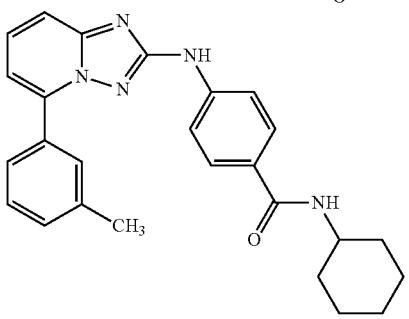
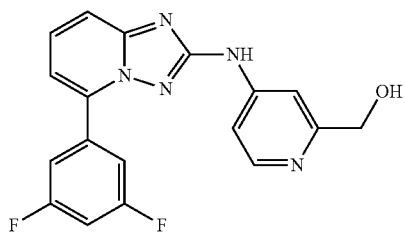
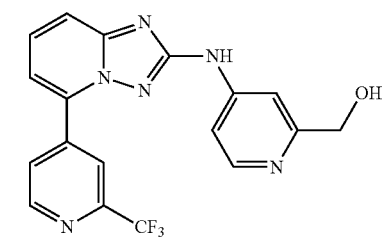
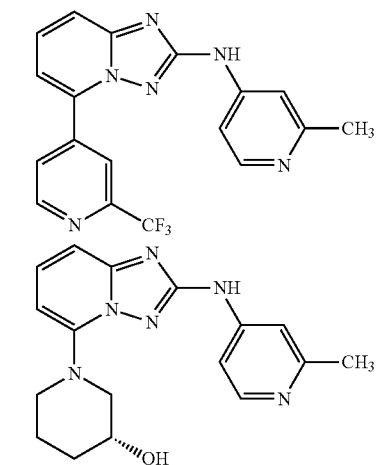

51
-continued
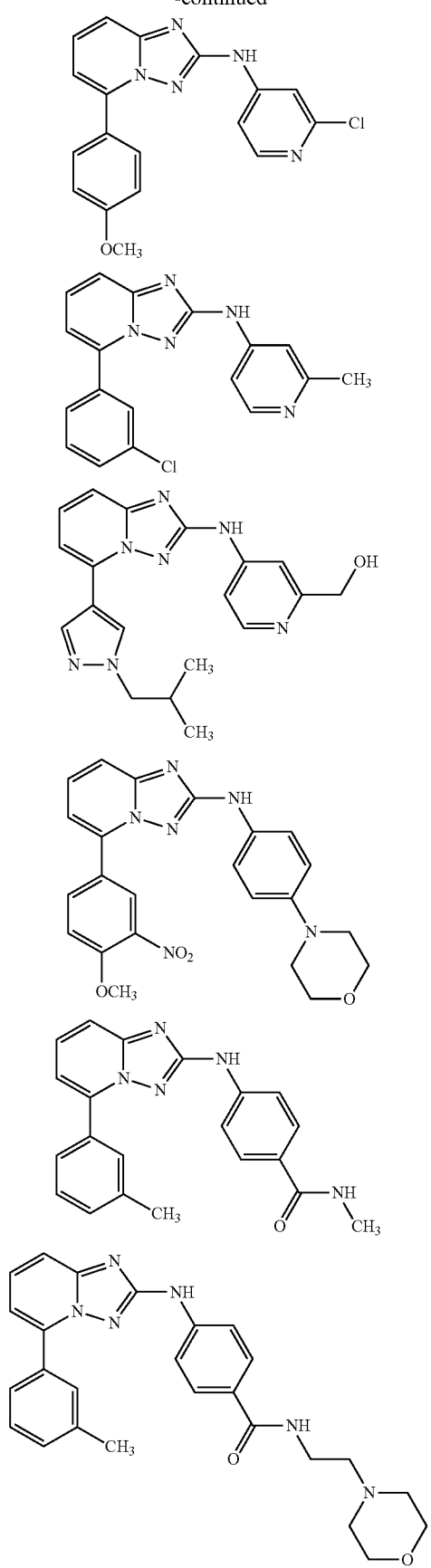
52
-continued
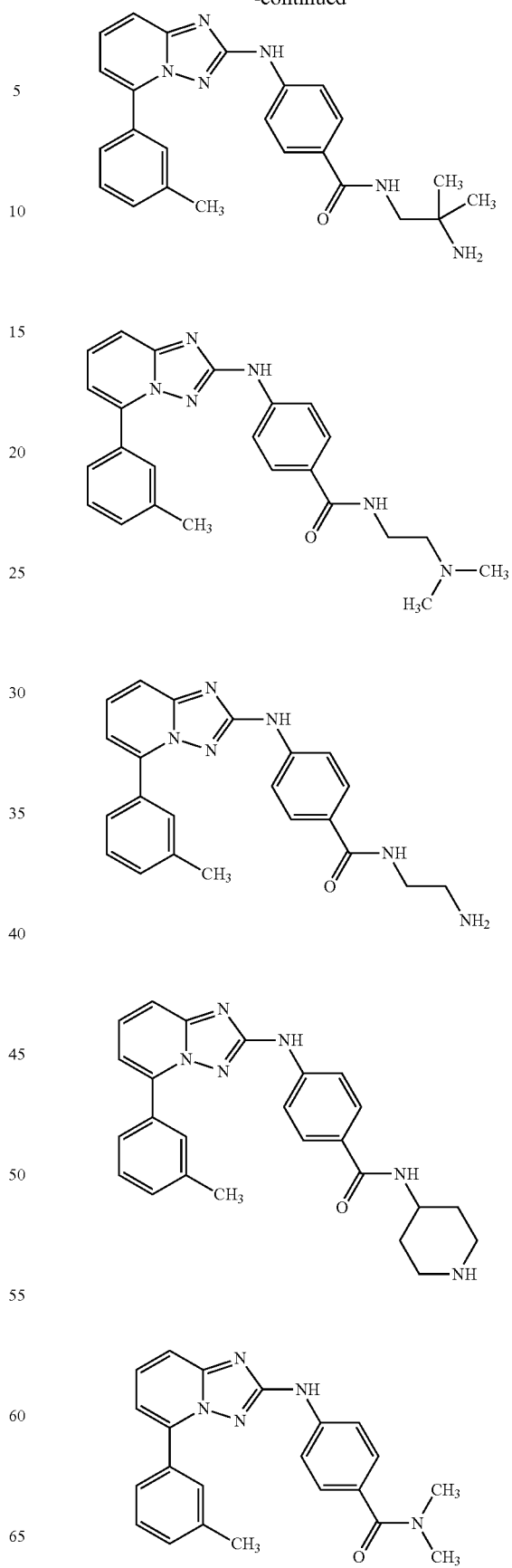

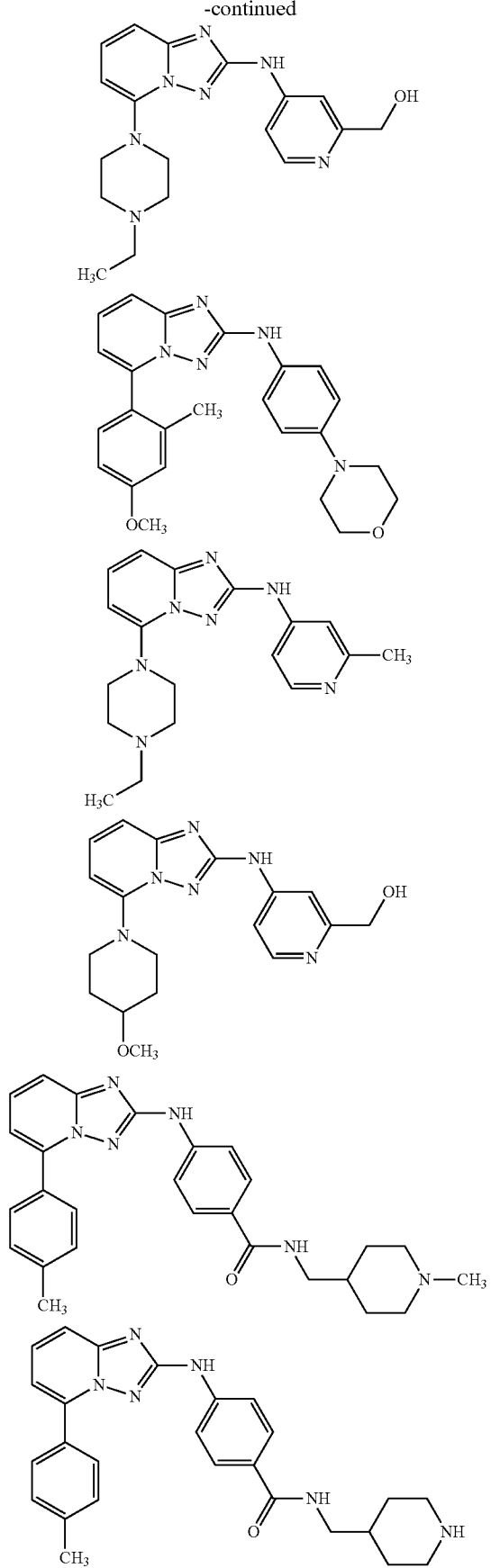
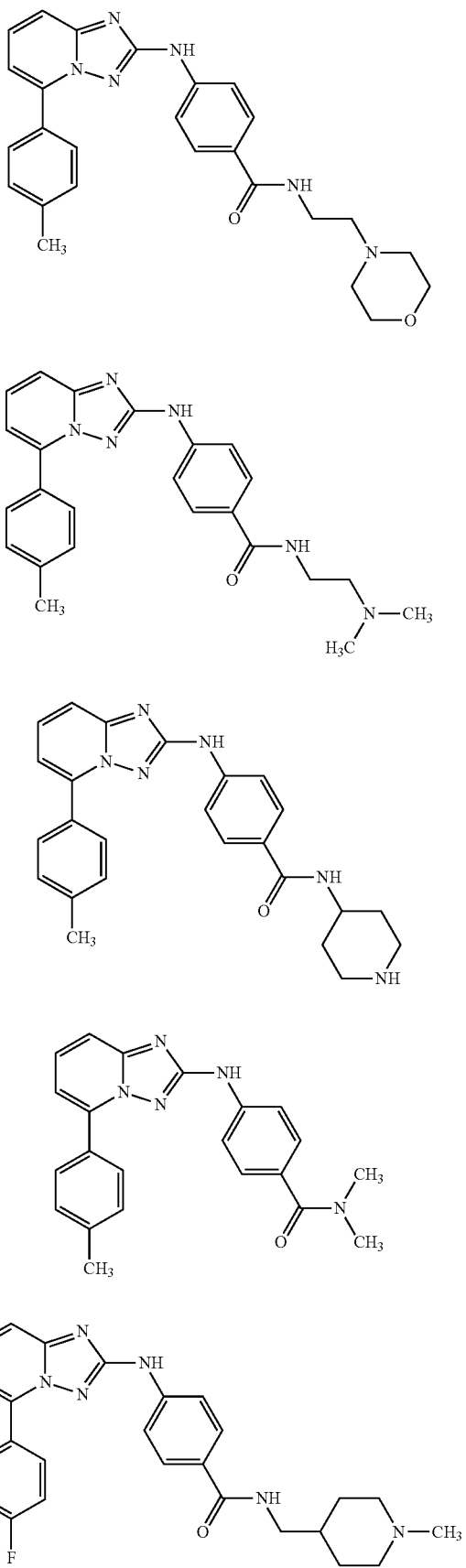

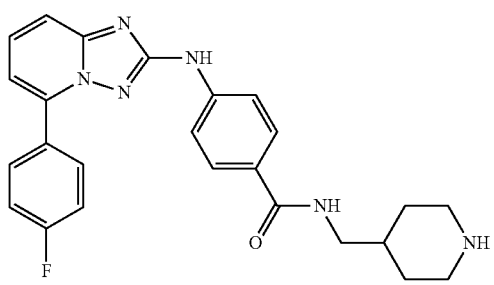
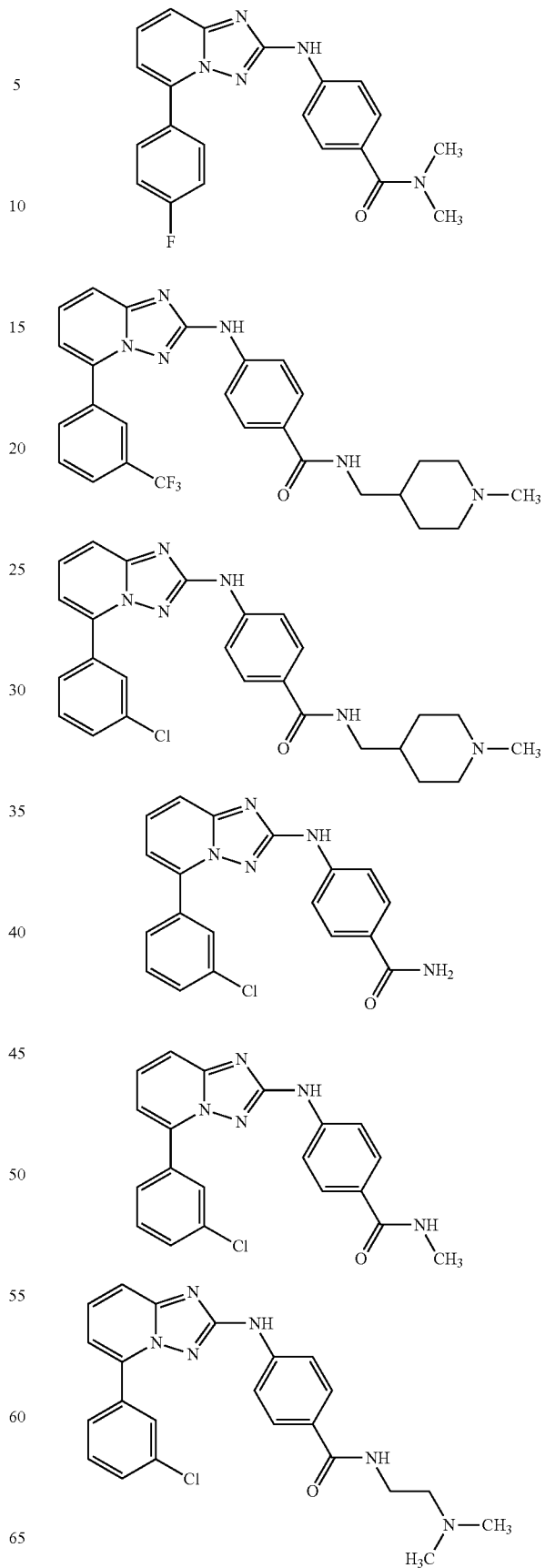

57
-continued
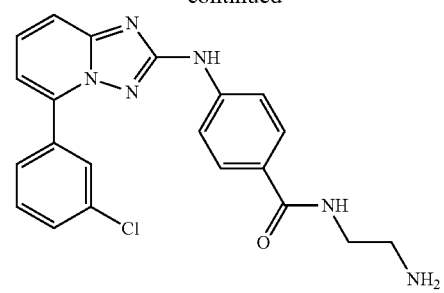
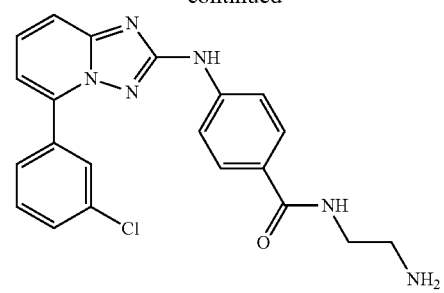
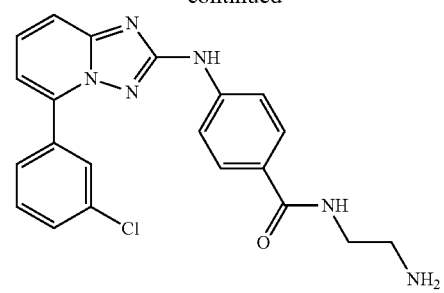
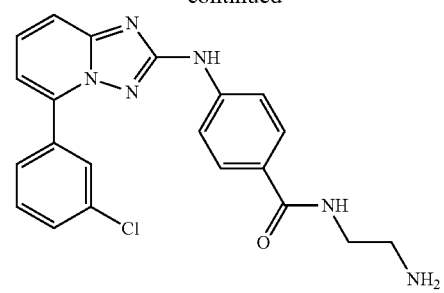
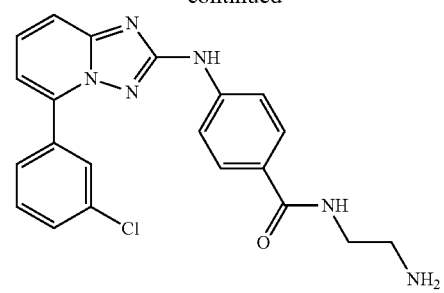
58
-continued
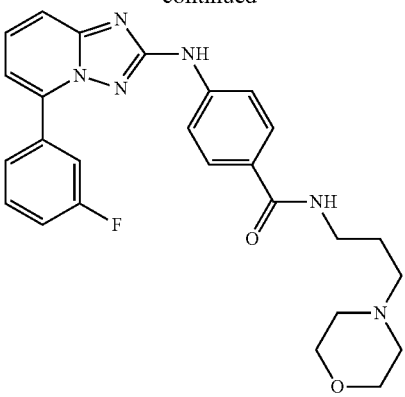
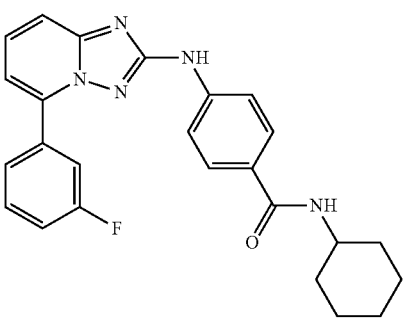
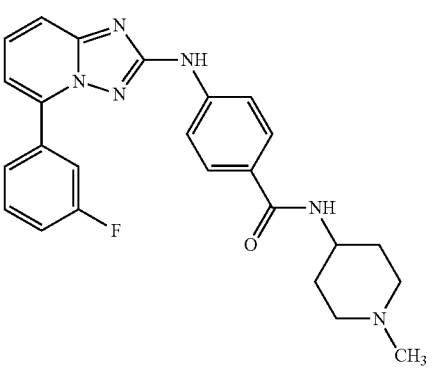
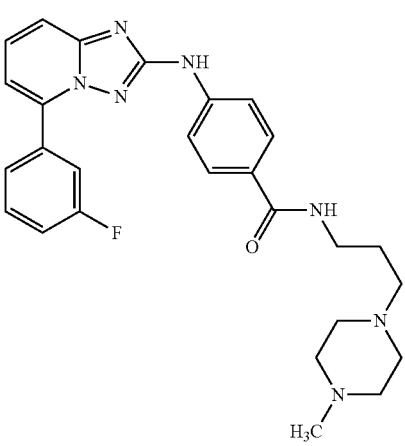

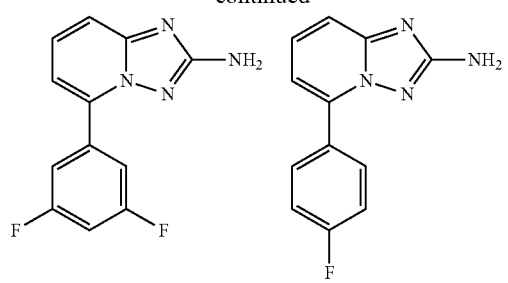
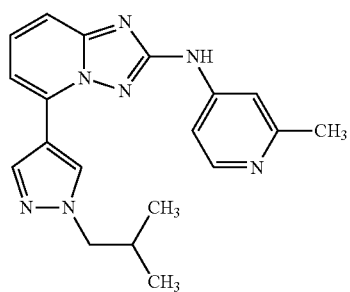
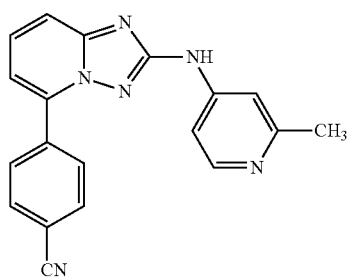
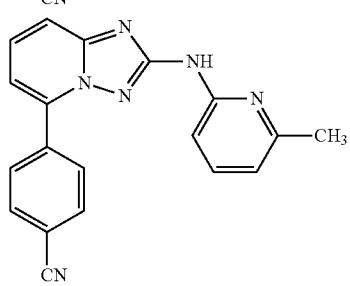
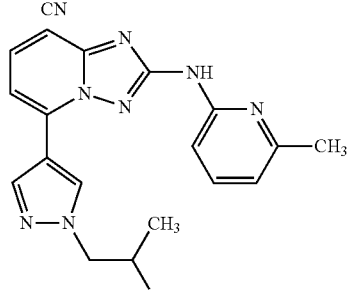
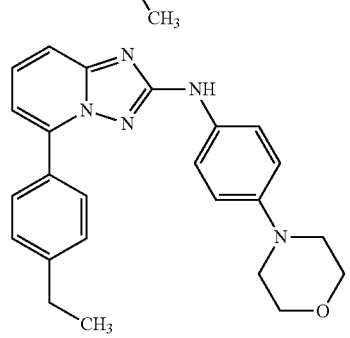
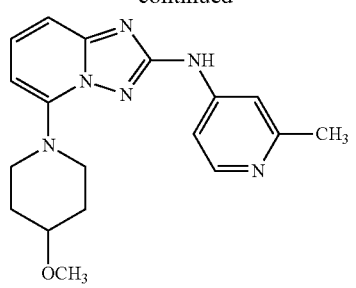
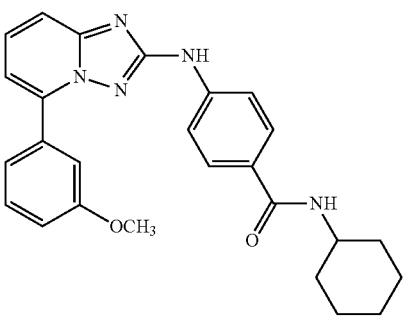
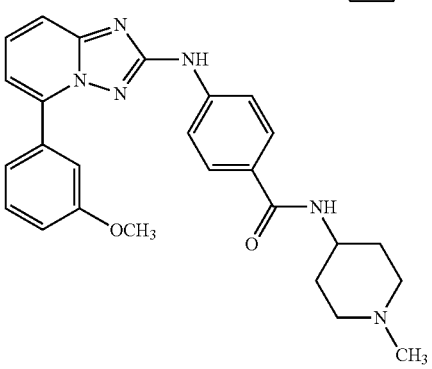
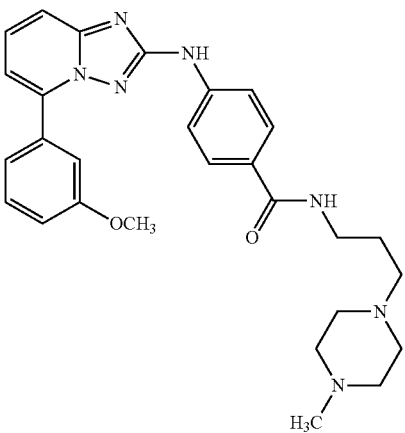
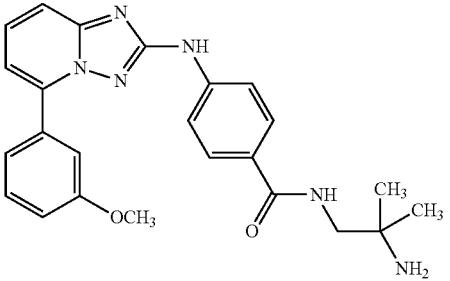

61
-continued
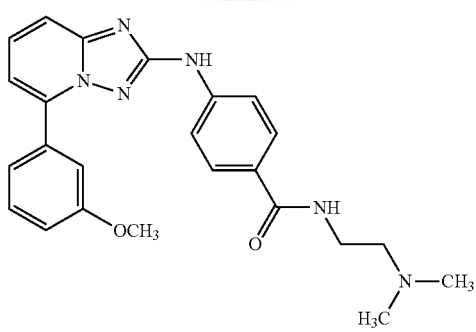
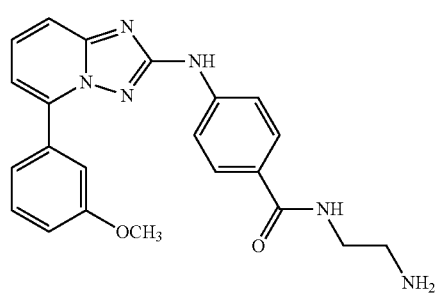
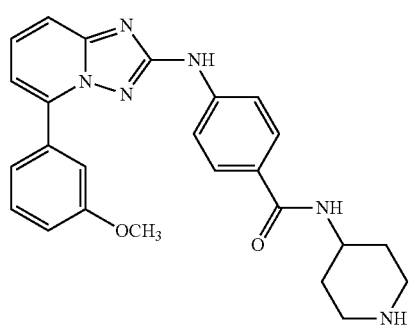
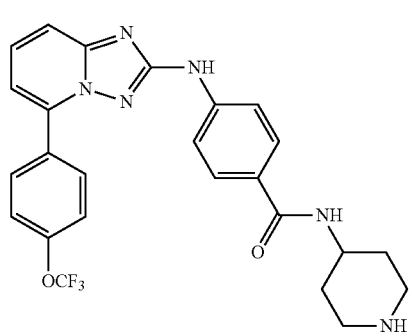
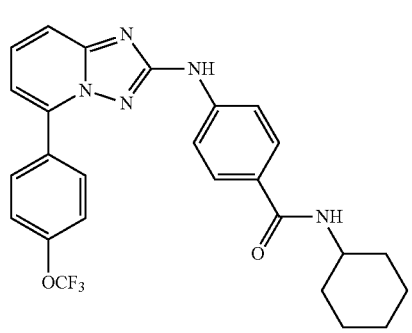
62
-continued
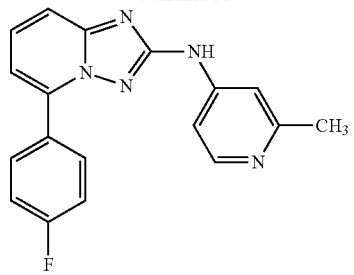
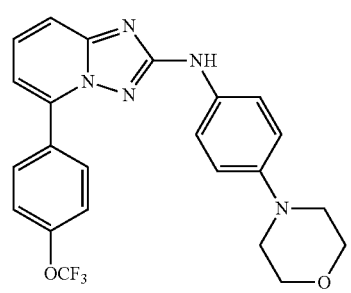
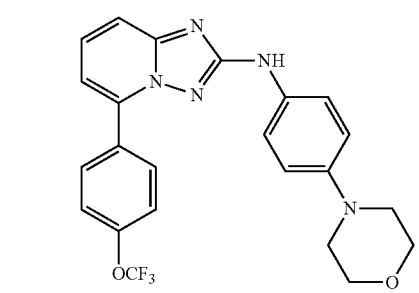
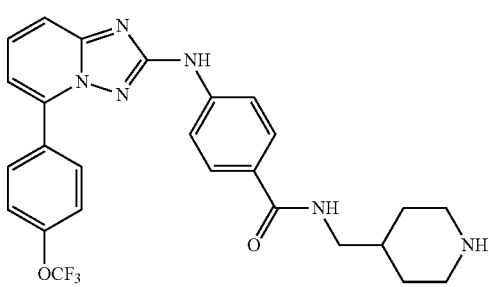
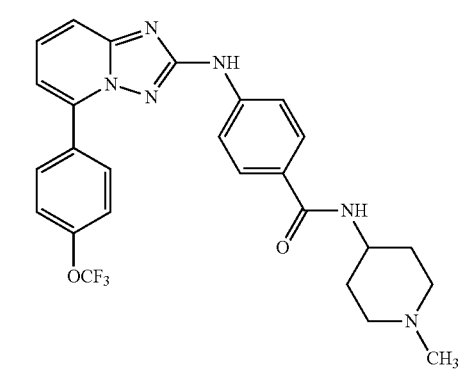
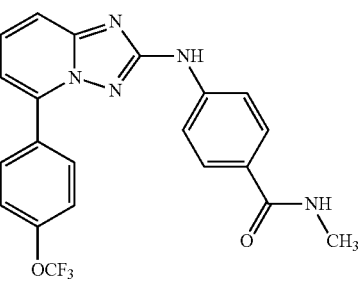

-continued
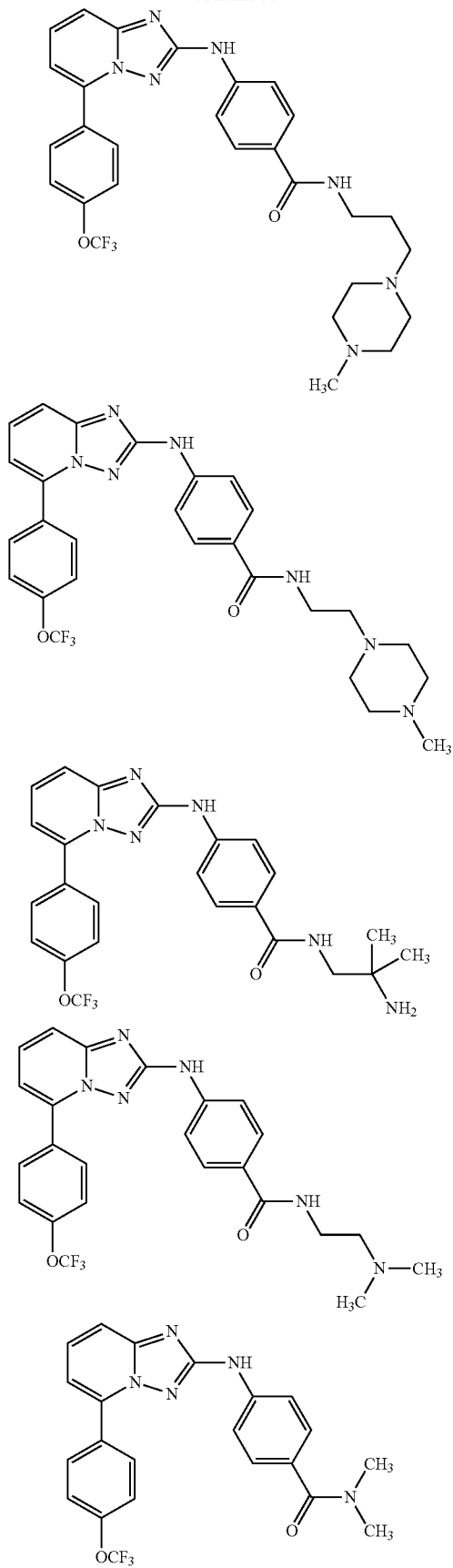
-continued
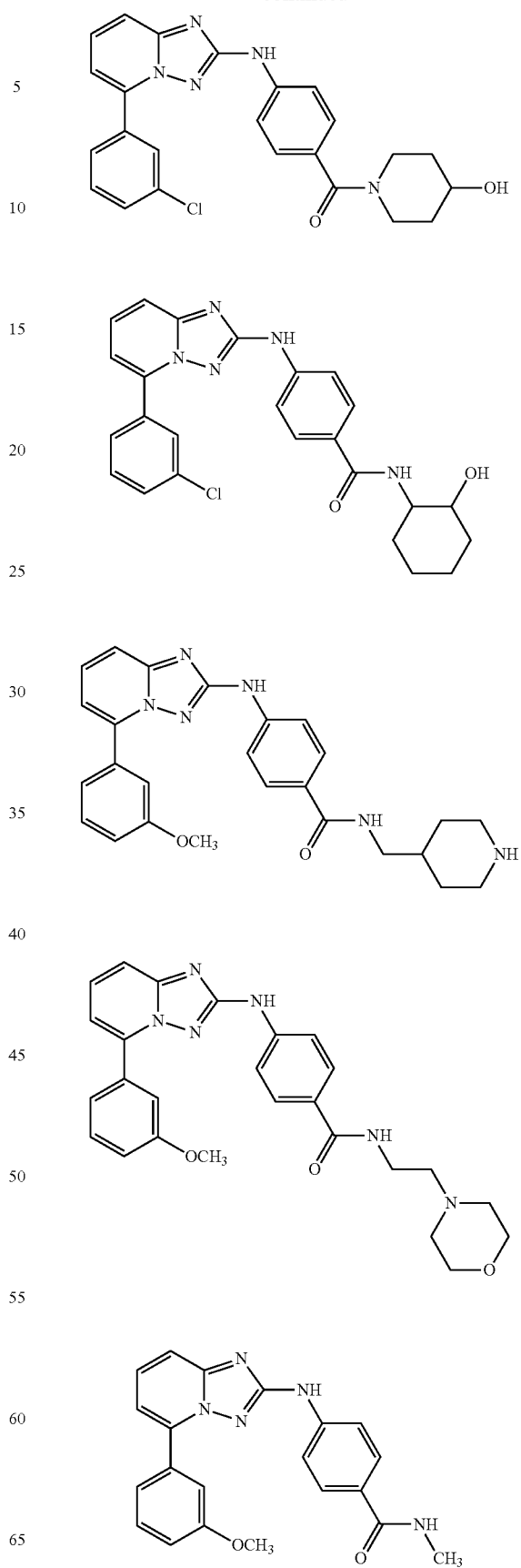

65
-continued
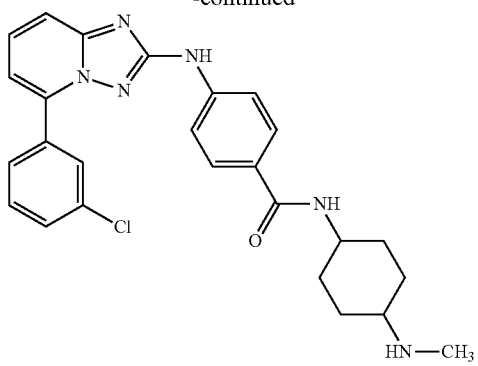
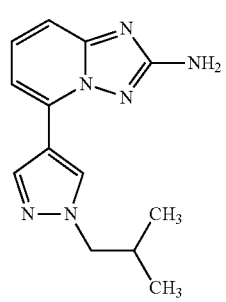
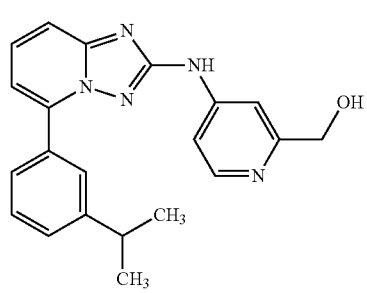
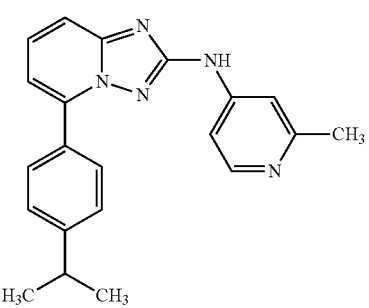
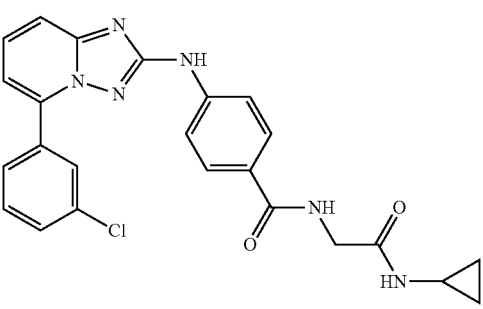
66
-continued
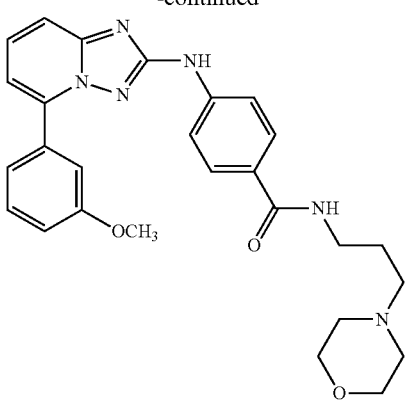
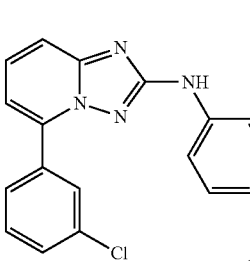
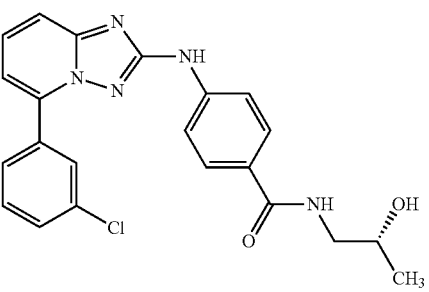
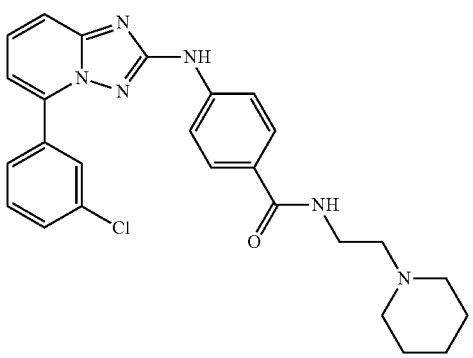

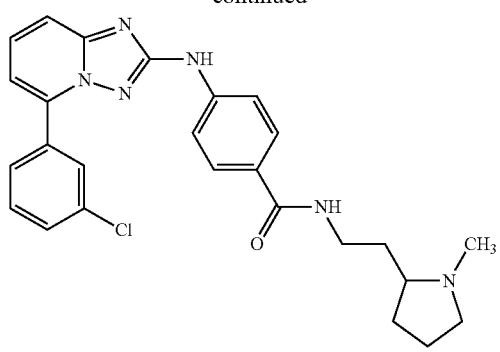
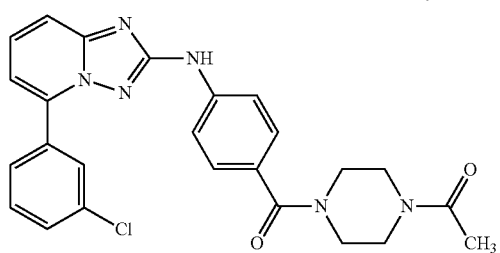
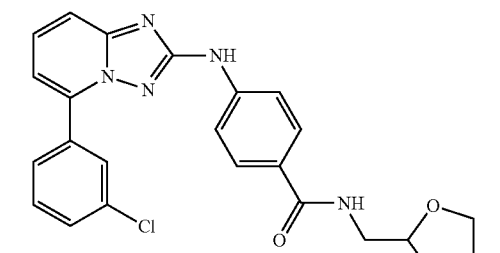
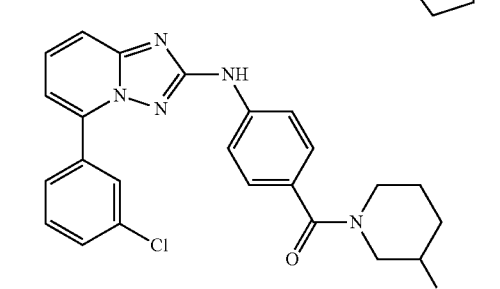
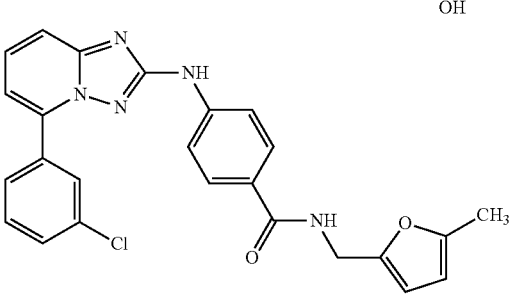
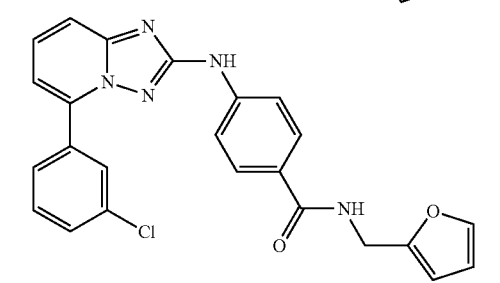
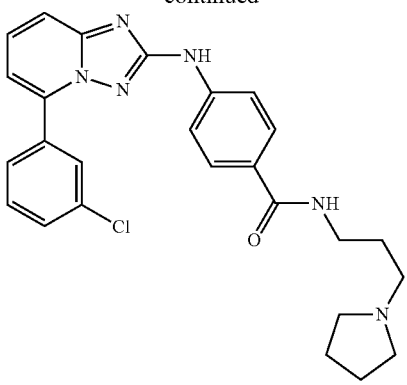
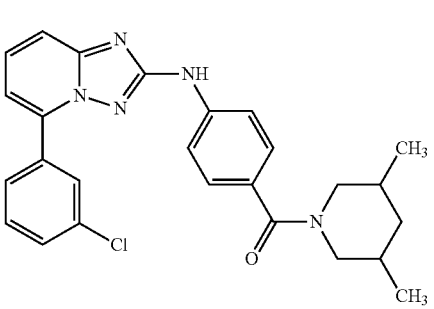
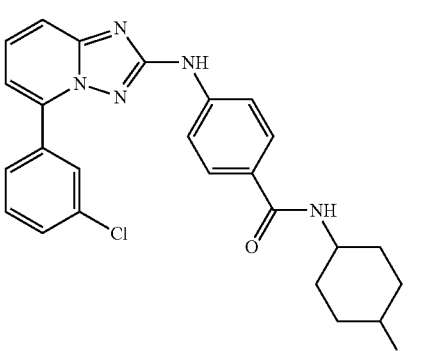
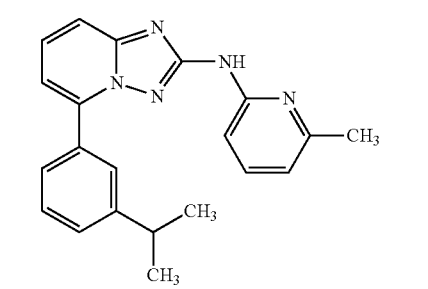
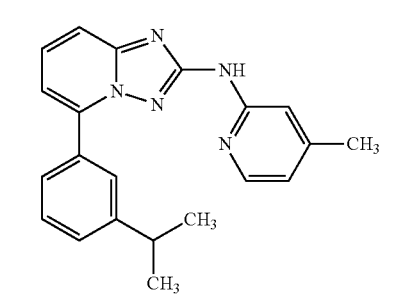

69
-continued
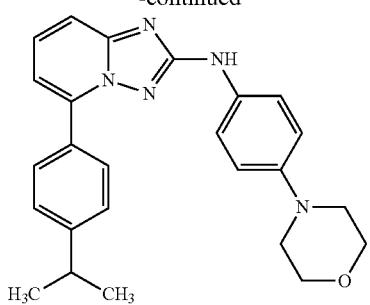
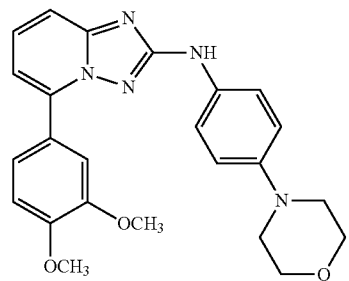
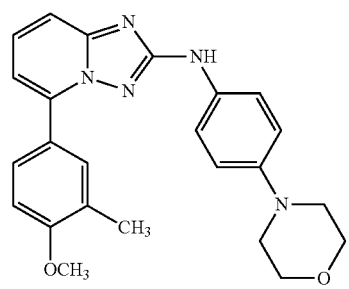
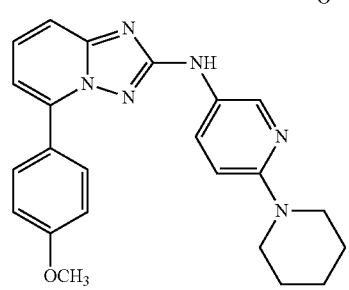
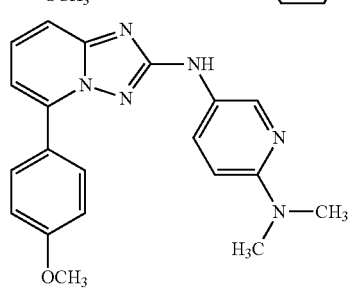
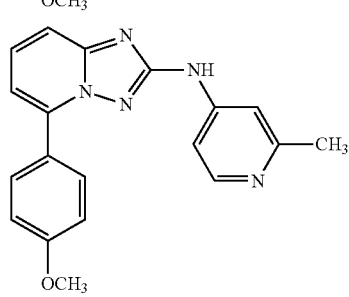
70
-continued
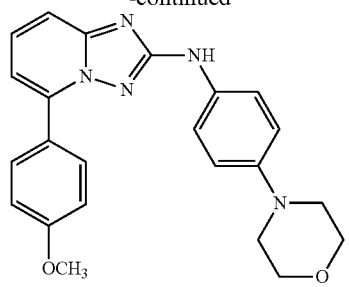
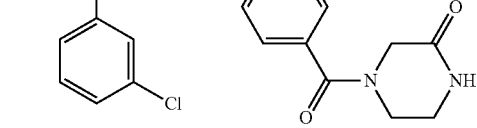
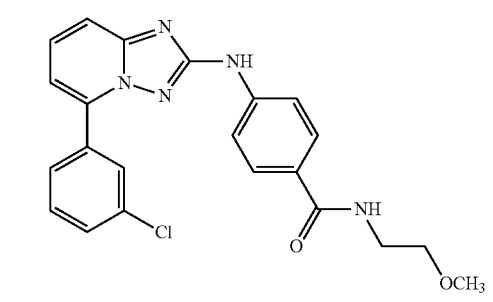
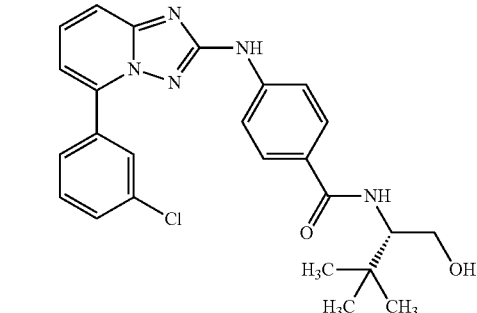

71
-continued
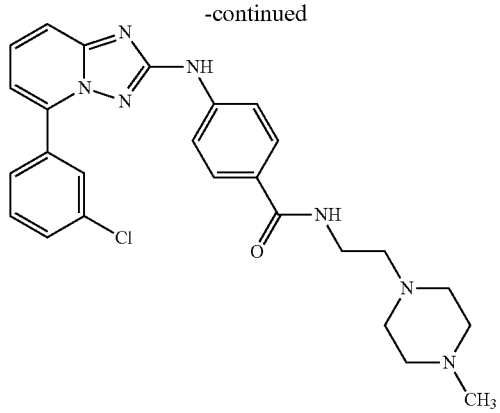
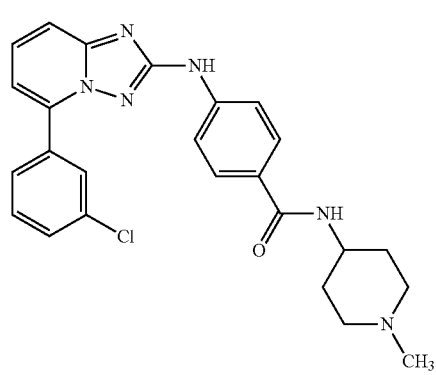
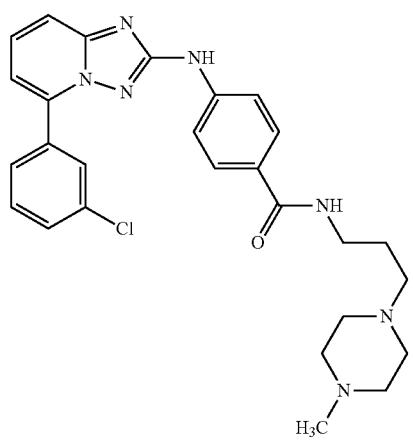
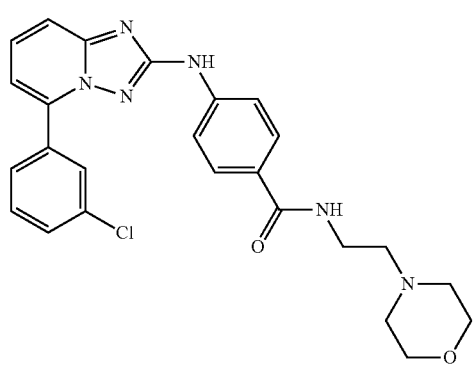
72
-continued
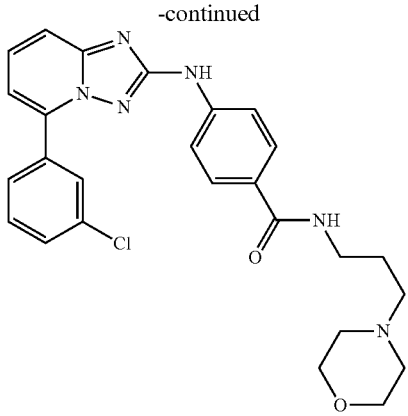
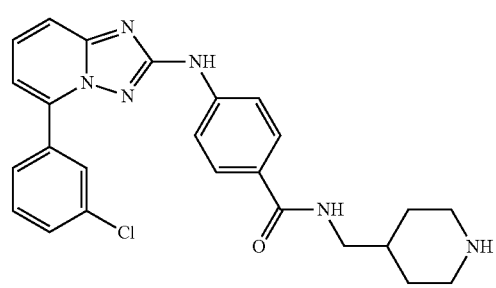
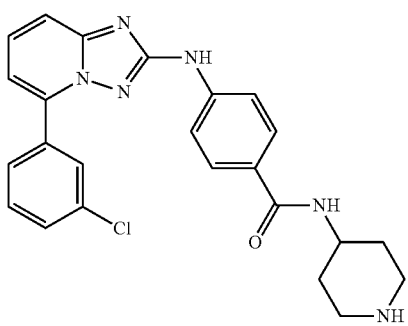
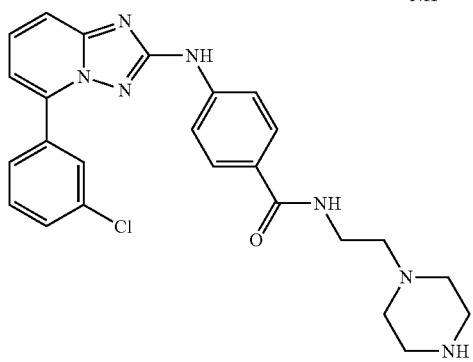
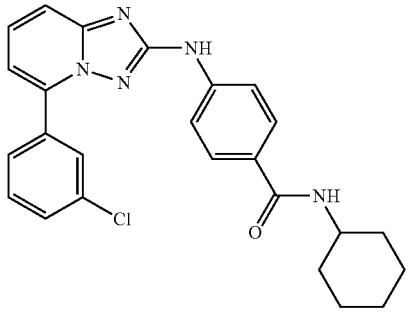

-continued
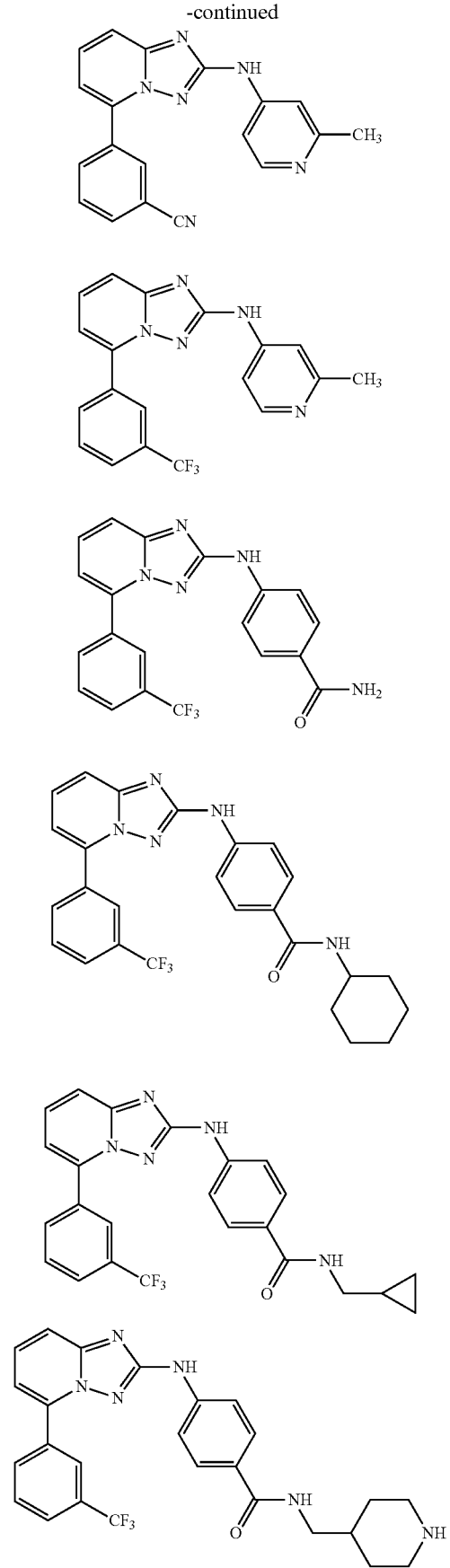
-continued
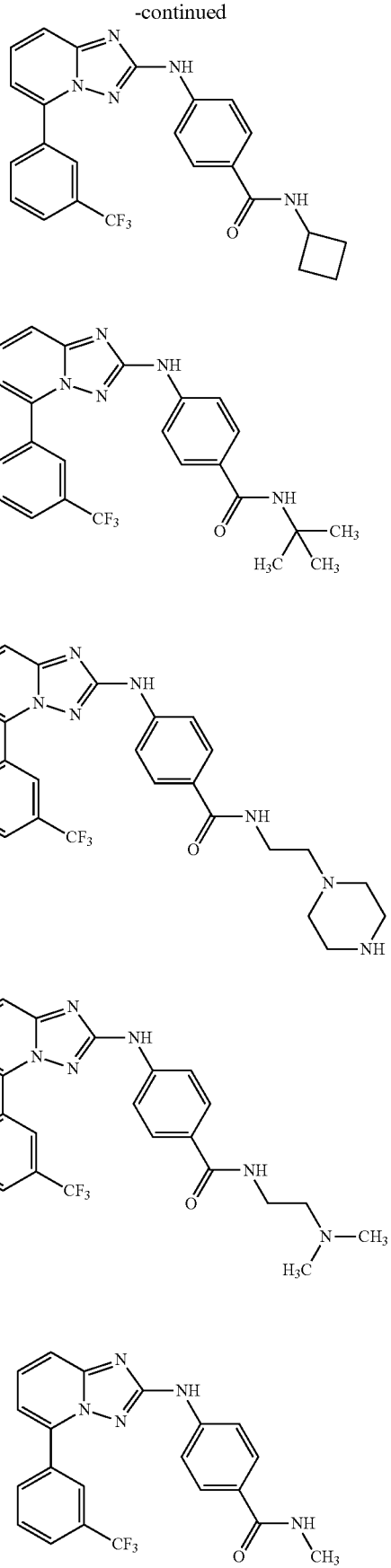

75
-continued
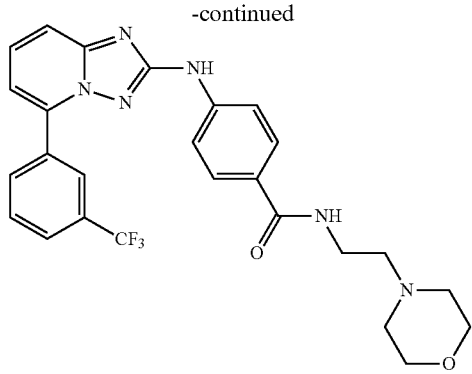
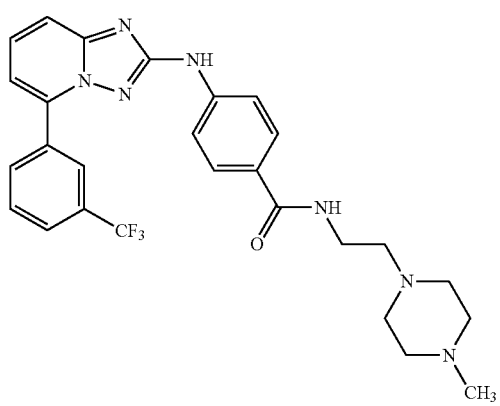
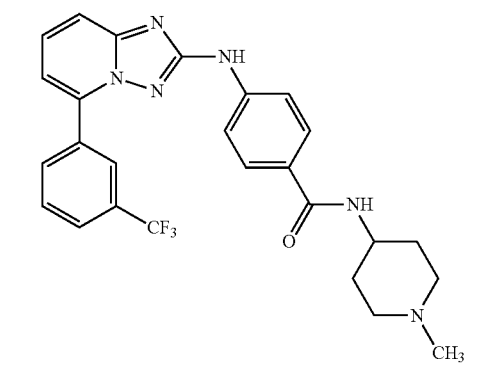
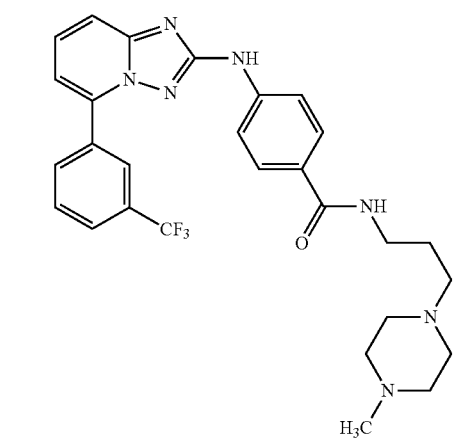
76
-continued
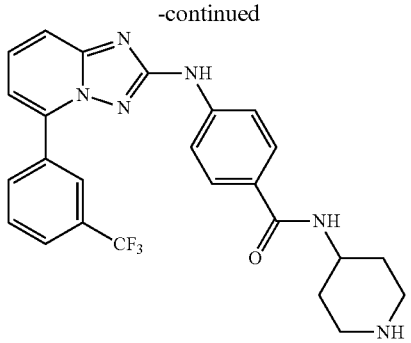
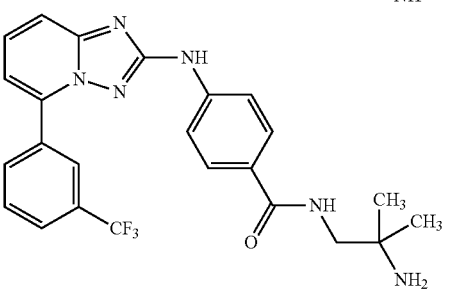
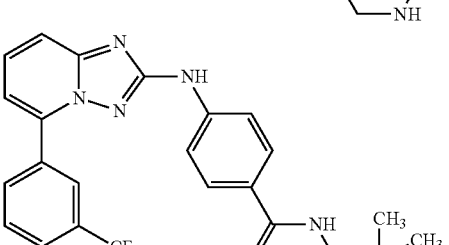
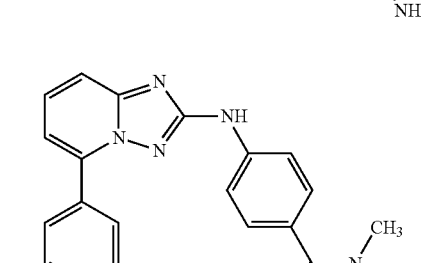
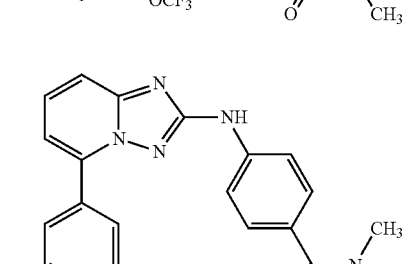
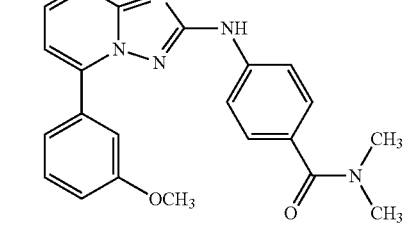

77
-continued
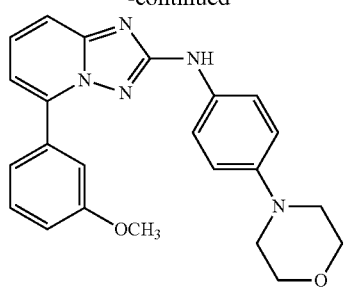
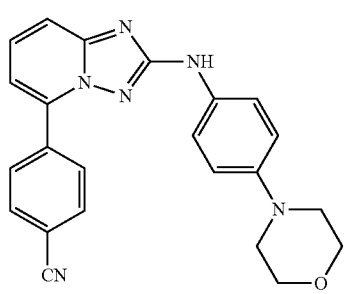
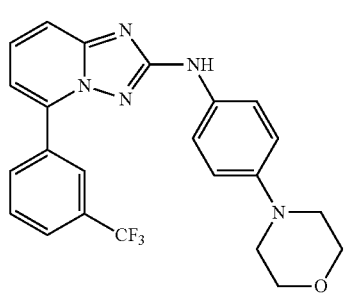
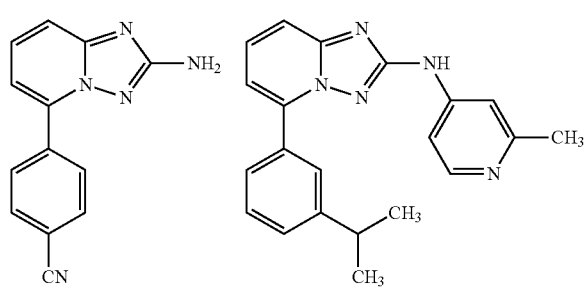
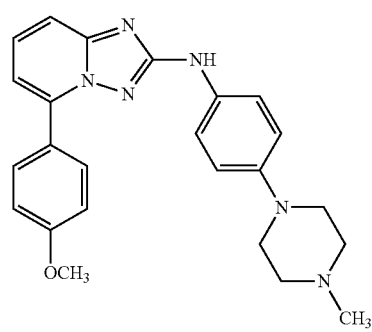
78
-continued
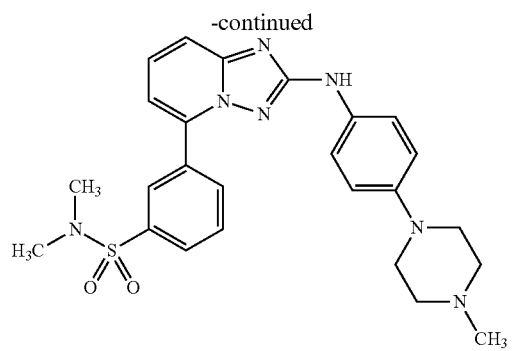
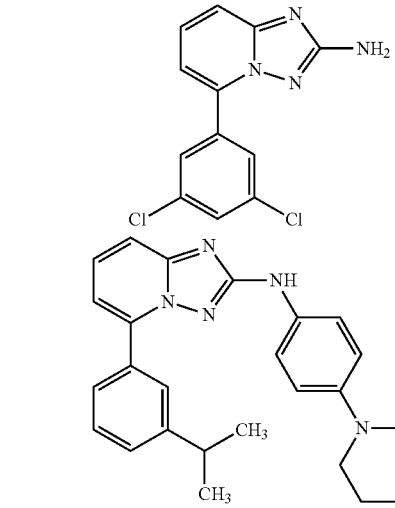
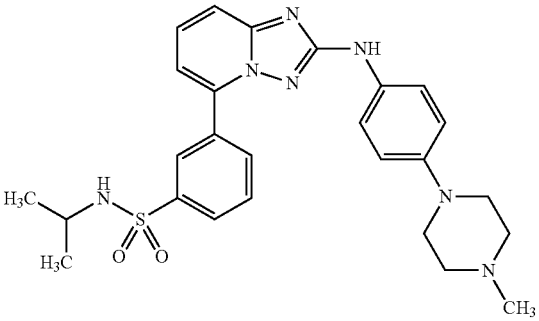
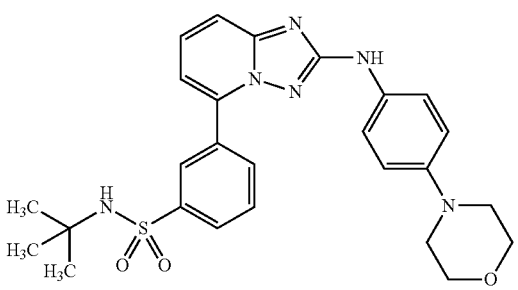
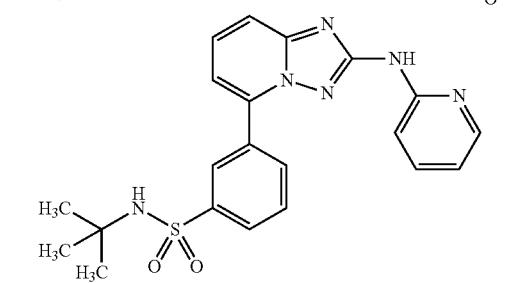

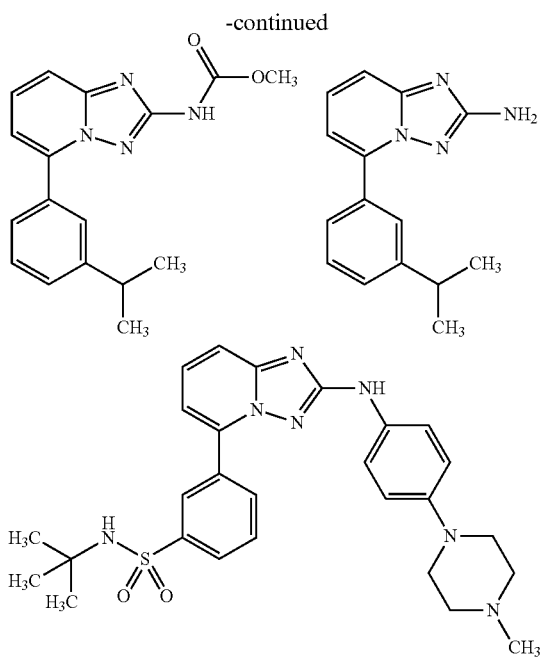

Another embodiment includes compounds of Formula I, selected from the compounds of Examples 1-438.

Another embodiment includes a compound of Formula I that has $K_i$ and/or $EC_{50}$ that is at least 15 fold, alternatively 10 fold, or 5 fold or more selective in inhibiting one Janus kinase activity over inhibiting each of the other Janus kinase activities.

In another embodiment, compounds of Formula I have $K_i$ for JAK2 inhibition that is at least about 10 fold selective over one, or any combination of, JAK1, JAK3 and TYK2. In one example, compounds of Formula I have $K_i$ for JAK2 inhibition that is at least about 10 fold selective over all JAK1, JAK3 and TYK2. In another example, compounds of Formula I have $K_i$ for JAK2 inhibition that is at least about 8 fold selective over all JAK1, JAK3 and TYK2. In another example, compounds of Formula I have $K_i$ for JAK2 inhibition that is at least about 5 fold selective over all JAK1, JAK3 and TYK2.

The compounds of Formula I may contain asymmetric or chiral centers, and, therefore, exist in different stereoisomeric forms. It is intended that all stereoisomeric forms of the compounds of Formula I, including but not limited to: diastereomers, enantiomers, and atropisomers as well as mixtures thereof such as racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of Formula I (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of Formula I may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of Formula I, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of Formula I include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$ respectively. Certain isotopically-labeled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of Formula I can generally be prepared by following procedures analogous to those disclosed in the Schemes and/or in the Examples herein below, by substituting an isotopically labeled reagent for a non-isotopically labeled reagent.

Synthesis of Triazolopyridine JAK Inhibitor Compounds

Compounds of Formula I may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984. Methods for triazolopyridine synthesis are also disclosed in: WO 02/38572 and WO 2006/038116.

Compounds of Formula I may be prepared singly or as compound libraries comprising at least 2, for example 5 to 1,000 compounds, or 10 to 100 compounds of Formula I. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, enantiomers, diasteriomers, tautomers or pharmaceutically acceptable salts thereof.

For illustrative purposes, reaction schemes 1-6 depicted below provide routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from readily available starting materials using the general methods illustrated in Reaction Schemes 1-6 below.

Reaction Scheme 1

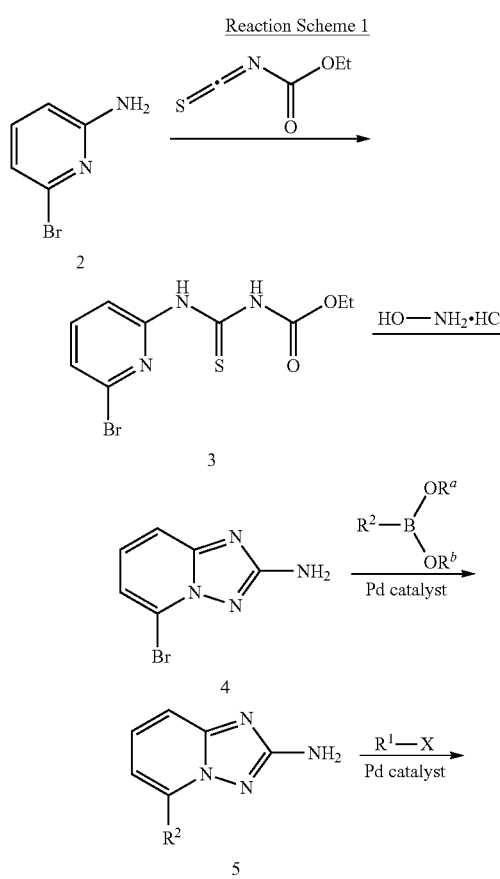

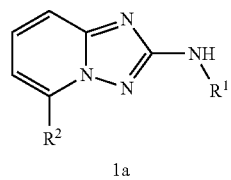

For example, compounds of Formula I can be synthesized as shown in Reaction Scheme 1. A common intermediate, 5-bromo[1,2,4]triazolo[1,5-a]pyridin-2-amine (4), which is available from 2-amino-6-bromopyridine (2), can be subjected to palladium-catalyzed coupling reactions such as the Suzuki reaction with boronic acids or boronate esters to form compounds of Formula 5. Palladium-catalyzed amination of aryl or heteroaryl halides with triazolopyridinamine 5 provides compounds of Formula 1a, wherein $R^a$, $R^b$, $R^1$ and $R^2$ are as defined above for Formula I.

Reaction Scheme 2

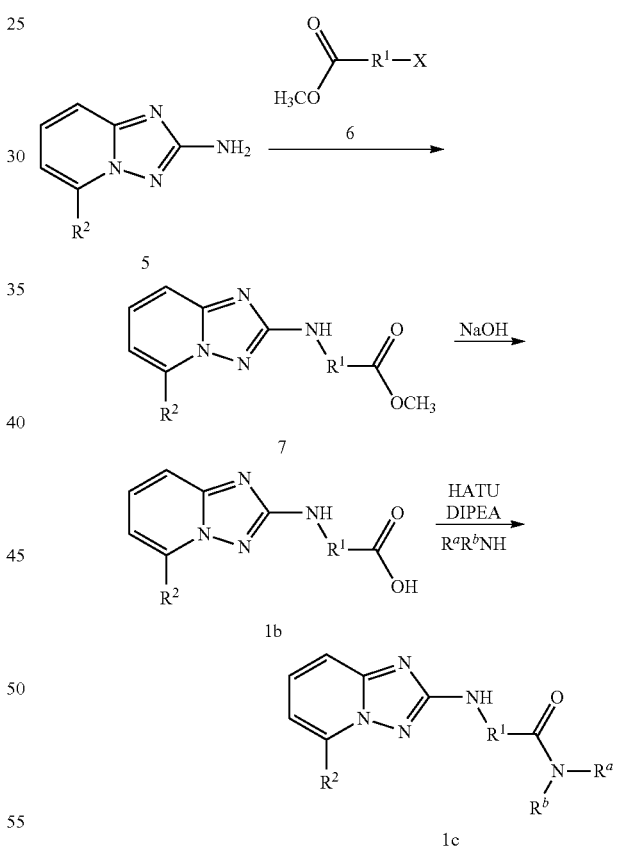

Reaction Scheme 2 illustrates the synthesis of compounds of Formulas 1b and 1c. Palladium-catalyzed amination of methoxycarbonyl substituted phenyl halides or methoxycarbonyl substituted heteroaryl halides 6 with triazolopyridinamine 5 provides compounds of Formula 7. Hydrolysis of the corresponding methyl esters affords carboxylic acids 1b, which can be subjected to standard amide formation methods to yield amides 1c, wherein $R^a$, $R^b$, $R^1$ and $R^2$ are as defined above for Formula I.

Reaction Scheme 3

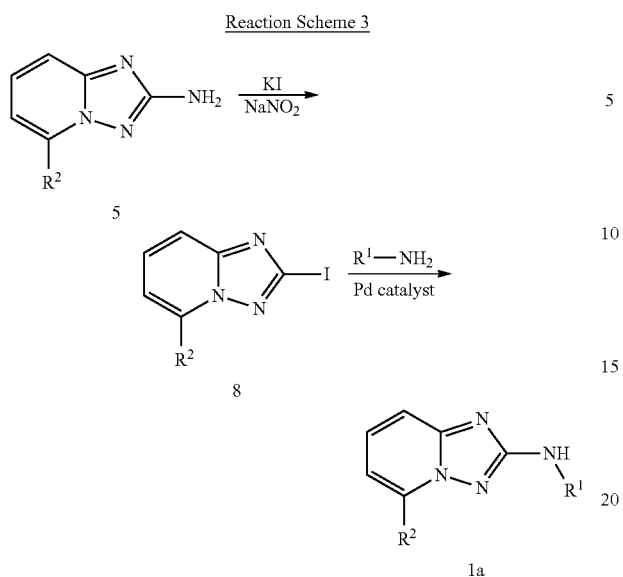

An alternative method for the synthesis of compounds of Formula I proceeds via the 2-iodotriazolopyridine 8 as shown in Reaction Scheme 3. Diazotization of triazolopyridinamine 5 and in situ iodide substitution provide iodotriazolopyridine 8. Palladium-catalyzed amination of iodotriazolopyridine 8 with amines affords compounds of Formula 1a, wherein $R^1$ and $R^2$ are as defined above for Formula I.

Reaction Scheme 4

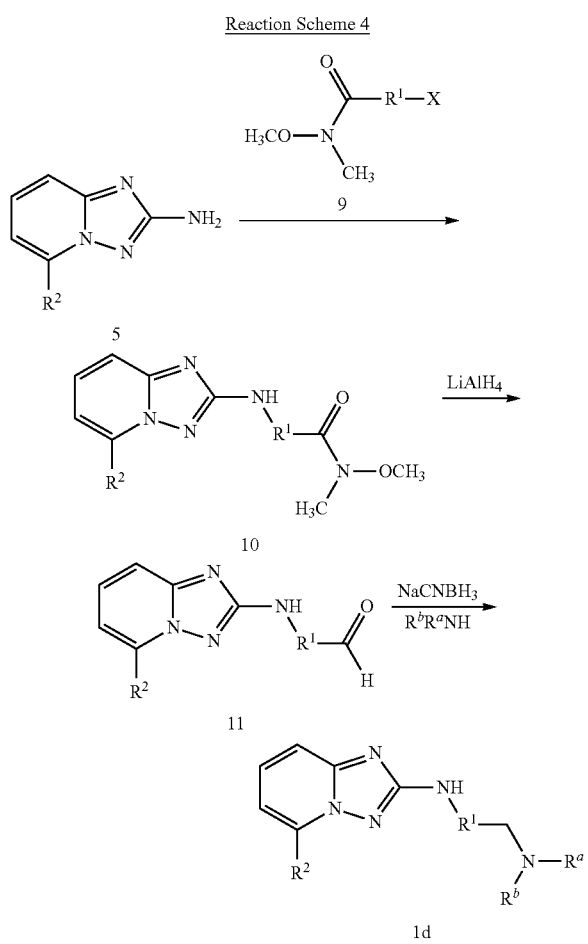

Reaction Scheme 4 illustrates the synthesis of compounds of Formula 1d. Palladium-catalyzed amination of triazolopyridinamine 5 with halophenyl or haloheteroaryl substituted N-methoxy-N-methyl amides furnishes compounds of Formula 10. Lithium aluminum hydride reduction of the N-methoxy-N-methyl amide 10 provides the corresponding aldehyde 11. Reductive amination of aldehyde 11 with amines and a reducing reagent such as sodium cyanoborohydride provides amine 1d, wherein $R^a$, $R^b$, $R^1$ and $R^2$ are as defined above for Formula I.

Reaction Scheme 5

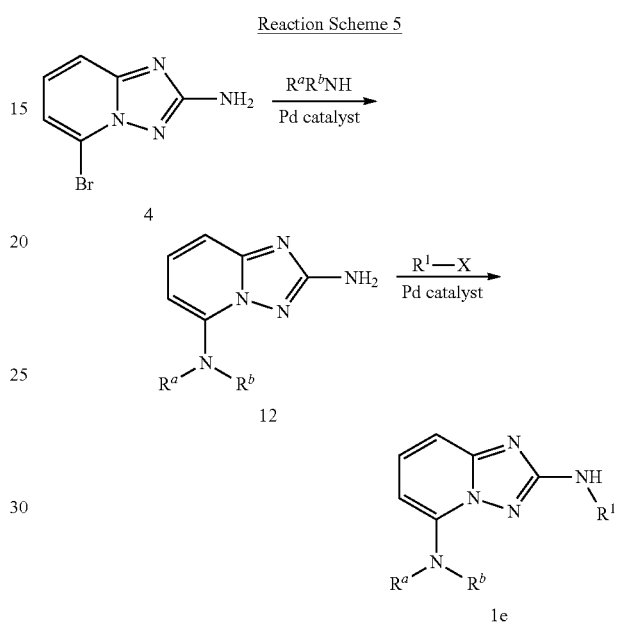

The synthesis of compounds of Formula 1e by sequential palladium-catalyzed aminations is shown is Reaction Scheme 5. Palladium-catalyzed amination of 5-bromo[1,2,4]triazolo[1,5-a]pyridin-2-amine (4) with amines $R^aR^bNH$ provides amino-substituted compounds of Formula 12. Subsequent palladium-catalyzed amination of triazolopyridinamine 12 with aryl halides or heteroaryl halides yields compounds of Formula 1e, wherein $R^a$, $R^b$ and $R^1$ are as defined above for Formula I.

Reaction Scheme 6

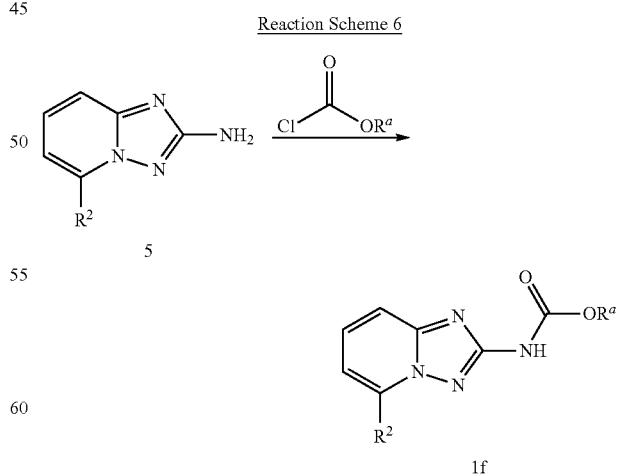

Carbamates of Formula 1f can be synthesized as illustrated in Reaction Scheme 6 by treatment of triazolopyridinamine 5 with chloroformates, wherein $R^a$ and $R^2$ are as defined above for Formula I.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

Positional isomers, for example E and Z forms, of compounds of Formula I, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Biological Evaluation

Previous studies have shown that the isolated kinase domains of human JAK1, JAK2, JAK3 or TYK2 phosphorylate peptide substrates in in vitro kinase assays (Saltzman et al., *Biochem. Biophys. Res. Commun.* 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP_004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., *Biochem. Biophys. Res. Commun.* 246:627-633 (2004)). The activity of the JAK1, JAK2, JAK3 or TYK2 kinase domains was measured in vitro by monitoring phosphorylation of JAK3 derived peptides using the Caliper LabChip technology (see Examples).

The compounds of the present invention are tested for their capacity to inhibit a Janus kinase activity and activation (primary assays) and for their biological effects on growing cells (secondary assays) as described herein. The compounds having $IC_{50}$ of less than 10 μM (preferably less than 5 μM, more preferably less than 1 μM, most preferably less than 0.5 μM) in the appropriate Janus kinase activity and activation assay (see Examples A and B), and $EC_{50}$ of less than 20 μM (preferably less than 10 μM, more preferably less than 5 μM, most preferably less than 1 μM) in the appropriate cellular assays (see Example C) are useful as Janus kinase inhibitors.

Administration of Triazolopyridine Compounds

Another embodiment includes a method of treating or lessening the severity of a disease or condition responsive to the inhibition of one or more Janus kinase activity, selected from JAK1, JAK2, JAK3 and TYK2, in a patient. The method includes administering to the patient a therapeutically effective amount of a compound of Formula I.

Another embodiment includes a method of treating or lessening the severity of a disease or condition responsive to the inhibition of JAK2 kinase activity in a patient. The method includes the step of administering to a patient a therapeutically effective amount of a compound of Formula I.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory diseases is rheumatoid arthritis, psoriasis, contact dermatitis or delayed hypersensitivity reactions.

In one embodiment, the inflammatory disease is inflammatory bowel disease,

In one embodiment, the autoimmune disease is lupus or multiple sclerosis.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology, Vol.* 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through one or more of the Janus kinase pathways in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House RV. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 68). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 69) determines the ability of compounds to inhibit the production of CD69 by B lymphocytes in human whole blood activated by crosslinking surface IgM with goat F(ab')2 anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology, Volume* 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

A compound of Formula I may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound of Formula I is administered orally, it may be formulated as a pill, capsule, tablet, etc. with a pharmaceutically acceptable carrier or excipient. Where the compound of Formula I is administered parenterally, it may be formulated with a pharmaceutically acceptable parenteral vehicle and in a unit dosage injectable form, as detailed below.

A dose to treat human patients may range from about 10 mg to about 1000 mg of a compound of Formula I. A typical dose may be about 100 mg to about 300 mg of a compound of Formula I. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Another embodiment of the invention aspect of this invention provides a compound of this invention for use as a medicament in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations of Triazolopyridine Compounds

Another embodiment includes a pharmaceutical composition that includes a compound of Formula I and a pharmaceutically acceptable carrier, adjuvant or vehicle.

In one embodiment, the pharmaceutical composition also includes an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

In one embodiment, a compound of Formula I is present in a pharmaceutical formulation in an amount to detectably inhibit JAK2 kinase activity and a pharmaceutically acceptable carrier, adjuvant or vehicle.

In one embodiment, a compound of Formula I is present in a pharmaceutical formulation in an amount to detectably inhibit JAK2 kinase activity and is at least 10 fold or more selective in inhibiting JAK2 kinase activity over inhibiting each of JAK1, JAK3 and Tyk-2 activity.

In one embodiment, a compound of Formula I is present in a pharmaceutical formulation in an amount to detectably inhibit a Janus kinase activity and is at least 15 fold, alternatively 10 fold, or 5 fold or more selective in inhibiting one Janus kinase activity over inhibiting each of the other JAK1, JAK2, JAK3 and/or Tyk-2 activity.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of a compound of Formula I may be prepared for various routes and types of administration. A compound of Formula I having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of the compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a compound of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of a compound of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

A compound of Formula I may be combined in a pharmaceutical combination formulation, or dosing regimen as combination therapy, with a second compound that has anti-hyperproliferative or chemotherapeutic properties, that is useful for treating a disease or disorder responsive to the inhibition of a JAK kinase, for example a hyperproliferative disorder (e.g. cancer), or that is useful in treating another disorder named herein. The second compound of the pharmaceutical combination formulation or dosing regimen preferably has complementary activities to a compound of Formula I of the combination such that they do not adversely affect each other. Such molecules are suitably present in combination in amounts that are effective for the purpose intended.

In another embodiment, a compound of Formulas I may be employed alone or in combination with other therapeutic agents for the treatment of a disease or disorder described herein, such as an immunologic disorder (e.g. psoriasis or inflammation). In certain embodiments, a compound of Formula I is combined in a pharmaceutical combination formulation, or dosing regimen as combination therapy, with a second therapeutic compound that has anti-inflammatory or that is useful for treating an inflammation, immune-response disorder. The second therapeutic agent may be a NSAID or other anti-inflammatory agent. In one embodiment, a composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

Another embodiment, therefore, includes a method of treating or lessening the severity of a disease or condition responsive to the inhibition of JAK2 kinase activity in a patient, comprising administering to said patient a therapeutically effective amount of a compound of Formula I, and further comprising, administering a second chemotherapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Triazolopyridine Compounds

Another embodiment includes in vivo metabolic products of an administered compound of Formula I. Such products may result for example from the oxidation, reduction, hydrolysis, amidation, deamidation, esterification, deesterification, enzymatic cleavage, and the like, of the administered compound.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of a compound of Formula I.

Articles of Manufacture

Another embodiment includes a kit for treating a disease or disorder responsive to the inhibition of a JAK kinase. The kit includes:

(a) a first pharmaceutical composition comprising a compound of Formula I; and (b) instructions for use.

In another embodiment, the kit further includes:

(c) a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of Formula I or formulation thereof which is effective for treating the condition and may have a sterile access port (for example the container may be an intravenous solution bag or a vial having a stopper pierceable by a hypodermic injection needle). The container includes a composition comprising at least one compound of Formula I. The label or package insert indicates that the composition is used for treating the condition of choice, such as cancer. In one embodiment, the label or package inserts indicates that the composition comprising the compound of Formula I can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of Formula I contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In an embodiment, the compounds of Formula I can be used to control JAK protein kinases, tyrosine kinases, additional serine/threonine kinases, and/or dual specificity kinases. Thus, they are useful as pharmacological standards for use in the development of new biological tests, assays and in the search for new pharmacological agents.

Compounds of Formula I may be assayed for the ability to modulate the activity of JAK protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formula I to bind to kinases and may be measured either by radiolabelling the compound of Formula I prior to binding, isolating the compound of Formula I/kinase complex and determining the amount of radiolabel bound, or by running a competition experiment where a compound of Formula I is incubated with known radiolabeled ligands. These and other useful in vitro assays are well known to those of skill in the art.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of Formula I, and alternative methods for preparing the compounds of Formula I are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

Compounds of Formula I may be assayed for the ability to modulate the activity of Janus protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formula I to bind to kinases and may be measured either by radiolabelling the compound of Formula I prior to binding, isolating the compound of Formula I/kinase complex and determining the amount of radiolabel bound, or by running a competition experiment where a compound of Formula I is incubated with known radiolabeled ligands. These and other useful in vitro assays are well known to those of skill in the art.

Previous studies have shown that the isolated kinase domains of human JAK1, JAK2, JAK3 or TYK2 phosphorylate peptide substrates in in vitro kinase assays (Saltzman et al., Biochem. Biophys. Res. Commun. 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP_004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., Biochem. Biophys. Res. Commun. 246:627-633 (2004)). The activity of the JAK1, JAK2, JAK3 or TYK2 kinase domains was measured in vitro by monitoring phosphorylation of JAK3 derived peptides using the Caliper LabChip technology (see Examples).

Example A

JAK2 Inhibition Assay Protocol

The activity of the isolated JAK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-438, compounds were diluted serially in DMSO and added to 50 µL kinase reactions containing 0.2 nM purified JAK2 enzyme, 100 mM Hepes pH7.2, 0.015% Brij-35, 1.5 µM peptide substrate, 25 µM ATP, 10 mM MgCl$_2$, 4 mM DTT at a final DMSO concentration of 2%. Reactions were incubated at 22° C. in 384-well polypropylene microtiter plates for 30 minutes and then stopped by addition of 25 µL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki value 70s were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example B

JAK1 and TYK2 Inhibition Assay Protocol

The activity of the isolated JAK1 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-438, compounds were diluted serially in DMSO and added to 50 uL kinase reactions containing 1.5 nM JAK1, 0.2 nM purified JAK2 or 1 nM purified TYK2 enzyme, 100 mM Hepes pH7.2, 0.015% Brij-35, 1.5 uM peptide substrate, 25 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example C

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labeled on the N-terminus with 5-carboxyfluorescein using the Caliper LabChip technology (Caliper Life Sciences, Hopkinton, Mass.). To determine the inhibition constants (Ki) of Examples 1-438, compounds were diluted serially in DMSO and added to 50 uL kinase reactions containing 5 nM purified JAK3 enzyme, 100 mM Hepes pH7.2, 0.015% Brij-35, 1.5 uM peptide substrate, 5 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example D

Cell-Based Pharmacology Assays

The activities of compounds I-443 were determined in cell-based assays that are designed to measure Janus kinase dependent signaling. Compounds were serially diluted in DMSO and incubated with Set-2 cells (German Collection of Microorganisms and Cell Cultures (DSMZ); Braunschweig, Germany), which express the JAK2V617F mutant protein, in 96-well microtiter plates for 1 hr at 37° C. in RPMI medium at a final cell density of $10^5$ cells per well and a final DMSO concentration of 0.57%. Compound-mediated effects on STAT5 phosphorylation were then measured in the lysates of incubated cells using the Meso Scale Discovery (MSD) technology (Gaithersburg, Md.) according to the manufacturer's protocol and $EC_{50}$ values were determined. Alternatively, serially diluted compounds were added to NK92 cells (American Type Culture Collection (ATCC); Manassas, Va.) in 96-well microtiter plates in RPMI medium at a final cell density of $10^5$ cells per well and a final DMSO concentration of 0.57%. Human recombinant IL-12 (R&D systems; Minneapolis, Minn.) was then added at a final concentration of 10 ng/ml to the microtiter plates containing the NK92 cells and compound and the plates were incubated for 1 hr at 37° C. Compound-mediated effects on STAT4 phosphorylation were then measured in the lysates of incubated cells using the Meso Scale Discovery (MSD) technology (Gaithersburg, Md.) according to the manufacturer's protocol and $EC_{50}$ values were determined.

Preparative Examples

Abbreviations $CD_3OD$ Deuterated Methanol
DCM Dichloromethane
DIPEA Diisopropylethylamine
DMSO Dimethylsulfoxide
DMF Dimethylformamide
EtOAc Ethyl Acetate
EtOH Ethanol
HCl Hydrochloric acid
HM-N Isolute® HM-N is a modified form of diatomaceous earth
IMS industrial methylated spirits
MeOH Methanol
$POCl_3$ Phosphorus oxychloride
NaH Sodium Hydride
$Na_2SO_4$ Sodium Sulfate
$NaHCO_3$ Sodium bicarbonate
NaOH Sodium hydroxide
$Pd(PPh_3)_4$ Tetrakis(triphenylphosphine)palladium(0)
$NEt_3$ Triethylamine
$Pd_2dba_3$ Tris-(dibenzylideneacetone)dipalladium(0)
Si-SPE Pre-packed Isolute® silica flash chromatography cartridge
Si-ISCO Pre-packed ISCO® silica flash chromatography cartridge
THF Tetrahydrofuran
General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP1100 LC system with diode array detector. This system uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Microwave experiments were carried out using a Biotage Initiator 60™ or CEM Explorer®. Temperature from 40-250° C. can be achieved, and pressures of up to 30 bar can be reached.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Combiflash system (Manufacturer: Teledyne Isco) having a silica gel column. $^1$H NMR spectra were recorded on a Varian instrument operating at 400 MHz. $^1$H NMR spectra were obtained as $CDCl_3$, $d_6$-DMSO or $d_4$ MeOH solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

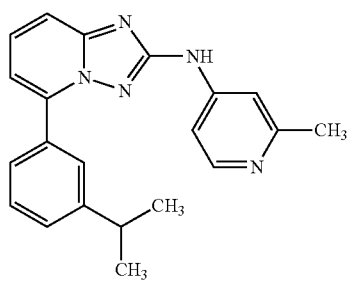

5-[3-(propan-2-yl)phenyl]-N-(2-methylpyridin-4-yl)[1,2,4]triazolo[1,5-a]pyridin-2-amine

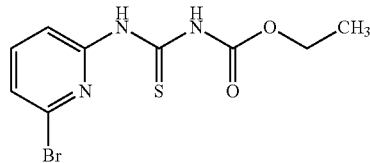 [SMILES: CCOC(=O)NC(=S)Nc1cccc(Br)n1]

Ethyl[(6-methylpyridin-2-yl)carbamothioyl]carbamate

To an ice-cooled solution of 2-amino-6-bromopyridine (25.0 g, 0.144 mmol, 1 equiv) in dichloromethane (400 mL) was added ethoxycarbonyl isothiocyanate (19.9 g, 0.152 mmol, 1.05 equiv) dropwise. The reaction mixture was warmed to 24° C. After 21 h, the reaction mixture was concentrated in vacuo (~20 mm Hg). The residue was diluted with ethyl acetate (600 mL), and the resulting organic solution was washed sequentially with water (2×200 mL) and saturated aqueous sodium chloride solution (200 mL). The organic was dried over magnesium sulfate, filtered, and concentrated to afford product as a yellow solid (43.7 g).

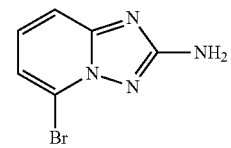 [SMILES: Nc1nc2cccc(Br)n2n1]

5-Bromo[1,2,4]triazolo[1,5-a]pyridin-2-amine

A solution was ethyl[(6-methylpyridin-2-yl)carbamothioyl]carbamate (43.7 g, 0.144 mmol, 1 equiv), hydroxylamine hydrochloride (51.3 g, 0.738 mmol, 5.13 equiv), and diisopropylethylamine (75.2 mL, 0.432 mmol, 3.00 equiv) in 1:1 methanol/ethanol (500 mL) was heated to 70° C. for 3.5 h. The reaction mixture was cooled to 24° C., and the resulting solids were filtered. The solids were rinsed with cold water (2×100 mL) and dried in vacuo (~1 mm Hg) to afford product as a white solid (24.4 g, 79.5%). $^1$H NMR (400 MHz, DMSO-$d_6$), δ: 7.32-7.38 (m, 2H), 7.21 (m, 1H), 6.23 (br s, 2H).

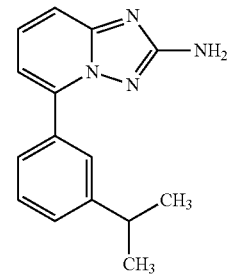 [SMILES: CC(C)c1cccc(-c2cccc3nc(N)nn23)c1]

5-[3-(propan-2-yl)phenyl][1,2,4]triazolo[1,5-a]pyridin-2-amine

A biphasic solution of 5-bromo[1,2,4]triazolo[1,5-a]pyridin-2-amine (0.800 g, 3.76 mmol, 1.00 equiv), 3-(2-propyl)phenyl boronic acid (0.739 g, 4.51 mmol, 1.20 equiv), bis(triphenylphosphine)palladium(II) chloride (0.264 g, 0.376 mmol, 0.100 equiv) in acetonitrile (6 mL) and 1.0M sodium carbonate aqueous solution (6 mL) was heated in the microwave to 160° C. for 2 min. The reaction mixture was partitioned between saturated aqueous sodium chloride solution (10 mL) and ethyl acetate (20 mL). The collected organic was dried over anhydrous magnesium sulfate, filtered, and concentrated. Purification by flash column chromatography (2.5% methanol in dichoromethane) afforded product as a sticky solid (567 mg, 63%). $^1$H NMR (500 MHz, CDCl$_3$), δ: 7.74 (m, 1H), 7.68 (m, 1H), 7.36-7.48 (m, 4H), 6.79 (dd, J=7.2, 1.3 Hz, 1H), 4.46 (br s, 2H), 3.01 (m, 1H), 1.31 (d, J=6.9 Hz, 6H).

5-[3-(propan-2-yl)phenyl]-N-(2-methylpyridin-4-yl)[1,2,4]triazolo[1,5-a]pyridin-2-amine A suspension of 5-[3-(propan-2-yl)phenyl][1,2,4]triazolo[1,5-a]pyridin-2-amine (88.9 mg, 0.352 mmol, 1.00 equiv), 4-chloro-2-methylpyridine (53.9 mg, 0.423 mmol, 1.20 equiv), 2-dicyclohexylphosphino-2',4',6'-triisopropylbiphenyl (17.6 mg, 0.0369 mmol, 0.105 equiv), cesium carbonate (237 mg, 0.727 mmol, 2.06 equiv), and tris(dibenzylideneacetone)dipalladium(0) (10.0 mg, 0.0109 mmol, 0.0310 equiv) in N,N-dimethylformamide (2 mL) was heated in the microwave to 210° C. for 20 min. The reaction mixture was concentrated in vacuo (~1 mm Hg). The resulting residue was partitioned between saturated aqueous sodium chloride solution (5 mL) and ethyl acetate (5 mL). The organic was separated, and the aqueous phase was extracted with ethyl acetate (2×5 mL). The collected organic was dried over anhydrous sodium sulfate, filtered, and concentrated. Purification by preparative HPLC yielded a white solid (65.5 mg, 54%). $^1$H NMR (400 MHz, DMSO-d$_6$), δ: 10.13 (s, 1H), 8.16 (m, 1H), 7.95 (s, 1H), 7.83 (m, 1H), 7.63-7.72 (m, 2H), 7.44-7.55 (m, 4H), 7.25 (dd, J=7.1, 1.3 Hz, 1H), 3.03 (m, 1H), 2.37 (s, 3H), 1.30 (d, J=6.9 Hz, 6H).

Example 2

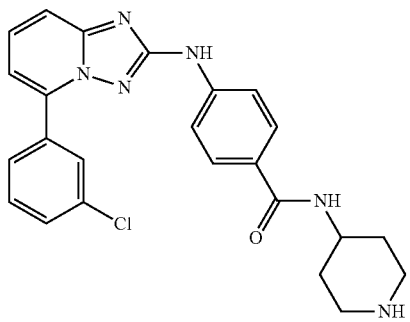 [SMILES: O=C(NC1CCNCC1)c1ccc(Nc2nc3cccc(-c4cccc(Cl)c4)n3n2)cc1]

4-(5-(3-chlorophenyl)-[1,2,4]triazolo[1,5-a]pyridin-2-ylamino)-N-(piperidin-4-yl)benzamide

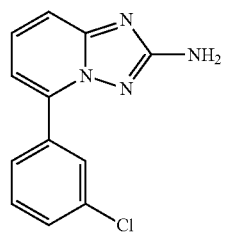 [SMILES: Nc1nc2cccc(-c3cccc(Cl)c3)n2n1]

5-(3-chlorophenyl)[1,2,4]triazolo[1,5-a]pyridin-2-amine

A suspension of 5-bromo[1,2,4]triazolo[1,5-c]pyridin-2-amine (5.1 g, 24 mmol, 1 equiv), 3-chlorophenylboronic acid (3.8 g, 24 mmol, 1.0 equiv), cesium carbonate (9.4 g, 29 mmol, 1.2 equiv), tetrakistriphenylphosphine palladium (2.7 g, 2.4 mmol, 0.1 equiv) was heated to 150° C. for 1 h under microwave irradiation. The reaction mixture was diluted with ethyl acetate and filtered through Celite. The filtrate was washed with saturated aqueous sodium chloride solution. The organic phase was dried over magnesium sulfate, filtered, and concentrated. Purification by flash column chromatography (30% ethyl acetate in petroleum ether) provided product as a solid (3.5 g, 61%). LCMS (ESI) m/z: 244.9.

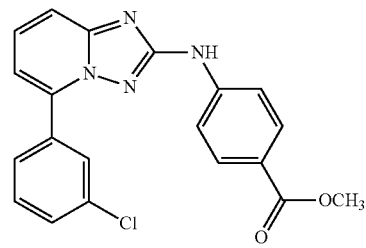 [SMILES: COC(=O)c1ccc(Nc2nc3cccc(-c4cccc(Cl)c4)n3n2)cc1]

Methyl 4-{[5-(3-chlorophenyl)[1,2,4]triazolo[1,5-a]pyridin-2-yl]amino}benzoate

A solution of 5-(3-chlorophenyl)[1,2,4]triazolo[1,5-a]pyridin-2-amine (1.46 g, 5.97 mmol, 1 equiv), methyl 4-iodobenzoate (1.57 g, 5.99 mmol, 1.00 equiv), palladium diacetate (134 mg, 0.597 mmol, 0.100 eq), cesium carbonate (1.96 g, 6.02 mmol, 1.01 equiv), and XantPhos (173 mg, 0.299 mmol, 0.050 eq) in 1,4-dioxane was heated at 80° C. overnight. The mixture was concentrated, and the residue was diluted with methanol and water. The resulting solid was filtered and rinsed with water, isopropanol, and hexanes. The crude product was used for the next step without further purification (1.85 g, 80%). LCMS (ESI) m/z: 379.0.

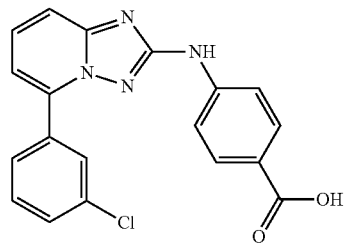 [SMILES: O=C(O)c1ccc(Nc2nc3cccc(-c4cccc(Cl)c4)n3n2)cc1]

4-{[5-(3-chlorophenyl)[1,2,4]triazolo[1,5-a]pyridin-2-yl]amino}benzoic acid

A solution of methyl 4-{[5-(3-chlorophenyl)[1,2,4]triazolo[1,5-a]pyridin-2-yl]amino}benzoate (0.50 g, 1.3 mmol, 1 equiv) in 2M sodium hydroxide aqueous solution and 1,4-dioxane was stirred at about 80-90° C. After 3 h, the reaction mixture was neutralized with 6N aqueous hydrochloride acid solution to pH=4-5. The resulting solid was filtered and rinsed sequentially with water, isopropanol, and hexanes. The resulting crude product was used for the next step without further purification (330 mg, >85% purity by HPLC). LCMS (ESI) m/z: 365.0.

4-(5-(3-Chlorophenyl)-[1,2,4]triazolo[1,5-a]pyridin-2-ylamino)-N-(piperidin-4-yl)benzamide To a solution of 4-{[5-(3-chlorophenyl)[1,2,4]triazolo[1,5-a]pyridin-2-yl]amino}benzoic acid (182 mg, 0.499 mmol, 1 equiv), O-(7-Azabenzotriazol-1-yl)-N,N,N',N'-tetramethyluronium hexafluorophosphate (228 mg, 0.600 mmol, 1.20 equiv), and diisopropylethylamine (97 mg, 0.75 mmol, 1.5 equiv) in 1:2 dichloromethane/tetrahydrofuran (5 mL) was added tert-butyl 4-amino-1-piperidine carboxylate (120 mg, 0.60 mmol, 1.2 equiv). The resulting mixture was stirred at 30° C. overnight, filtered, concentrated to give crude product. The crude product was dissolved in 1:1 trifluoroacetic acid/tetrahydrofuran (10 ml) and stirred at room temperature for 2 h. After removal of the solvent, the resulting residue was purified by preparative HPLC to give the desired product (39.5 mg, 17%). $^1$H NMR (400 MHz, DMSO-$d_6$), δ: 9.98 (s, 1H), 8.24 (s, 1H), 7.94-7.97 (m, 1H), 7.86 (s, 3H), 7.61-7.75 (m, 6H), 7.29-7.32 (m, 3H), 3.30-3.40 (m, 3H), 3.00 (m, 2H), 1.89 (m, 2H), 1.40 (m, 2H). LCMS (ESI) m/z: 447.0.

Example 3

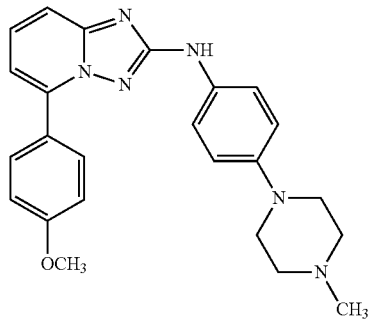 [SMILES: COc1ccc(-c2cccc3nc(Nc4ccc(N5CCN(C)CC5)cc4)nn23)cc1]

5-(4-methoxyphenyl)-N-(4-(4-methylpiperazin-1-yl)phenyl)-[1,2,4]triazolo[1,5-a]pyridin-2-amine

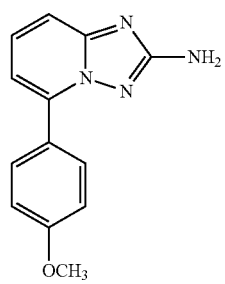 [SMILES: COc1ccc(-c2cccc3nc(N)nn23)cc1]

5-(4-methoxyphenyl)-[1,2,4]triazolo[1,5-a]pyridin-2-amine

A solution of 5-bromo-[1,2,4]triazolo[1,5-a]pyridin-2-amine (1.5 g, 7.0 mmol, 1 equiv) and bis(triphenylphosphine) palladium(II) chloride (500 mg, 0.7 mmol 0.1 equiv) in acetonitrile (10 mL) and 1M aqueous sodium carbonate solution (10 mL) was heated at 120° C. for 3 min in the microwave. The reaction mixture was diluted with ethyl acetate, and the resulting solution was washed water (2×) and saturated aqueous sodium chloride solution. Purification by flash column chromatography (2→10% methanol in dichloromethane) provided product (1.4 g, 83%). $^1$H NMR (400 MHz, CDCl$_3$), δ: 7.90 (d, 2H), 7.48 (m, 1H), 7.39 (m, 1H), 7.05 (d, 2H), 6.88 (dd, 1H), 4.25 (s, 2H); ES-MS m/z 241.0.

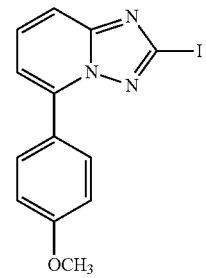 [SMILES: COc1ccc(-c2cccc3nc(I)nn23)cc1]

2-iodo-5-(4-methoxyphenyl)[1,2,4]triazolo[1,5-a]pyridine

To a solution of 5-(4-methoxyphenyl)[1,2,4]triazolo[1,5-a]pyridin-2-amine (825 mg, 3.43 mmol) and p-toluene sulphonic acid (1.77 g, 10.3 mmol) in acetonitrile (40 mL) was added a solution of potassium iodide (1.42 g, 8.55 mmol) and sodium nitrite (474 mg, 6.87 mmol) in water (2 mL) at 24° C. After 18 h, ethyl acetate was added to the reaction mixture. The resulting solution was washed with water (2×) and saturated aqueous sodium chloride solution. The organic was dried over magnesium sulfate, filtered, and concentrated. Purification using ISCO CombiFlash (2→5% methanol in dichloromethane) afforded 2-iodo-5-(4-methoxyphenyl)-[1,2,4]triazolo[1,5-a]pyridine (950 mg, 71%). $^1$H NMR (400 MHz, CDCl$_3$), δ: 7.90 (d, 2H), 7.64 (m, 1H), 7.57 (t, 1H), 7.05 (t, 3H); ES-MS m/z 351.9.

5-(4-Methoxyphenyl)-N-(4-(4-methylpiperazin-1-yl)phenyl)-[1,2,4]triazolo[1,5-a]pyridin-2-amine A solution of 4-(4-aminophenyl)-1-methylpiperazine (163 mg, 0.86 mmol), 2-dicyclohexylphosphino-2',4',6'-triisopropylbiphenyl (54 mg, 0.11 mmol), sodium tert-butoxide (103 mg, 1 mmol), and 2-iodo-5-(4-methoxyphenyl)-[1,2,4]triazolo[1,5-a]pyridine (150 mg, 0.43 mmol) in dimethylformamide (4 mL) was degassed by evacuation of the reaction vessel followed by N$_2$ purge (3×). To this mixture was added trisdibenzylideneacetone-bispalladium (52 mg, 0.06 mmol), and the reaction mixture was further degassed. The reaction mixture was heated to 100° C. After 2 h, acetic acid (60 mg, 1 mmol) was added, the resulting mixture was filtered and concentrated. Purification by reverse phase HPLC provided product (60 mg, 30%). $^1$H NMR (400 MHz, CD$_3$OD), δ: 8.10 (d, 2H), 7.7 (m, 1H), 7.6 (d, 2H), 7.35 (t, 1H), 7.20 (m, 3H), 7.0 (d, 2H), 3.9 (s, 3H), 3.2 (t, 4H), 2.7 (t, 4H), 2.4 (s, 3H); ES-MS m/z 415.3.

Example 4

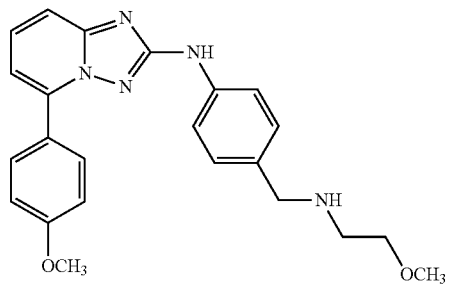 [SMILES: COCCNCc1ccc(Nc2nc3cccc(-c4ccc(OC)cc4)n3n2)cc1]

N-(4-((2-methoxyethylamino)methyl)phenyl)-5-(4-methoxyphenyl)-[1,2,4]triazolo[1,5-a]pyridin-2-amine

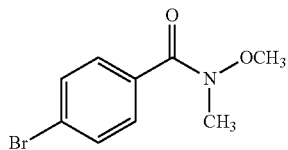

4-bromo-N-methoxy-N-methylbenzamide

A solution of 4-bromobenzoyl chloride (4.67 g, 21.3 mmol), diisopropylethylamine (3.78 mL, 46.8 mmol), and N,O-dimethylhydroxylamine (2.18 g, 22.3 mmol) in ethyl acetate (100 mL) was heated to 45° C. After 1 h, the reaction mixture was diluted with ethyl acetate (100 mL). The resulting solution was washed sequentially with water and saturated aqueous sodium chloride solution. The collected organic was dried over magnesium sulfate, filtered, and concentrated. Purification by flash column chromatography (hexanes→ethyl acetate in hexanes) provided producted as a tan solid (4.12 g, 79%). LCMS (ESI) m/z: 244.

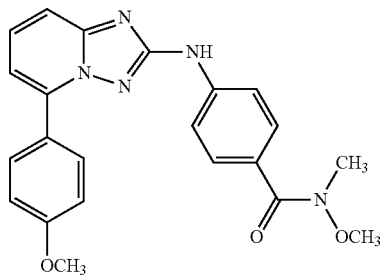 [SMILES: COc1ccc(-c2cccc3nc(Nc4ccc(C(=O)N(C)OC)cc4)nn23)cc1]

N-methoxy-4-(5-(4-methoxyphenyl)-[1,2,4]triazolo[1,5-a]pyridin-2-ylamino)-N-methylbenzamide Made by following the procedure described for the preparation of 5-[3-(propan-2-yl)phenyl]-N-(2-methylpyridin-4-yl)[1,2,4]triazolo[1,5-a]pyridin-2-amine, in Example 1, but substituting 4-bromo-N-methoxy-N-methylbenzamide and 5-(4-methoxyphenyl)-[1,2,4]triazolo[1,5-c]pyridin-2-amine. LCMS (ESI) m/z: 404.

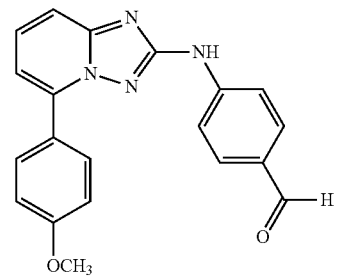 [SMILES: COc1ccc(-c2cccc3nc(Nc4ccc(C=O)cc4)nn23)cc1]

4-(5-(4-methoxyphenyl)-[1,2,4]triazolo[1,5-a]pyridin-2-ylamino)benzaldehyde

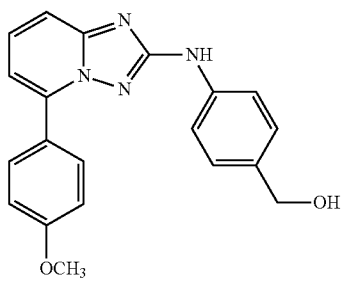 [SMILES: COc1ccc(-c2cccc3nc(Nc4ccc(CO)cc4)nn23)cc1]

(4-(5-(4-methoxyphenyl)-[1,2,4]triazolo[1,5-a]pyridin-2-ylamino)phenyl)methanol

To a solution lithium aluminum hydride (20 mmol, 1M in tetrahydrofuran) at −78° C. was added a solution of N-methoxy-4-(5-(4-methoxyphenyl)-[1,2,4]triazolo[1,5-a]pyridin-2-ylamino)-N-methylbenzamide (215 mg, 0.53 mmol) in tetrahydrofuran (4.5 mL) over 25 min. After 1 h, excess lithium aluminum hydride was quenched by the addition of water, and ethyl acetate was added. The resulting mixture was washed sequentially with 1M hydrochloric acid and saturated aqueous sodium chloride solution. The organic was dried over magnesium sulfate, filtered, and concentrated. Purification by flash column chromatography (hexanes→ethyl acetate in hexanes) afforded aldehyde was as a yellow solid (56 mg, 30%), LCMS (ESI) m/z: 345 and alcohol as a white solid (10.8 mg, 9%), LCMS (ESI) m/z: 347.

N-(4-((2-methoxyethylamino)methyl)phenyl)-5-(4-methoxyphenyl)-[1,2,4]triazolo[1,5-a]pyridin-2-amine A solution of 4-(5-(4-methoxyphenyl)-[1,2,4]triazolo[1,5-a]pyridin-2-ylamino)benzaldehyde (47 mg, 0.14 mmol) and 2-methoxyethylamine (65 μL, 0.70 mmol) and 4 Å molecular sieves in tetrahydrofuran (5 mL) was stirred at 24° C. After 18 h, sodium cyanoborohydride (100 mg, 2 mmol) was added to the reaction mixture. After 1 h, the reaction mixture was partitioned between ethyl acetate (20 mL) and water (10 mL). The organic was separated and washed with saturated aqueous sodium chloride solution (10 mL). The collected organic was dried over magnesium sulfate, filtered, and concentrated.

Purification by preparative HPLC provided a tan solid (18.6 mg, 34%). LCMS (ESI) m/z: 404. $^1$H NMR (400 MHz, DMSO-$d_6$), δ: 9.51 (s, 1H), 8.05 (d, J=8.8, 2 H), 7.62 (m, 3H), 7.52 (d, J=8.7, 1H), 7.20 (d, J=8.4, 2H), 7.16-7.10 (m, 3H), 3.87 (s, 3H), 3.62 (s, 2H), 3.39 (t, J=5.7, 2H), 3.23 (s, 3H), 3.17 (d, J=5.2, 2H), 2.63 (t, J=5.7, 2H).

Example 5

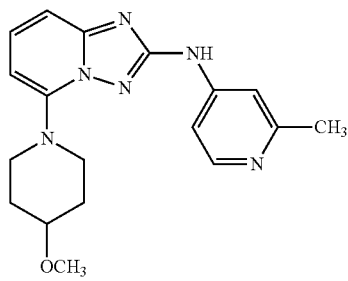 [SMILES: COC1CCN(c2cccc3nc(Nc4ccnc(C)c4)nn23)CC1]

5-(4-methoxypiperidin-1-yl)-N-(2-methylpyridin-4-yl)-[1,2,4]triazolo[1,5-a]pyridin-2-amine

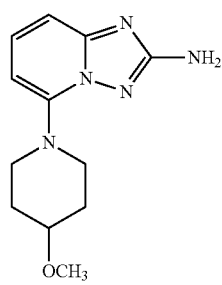 [SMILES: COC1CCN(c2cccc3nc(N)nn23)CC1]

5-(4-methoxypiperidin-1-yl)-[1,2,4]triazolo[1,5-a]pyridin-2-amine

A suspension of 5-bromo[1,2,4]triazolo[1,5-a]pyridin-2-amine (69.2 mg, 0.325 mmol, 1 equiv), 4-methoxypiperidine (150 mg, 1.3 mmol, 4.0 equiv), cesium carbonate (212 mg, 0.652 mmol, 2.00 equiv), XPhos (16.9 mg, 0.0354 mmol, 0.109 equiv), and tris(dibenzylideneacetone)dipalladium (0) (9.3 mg, 0.010 mmol, 0.031 equiv) in N,N-dimethylformamide (2 mL) was heated to 180° C. in the microwave for 15 min. The reaction mixture was concentrated in vacuo. The resulting residue was partitioned between ethyl acetate (5 mL) and saturated aqueous sodium chloride solution (5 mL). The aqueous was extracted with ethyl acetate (2×5 mL). The combine organic was dried over anhydrous sodium sulfate, filtered, and concentrated. Purification by flash column chromotagraphy (95:5 dichloromethane/methanol) afforded a white solid (557 mg, 67%). LCMS (ESI) m/z: 248.3. NMR (500 MHz, CDCl$_3$), δ: 7.32 (m, 1H), 7.05 (m, 1H), 6.23 (m, 1H), 4.39 (br s, 2H), 3.66 (m, 2H), 3.48 (m, 1H), 3.41 (s, 3H), 3.18 (m, 2H), 2.08 (m, 2H), 1.89 (m, 2H).

5-(4-methoxypiperidin-1-yl)-N-(2-methylpyridin-4-yl)-[1,2,4]triazolo[1,5-a]pyridin-2-amine Made by following the procedure described for the preparation of 5-[3-(propan-2-yl)phenyl]-N-(2-methylpyridin-4-yl)[1,2,4]triazolo[1,5-a]pyridin g-amine, in Example 1, but substituting 5-(4-methoxypiperidin-1-yl)-[1,2,4]triazolo[1,5-a]pyridin-2-amine. LCMS (ESI) m/z: 339.3. $^1$H NMR (400 MHz, DMSO-$d_6$), δ: 10.01 (s, 1H), 8.19-8.22 (m, 2H), 7.67 (s, 1H), 7.53 (m, 1H), 7.39 (m, 1H), 7.18 (d, J=8.7 Hz, 1H), 6.48 (d, J=7.8 Hz, 1H), 3.74 (m, 2H), 3.49 (m, 2H), 3.32 (s, 3H), 3.19 (m, 1H), 2.41 (s, 3H), 2.08 (m, 2H), 1.73 (m, 2H).

Example 6

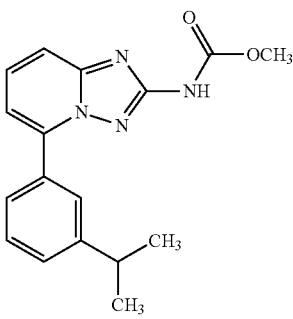 [SMILES: COC(=O)Nc1nc2cccc(-c3cccc(C(C)C)c3)n2n1]

[5-(3-Isopropyl-phenyl)-[1,2,4]triazolo[1,5-a]pyridin-2-yl]-carbamic acid methyl ester To a solution of 5-[3-(propan-2-yl)phenyl][1,2,4]triazolo[1,5-a]pyridin-2-amine (23.6 mg, 0.0935 mmol, 1 equiv) in pyridine was added methyl chloroformate (36.1 uL, 0.468 mmol, 5.00 equiv) at 24° C. After 3 h, the reaction mixture was concentrated in vacuo. The resulting residue was partitioned between saturated aqueous sodium bicarbonate solution (5 mL) and ethyl acetate (5 mL). The aqueous layer was extracted with ethyl acetate (2×5 mL). The combined organic extracts were dried over magnesium sulfate, filtered, and concentrated. Purification by preparative HPLC provided a white solid (17.7 mg, 61%). LCMS (ESI) m/z: 311.2. $^1$H NMR (500 MHz, DMSO-$d_6$), δ: 10.45 (s, 1H), 7.88 (m, 1H), 7.81 (m, 1H), 7.65-7.72 (m, 2H), 7.48 (t, J=7.6 Hz, 1H), 7.42 (m, 1H), 7.28 (dd, J=7.0, 1.6 Hz, 1H), 3.67 (s, 3H), 3.00 (m, 1H), 1.28 (d, J=6.9 Hz, 6H).

Examples 7-230 shown in Table 1 were prepared generally following the above-described Examples. For each compound shown in Table 1, the Example number followed is given in the Method column.

TABLE 1

| Ex | Structure | Name | Method | LCMS (ESI) m/z |
|---|---|---|---|---|
| 7 | 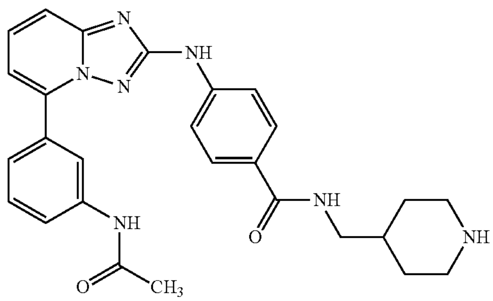 [SMILES: CC(=O)Nc1cccc(-c2cccc3nc(Nc4ccc(C(=O)NCC5CCNCC5)cc4)nn23)c1] | 4-[5-(3-Acetylamino-phenyl)-[1,2,4]triazolo[1,5-a]pyridin-2-ylamino]-N-piperidin-4-ylmethyl-benzamide | 2 | 484.3 |
| 8 | 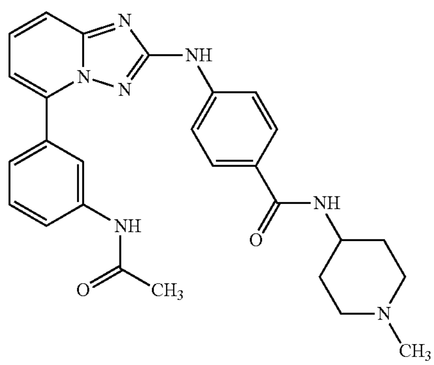 [SMILES: CC(=O)Nc1cccc(-c2cccc3nc(Nc4ccc(C(=O)NC5CCN(C)CC5)cc4)nn23)c1] | 4-[5-(3-Acetylamino-phenyl)-[1,2,4]triazolo[1,5-a]pyridin-2-ylamino]-N-(1-methyl-piperidin-4-yl)-benzamide | 2 | 484.2 |
| 9 | 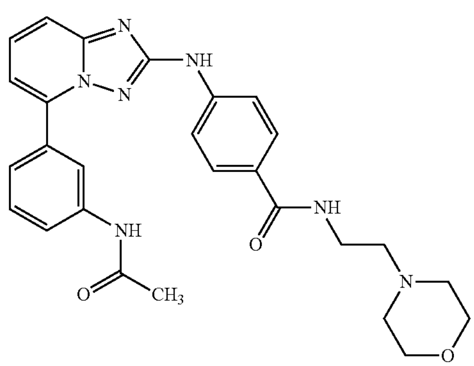 [SMILES: CC(=O)Nc1cccc(-c2cccc3nc(Nc4ccc(C(=O)NCCN5CCOCC5)cc4)nn23)c1] | 4-[5-(3-Acetylamino-phenyl)-[1,2,4]triazolo[1,5-a]pyridin-2-ylamino]-N-(2-morpholin-4-yl-ethyl)-benzamide | 2 | 500.3 |
| 10 | 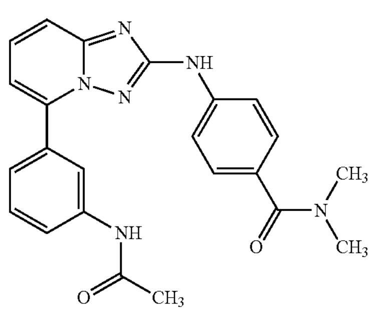 [SMILES: CC(=O)Nc1cccc(-c2cccc3nc(Nc4ccc(C(=O)N(C)C)cc4)nn23)c1] | 4-[5-(3-Acetylamino-phenyl)-[1,2,4]triazolo[1,5-a]pyridin-2-ylamino]-N,N-dimethyl-benzamide | 2 | 415.1 |

TABLE 1-continued

| Ex | Structure | Name | Method | LCMS (ESI) m/z |
|---|---|---|---|---|
| 11 | 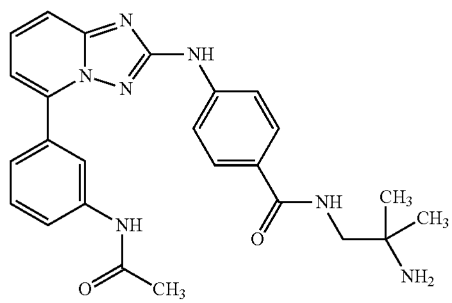 [SMILES: CC(=O)Nc1cccc(-c2cccc3nc(Nc4ccc(C(=O)NCC(C)(C)N)cc4)nn23)c1] | 4-[5-(3-Acetylamino-phenyl)-[1,2,4]triazolo[1,5-a]pyridin-2-ylamino]-N-(2-amino-2-methyl-propyl)-benzamide | 2 | 458.3 |
| 12 | 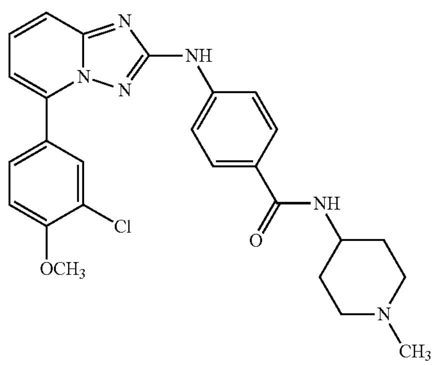 [SMILES: COc1ccc(-c2cccc3nc(Nc4ccc(C(=O)NC5CCN(C)CC5)cc4)nn23)cc1Cl] | 4-[5-(3-Chloro-4-methoxy-phenyl)-[1,2,4]triazolo[1,5-a]pyridin-2-ylamino]-N-(1-methyl-piperidin-4-yl)-benzamide | 2 | 491.2 |
| 13 | 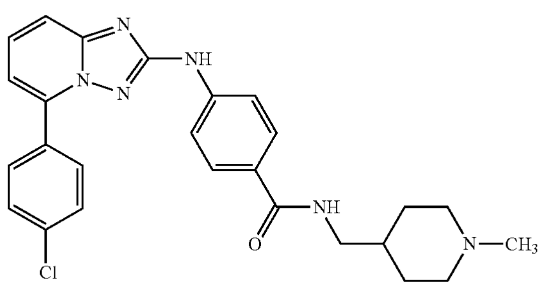 [SMILES: CN1CCC(CNC(=O)c2ccc(Nc3nc4cccc(-c5ccc(Cl)cc5)n4n3)cc2)CC1] | 4-[5-(4-Chloro-phenyl)-[1,2,4]triazolo[1,5-a]pyridin-2-ylamino]-N-(1-methyl-piperidin-4-ylmethyl)-benzamide | 2 | 475.2 |
| 14 | 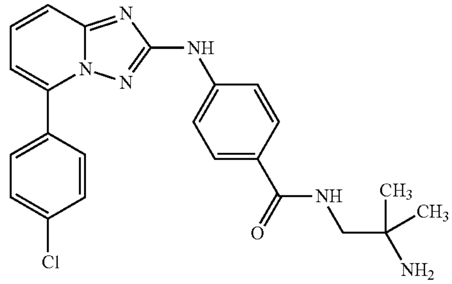 [SMILES: CC(C)(N)CNC(=O)c1ccc(Nc2nc3cccc(-c4ccc(Cl)cc4)n3n2)cc1] | N-(2-Amino-2-methyl-propyl)-4-[5-(4-chloro-phenyl)-[1,2,4]triazolo[1,5-a]pyridin-2-ylamino]-benzamide | 2 | 435.2 |

TABLE 1-continued

| Ex | Structure | Name | Method | LCMS (ESI) m/z |
|---|---|---|---|---|
| 15 | 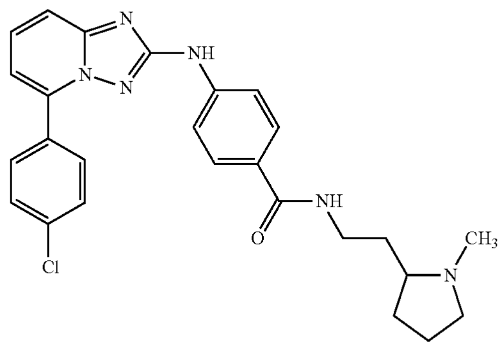 [SMILES: CN1CCCC1CCNC(=O)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N-[2-(1-methyl-pyrrolidin-2-yl)-ethyl]-benzamide | 2 | 475.2 |
| 16 | 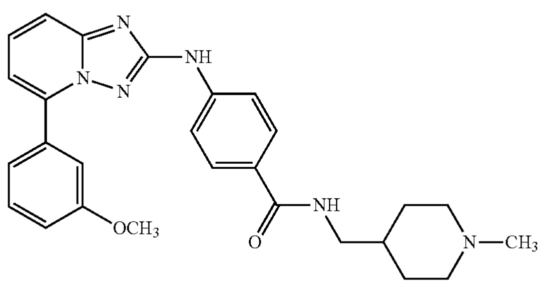 [SMILES: COc1cccc(-c2cccc3nc(Nc4ccc(C(=O)NCC5CCN(C)CC5)cc4)nn23)c1] | 4-[5-(3-Methoxy-phenyl)-[1,2,4]triazolo[1,5-a]pyridin-2-ylamino]-N-(1-methyl-piperidin-4-ylmethyl)-benzamide | 2 | 471.2 |
| 17 | 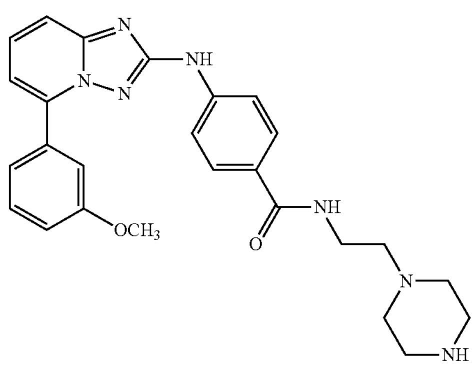 | 4-[5-(3-Methoxy-phenyl)-[1,2,4]triazolo[1,5-a]pyridin-2-ylamino]-N-(2-piperazin-1-yl-ethyl)-benzamide | 2 | 472.3 |
| 18 | 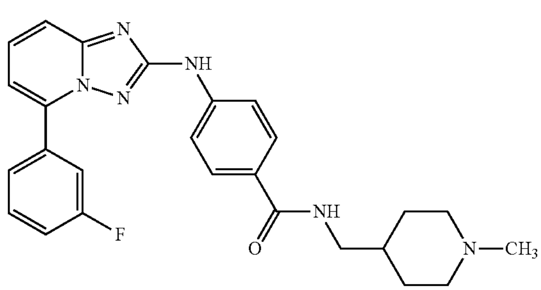 [SMILES: CN1CCC(CNC(=O)c2ccc(Nc3nc4cccc(-c5cccc(F)c5)n4n3)cc2)CC1] | 4-[5-(3-Fluoro-phenyl)-[1,2,4]triazolo[1,5-a]pyridin-2-ylamino]-N-(1-methyl-piperidin-4-ylmethyl)-benzamide | 2 | 459.1 |

TABLE 1-continued

| Ex | Structure | Name | Method | LCMS (ESI) m/z |
|---|---|---|---|---|
| 19 | 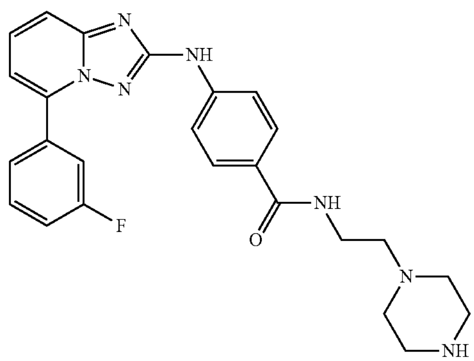 | 4-[5-(3-Fluoro-phenyl)-[1,2,4]triazolo[1,5-a]pyridin-2-ylamino]-N-(2-piperazin-1-yl-ethyl)-benzamide | 2 | 460.2 |
| 20 | 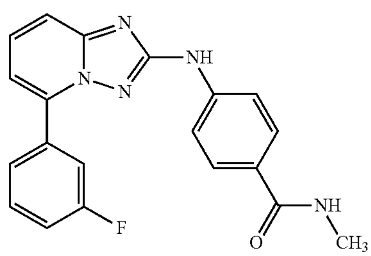 [SMILES: CNC(=O)c1ccc(Nc2nc3cccc(-c4cccc(F)c4)n3n2)cc1] | 4-[5-(3-Fluoro-phenyl)-[1,2,4]triazolo[1,5-a]pyridin-2-ylamino]-N-methyl-benzamide | 2 | 362.1 |
| 21 | 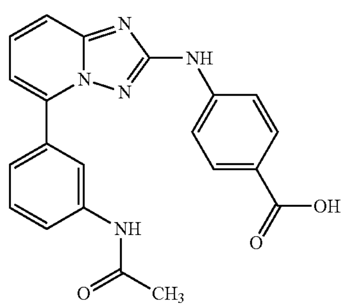 [SMILES: CC(=O)Nc1cccc(-c2cccc3nc(Nc4ccc(C(=O)O)cc4)nn23)c1] | 4-[5-(3-Acetylamino-phenyl)-[1,2,4]triazolo[1,5-a]pyridin-2-ylamino]-benzoic acid | 2 | 388.0 |
| 22 | 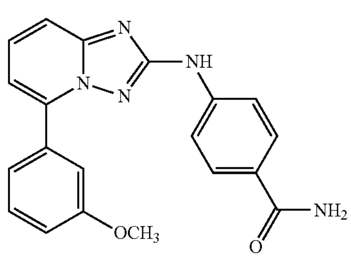 | 4-[5-(3-Methoxy-phenyl)-[1,2,4]triazolo[1,5-a]pyridin-2-ylamino]-benzamide | 2 | 360.1 |
| 23 | 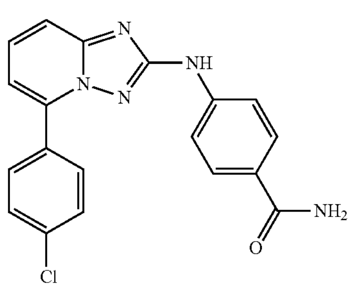 [SMILES: NC(=O)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-benzamide | 2 | 363.9 |

TABLE 1-continued

| Ex | Structure | Name | Method | LCMS (ESI) m/z |
|---|---|---|---|---|
| 24 | 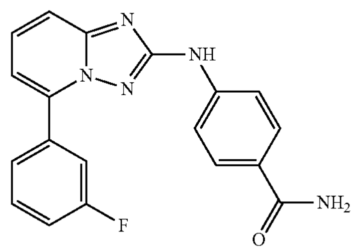 [SMILES: NC(=O)c1ccc(Nc2nc3cccc(-c4cccc(F)c4)n3n2)cc1] | 4-[5-(3-Fluoro-phenyl)-[1,2,4]triazolo[1,5-a]pyridin-2-ylamino]-benzamide | 2 | 348.0 |
| 25 | 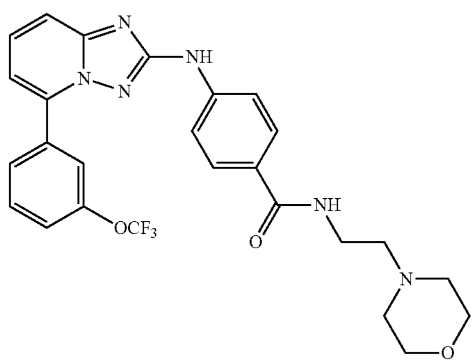 | N-(2-Morpholin-4-yl-ethyl)-4-[5-(3-trifluoromethoxy-phenyl)-[1,2,4]triazolo[1,5-a]pyridin-2-ylamino]-benzamide | 2 | 527.0 |
| 26 | 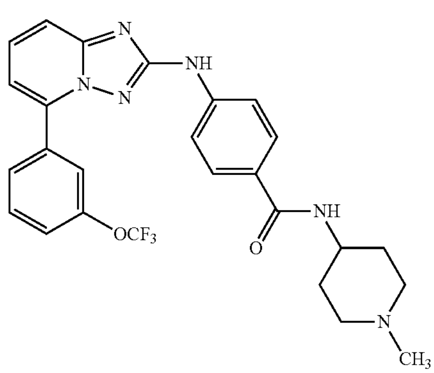 | N-(1-Methyl-piperidin-4-yl)-4-[5-(3-trifluoromethoxy-phenyl)-[1,2,4]triazolo[1,5-a]pyridin-2-ylamino]-benzamide | 2 | 511.0 |
| 27 | 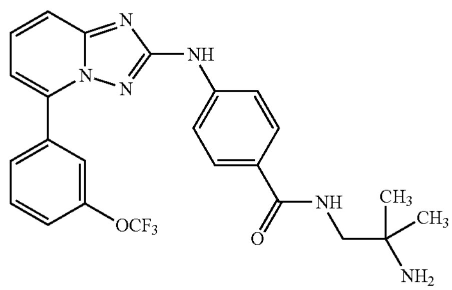 [SMILES: CC(C)(N)CNC(=O)c1ccc(Nc2nc3cccc(-c4cccc(OC(F)(F)F)c4)n3n2)cc1] | N-(2-Amino-2-methyl-propyl)-4-[5-(3-trifluoromethoxy-phenyl)-[1,2,4]triazolo[1,5-a]pyridin-2-ylamino]-benzamide | 2 | 485.0 |

TABLE 1-continued

| Ex | Structure | Name | Method | LCMS (ESI) m/z |
|---|---|---|---|---|
| 28 | 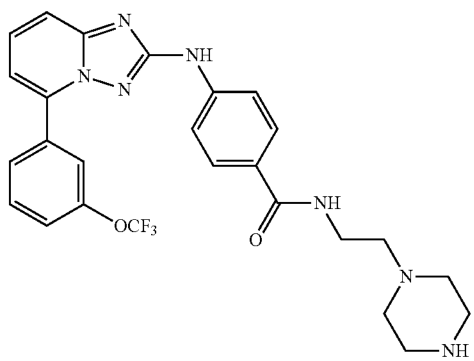 | N-(2-Piperazin-1-yl-ethyl)-4-[5-(3-trifluoromethoxy-phenyl)-[1,2,4]triazolo[1,5-a]pyridin-2-ylamino]-benzamide | 2 | 526.1 |
| 29 | 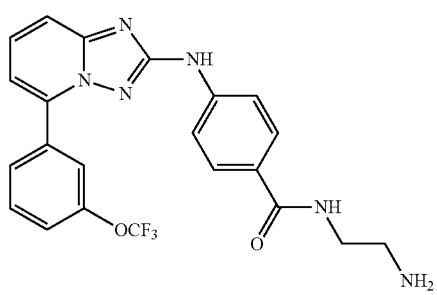 | N-(2-Amino-ethyl)-4-[5-(3-trifluoromethoxy-phenyl)-[1,2,4]triazolo[1,5-a]pyridin-2-ylamino]-benzamide | 2 | 457.0 |
| 30 | 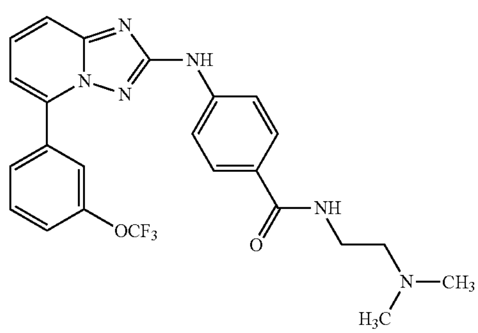 [SMILES: CN(C)CCNC(=O)c1ccc(Nc2nc3cccc(-c4cccc(OC(F)(F)F)c4)n3n2)cc1] | N-(2-Dimethylamino-ethyl)-4-[5-(3-trifluoromethoxy-phenyl)-[1,2,4]triazolo[1,5-a]pyridin-2-ylamino]-benzamide | 2 | 485.1 |
| 31 | 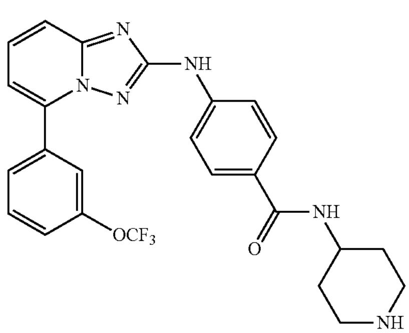 | N-Piperidin-4-yl-4-[5-(3-trifluoromethoxy-phenyl)-[1,2,4]triazolo[1,5-a]pyridin-2-ylamino]-benzamide | 2 | 497.3 |

TABLE 1-continued

| Ex | Structure | Name | Method | LCMS (ESI) m/z |
|---|---|---|---|---|
| 32 | 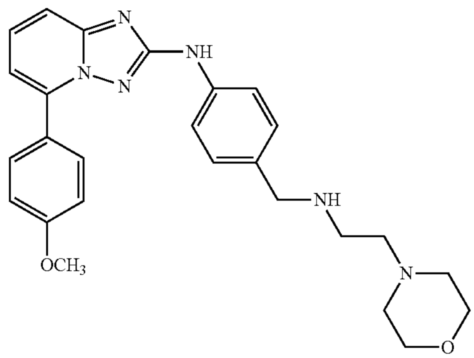 [SMILES: COc1ccc(-c2cccc3nc(Nc4ccc(CNCCN5CCOCC5)cc4)nn23)cc1] | [5-(4-Methoxy-phenyl)-[1,2,4]triazolo[1,5-a]pyridin-2-yl]-{4-[(2-morpholin-4-yl-ethylamino)-methyl]-phenyl}-amine | 4 | 459 |
| 33 | 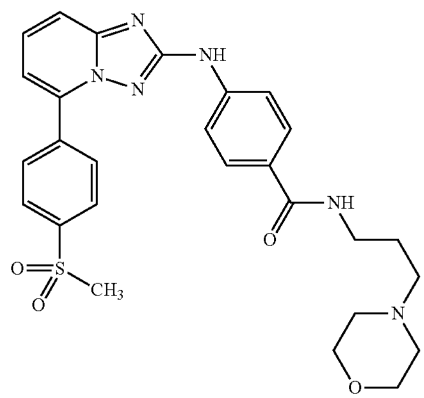 [SMILES: CS(=O)(=O)c1ccc(-c2cccc3nc(Nc4ccc(C(=O)NCCCN5CCOCC5)cc4)nn23)cc1] | 4-[5-(4-Methanesulfonyl-phenyl)-[1,2,4]triazolo[1,5-a]pyridin-2-ylamino]-N-(3-morpholin-4-yl-propyl)-benzamide | 2 | 535.1 |
| 34 | 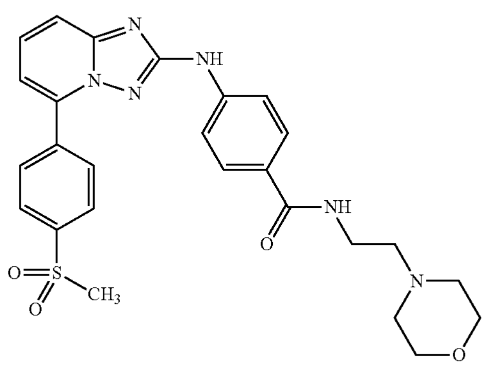 [SMILES: CS(=O)(=O)c1ccc(-c2cccc3nc(Nc4ccc(C(=O)NCCN5CCOCC5)cc4)nn23)cc1] | 4-[5-(4-Methanesulfonyl-phenyl)-[1,2,4]triazolo[1,5-a]pyridin-2-ylamino]-N-(2-morpholin-4-yl-ethyl)-benzamide | 2 | 521.1 |
| 35 | 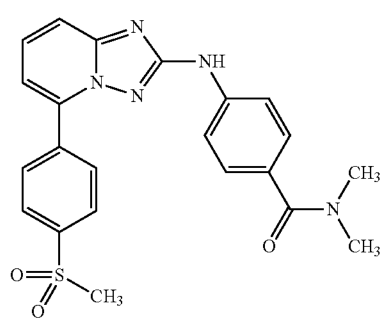 [SMILES: CN(C)C(=O)c1ccc(Nc2nc3cccc(-c4ccc(S(C)(=O)=O)cc4)n3n2)cc1] | 4-[5-(4-Methanesulfonyl-phenyl)-[1,2,4]triazolo[1,5-a]pyridin-2-ylamino]-N,N-dimethyl-benzamide | 2 | 436.1 |

TABLE 1-continued

| Ex | Structure | Name | Method | LCMS (ESI) m/z |
|---|---|---|---|---|
| 36 | 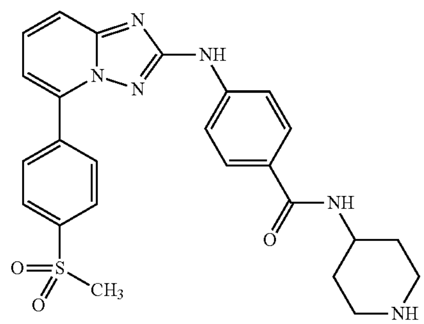 [SMILES: CS(=O)(=O)c1ccc(-c2cccc3nc(Nc4ccc(C(=O)NC5CCNCC5)cc4)nn23)cc1] | 4-[5-(4-Methanesulfonyl-phenyl)-[1,2,4]triazolo[1,5-a]pyridin-2-ylamino]-N-piperidin-4-yl-benzamide | 2 | 491.3 |
| 37 | 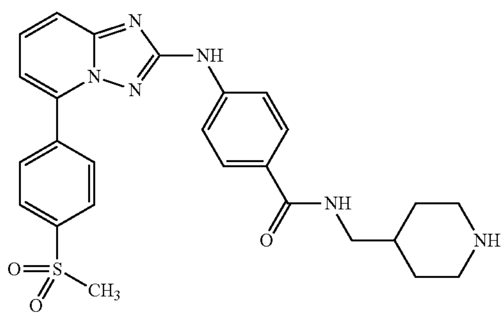 [SMILES: CS(=O)(=O)c1ccc(-c2cccc3nc(Nc4ccc(C(=O)NCC5CCNCC5)cc4)nn23)cc1] | 4-[5-(4-Methanesulfonyl-phenyl)-[1,2,4]triazolo[1,5-a]pyridin-2-ylamino]-N-piperidin-4-ylmethyl-benzamide | 2 | 505.1 |
| 38 | 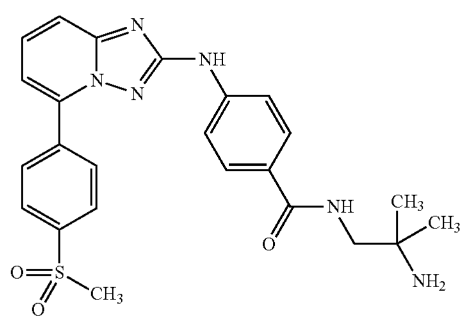 [SMILES: CC(C)(N)CNC(=O)c1ccc(Nc2nc3cccc(-c4ccc(S(C)(=O)=O)cc4)n3n2)cc1] | N-(2-Amino-2-methyl-propyl)-4-[5-(4-methanesulfonyl-phenyl)-[1,2,4]triazolo[1,5-a]pyridin-2-ylamino]-benzamide | 2 | 479.9 |
| 39 | 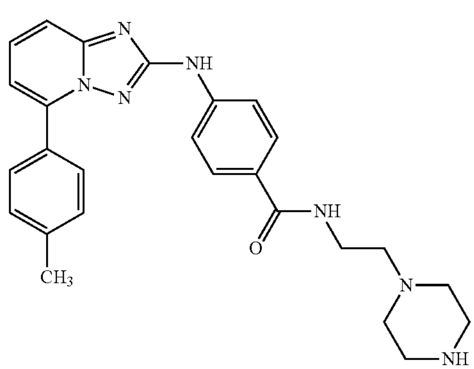 | N-(2-Piperazin-1-yl-ethyl)-4-(5-p-tolyl-[1,2,4]triazolo[1,5-a]pyridin-2-ylamino)-benzamide | 2 | 456.0 |

TABLE 1-continued

| Ex | Structure | Name | Method | LCMS (ESI) m/z |
|---|---|---|---|---|
| 40 | 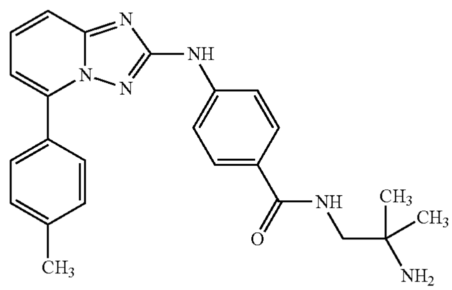 | N-(2-Amino-2-methyl-propyl)-4-(5-p-tolyl-[1,2,4]triazolo[1,5-a]pyridin-2-ylamino)-benzamide | 2 | 415.0 |
| 41 | 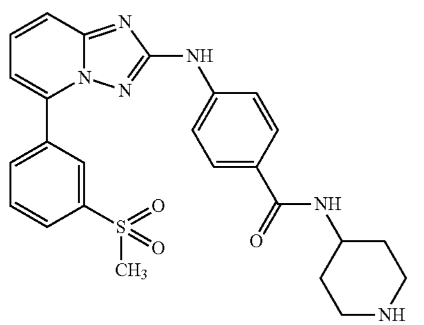 [SMILES: CS(=O)(=O)c1cccc(-c2cccc3nc(Nc4ccc(C(=O)NC5CCNCC5)cc4)nn23)c1] | 4-[5-(3-Methanesulfonyl-phenyl)-[1,2,4]triazolo[1,5-a]pyridin-2-ylamino]-N-piperidin-4-yl-benzamide | 2 | 491.0 |
| 42 | 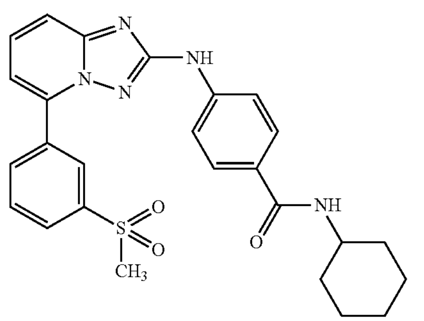 [SMILES: CS(=O)(=O)c1cccc(-c2cccc3nc(Nc4ccc(C(=O)NC5CCCCC5)cc4)nn23)c1] | N-Cyclohexyl-4-[5-(3-methanesulfonyl-phenyl)-[1,2,4]triazolo[1,5-a]pyridin-2-ylamino]-benzamide | 2 | 489.9 |
| 43 | 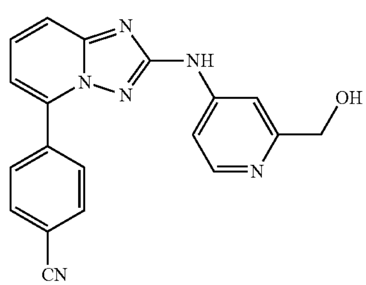 [SMILES: N#Cc1ccc(-c2cccc3nc(Nc4ccnc(CO)c4)nn23)cc1] | 4-[2-(2-Hydroxymethyl-pyridin-4-ylamino)-[1,2,4]triazolo[1,5-a]pyridin-5-yl]-benzonitrile | 1 | 343 |
| 44 | 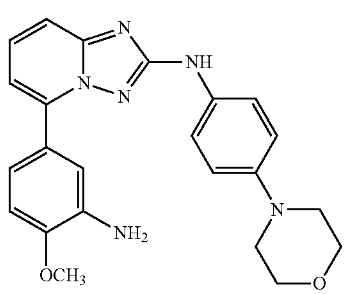 | [5-(3-Amino-4-methoxy-phenyl)-[1,2,4]triazolo[1,5-a]pyridin-2-yl]-(4-morpholin-4-yl-phenyl)-amine | 1 | 417.2 |

TABLE 1-continued

| Ex | Structure | Name | Method | LCMS (ESI) m/z |
|---|---|---|---|---|
| 45 | 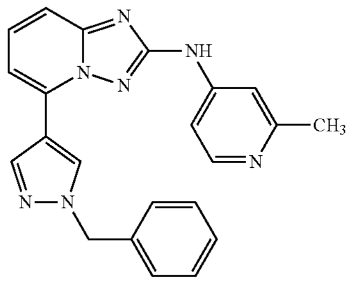 [SMILES: Cc1cc(Nc2nc3cccc(-c4cnn(Cc5ccccc5)c4)n3n2)ccn1] | [5-(1-Benzyl-1H-pyrazol-4-yl)-[1,2,4]triazolo[1,5-a]pyridin-2-yl]-(2-methyl-pyridin-4-yl)-amine | 1 | 382 |
| 46 | 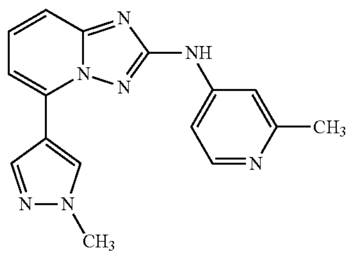 [SMILES: Cc1cc(Nc2nc3cccc(-c4cnn(C)c4)n3n2)ccn1] | [5-(1-Methyl-1H-pyrazol-4-yl)-[1,2,4]triazolo[1,5-a]pyridin-2-yl]-(2-methyl-pyridin-4-yl)-amine | 1 | 306 |
| 47 | 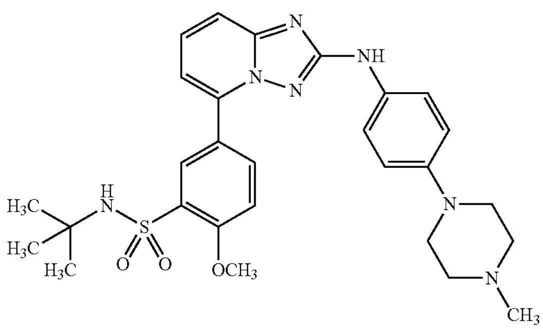 [SMILES: COc1ccc(-c2cccc3nc(Nc4ccc(N5CCN(C)CC5)cc4)nn23)cc1S(=O)(=O)NC(C)(C)C] | N-tert-Butyl-2-methoxy-5-{2-[4-(4-methyl-piperazin-1-yl)-phenylamino]-[1,2,4]triazolo[1,5-a]pyridin-5-yl}-benzenesulfonamide | 3 | 550 |
| 48 | 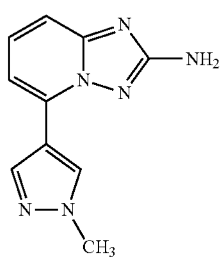 [SMILES: Cn1cc(-c2cccc3nc(N)nn23)cn1] | 5-(1-Methyl-1H-pyrazol-4-yl)-[1,2,4]triazolo[1,5-a]pyridin-2-ylamine | 1 | 215 |
| 49 | 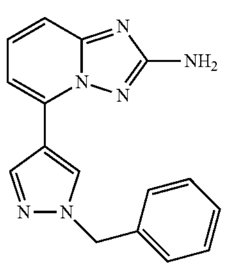 [SMILES: Nc1nc2cccc(-c3cnn(Cc4ccccc4)c3)n2n1] | 5-(1-Benzyl-1H-pyrazol-4-yl)-[1,2,4]triazolo[1,5-a]pyridin-2-ylamine | 1 | 291 |

TABLE 1-continued

| Ex | Structure | Name | Method | LCMS (ESI) m/z |
|---|---|---|---|---|
| 50 | 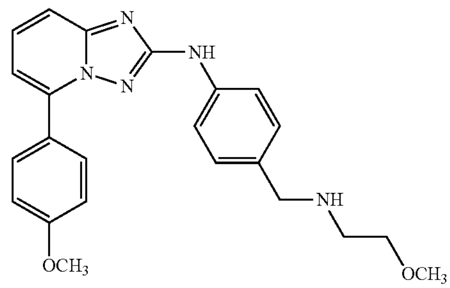 [SMILES: COCCNCc1ccc(Nc2nc3cccc(-c4ccc(OC)cc4)n3n2)cc1] | {4-[(2-Methoxy-ethylamino)-methyl]-phenyl}-[5-(4-methoxy-phenyl)-[1,2,4]triazolo[1,5-a]pyridin-2-yl]-amine | 4 | 404 |
| 51 | 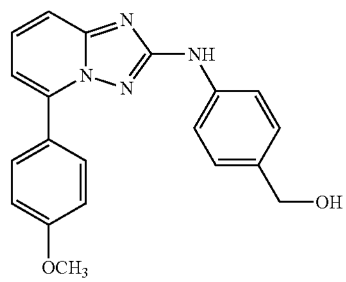 [SMILES: COc1ccc(-c2cccc3nc(Nc4ccc(CO)cc4)nn23)cc1] | {4-[5-(4-Methoxy-phenyl)-[1,2,4]triazolo[1,5-a]pyridin-2-ylamino]-phenyl}-methanol | 4 | 347 |
| 52 | 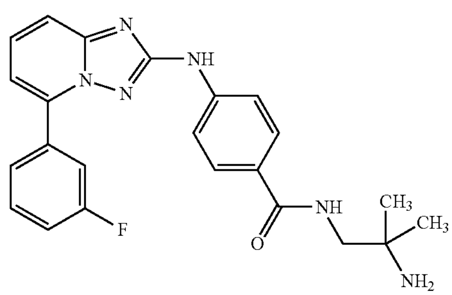 | N-(2-Amino-2-methyl-propyl)-4-[5-(3-fluoro-phenyl)-[1,2,4]triazolo[1,5-a]pyridin-2-ylamino]-benzamide | 2 | 491.1 |
| 53 | 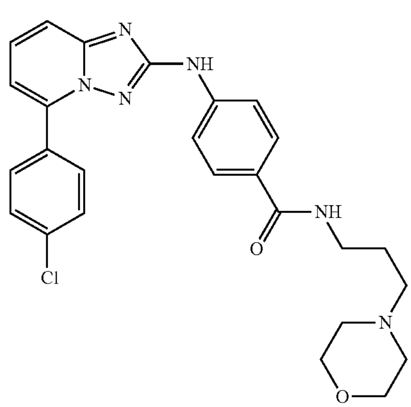 [SMILES: O=C(NCCCN1CCOCC1)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N-(3-morpholin-4-yl-propyl)-benzamide | 2 | 491.2 |

TABLE 1-continued

| Ex | Structure | Name | Method | LCMS (ESI) m/z |
|---|---|---|---|---|
| 54 | 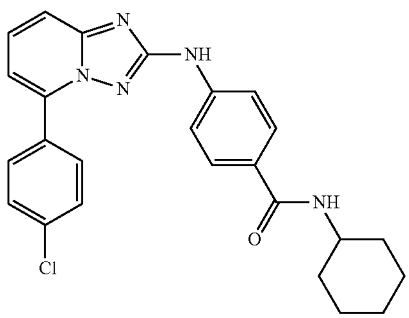 [SMILES: O=C(NC1CCCCC1)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N-cyclohexyl-benzamide | 2 | 446.2 |
| 55 | 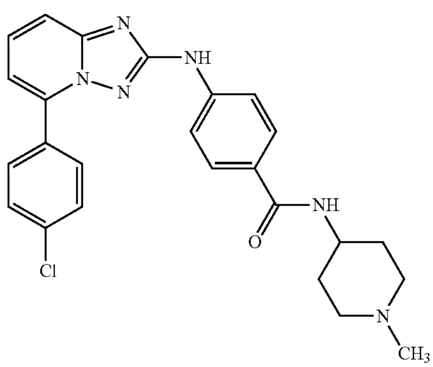 [SMILES: CN1CCC(NC(=O)c2ccc(Nc3nc4cccc(-c5ccc(Cl)cc5)n4n3)cc2)CC1] | 4-[5-(4-Chloro-phenyl)-[1,2,4]triazolo[1,5-a]pyridin-2-ylamino]-N-(1-methyl-piperidin-4-yl)-benzamide | 2 | 461.1 |
| 56 | 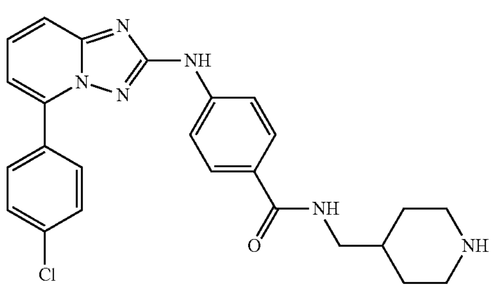 | 4-[5-(4-Chloro-phenyl)-[1,2,4]triazolo[1,5-a]pyridin-2-ylamino]-N-piperidin-4-ylmethyl-benzamide | 2 | 461.1 |
| 57 | 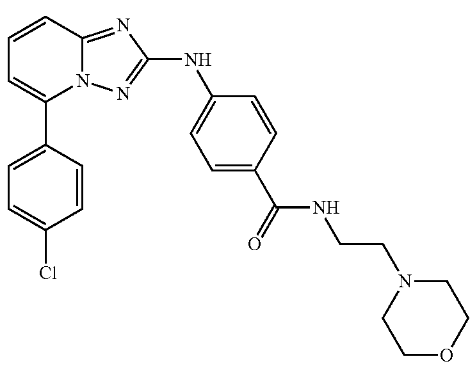 [SMILES: O=C(NCCN1CCOCC1)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N-(2-morpholin-4-yl-ethyl)-benzamide | 2 | 477.1 |

TABLE 1-continued

| Ex | Structure | Name | Method | LCMS (ESI) m/z |
|---|---|---|---|---|
| 58 | 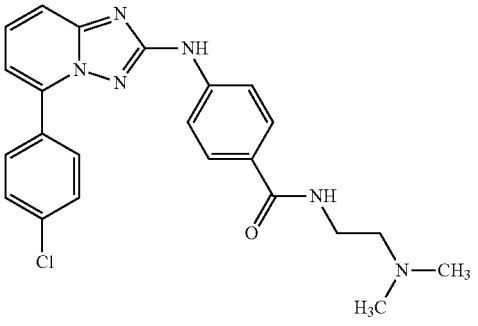 | 4-[5-(4-Chloro-phenyl)-[1,2,4]triazolo[1,5-a]pyridin-2-ylamino]-N-(2-dimethylamino-ethyl)-benzamide | 2 | 435.1 |
| 59 | 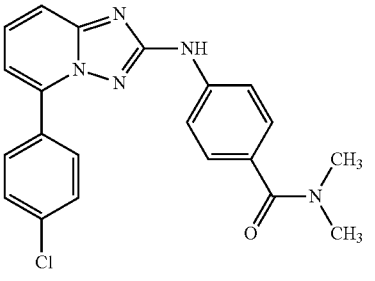 [SMILES: CN(C)C(=O)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N,N-dimethyl-benzamide | 2 | 392.2 |
| 60 | 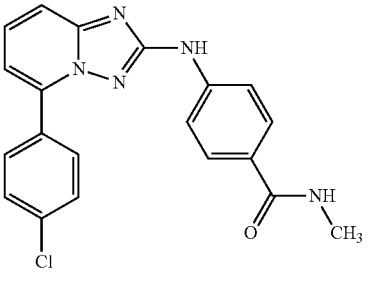 [SMILES: CNC(=O)c1ccc(Nc2nc3cccc(-c4ccc(Cl)cc4)n3n2)cc1] | 4-[5-(4-Chloro-phenyl)-[1,2,4]triazolo[1,5-a]pyridin-2-ylamino]-N-methyl-benzamide | 2 | 378.2 |
| 61 | 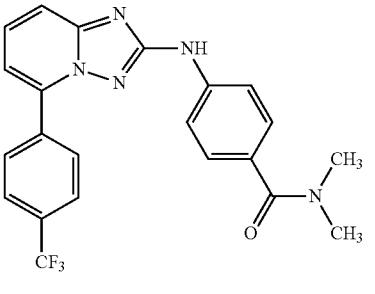 | N,N-Dimethyl-4-[5-(4-trifluoromethyl-phenyl)-[1,2,4]triazolo[1,5-a]pyridin-2-ylamino]-benzamide | 2 | 426.2 |
| 62 | 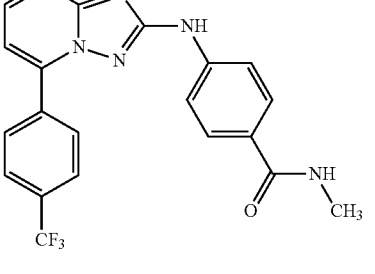 | N-Methyl-4-[5-(4-trifluoromethyl-phenyl)-[1,2,4]triazolo[1,5-a]pyridin-2-ylamino]-benzamide | 2 | 412.2 |

TABLE 1-continued

| Ex | Structure | Name | Method | LCMS (ESI) m/z |
|---|---|---|---|---|
| 63 | 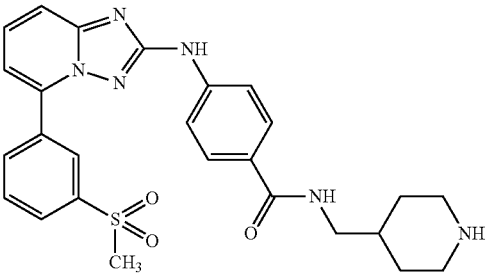 | N-Piperidin-4-ylmethyl-4-[5-(4-trifluoromethyl-phenyl)-[1,2,4]triazolo[1,5-a]pyridin-2-ylamino]-benzamide | 2 | 495.2 |
| 64 | 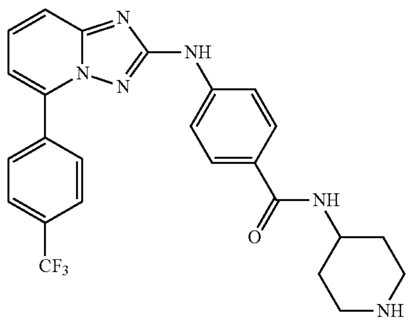 [SMILES: O=C(NC1CCNCC1)c1ccc(Nc2nc3cccc(-c4ccc(C(F)(F)F)cc4)n3n2)cc1] | N-Piperidin-4-yl-4-[5-(4-trifluoromethyl-phenyl)-[1,2,4]triazolo[1,5-a]pyridin-2-ylamino]-benzamide | 2 | 481.1 |
| 65 | 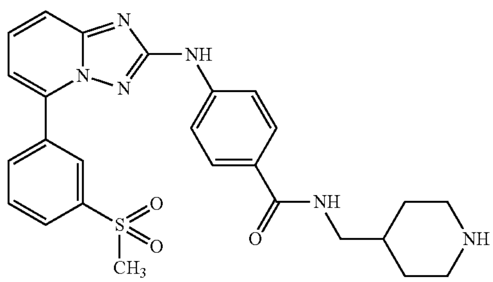 [SMILES: CS(=O)(=O)c1cccc(-c2cccc3nc(Nc4ccc(C(=O)NCC5CCNCC5)cc4)nn23)c1] | 4-[5-(3-Methanesulfonyl-phenyl)-[1,2,4]triazolo[1,5-a]pyridin-2-ylamino]-N-piperidin-4-ylmethyl-benzamide | 2 | 505.1 |
| 66 | 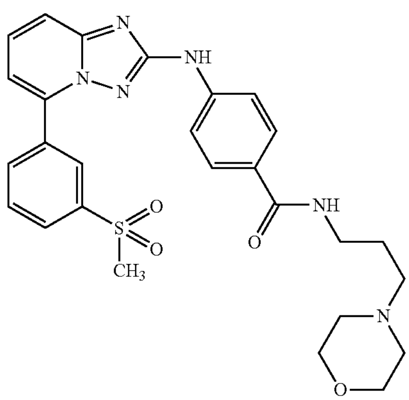 [SMILES: CS(=O)(=O)c1cccc(-c2cccc3nc(Nc4ccc(C(=O)NCCCN5CCOCC5)cc4)nn23)c1] | 4-[5-(3-Methanesulfonyl-phenyl)-[1,2,4]triazolo[1,5-a]pyridin-2-ylamino]-N-(3-morpholin-4-yl-propyl)-benzamide | 2 | 535.2 |
| 67 | 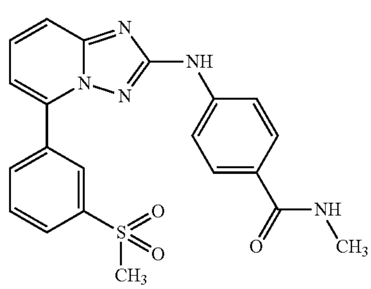 [SMILES: CNC(=O)c1ccc(Nc2nc3cccc(-c4cccc(S(C)(=O)=O)c4)n3n2)cc1] | 4-[5-(3-Methanesulfonyl-phenyl)-[1,2,4]triazolo[1,5-a]pyridin-2-ylamino]-N-methyl-benzamide | 2 | 422.0 |

TABLE 1-continued

| Ex | Structure | Name | Method | LCMS (ESI) m/z |
|---|---|---|---|---|
| 68 | 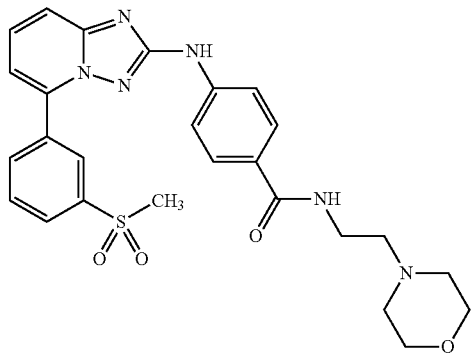 [SMILES: CS(=O)(=O)c1cccc(-c2cccc3nc(Nc4ccc(C(=O)NCCN5CCOCC5)cc4)nn23)c1] | 4-[5-(3-Methanesulfonyl-phenyl)-[1,2,4]triazolo[1,5-a]pyridin-2-ylamino]-N-(2-morpholin-4-yl-ethyl)-benzamide | 2 | 521.1 |
| 69 | 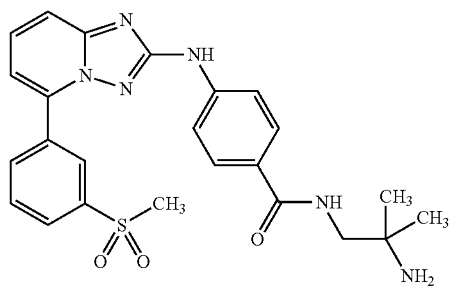 [SMILES: CC(C)(N)CNC(=O)c1ccc(Nc2nc3cccc(-c4cccc(S(C)(=O)=O)c4)n3n2)cc1] | N-(2-Amino-2-methyl-propyl)-4-[5-(3-methanesulfonyl-phenyl)-[1,2,4]triazolo[1,5-a]pyridin-2-ylamino]-benzamide | 2 | 479.0 |
| 70 | 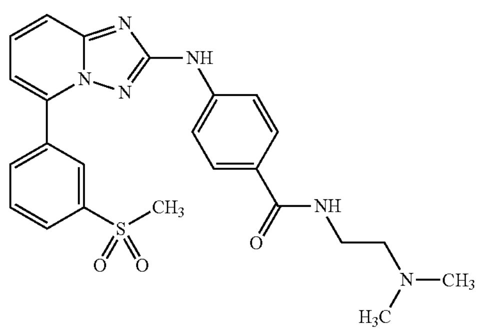 [SMILES: CN(C)CCNC(=O)c1ccc(Nc2nc3cccc(-c4cccc(S(C)(=O)=O)c4)n3n2)cc1] | N-(2-Dimethylamino-ethyl)-4-[5-(3-methanesulfonyl-phenyl)-[1,2,4]triazolo[1,5-a]pyridin-2-ylamino]-benzamide | 2 | 479.1 |
| 71 | 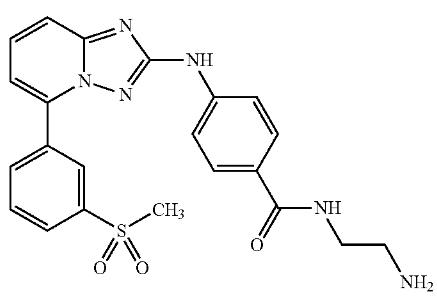 [SMILES: CS(=O)(=O)c1cccc(-c2cccc3nc(Nc4ccc(C(=O)NCCN)cc4)nn23)c1] | N-(2-Amino-ethyl)-4-[5-(3-methanesulfonyl-phenyl)-[1,2,4]triazolo[1,5-a]pyridin-2-ylamino]-benzamide | 2 | 450.9 |
| 72 | 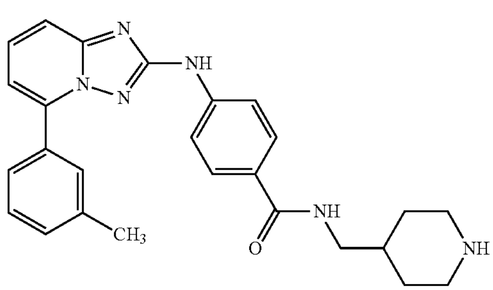 | N-Piperidin-4-ylmethyl-4-(5-m-tolyl-[1,2,4]triazolo[1,5-a]pyridin-2-ylamino)-benzamide | 2 | 441.1 |

TABLE 1-continued

| Ex | Structure | Name | Method | LCMS (ESI) m/z |
|---|---|---|---|---|
| 73 | 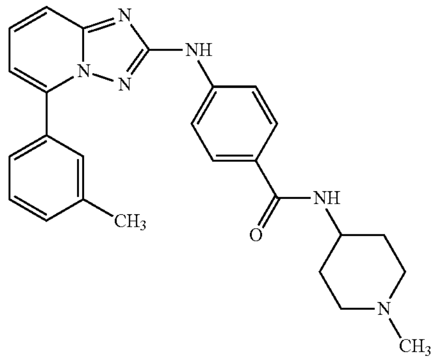 [SMILES: Cc1cccc(-c2cccc3nc(Nc4ccc(C(=O)NC5CCN(C)CC5)cc4)nn23)c1] | N-(1-Methyl-piperidin-4-yl)-4-(5-m-tolyl-[1,2,4]triazolo[1,5-a]pyridin-2-ylamino)-benzamide | 2 | 441.1 |
| 74 | 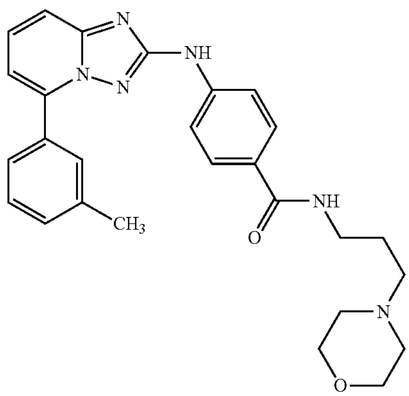 [SMILES: Cc1cccc(-c2cccc3nc(Nc4ccc(C(=O)NCCCN5CCOCC5)cc4)nn23)c1] | N-(3-Morpholin-4-yl-propyl)-4-(5-m-tolyl-[1,2,4]triazolo[1,5-a]pyridin-2-ylamino)-benzamide | 2 | 471.2 |
| 75 | 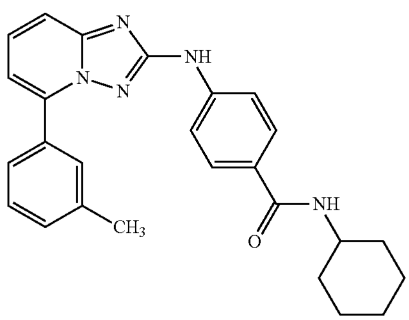 [SMILES: Cc1cccc(-c2cccc3nc(Nc4ccc(C(=O)NC5CCCCC5)cc4)nn23)c1] | N-Cyclohexyl-4-(5-m-tolyl-[1,2,4]triazolo[1,5-a]pyridin-2-ylamino)-benzamide | 2 | 426.1 |
| 76 | 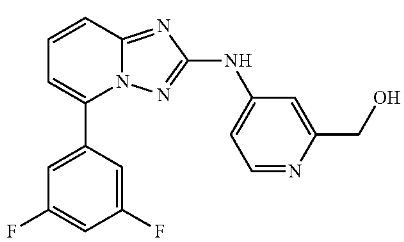 [SMILES: OCc1cc(Nc2nc3cccc(-c4cc(F)cc(F)c4)n3n2)ccn1] | {4-[5-(3,5-Difluoro-phenyl)-[1,2,4]triazolo[1,5-a]pyridin-2-ylamino]-pyridin-2-yl}-methanol | 1 | 354 |
| 78 | 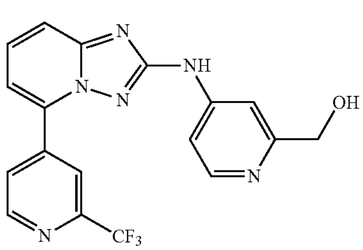 [SMILES: OCc1cc(Nc2nc3cccc(-c4ccnc(C(F)(F)F)c4)n3n2)ccn1] | {4-[5-(2-Trifluoromethyl-pyridin-4-yl)-[1,2,4]triazolo[1,5-a]pyridin-2-ylamino]-pyridin-2-yl}-methanol | 1 | 387 |

TABLE 1-continued

| Ex | Structure | Name | Method | LCMS (ESI) m/z |
|---|---|---|---|---|
| 79 | 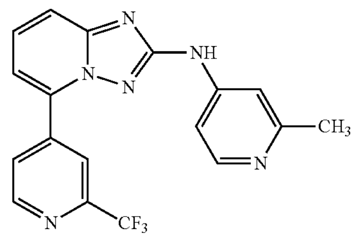 | (2-Methyl-pyridin-4-yl)-[5-(2-trifluoromethyl-pyridin-4-yl)-[1,2,4]triazolo[1,5-a]pyridin-2-yl]-amine | 1 | 371 |
| 80 | 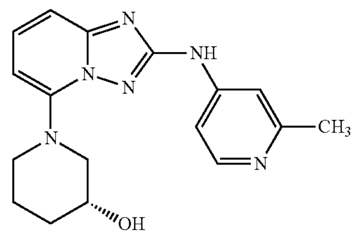 [SMILES: Cc1cc(Nc2nc3cccc(N4CCC[C@@H](O)C4)n3n2)ccn1] | (R)-1-[2-(2-Methyl-pyridin-4-ylamino)-[1,2,4]triazolo[1,5-a]pyridin-5-yl]-piperidin-3-ol | 1 | 325.2 |
| 81 | 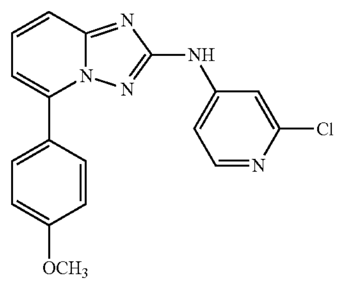 [SMILES: COc1ccc(-c2cccc3nc(Nc4ccnc(Cl)c4)nn23)cc1] | (2-Chloro-pyridin-4-yl)-[5-(4-methoxy-phenyl)-[1,2,4]triazolo[1,5-a]pyridin-2-yl]-amine | 1 | 352 |
| 82 | 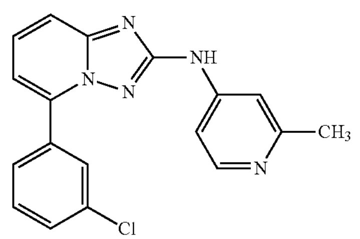 [SMILES: Cc1cc(Nc2nc3cccc(-c4cccc(Cl)c4)n3n2)ccn1] | [5-(3-Chloro-phenyl)-[1,2,4]triazolo[1,5-a]pyridin-2-yl]-(2-methyl-pyridin-4-yl)-amine | 1 | 337 |
| 83 | 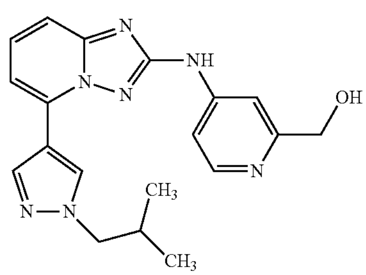 [SMILES: CC(C)Cn1cc(-c2cccc3nc(Nc4ccnc(CO)c4)nn23)cn1] | {4-[5-(1-Isobutyl-1H-pyrazol-4-yl)-[1,2,4]triazolo[1,5-a]pyridin-2-ylamino]-pyridin-2-yl}-methanol | 1 | 364 |
| 84 | 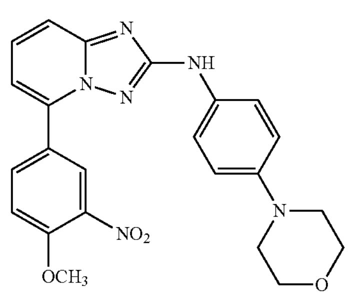 [SMILES: COc1ccc(-c2cccc3nc(Nc4ccc(N5CCOCC5)cc4)nn23)cc1[N+](=O)[O-]] | [5-(4-Methoxy-3-nitro-phenyl)-[1,2,4]triazolo[1,5-a]pyridin-2-yl]-(4-morpholin-4-yl-phenyl)-amine | 1 | 447.2 |

TABLE 1-continued

| Ex | Structure | Name | Method | LCMS (ESI) m/z |
|---|---|---|---|---|
| 85 | 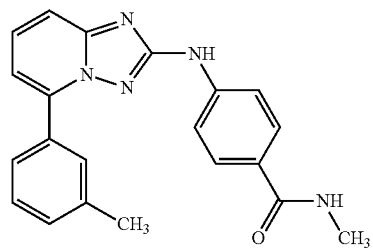 | N-Methyl-4-(5-m-tolyl-[1,2,4]triazolo[1,5-a]pyridin-2-ylamino)-benzamide | 2 | 358.0 |
| 86 | 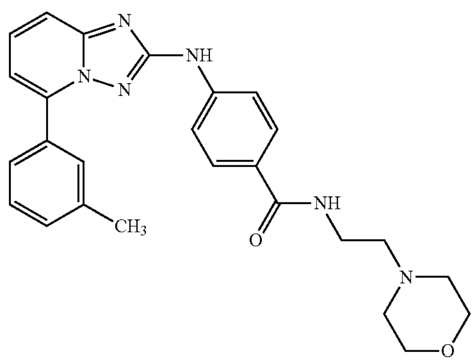 | N-(2-Morpholin-4-yl-ethyl)-4-(5-m-tolyl-[1,2,4]triazolo[1,5-a]pyridin-2-ylamino)-benzamide | 2 | 457.1 |
| 87 | 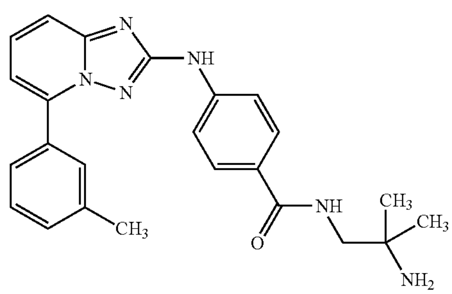 | N-(2-Amino-2-methyl-propyl)-4-(5-m-tolyl-[1,2,4]triazolo[1,5-a]pyridin-2-ylamino)-benzamide | 2 | 415.0 |
| 88 | 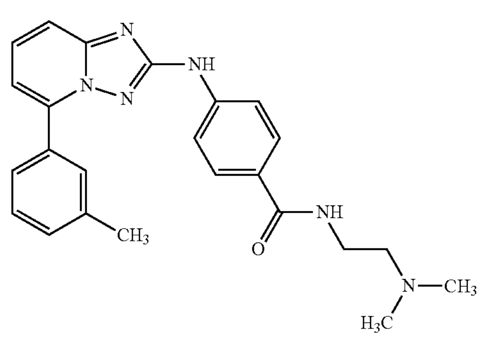 [SMILES: Cc1cccc(-c2cccc3nc(Nc4ccc(C(=O)NCCN(C)C)cc4)nn23)c1] | N-(2-Dimethylamino-ethyl)-4-(5-m-tolyl-[1,2,4]triazolo[1,5-a]pyridin-2-ylamino)-benzamide | 2 | 415.2 |
| 89 | 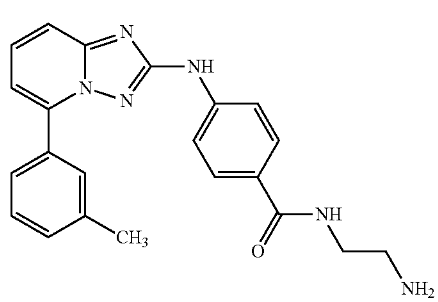 | N-(2-Amino-ethyl)-4-(5-m-tolyl-[1,2,4]triazolo[1,5-a]pyridin-2-ylamino)-benzamide | 2 | 387.1 |

TABLE 1-continued

| Ex | Structure | Name | Method | LCMS (ESI) m/z |
|---|---|---|---|---|
| 90 | 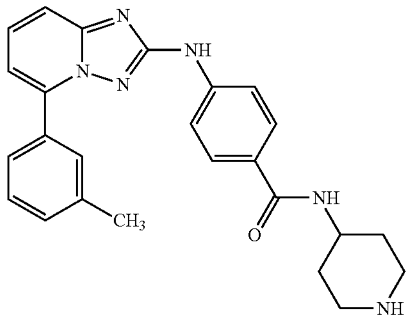 [SMILES: Cc1cccc(-c2cccc3nc(Nc4ccc(C(=O)NC5CCNCC5)cc4)nn23)c1] | N-Piperidin-4-yl-4-(5-m-tolyl-[1,2,4]triazolo[1,5-a]pyridin-2-ylamino)-benzamide | 2 | 427.1 |
| 91 | 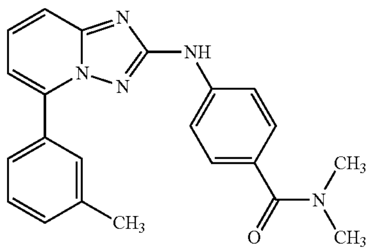 [SMILES: Cc1cccc(-c2cccc3nc(Nc4ccc(C(=O)N(C)C)cc4)nn23)c1] | N,N-Dimethyl-4-(5-m-tolyl-[1,2,4]triazolo[1,5-a]pyridin-2-ylamino)-benzamide | 2 | 372.0 |
| 92 | 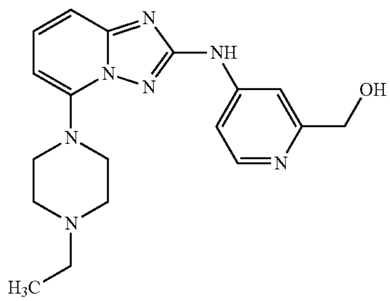 [SMILES: CCN1CCN(c2cccc3nc(Nc4ccnc(CO)c4)nn23)CC1] | {4-[5-(4-Ethyl-piperazin-1-yl)-[1,2,4]triazolo[1,5-a]pyridin-2-ylamino]-pyridin-2-yl}-methanol | 5 | 354.3 |
| 93 | 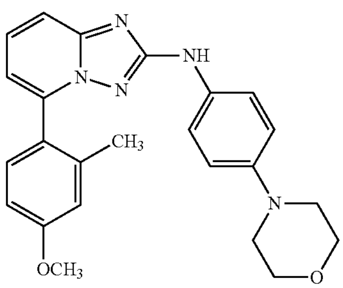 [SMILES: COc1ccc(-c2cccc3nc(Nc4ccc(N5CCOCC5)cc4)nn23)c(C)c1] | [5-(4-Methoxy-2-methyl-phenyl)-[1,2,4]triazolo[1,5-a]pyridin-2-yl]-(4-morpholin-4-yl-phenyl)-amine | 1 | 416.2 |
| 94 | 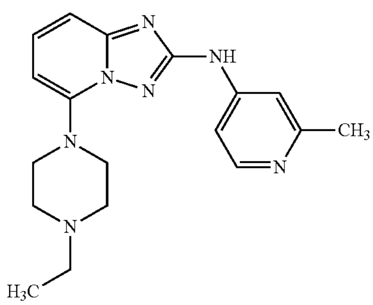 [SMILES: CCN1CCN(c2cccc3nc(Nc4ccnc(C)c4)nn23)CC1] | [5-(4-Ethyl-piperazin-1-yl)-[1,2,4]triazolo[1,5-a]pyridin-2-yl]-(2-methyl-pyridin-4-yl)-amine | 5 | 338.3 |

TABLE 1-continued

| Ex | Structure | Name | Method | LCMS (ESI) m/z |
|---|---|---|---|---|
| 95 | 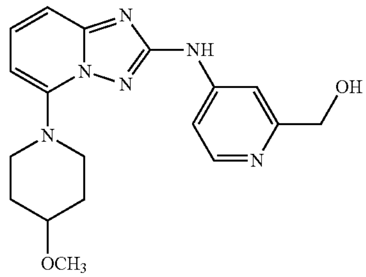 [SMILES: COC1CCN(c2cccc3nc(Nc4ccnc(CO)c4)nn23)CC1] | {4-[5-(4-Methoxy-piperidin-1-yl)-[1,2,4]triazolo[1,5-a]pyridin-2-ylamino]-pyridin-2-yl}-methanol | 5 | 355.2 |
| 96 | 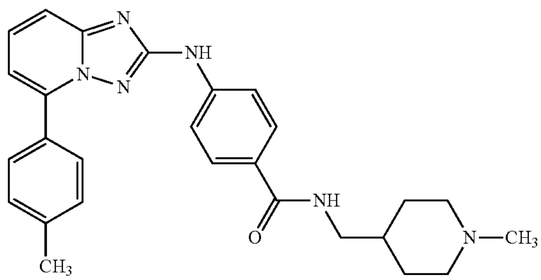 | N-(1-Methyl-piperidin-4-ylmethyl)-4-(5-p-tolyl-[1,2,4]triazolo[1,5-a]pyridin-2-ylamino)-benzamide | 2 | 455.3 |
| 97 | 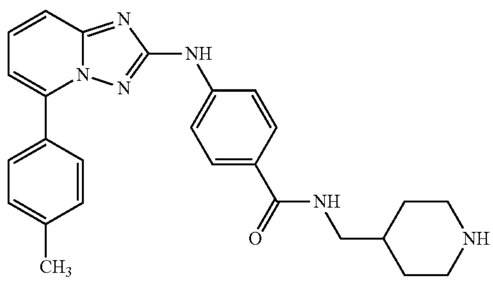 | N-Piperidin-4-ylmethyl-4-(5-p-tolyl-[1,2,4]triazolo[1,5-a]pyridin-2-ylamino)-benzamide | 2 | 441.1 |
| 98 | 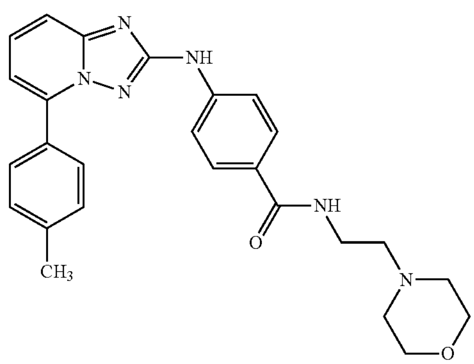 [SMILES: Cc1ccc(-c2cccc3nc(Nc4ccc(C(=O)NCCN5CCOCC5)cc4)nn23)cc1] | N-(2-Morpholin-4-yl-ethyl)-4-(5-p-tolyl-[1,2,4]triazolo[1,5-a]pyridin-2-ylamino)-benzamide | 2 | 457.2 |
| 99 | 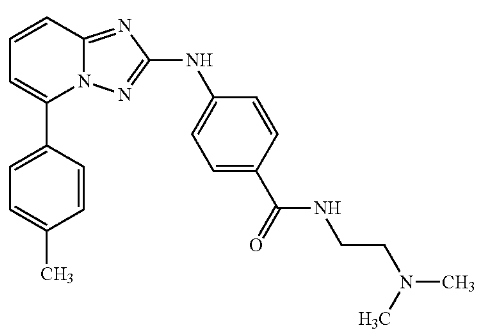 [SMILES: Cc1ccc(-c2cccc3nc(Nc4ccc(C(=O)NCCN(C)C)cc4)nn23)cc1] | N-(2-Dimethylamino-ethyl)-4-(5-p-tolyl-[1,2,4]triazolo[1,5-a]pyridin-2-ylamino)-benzamide | 2 | 415.2 |

TABLE 1-continued

| Ex | Structure | Name | Method | LCMS (ESI) m/z |
|---|---|---|---|---|
| 100 | 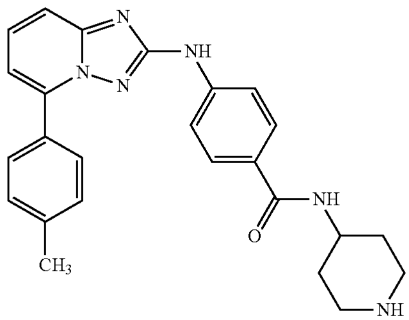 | N-Piperidin-4-yl-4-(5-p-tolyl-[1,2,4]triazolo[1,5-a]pyridin-2-ylamino)-benzamide | 2 | 427.3 |
| 101 | 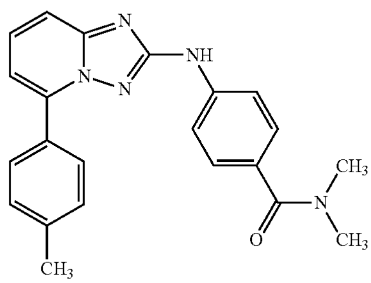 | N,N-Dimethyl-4-(5-p-tolyl-[1,2,4]triazolo[1,5-a]pyridin-2-ylamino)-benzamide | 2 | 372.1 |
| 102 | 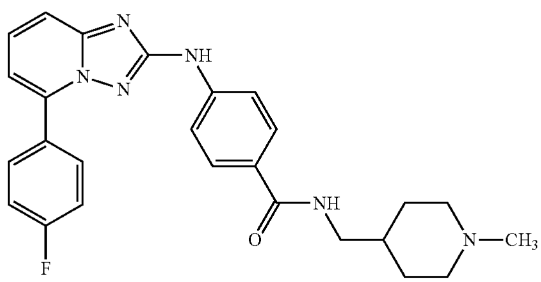 [SMILES: CN1CCC(CNC(=O)c2ccc(Nc3nc4cccc(-c5ccc(F)cc5)n4n3)cc2)CC1] | 4-[5-(4-Fluoro-phenyl)-[1,2,4]triazolo[1,5-a]pyridin-2-ylamino]-N-(1-methyl-piperidin-4-ylmethyl)-benzamide | 2 | 459.2 |
| 103 | 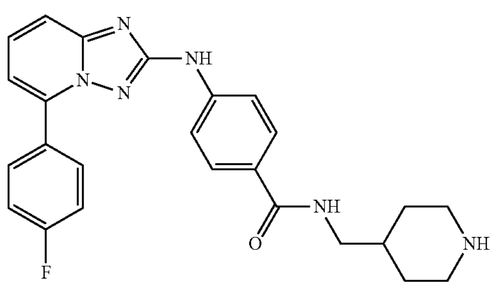 [SMILES: O=C(NCC1CCNCC1)c1ccc(Nc2nc3cccc(-c4ccc(F)cc4)n3n2)cc1] | 4-[5-(4-Fluoro-phenyl)-[1,2,4]triazolo[1,5-a]pyridin-2-ylamino]-N-piperidin-4-ylmethyl-benzamide | 2 | 445.3 |
| 104 | 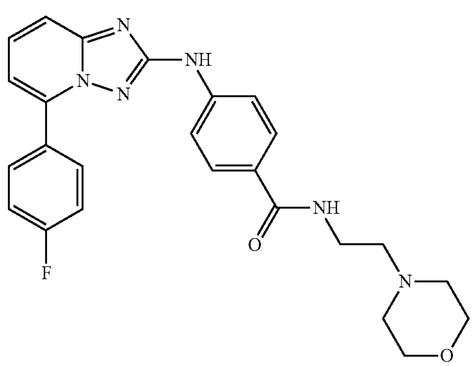 [SMILES: O=C(NCCN1CCOCC1)c1ccc(Nc2nc3cccc(-c4ccc(F)cc4)n3n2)cc1] | 4-[5-(4-Fluoro-phenyl)-[1,2,4]triazolo[1,5-a]pyridin-2-ylamino]-N-(2-morpholin-4-yl-ethyl)-benzamide | 2 | 461.2 |

TABLE 1-continued

| Ex | Structure | Name | Method | LCMS (ESI) m/z |
|---|---|---|---|---|
| 105 | 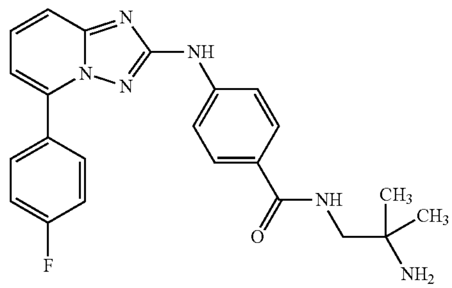 | N-(2-Amino-2-methyl-propyl)-4-[5-(4-fluoro-phenyl)-[1,2,4]triazolo[1,5-a]pyridin-2-ylamino]-benzamide | 2 | 419.2 |
| 106 | 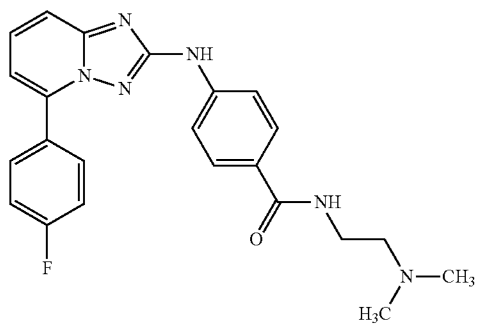 [SMILES: CN(C)CCNC(=O)c1ccc(Nc2nc3cccc(-c4ccc(F)cc4)n3n2)cc1] | N-(2-Dimethylamino-ethyl)-4-[5-(4-fluoro-phenyl)-[1,2,4]triazolo[1,5-a]pyridin-2-ylamino]-benzamide | 2 | 419.2 |
| 107 | 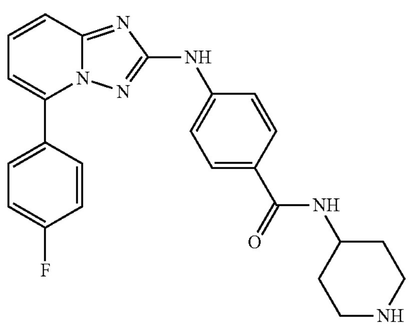 [SMILES: O=C(NC1CCNCC1)c1ccc(Nc2nc3cccc(-c4ccc(F)cc4)n3n2)cc1] | 4-[5-(4-Fluoro-phenyl)-[1,2,4]triazolo[1,5-a]pyridin-2-ylamino]-N-piperidin-4-yl-benzamide | 2 | 431.1 |
| 108 | 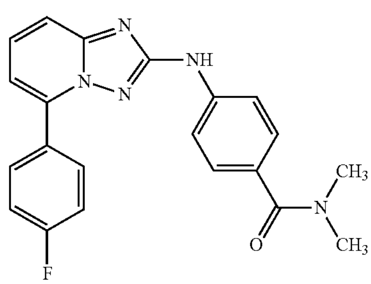 | 4-[5-(4-Fluoro-phenyl)-[1,2,4]triazolo[1,5-a]pyridin-2-ylamino]-N,N-dimethyl-benzamide | 2 | 376.1 |
| 109 | 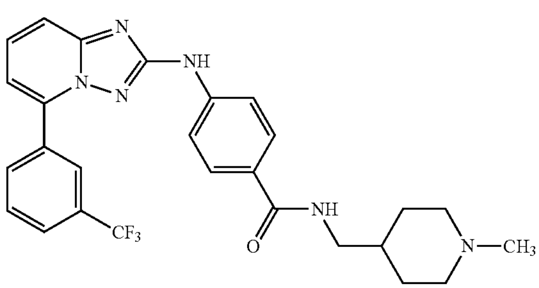 [SMILES: CN1CCC(CNC(=O)c2ccc(Nc3nc4cccc(-c5cccc(Cl)c5)n4n3)cc2)CC1] | N-(1-Methyl-piperidin-4-ylmethyl)-4-[5-(3-trifluoromethyl-phenyl)-[1,2,4]triazolo[1,5-a]pyridin-2-ylamino]-benzamide | 2 | 509.2 |

TABLE 1-continued

| Ex | Name | Method | LCMS (ESI) m/z |
|---|---|---|---|
| 110 | 4-[5-(3-Chloro-phenyl)-[1,2,4]triazolo[1,5-a]pyridin-2-ylamino]-N-(1-methyl-piperidin-4-ylmethyl)-benzamide | 2 | 475.2 |
| 111 | 4-[5-(3-Chloro-phenyl)-[1,2,4]triazolo[1,5-a]pyridin-2-ylamino]-benzamide | 2 | 364.1 |
| 112 | 4-[5-(3-Chloro-phenyl)-[1,2,4]triazolo[1,5-a]pyridin-2-ylamino]-N-methyl-benzamide | 2 | 378.0 |
| 113 | 4-[5-(3-Chloro-phenyl)-[1,2,4]triazolo[1,5-a]pyridin-2-ylamino]-N-(2-dimethylamino-ethyl)-benzamide | 2 | 435.2 |
| 114 | N-(2-Amino-ethyl)-4-[5-(3-chloro-phenyl)-[1,2,4]triazolo[1,5-a]pyridin-2-ylamino]-benzamide | 2 | 407.1 |

TABLE 1-continued

| Ex | Structure | Name | Method | LCMS (ESI) m/z |
|---|---|---|---|---|
| 115 | 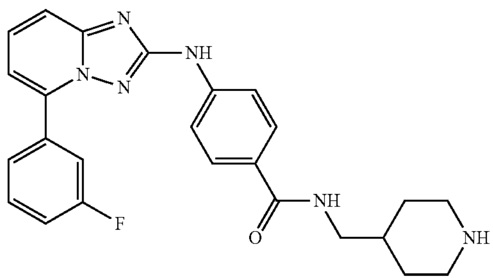 | 4-[5-(3-Fluorophenyl)-[1,2,4]triazolo[1,5-a]pyridin-2-ylamino]-N-piperidin-4-ylmethyl-benzamide | 2 | 445.0 |
| 116 | 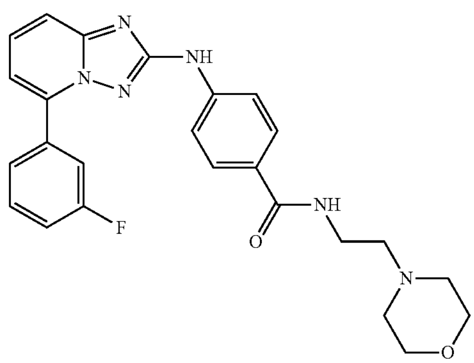 [SMILES: O=C(NCCN1CCOCC1)c1ccc(Nc2nc3cccc(-c4cccc(F)c4)n3n2)cc1] | 4-[5-(3-Fluorophenyl)-[1,2,4]triazolo[1,5-a]pyridin-2-ylamino]-N-(2-morpholin-4-yl-ethyl)-benzamide | 2 | 461.1 |
| 117 | 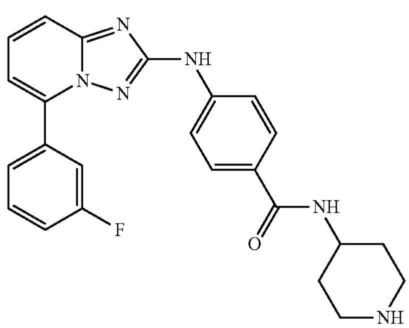 [SMILES: O=C(NC1CCNCC1)c1ccc(Nc2nc3cccc(-c4cccc(F)c4)n3n2)cc1] | 4-[5-(3-Fluorophenyl)-[1,2,4]triazolo[1,5-a]pyridin-2-ylamino]-N-piperidin-4-yl-benzamide | 2 | 431.0 |
| 118 | 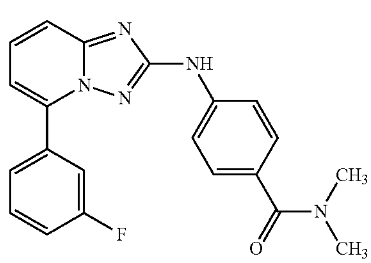 | 4-[5-(3-Fluorophenyl)-[1,2,4]triazolo[1,5-a]pyridin-2-ylamino]-N,N-dimethyl-benzamide | 2 | 376.1 |

TABLE 1-continued

| Ex | Structure | Name | Method | LCMS (ESI) m/z |
|---|---|---|---|---|
| 119 | 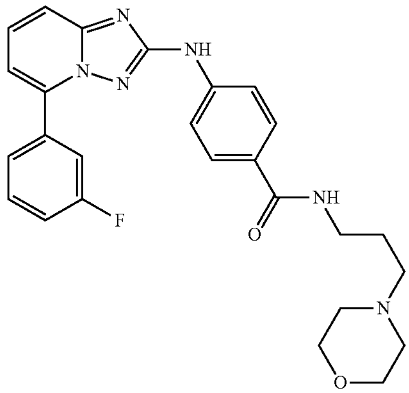 [SMILES: O=C(NCCCN1CCOCC1)c1ccc(Nc2nc3cccc(-c4cccc(F)c4)n3n2)cc1] | 4-[5-(3-Fluoro-phenyl)-[1,2,4]triazolo[1,5-a]pyridin-2-ylamino]-N-(3-morpholin-4-yl-propyl)-benzamide | 2 | 475.1 |
| 120 | 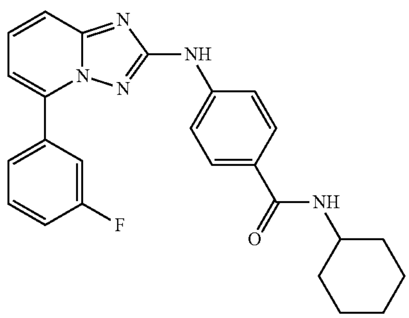 | N-Cyclohexyl-4-[5-(3-fluoro-phenyl)-[1,2,4]triazolo[1,5-a]pyridin-2-ylamino]-benzamide | 2 | 430.2 |
| 121 | 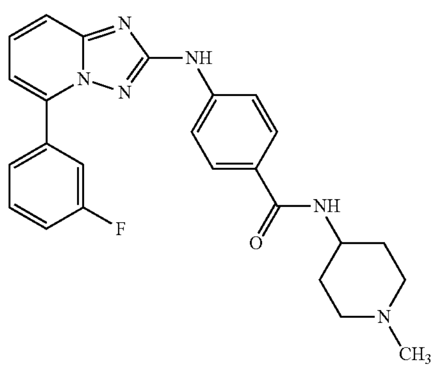 [SMILES: CN1CCC(NC(=O)c2ccc(Nc3nc4cccc(-c5cccc(F)c5)n4n3)cc2)CC1] | 4-[5-(3-Fluoro-phenyl)-[1,2,4]triazolo[1,5-a]pyridin-2-ylamino]-N-(1-methyl-piperidin-4-yl)-benzamide | 2 | 445.0 |
| 122 | 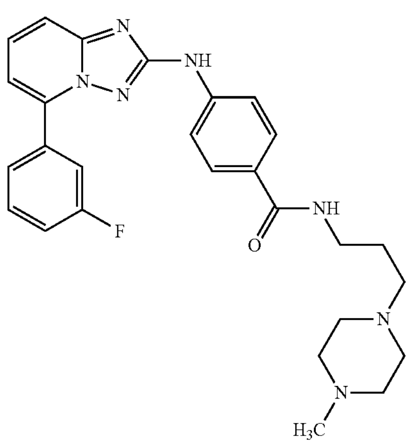 [SMILES: CN1CCN(CCCNC(=O)c2ccc(Nc3nc4cccc(-c5cccc(F)c5)n4n3)cc2)CC1] | 4-[5-(3-Fluoro-phenyl)-[1,2,4]triazolo[1,5-a]pyridin-2-ylamino]-N-[3-(4-methyl-piperazin-1-yl)-propyl]-benzamide | 2 | 488.1 |

TABLE 1-continued

| Ex | Structure | Name | Method | LCMS (ESI) m/z |
|---|---|---|---|---|
| 123 | 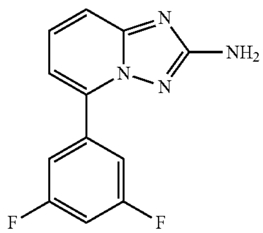 [SMILES: Nc1nc2cccc(-c3cc(F)cc(F)c3)n2n1] | 5-(3,5-Difluoro-phenyl)-[1,2,4]triazolo[1,5-a]pyridin-2-ylamine | 1 | 247 |
| 124 | 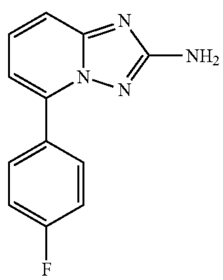 [SMILES: Nc1nc2cccc(-c3ccc(F)cc3)n2n1] | 5-(4-Fluoro-phenyl)-[1,2,4]triazolo[1,5-a]pyridin-2-ylamine | 1 | 229 |
| 125 | 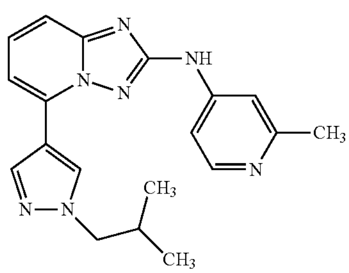 [SMILES: Cc1cc(Nc2nc3cccc(-c4cnn(CC(C)C)c4)n3n2)ccn1] | [5-(1-Isobutyl-1H-pyrazol-4-yl)-[1,2,4]triazolo[1,5-a]pyridin-2-yl]-(2-methyl-pyridin-4-yl)-amine | 1 | 348 |
| 126 | 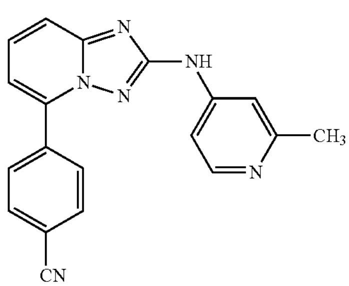 [SMILES: Cc1cc(Nc2nc3cccc(-c4ccc(C#N)cc4)n3n2)ccn1] | 4-[2-(2-Methyl-pyridin-4-ylamino)-[1,2,4]triazolo[1,5-a]pyridin-5-yl]-benzonitrile | 1 | 327 |
| 127 | 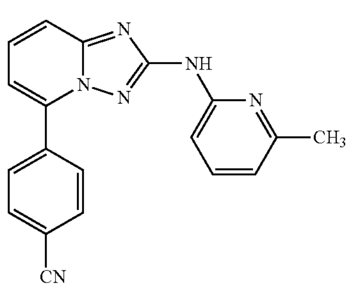 [SMILES: Cc1cccc(Nc2nc3cccc(-c4ccc(C#N)cc4)n3n2)n1] | 4-[2-(6-Methyl-pyridin-2-ylamino)-[1,2,4]triazolo[1,5-a]pyridin-5-yl]-benzonitrile | 1 | 327 |

TABLE 1-continued

| Ex | Structure | Name | Method | LCMS (ESI) m/z |
|---|---|---|---|---|
| 128 | 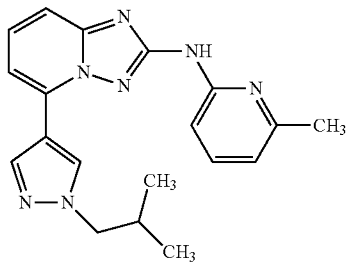 [SMILES: Cc1cccc(Nc2nc3cccc(-c4cnn(CC(C)C)c4)n3n2)n1] | [5-(1-Isobutyl-1H-pyrazol-4-yl)-[1,2,4]triazolo[1,5-a]pyridin-2-yl]-(6-methyl-pyridin-2-yl)-amine | 1 | 348 |
| 129 | 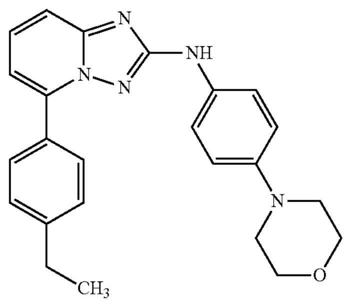 [SMILES: CCc1ccc(-c2cccc3nc(Nc4ccc(N5CCOCC5)cc4)nn23)cc1] | [5-(4-Ethyl-phenyl)-[1,2,4]triazolo[1,5-a]pyridin-2-yl]-(4-morpholin-4-yl-phenyl)-amine | 1 | 400.3 |
| 130 | 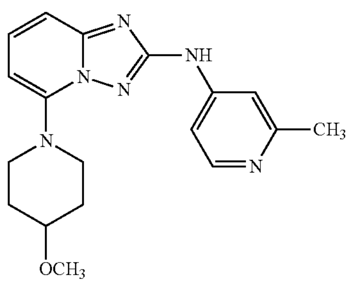 [SMILES: COC1CCN(c2cccc3nc(Nc4ccnc(C)c4)nn23)CC1] | [5-(4-Methoxy-piperidin-1-yl)-[1,2,4]triazolo[1,5-a]pyridin-2-yl]-(2-methyl-pyridin-4-yl)-amine | 5 | 339.3 |
| 131 | 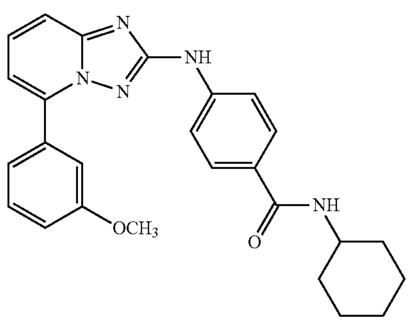 [SMILES: COc1cccc(-c2cccc3nc(Nc4ccc(C(=O)NC5CCCCC5)cc4)nn23)c1] | N-Cyclohexyl-4-[5-(3-methoxy-phenyl)-[1,2,4]triazolo[1,5-a]pyridin-2-ylamino]-benzamide | 2 | 442.2 |
| 132 | 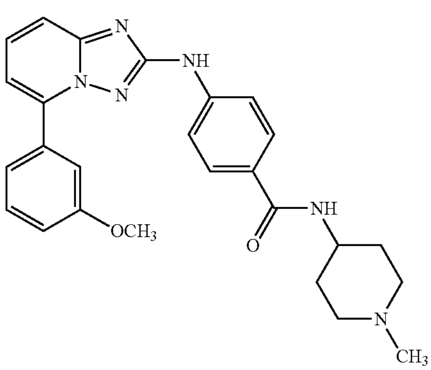 [SMILES: COc1cccc(-c2cccc3nc(Nc4ccc(C(=O)NC5CCN(C)CC5)cc4)nn23)c1] | 4-[5-(3-Methoxy-phenyl)-[1,2,4]triazolo[1,5-a]pyridin-2-ylamino]-N-(1-methyl-piperidin-4-yl)-benzamide | 2 | 457.1 |

TABLE 1-continued

| Ex | Structure | Name | Method | LCMS (ESI) m/z |
|---|---|---|---|---|
| 133 | 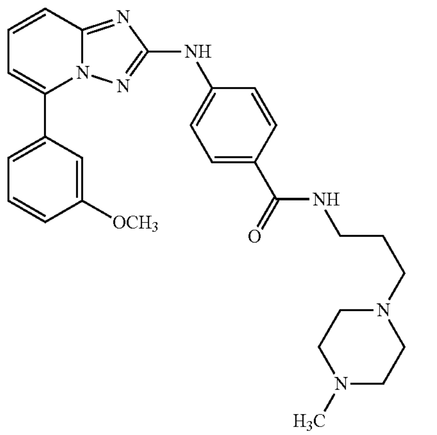 | 4-[5-(3-Methoxy-phenyl)-[1,2,4]triazolo[1,5-a]pyridin-2-ylamino]-N-[3-(4-methyl-piperazin-1-yl)-propyl]-benzamide | 2 | 500.2 |
| 134 | 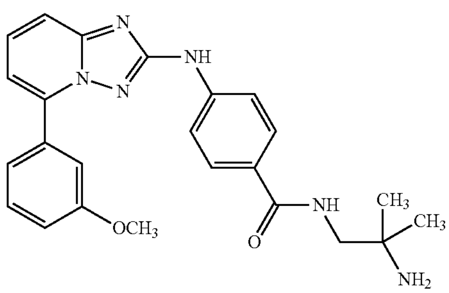 | N-(2-Amino-2-methyl-propyl)-4-[5-(3-methoxy-phenyl)-[1,2,4]triazolo[1,5-a]pyridin-2-ylamino]-benzamide | 2 | 431.1 |
| 135 | 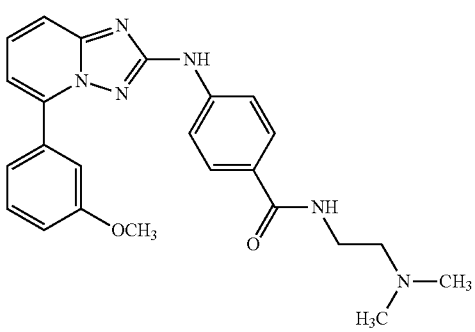 | N-(2-Dimethylamino-ethyl)-4-[5-(3-methoxy-phenyl)-[1,2,4]triazolo[1,5-a]pyridin-2-ylamino]-benzamide | 2 | 431.1 |
| 136 | 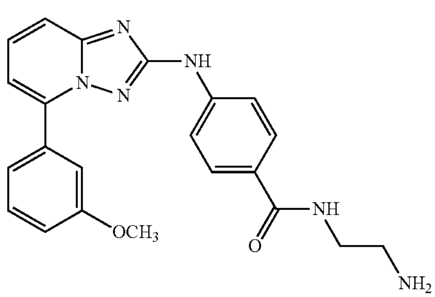 | N-(2-Amino-ethyl)-4-[5-(3-methoxy-phenyl)-[1,2,4]triazolo[1,5-a]pyridin-2-ylamino]-benzamide | 2 | 403.0 |

TABLE 1-continued

| Ex | Structure | Name | Method | LCMS (ESI) m/z |
|---|---|---|---|---|
| 137 | 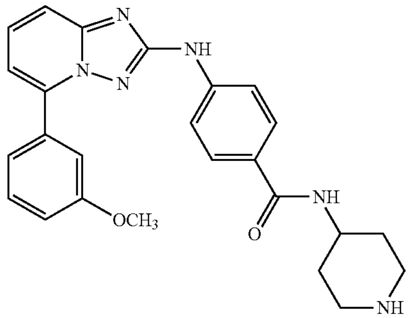 [SMILES: COc1cccc(-c2cccc3nc(Nc4ccc(C(=O)NC5CCNCC5)cc4)nn23)c1] | 4-[5-(3-Methoxy-phenyl)-[1,2,4]triazolo[1,5-a]pyridin-2-ylamino]-N-piperidin-4-yl-benzamide | 2 | 443.1 |
| 138 | 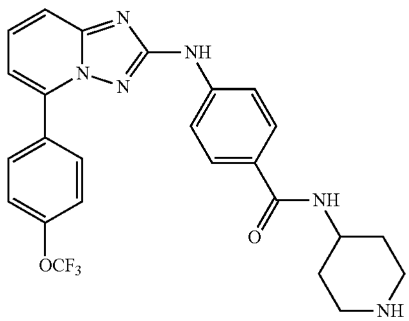 | N-Piperidin-4-yl-4-[5-(4-trifluoromethoxy-phenyl)-[1,2,4]triazolo[1,5-a]pyridin-2-ylamino]-benzamide | 2 | 497.1 |
| 139 | 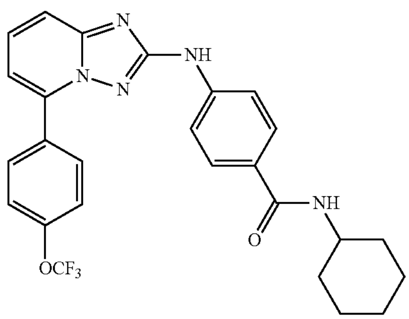 [SMILES: O=C(NC1CCCCC1)c1ccc(Nc2nc3cccc(-c4ccc(OC(F)(F)F)cc4)n3n2)cc1] | N-Cyclohexyl-4-[5-(4-trifluoromethoxy-phenyl)-[1,2,4]triazolo[1,5-a]pyridin-2-ylamino]-benzamide | 2 | 496.2 |
| 140 | 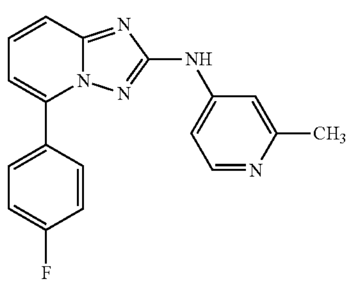 [SMILES: Cc1cc(Nc2nc3cccc(-c4ccc(F)cc4)n3n2)ccn1] | [5-(4-Fluoro-phenyl)-[1,2,4]triazolo[1,5-a]pyridin-2-yl]-(2-methyl-pyridin-4-yl)-amine | 1 | 320 |
| 141 | 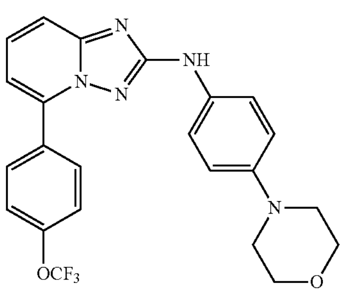 [SMILES: FC(F)(F)Oc1ccc(-c2cccc3nc(Nc4ccc(N5CCOCC5)cc4)nn23)cc1] | (4-Morpholin-4-yl-phenyl)-[5-(4-trifluoromethoxy-phenyl)-[1,2,4]triazolo[1,5-a]pyridin-2-yl]-amine | 1 | 456.3 |

US 8,889,673 B2

TABLE 1-continued

| Ex | Structure | Name | Method | LCMS (ESI) m/z |
|---|---|---|---|---|
| 142 | 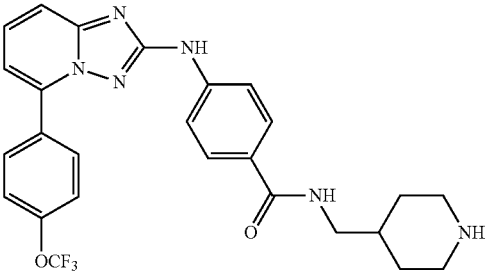 [SMILES: O=C(NCC1CCNCC1)c1ccc(Nc2nc3cccc(-c4ccc(OC(F)(F)F)cc4)n3n2)cc1] | N-Piperidin-4-ylmethyl-4-[5-(4-trifluoromethoxy-phenyl)-[1,2,4]triazolo[1,5-a]pyridin-2-ylamino]-benzamide | 2 | 511.1 |
| 143 | 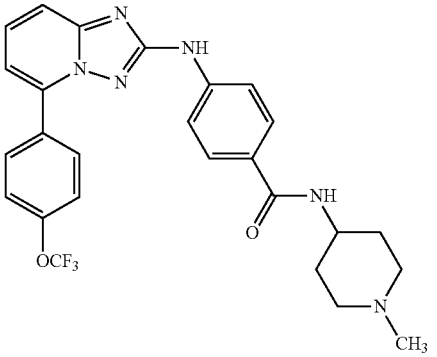 [SMILES: CN1CCC(NC(=O)c2ccc(Nc3nc4cccc(-c5ccc(OC(F)(F)F)cc5)n4n3)cc2)CC1] | N-(1-Methyl-piperidin-4-yl)-4-[5-(4-trifluoromethoxy-phenyl)-[1,2,4]triazolo[1,5-a]pyridin-2-ylamino]-benzamide | 2 | 511.1 |
| 144 | 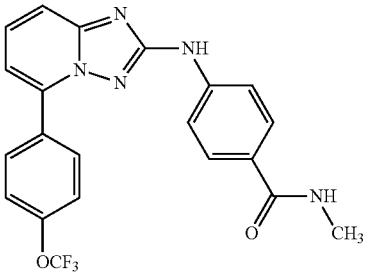 [SMILES: CNC(=O)c1ccc(Nc2nc3cccc(-c4ccc(OC(F)(F)F)cc4)n3n2)cc1] | N-Methyl-4-[5-(4-trifluoromethoxy-phenyl)-[1,2,4]triazolo[1,5-a]pyridin-2-ylamino]-benzamide | 2 | 428.2 |
| 145 | 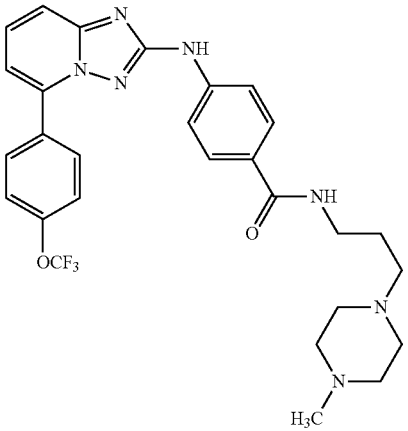 [SMILES: CN1CCN(CCCNC(=O)c2ccc(Nc3nc4cccc(-c5ccc(OC(F)(F)F)cc5)n4n3)cc2)CC1] | N-[3-(4-Methyl-piperazin-1-yl)-propyl]-4-[5-(4-trifluoromethoxy-phenyl)-[1,2,4]triazolo[1,5-a]pyridin-2-ylamino]-benzamide | 2 | 554.2 |

TABLE 1-continued

| Ex | Structure | Name | Method | LCMS (ESI) m/z |
|---|---|---|---|---|
| 146 | 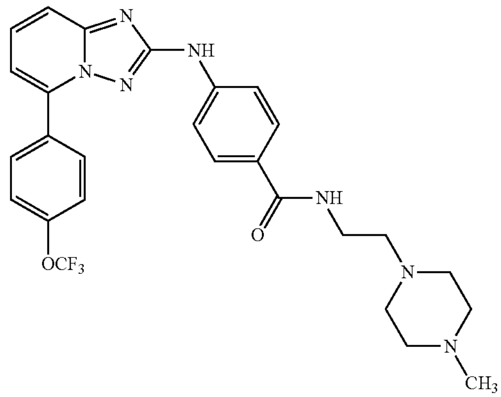 [SMILES: CN1CCN(CCNC(=O)c2ccc(Nc3nc4cccc(-c5ccc(OC(F)(F)F)cc5)n4n3)cc2)CC1] | N-[2-(4-Methyl-piperazin-1-yl)-ethyl]-4-[5-(4-trifluoromethoxy-phenyl)-[1,2,4]triazolo[1,5-a]pyridin-2-ylamino]-benzamide | 2 | 540.1 |
| 147 | 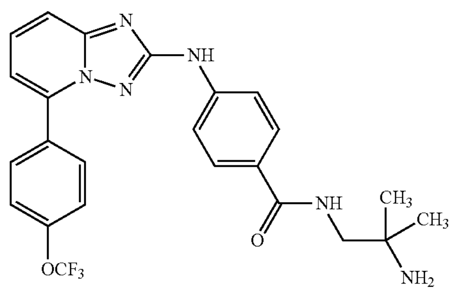 | N-(2-Amino-2-methyl-propyl)-4-[5-(4-trifluoromethoxy-phenyl)-[1,2,4]triazolo[1,5-a]pyridin-2-ylamino]-benzamide | 2 | 485.1 |
| 148 | 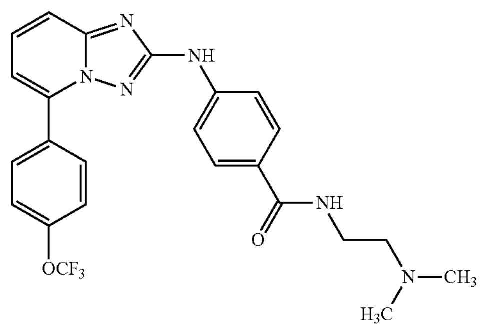 | N-(2-Dimethylamino-ethyl)-4-[5-(4-trifluoromethoxy-phenyl)-[1,2,4]triazolo[1,5-a]pyridin-2-ylamino]-benzamide | 2 | 485.2 |
| 149 | 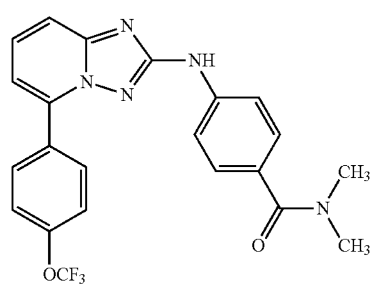 [SMILES: CN(C)C(=O)c1ccc(Nc2nc3cccc(-c4ccc(OC(F)(F)F)cc4)n3n2)cc1] | N,N-Dimethyl-4-[5-(4-trifluoromethoxy-phenyl)-[1,2,4]triazolo[1,5-a]pyridin-2-ylamino]-benzamide | 2 | 442.2 |
| 150 | 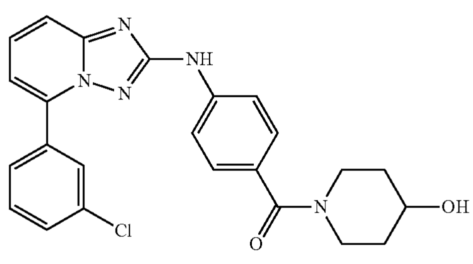 [SMILES: O=C(c1ccc(Nc2nc3cccc(-c4cccc(Cl)c4)n3n2)cc1)N1CCC(O)CC1] | {4-[5-(3-Chloro-phenyl)-[1,2,4]triazolo[1,5-a]pyridin-2-ylamino]-phenyl}-(4-hydroxy-piperidin-1-yl)-methanone | 2 | 448.1 |

TABLE 1-continued
| Ex | Structure | Name | Method | LCMS (ESI) m/z |
|---|---|---|---|---|
| 151 | 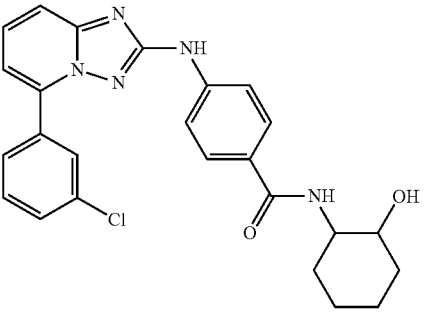 [SMILES: O=C(NC1CCCCC1O)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-hydroxy-cyclohexyl)-benzamide | 2 | 462.2 |
| 152 | 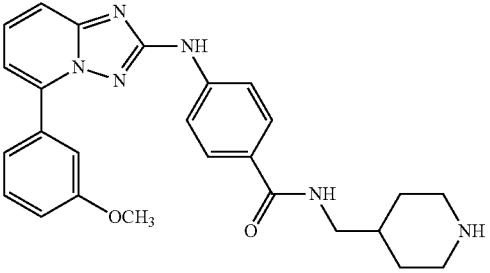 [SMILES: COc1cccc(-c2cccc3nc(Nc4ccc(C(=O)NCC5CCNCC5)cc4)nn23)c1] | 4-[5-(3-Methoxy-phenyl)-[1,2,4]triazolo[1,5-a]pyridin-2-ylamino]-N-piperidin-4-ylmethyl-benzamide | 2 | 457.1 |
| 153 | 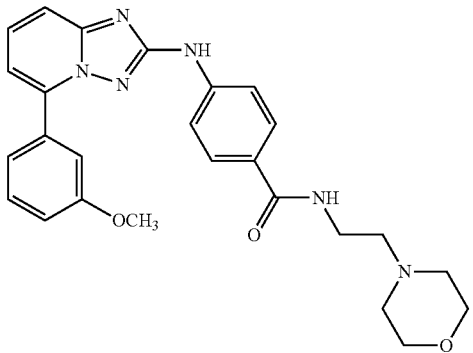 | 4-[5-(3-Methoxy-phenyl)-[1,2,4]triazolo[1,5-a]pyridin-2-ylamino]-N-(2-morpholin-4-yl-ethyl)-benzamide | 2 | 473.1 |
| 154 | 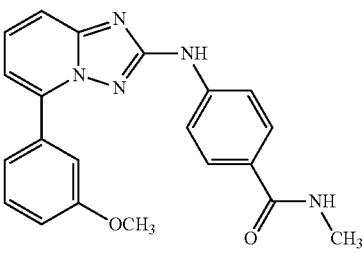 | 4-[5-(3-Methoxy-phenyl)-[1,2,4]triazolo[1,5-a]pyridin-2-ylamino]-N-methyl-benzamide | 2 | 374.2 |

TABLE 1-continued

| Ex | Structure | Name | Method | LCMS (ESI) m/z |
|---|---|---|---|---|
| 155 | 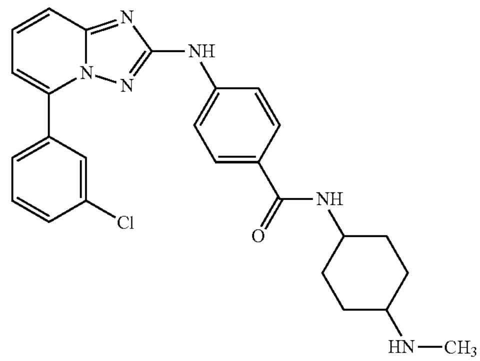 [SMILES: CNC1CCC(NC(=O)c2ccc(Nc3nc4cccc(-c5cccc(Cl)c5)n4n3)cc2)CC1] | 4-[5-(3-Chloro-phenyl)-[1,2,4]triazolo[1,5-a]pyridin-2-ylamino]-N-(4-methylamino-cyclohexyl)-benzamide | 2 | 475.3 |
| 156 | 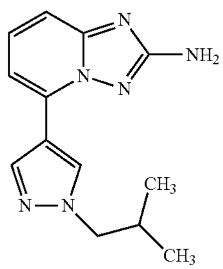 [SMILES: CC(C)Cn1cc(-c2cccc3nc(N)nn23)cn1] | 5-(1-Isobutyl-1H-pyrazol-4-yl)-[1,2,4]triazolo[1,5-a]pyridin-2-ylamine | 1 | 257 |
| 157 | 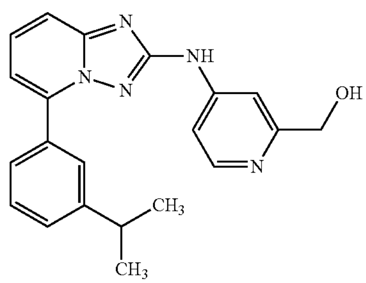 [SMILES: CC(C)c1cccc(-c2cccc3nc(Nc4ccnc(CO)c4)nn23)c1] | {4-[5-(3-Isopropyl-phenyl)-[1,2,4]triazolo[1,5-a]pyridin-2-ylamino]-pyridin-2-yl}-methanol | 1 | 360.2 |
| 158 | 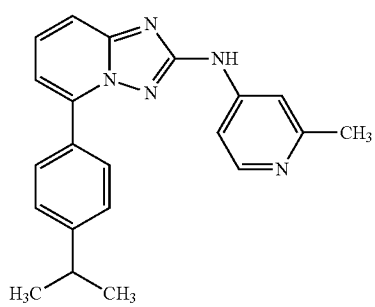 [SMILES: Cc1cc(Nc2nc3cccc(-c4ccc(C(C)C)cc4)n3n2)ccn1] | [5-(4-Isopropyl-phenyl)-[1,2,4]triazolo[1,5-a]pyridin-2-yl]-(2-methyl-pyridin-4-yl)-amine | 1 | 344.2 |
| 159 | 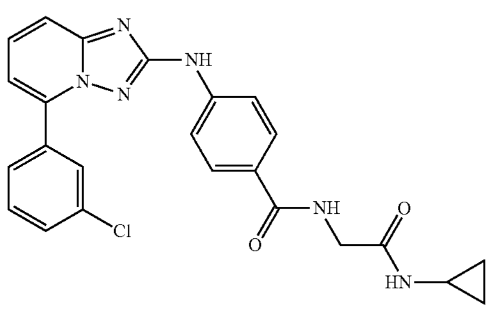 [SMILES: O=C(CNC(=O)c1ccc(Nc2nc3cccc(-c4cccc(Cl)c4)n3n2)cc1)NC1CC1] | 4-[5-(3-Chloro-phenyl)-[1,2,4]triazolo[1,5-a]pyridin-2-ylamino]-N-cyclopropyl-carbamoylmethyl-benzamide | 1 | 461.2 |

TABLE 1-continued

| Ex | Structure | Name | Method | LCMS (ESI) m/z |
|---|---|---|---|---|
| 160 | 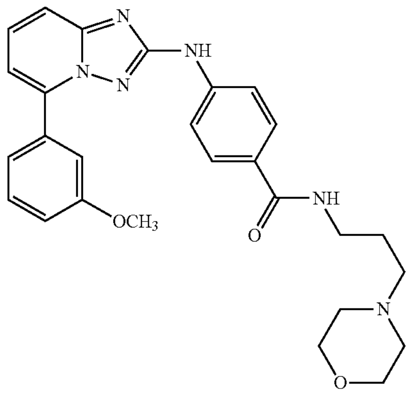 [SMILES: COc1cccc(-c2cccc3nc(Nc4ccc(C(=O)NCCCN5CCOCC5)cc4)nn23)c1] | 4-[5-(3-Methoxy-phenyl)-[1,2,4]triazolo[1,5-a]pyridin-2-ylamino]-N-(3-morpholin-4-yl-propyl)-benzamide | 2 | 487.2 |
| 161 | 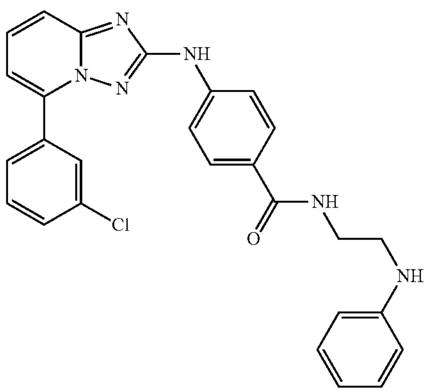 [SMILES: O=C(NCCNc1ccccc1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-phenylamino-ethyl)-benzamide | 2 | 483.2 |
| 162 | 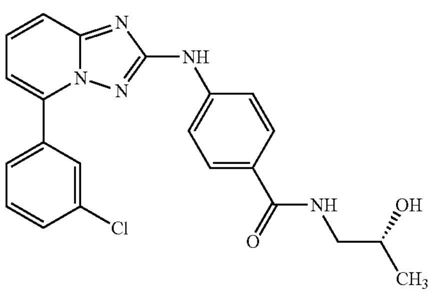 | 4-[5-(3-Chloro-phenyl)-[1,2,4]triazolo[1,5-a]pyridin-2-ylamino]-N-((R)-2-hydroxy-propyl)-benzamide | 2 | 422.2 |
| 163 | 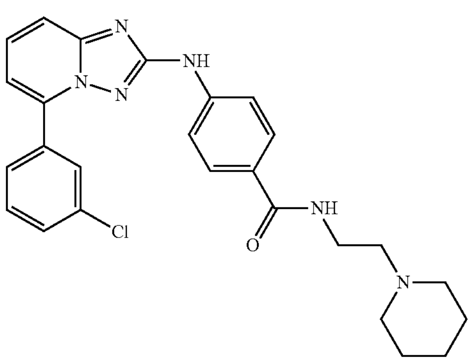 [SMILES: O=C(NCCN1CCCCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-piperidin-1-yl-ethyl)-benzamide | 2 | 475.2 |

TABLE 1-continued

| Ex | Structure | Name | Method | LCMS (ESI) m/z |
|---|---|---|---|---|
| 164 | 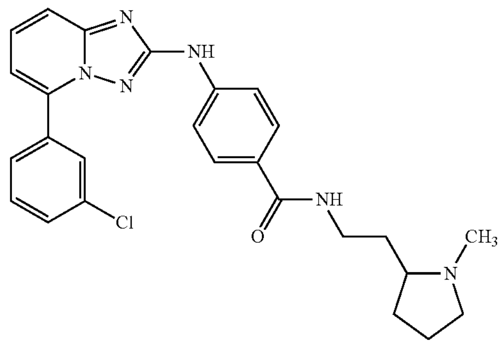 [SMILES: CN1CCCC1CCNC(=O)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-[2-(1-methyl-pyrrolidin-2-yl)-ethyl]-benzamide | 2 | 475.2 |
| 165 | 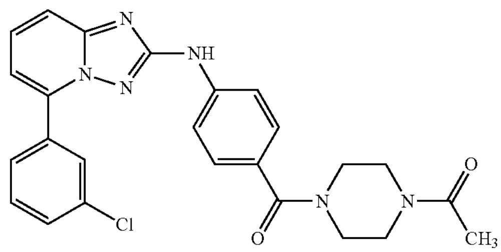 [SMILES: CC(=O)N1CCN(C(=O)c2ccc(Nc3nc4cccc(-c5cccc(Cl)c5)n4n3)cc2)CC1] | 1-(4-{4-[5-(3-Chloro-phenyl)-[1,2,4]triazolo[1,5-a]pyridin-2-ylamino]-benzoyl}-piperazin-1-yl)-ethanone | 2 | 475.2 |
| 166 | 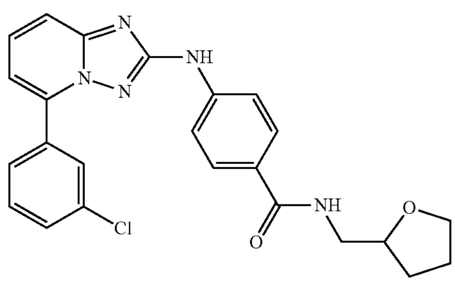 [SMILES: O=C(NCC1CCCO1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(tetrahydro-furan-2-ylmethyl)-benzamide | 2 | 448.2 |
| 167 | 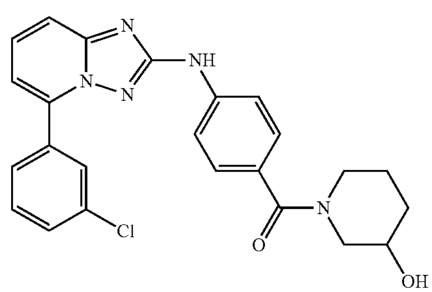 [SMILES: O=C(c1ccc(Nc2nc3cccc(-c4cccc(Cl)c4)n3n2)cc1)N1CCCC(O)C1] | {4-[5-(3-Chloro-phenyl)-[1,2,4]triazolo[1,5-a]pyridin-2-ylamino]-phenyl}-(3-hydroxy-piperidin-1-yl)-methanone | 2 | 448.1 |
| 168 | 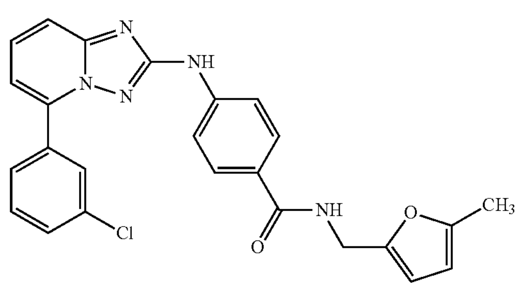 [SMILES: Cc1ccc(CNC(=O)c2ccc(Nc3nc4cccc(-c5cccc(Cl)c5)n4n3)cc2)o1] | 4-[5-(3-Chloro-phenyl)-[1,2,4]triazolo[1,5-a]pyridin-2-ylamino]-N-(5-methyl-furan-2-ylmethyl)-benzamide | 2 | 458.2 |

| Ex | Structure | Name | Method | LCMS (ESI) m/z |
|---|---|---|---|---|
| 169 | 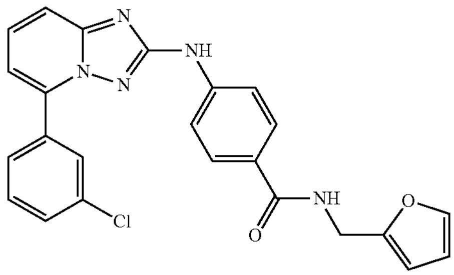 [SMILES: O=C(NCc1ccco1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-furan-2-ylmethyl-benzamide | 2 | 444.1 |
| 170 | 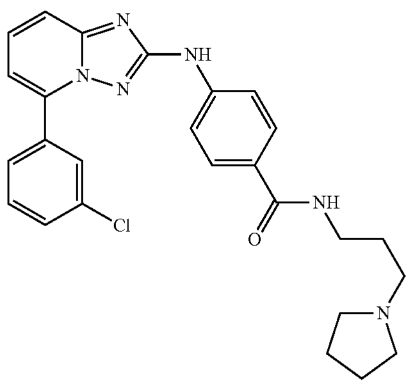 [SMILES: O=C(NCCCN1CCCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(3-pyrrolidin-1-yl-propyl)-benzamide | 2 | 475.2 |
| 171 | 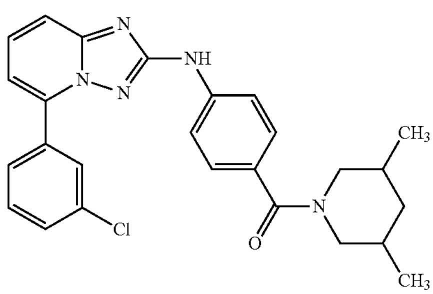 [SMILES: CC1CC(C)CN(C(=O)c2ccc(Nc3nc4cccc(-c5cccc(Cl)c5)n4n3)cc2)C1] | {4-[5-(3-Chloro-phenyl)-[1,2,4]triazolo[1,5-a]pyridin-2-ylamino]-phenyl}-(3,5-dimethyl-piperidin-1-yl)-methanone | 2 | 460.2 |
| 172 | 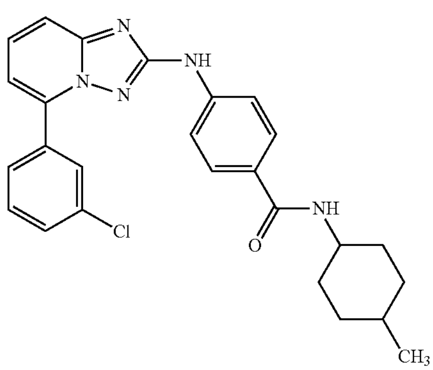 | 4-[5-(3-Chloro-phenyl)-[1,2,4]triazolo[1,5-a]pyridin-2-ylamino]-N-(4-methyl-cyclohexyl)-benzamide | 2 | 460.2 |

TABLE 1-continued

| Ex | Structure | Name | Method | LCMS (ESI) m/z |
|---|---|---|---|---|
| 173 | 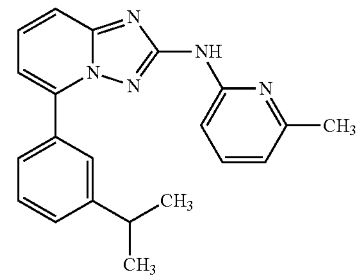 [SMILES: Cc1cccc(Nc2nc3cccc(-c4cccc(C(C)C)c4)n3n2)n1] | [5-(3-Isopropyl-phenyl)-[1,2,4]triazolo[1,5-a]pyridin-2-yl]-(6-methyl-pyridin-2-yl)-amine | 1 | 344.2 |
| 174 | 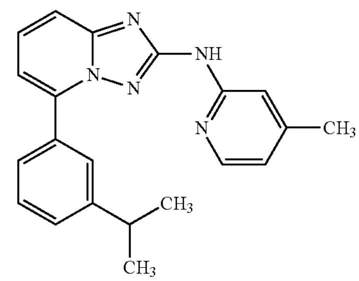 [SMILES: Cc1ccnc(Nc2nc3cccc(-c4cccc(C(C)C)c4)n3n2)c1] | [5-(3-Isopropyl-phenyl)-[1,2,4]triazolo[1,5-a]pyridin-2-yl]-(4-methyl-pyridin-2-yl)-amine | 1 | 344.2 |
| 175 | 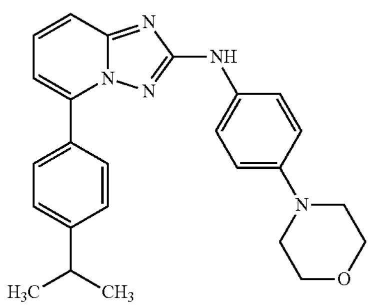 [SMILES: CC(C)c1ccc(-c2cccc3nc(Nc4ccc(N5CCOCC5)cc4)nn23)cc1] | [5-(4-Isopropyl-phenyl)-[1,2,4]triazolo[1,5-a]pyridin-2-yl]-(4-morpholin-4-yl-phenyl)-amine | 1 | 415.3 |
| 176 | 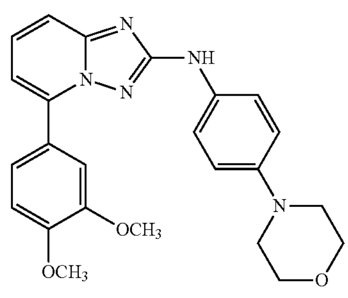 [SMILES: COc1ccc(-c2cccc3nc(Nc4ccc(N5CCOCC5)cc4)nn23)cc1OC] | [5-(3,4-Dimethoxy-phenyl)-[1,2,4]triazolo[1,5-a]pyridin-2-yl]-(4-morpholin-4-yl-phenyl)-amine | 1 | 432.3 |
| 177 | 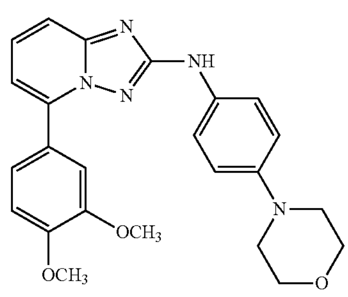 [SMILES: COc1ccc(-c2cccc3nc(Nc4ccc(N5CCOCC5)cc4)nn23)cc1OC] | [5-(4-Methoxy-3-methyl-phenyl)-[1,2,4]triazolo[1,5-a]pyridin-2-yl]-(4-morpholin-4-yl-phenyl)-amine | 1 | 416.3 |

TABLE 1-continued

| Ex | Structure | Name | Method | LCMS (ESI) m/z |
|---|---|---|---|---|
| 178 | 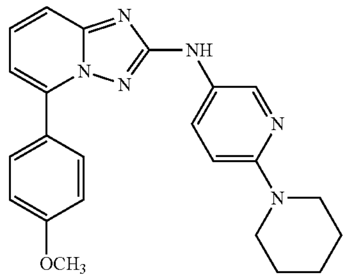 [SMILES: COc1ccc(-c2cccc3nc(Nc4ccc(N5CCCCC5)nc4)nn23)cc1] | [5-(4-Methoxy-phenyl)-[1,2,4]triazolo[1,5-a]pyridin-2-yl]-(3,4,5,6-tetrahydro-2H-[1,2']bipyridinyl-5'-yl)-amine | 1 | 401 |
| 179 | 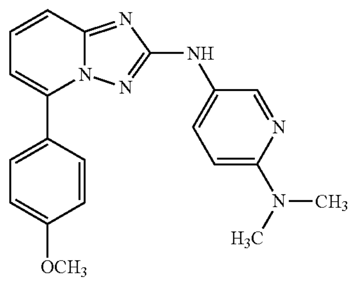 [SMILES: COc1ccc(-c2cccc3nc(Nc4ccc(N(C)C)nc4)nn23)cc1] | N%5&-[5-(4-Methoxy-phenyl)-[1,2,4]triazolo[1,5-a]pyridin-2-yl]-N%2&,N%2&-dimethyl-pyridine-2,5-diamine | 1 | 361 |
| 180 | 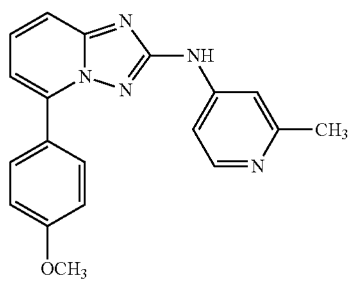 [SMILES: COc1ccc(-c2cccc3nc(Nc4ccnc(C)c4)nn23)cc1] | [5-(4-Methoxy-phenyl)-[1,2,4]triazolo[1,5-a]pyridin-2-yl]-(2-methyl-pyridin-4-yl)-amine | 1 | 332 |
| 181 | 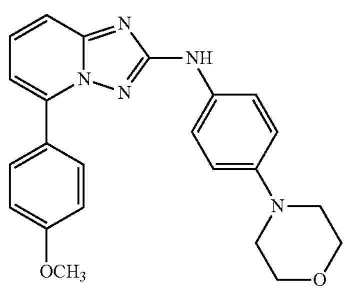 | [5-(4-Methoxy-phenyl)-[1,2,4]triazolo[1,5-a]pyridin-2-yl]-(4-morpholin-4-yl-phenyl)-amine | 1 | 402 |
| 182 | 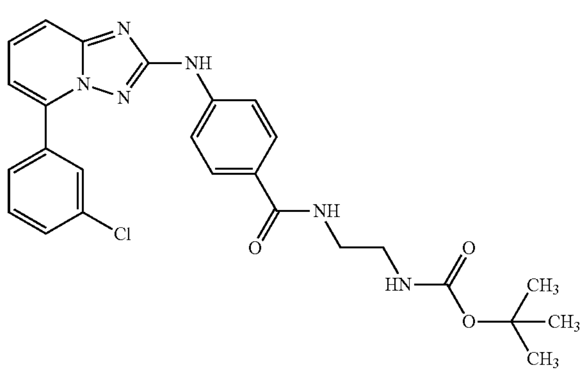 [SMILES: CC(C)(C)OC(=O)NCCNC(=O)c1ccc(Nc2nc3cccc(-c4cccc(Cl)c4)n3n2)cc1] | (2-{4-[5-(3-Chloro-phenyl)-[1,2,4]triazolo[1,5-a]pyridin-2-ylamino]-benzoylamino}-ethyl)-carbamic acid tert-butyl ester | 2 | 507.2 |

TABLE 1-continued

| Ex | Structure | Name | Method | LCMS (ESI) m/z |
|---|---|---|---|---|
| 183 | 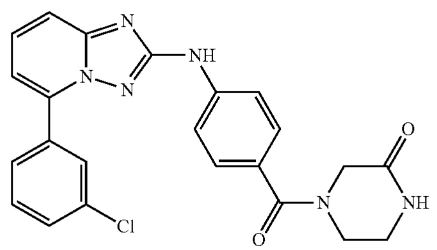 [SMILES: O=C1CN(C(=O)c2ccc(Nc3nc4cccc(-c5cccc(Cl)c5)n4n3)cc2)CCN1] | 4-{4-[5-(3-Chloro-phenyl)-[1,2,4]triazolo[1,5-a]pyridin-2-ylamino]-benzoyl}-piperazin-2-one | 2 | 447.1 |
| 184 | 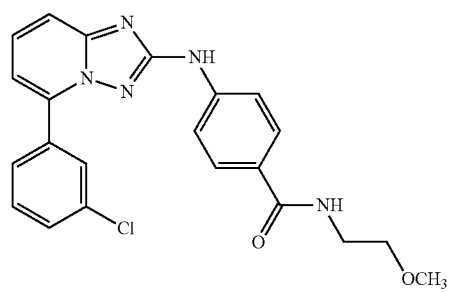 [SMILES: COCCNC(=O)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-methoxy-ethyl)-benzamide | 2 | 422.1 |
| 185 | 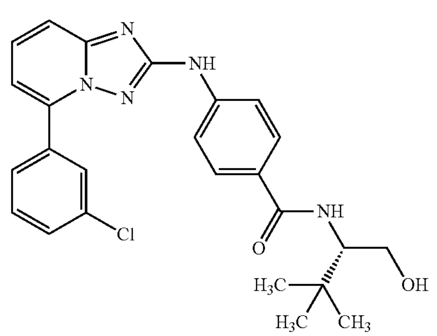 [SMILES: CC(C)(C)[C@@H](CO)NC(=O)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-((S)-1-hydroxymethyl-2,2-dimethyl-propyl)-benzamide | 2 | 464.2 |
| 186 | 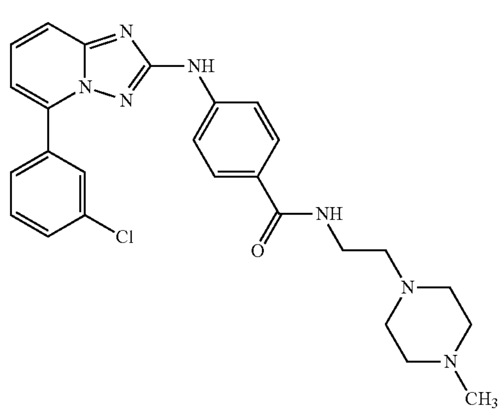 [SMILES: CN1CCN(CCNC(=O)c2ccc(Nc3nc4cccc(-c5cccc(Cl)c5)n4n3)cc2)CC1] | 4-[5-(3-Chloro-phenyl)-[1,2,4]triazolo[1,5-a]pyridin-2-ylamino]-N-[2-(4-methyl-piperazin-1-yl)-ethyl]-benzamide | 2 | 490.1 |

TABLE 1-continued

| Ex | Structure | Name | Method | LCMS (ESI) m/z |
|---|---|---|---|---|
| 187 | 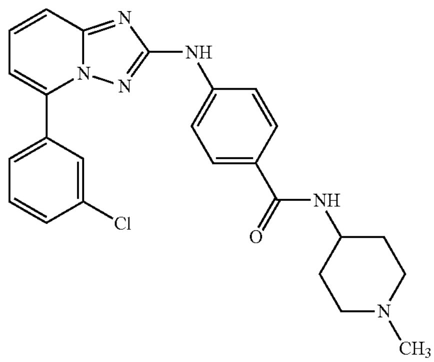 | 4-[5-(3-Chloro-phenyl)-[t,2,4]triazolo[1,5-a]pyridin-2-ylamino]-N-(1-methyl-piperidin-4-yl)-benzamide | 2 | 461.2 |
| 188 | 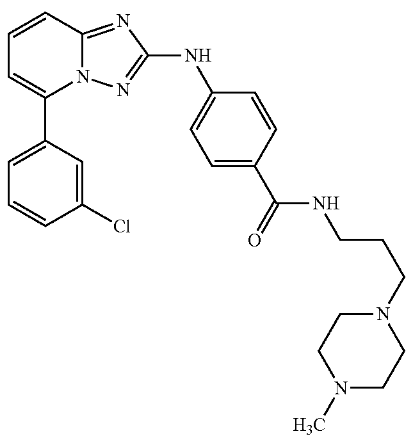 | 4-[5-(3-Chloro-phenyl)-[1,2,4]triazolo[1,5-a]pyridin-2-ylamino]-N-[3-(4-methyl-piperazin-1-yl)-propyl]-benzamide | 2 | 504.1 |
| 189 | 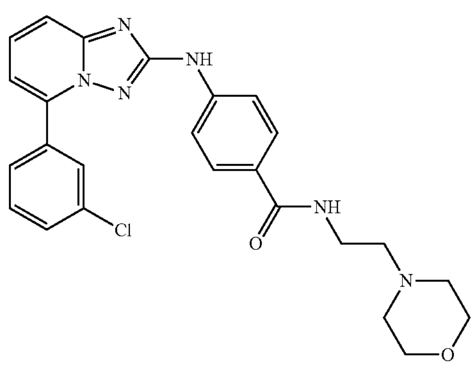 [SMILES: O=C(NCCN1CCOCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-morpholin-4-yl-ethyl)-benzamide | 2 | 477.0 |
| 190 | 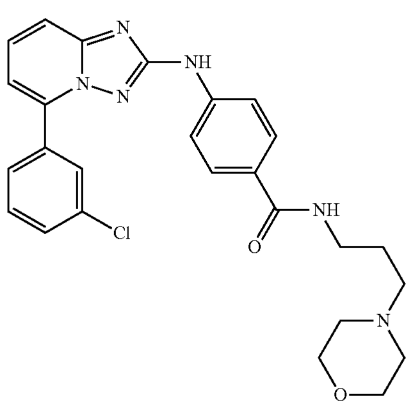 | 4-[5-(3-Chloro-phenyl)-[1,2,4]triazolo[1,5-a]pyridin-2-ylamino]-N-(3-morpholin-4-yl-propyl)-benzamide | 2 | 491.0 |

TABLE 1-continued

| Ex | Structure | Name | Method | LCMS (ESI) m/z |
|---|---|---|---|---|
| 191 | 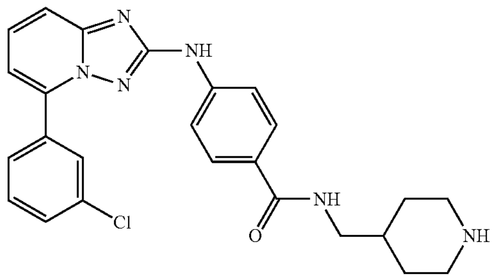 [SMILES: O=C(NCC1CCNCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-piperidin-4-ylmethyl-benzamide | 2 | 461.0 |
| 192 | 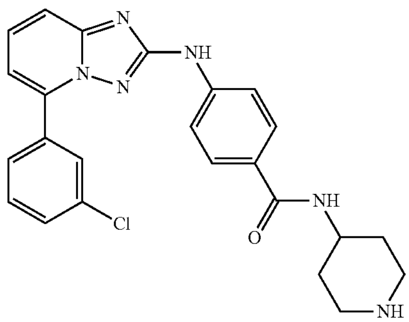 [SMILES: O=C(NC1CCNCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-piperidin-4-yl-benzamide | 2 | 447.0 |
| 193 | 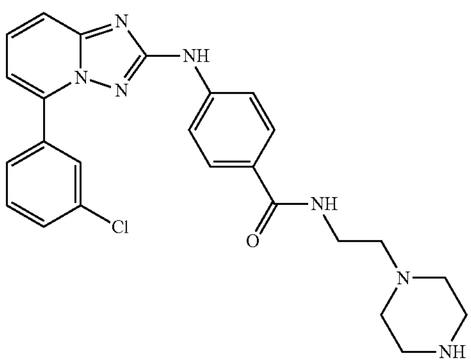 [SMILES: O=C(NCCN1CCNCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-(2-piperazin-1-yl-ethyl)-benzamide | 2 | 476.2 |
| 194 | 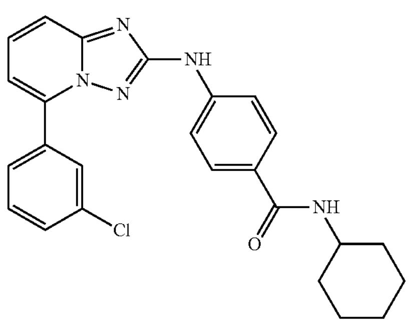 [SMILES: O=C(NC1CCCCC1)c1ccc(Nc2nc3cccc(-c4cccc(Cl)c4)n3n2)cc1] | 4-[5-(3-Chloro-phenyl)-[1,2,4]triazolo[1,5-a]pyridin-2-ylamino]-N-cyclohexyl-benzamide | 2 | 445.9 |
| 195 | 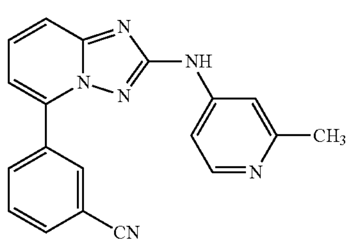 [SMILES: Cc1cc(Nc2nc3cccc(-c4cccc(C#N)c4)n3n2)ccn1] | 3-[2-(2-Methyl-pyridin-4-ylamino)-[1,2,4]triazolo[1,5-a]pyridin-5-yl]-benzonitrile | 1 | 327.2 |

TABLE 1-continued

| Ex | Name | Method | LCMS (ESI) m/z |
|---|---|---|---|
| 196 | (2-Methyl-pyridin-4-yl)-[5-(3-trifluoromethyl-phenyl)-[1,2,4]triazolo[1,5-a]pyridin-2-yl]-amine | 1 | 370.2 |
| 197 | 4-[5-(3-Trifluoromethyl-phenyl)-[1,2,4]triazolo[1,5-a]pyridin-2-ylamino]-benzamide | 2 | 398.0 |
| 198 | N-Cyclohexyl-4-[5-(3-trifluoromethyl-phenyl)-[1,2,4]triazolo[1,5-a]pyridin-2-ylamino]-benzamide | 2 | 480.2 |
| 199 | N-Cyclopropylmethyl-4-[5-(3-trifluoromethyl-phenyl)-[1,2,4]triazolo[1,5-a]pyridin-2-ylamino]-benzamide | 2 | 452.2 |
| 200 | N-Piperidin-4-ylmethyl-4-[5-(3-trifluoromethyl-phenyl)-[1,2,4]triazolo[1,5-a]pyridin-2-ylamino]-benzamide | 2 | 495.2 |

TABLE 1-continued

| Ex | Structure | Name | Method | LCMS (ESI) m/z |
|---|---|---|---|---|
| 201 | 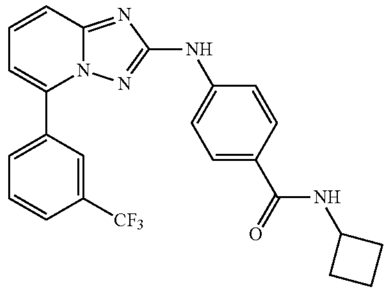 [SMILES: O=C(NC1CCC1)c1ccc(Nc2nc3cccc(-c4cccc(C(F)(F)F)c4)n3n2)cc1] | N-Cyclobutyl-4-[5-(3-trifluoromethyl-phenyl)-[1,2,4]triazolot[1,5-a]pyridin-2-ylamino]-benzamide | 2 | 452.1 |
| 202 | 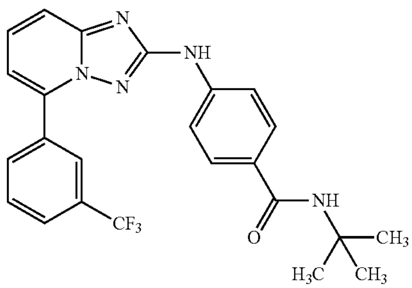 [SMILES: CC(C)(C)NC(=O)c1ccc(Nc2nc3cccc(-c4cccc(C(F)(F)F)c4)n3n2)cc1] | N-tert-Butyl-4-[5-(3-trifluoromethyl-phenyl)-[1,2,4]triazolo[1,5-a]pyridin-2-ylamino]-benzamide | 2 | 454.1 |
| 203 | 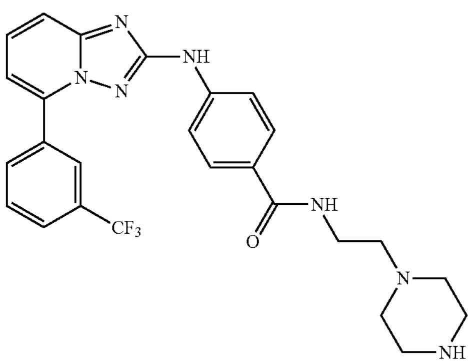 | N-(2-Piperazin-1-yl-ethyl)-4-[5-(3-trifluoromethyl-phenyl)-[1,2,4]triazolo[1,5-a]pyridin-2-ylamino]-benzamide | 2 | 510.2 |
| 204 | 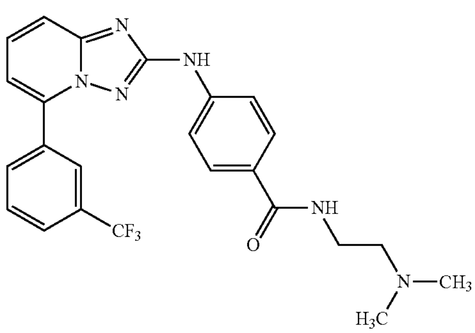 | N-(2-Dimethylamino-ethyl)-4-[5-(3-trifluoromethyl-phenyl)-[1,2,4]triazolo[1,5-a]pyridin-2-ylamino]-benzamide | 2 | 469.2 |
| 205 | 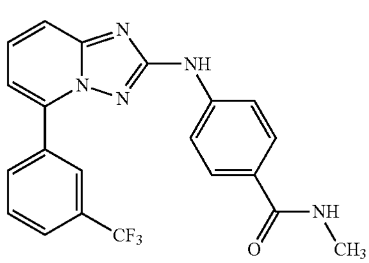 [SMILES: CNC(=O)c1ccc(Nc2nc3cccc(-c4cccc(C(F)(F)F)c4)n3n2)cc1] | N-Methyl-4-[5-(3-trifluoromethyl-phenyl)-[1,2,4]triazolo[1,5-a]pyridin-2-ylamino]-benzamide | 2 | 412.1 |

TABLE 1-continued

| Ex | Structure | Name | Method | LCMS (ESI) m/z |
|---|---|---|---|---|
| 206 | 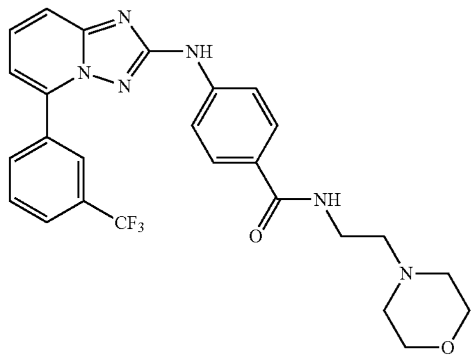 | N-(2-Morpholin-4-yl-ethyl)-4-[5-(3-trifluoromethyl-phenyl)-[1,2,4]triazolo[1,5-a]pyridin-2-ylamino]-benzamide | 2 | 511.0 |
| 207 | 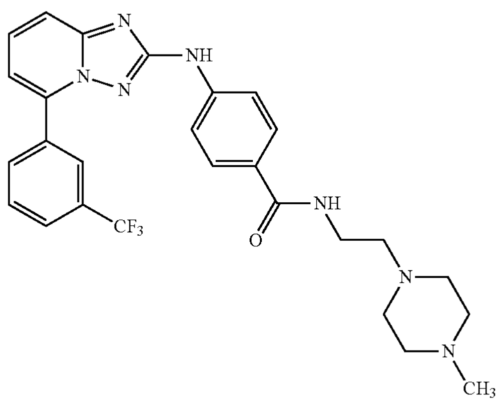 | N-[2-(4-Methyl-piperazin-1-yl)-ethyl]-4-[5-(3-trifluoromethyl-phenyl)-[1,2,4]triazolo[1,5-a]pyridin-2-ylamino]-benzamide | 2 | 524.1 |
| 208 | 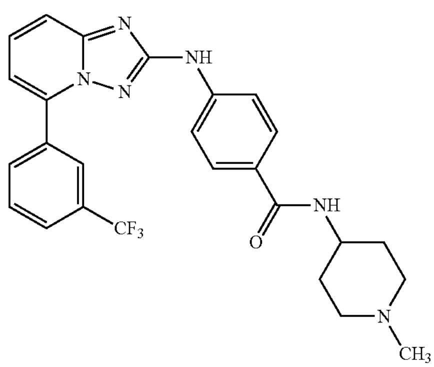 [SMILES: CN1CCC(NC(=O)c2ccc(Nc3nc4cccc(-c5cccc(C(F)(F)F)c5)n4n3)cc2)CC1] | N-(1-Methyl-piperidin-4-yl)-4-[5-(3-trifluoromethyl-phenyl)-[1,2,4]triazolo[1,5-a]pyridin-2-ylamino]-benzamide | 2 | 495.1 |
| 209 | 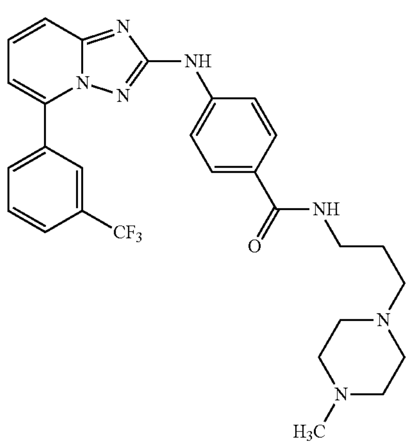 [SMILES: CN1CCN(CCCNC(=O)c2ccc(Nc3nc4cccc(-c5cccc(C(F)(F)F)c5)n4n3)cc2)CC1] | N-[3-(4-Methyl-piperazin-1-yl)-propyl]-4-[5-(3-trifluoromethyl-phenyl)-[1,2,4]triazolo[1,5-a]pyridin-2-ylamino]-benzamide | 2 | 538.3 |

TABLE 1-continued

| Ex | Structure | Name | Method | LCMS (ESI) m/z |
|---|---|---|---|---|
| 210 | 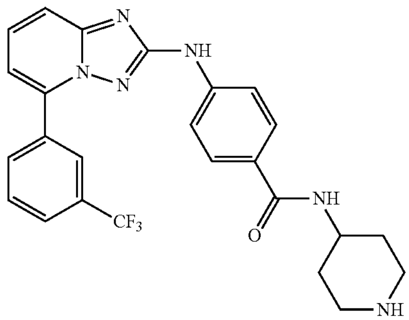 [SMILES: O=C(NC1CCNCC1)c1ccc(Nc2nc3cccc(-c4cccc(C(F)(F)F)c4)n3n2)cc1] | N-Piperidin-4-yl-4-[5-(3-trifluoromethyl-phenyl)-[1,2,4]triazolo[1,5-a]pyridin-2-ylamino]-benzamide | 2 | 481.0 |
| 211 | 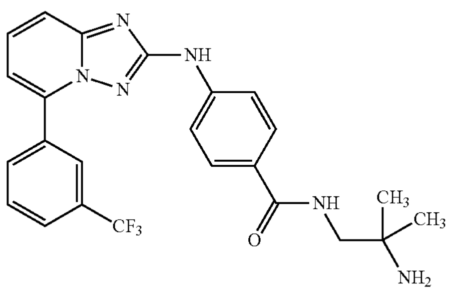 | N-(2-Amino-2-methyl-propyl)-4-[5-(3-trifluoromethyl-phenyl)-[1,2,4]triazolo[1,5-a]pyridin-2-ylamino]-benzamide | 2 | 469.2 |
| 212 | 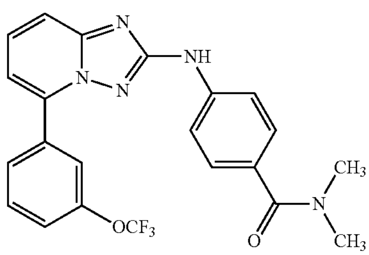 | N,N-Dimethyl-4-[5-(3-trifluoromethoxy-phenyl)-[1,2,4]triazolo[1,5-a]pyridin-2-ylamino]-benzamide | 2 | |
| 213 | 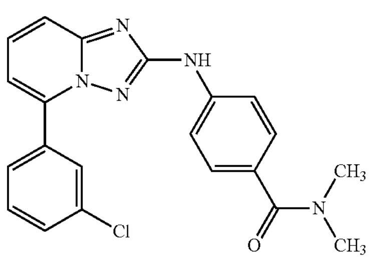 | 4-[5-(3-Chloro-phenyl)-[1,2,4]triazolo[1,5-a]pyridin-2-ylamino]-N,N-dimethyl-benzamide | 2 | |
| 214 | 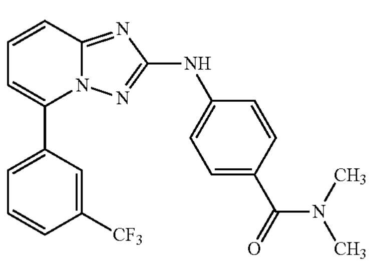 | N,N-Dimethyl-4-[5-(3-trifluoromethyl-phenyl)-[1,2,4]triazolo[1,5-a]pyridin-2-ylamino]-benzamide | 2 | |

TABLE 1-continued

| Ex | Structure | Name | Method | LCMS (ESI) m/z |
|---|---|---|---|---|
| 215 | 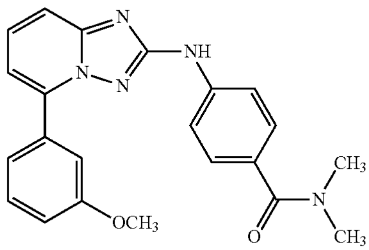 | 4-[5-(3-Methoxy-phenyl)-[1,2,4]triazolo[1,5-a]pyridin-2-ylamino]-N,N-dimethyl-benzamide | 2 | |
| 216 | 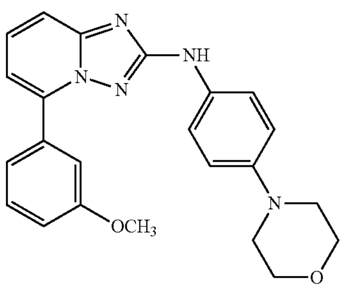 | [5-(3-Methoxy-phenyl)-[1,2,4]triazolo[1,5-a]pyridin-2-yl]-(4-morpholin-4-yl-phenyl)-amine | 1 | 402.3 |
| 217 | 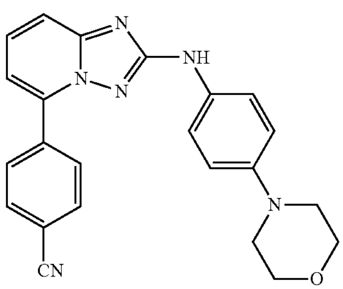 [SMILES: N#Cc1ccc(-c2cccc3nc(Nc4ccc(N5CCOCC5)cc4)nn23)cc1] | 4-[2-(4-Morpholin-4-yl-phenylamino)-[1,2,4]triazolo[1,5-a]pyridin-5-yl]-benzonitrile | 1 | 397.2 |
| 218 | 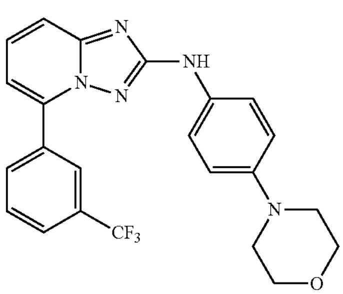 [SMILES: FC(F)(F)c1cccc(-c2cccc3nc(Nc4ccc(N5CCOCC5)cc4)nn23)c1] | (4-Morpholin-4-yl-phenyl)-[5-(3-trifluoromethyl-phenyl)-[1,2,4]triazolo[1,5-a]pyridin-2-yl]-amine | 1 | 440.2 |
| 219 | 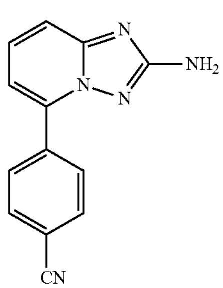 [SMILES: N#Cc1ccc(-c2cccc3nc(N)nn23)cc1] | 4-(2-Amino-[1,2,4]triazolo[1,5-a]pyridin-5-yl)-benzonitrile | 1 | 236.1 |

TABLE 1-continued

| Ex | Structure | Name | Method | LCMS (ESI) m/z |
|---|---|---|---|---|
| 220 | 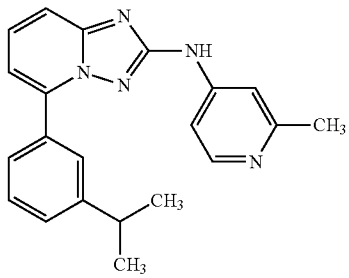 | [5-(3-Isopropyl-phenyl)-[1,2,4]triazolo[1,5-a]pyridin-2-yl]-(2-methyl-pyridin-4-yl)-amine | 1 | 344.2 |
| 221 | 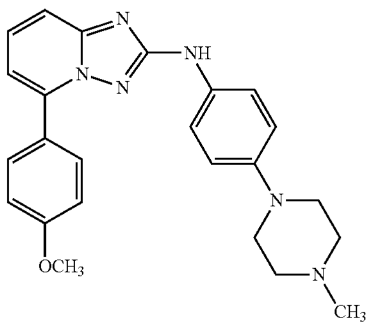 [SMILES: COc1ccc(-c2cccc3nc(Nc4ccc(N5CCN(C)CC5)cc4)nn23)cc1] | [5-(4-Methoxy-phenyl)-[1,2,4]triazolo[1,5-a]pyridin-2-yl]-[4-(4-methyl-piperazin-1-yl)-phenyl]-amine | 3 | 415.3 |
| 222 | 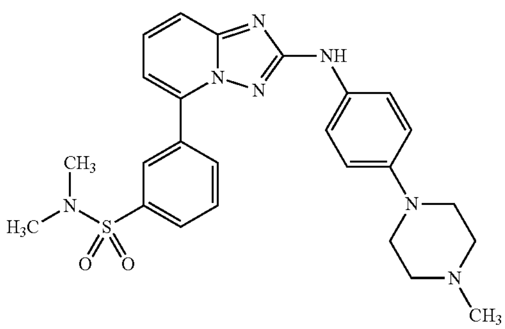 | N,N-Dimethyl-3-{2-[4-(4-methyl-piperazin-1-yl)-phenylamino]-[1,2,4]triazolo[1,5-a]pyridin-5-yl}-benzenesulfonamide | 3 | 492.3 |
| 223 | 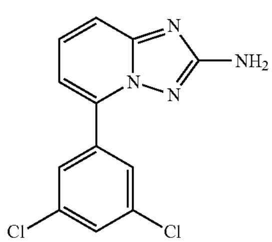 [SMILES: Nc1nc2cccc(-c3cc(Cl)cc(Cl)c3)n2n1] | 5-(3,5-Dichloro-phenyl)-[1,2,4]triazolo[1,5-a]pyridin-2-ylamine | 1 | 279.1 |
| 224 | 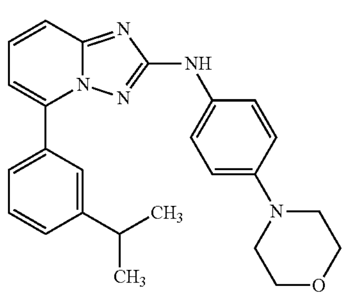 [SMILES: CC(C)c1cccc(-c2cccc3nc(Nc4ccc(N5CCOCC5)cc4)nn23)c1] | [5-(3-Isopropyl-phenyl)-[1,2,4]triazolo[1,5-a]pyridin-2-yl]-(4-morpholin-4-yl-phenyl)-amine | 1 | 414.3 |

TABLE 1-continued

| Ex | Name | Method | LCMS (ESI) m/z |
|---|---|---|---|
| 225 | N-Isopropyl-3-{2-[4-(4-methyl-piperazin-1-yl)-phenylamino]-[1,2,4]triazolo[1,5-a]pyridin-5-yl}-benzenesulfonamide | 3 | 506.3 |
| 226 | N-tert-Butyl-3-[2-(4-morpholin-4-yl-phenylamino)-[1,2,4]triazolo[1,5-a]pyridin-5-yl]-benzenesulfonamide | 3 | 507.4 |
| 227 | N-tert-Butyl-3-[2-(pyridin-2-ylamino)-[1,2,4]triazolo[1,5-a]pyridin-5-yl]-benzenesulfonamide | 1 | 423.3 |
| 228 | [5-(3-Isopropyl-phenyl)-[1,2,4]triazolo[1,5-a]pyridin-2-yl]-carbamic acid methyl ester | 6 | 311.2 |
| 229 | 5-(3-Isopropyl-phenyl)-[1,2,4]triazolo[1,5-a]pyridin-2-ylamine | 1 | 253.1 |

TABLE 1-continued

| Ex | Structure | Name | Method | LCMS (ESI) m/z |
|---|---|---|---|---|
| 230 | 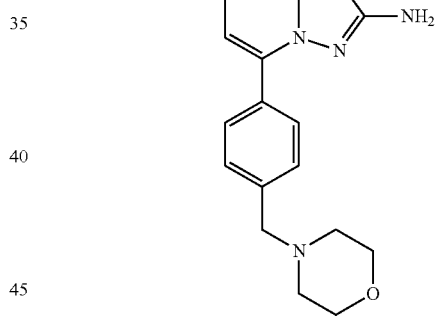 | N-tert-Butyl-3-{2-[4-(4-methyl-piperazin-1-yl)-phenylamino]-[1,2,4]triazolo[1,5-a]pyridin-5-yl}-benzenesulfonamide | 3 | 520.3 |

Example 231

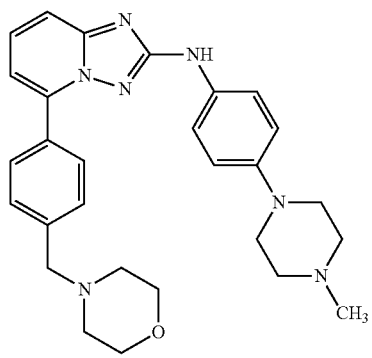 [SMILES: CN1CCN(c2ccc(Nc3nc4cccc(-c5ccc(CN6CCOCC6)cc5)n4n3)cc2)CC1]

N-(4-(4-Methylpiperazin-1-yl)phenyl)-5-(4-(morpholinomethyl)phenyl)-[1,2,4]triazolo[1,5-a]pyridin-2-amine

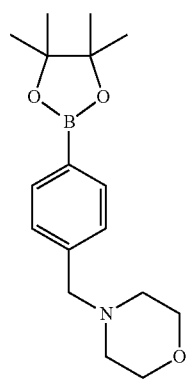 [SMILES: CC1(C)OB(c2ccc(CN3CCOCC3)cc2)OC1(C)C]

4-(4-(4,4,5,5-tetramethyl-1,3,2-dioxaborolan-2-yl)benzyl)morpholine

A solution of 4-(4-bromobenzyl)morpholine (2.0 g, 7.8 mmol), bis(pinacolato)diboron (2.4 g, 9.4 mmol), potassium acetate (1.1 g, 12 mmol) and 1,1'-bis(diphenylphosphino)ferrocenepalladium(II) chloride (660 mg, 0.1 mmol) in DMF was heated at 80° C. overnight. The reaction mixture was cooled to room temperature and diluted with ethyl acetate (100 mL). The resulting solution was washed with saturated aqueous sodium chloride (3×50 mL). The collected organic fraction was dried over anhydrous sodium sulfate, filtered, and concentrated in vacuo to afford the desired product which was used without further purification (2 g, 84% yield).

5-(4-(morpholinomethyl)phenyl)-[1,2,4]triazolo[1,5-a]pyridin-2-amine

A solution of 4-(4-(4,4,5,5-tetramethyl-1,3,2-dioxaborolan-2-yl)benzyl)morpholine (1.9 g, 6.3 mmol), 5-bromo-[1,2,4]triazolo[1,5-a]pyridine-2-amine (1 g, 5 mmol), 1,1'-bis(diphenylphosphino)ferrocenepalladium(II) chloride (250 mg, 0.63 mmol), and cesium carbonate (4.1 g, 12.6 mmol) in 10:1 dimethoxyethane/water (11 mL) was heated at 140° C. under microwave radiation for 1 h. The reaction mixture was diluted with ethyl acetate (200 mL), and the resulting suspension was filtered through celite. The filtrate was concentrated, and the resulting residue was purified by flash column chromatography (petroleum ether→ethyl acetate) to provide product (1 g, 69% yield). LCMS (ESI) m/z: 310.

211

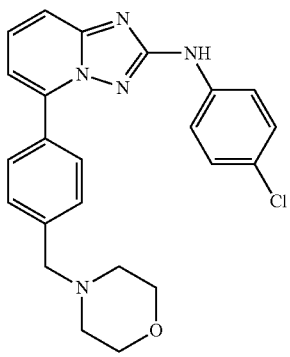 [SMILES: Clc1ccc(Nc2nc3cccc(-c4ccc(CN5CCOCC5)cc4)n3n2)cc1]

N-(4-chlorophenyl)-5-(4-(morpholinomethyl)phenyl)-[1,2,4]triazolo[1,5-a]pyridin-2-amine A suspension of 5-(4-(morpholinomethyl)phenyl)-[1,2,4]triazolo[1,5-a]pyridin-2-amine (0.50 g, 1.6 mmol), 1-bromo-4-chlorobenzene (340 mg, 1.8 mmol), tris(dibenzylideneacetone)dipalladium (0) (147 mg, 0.16 mmol), cesium carbonate (782 mg, 2.4 mmol), and 4,5-bis(diphenylphosphino)-9,9-dimethylxanthene (94 mg, 0.16 mmol) in 1,4-dioxane (50 mL) was heated to reflux for 2 days. The reaction mixture was diluted with ethyl acetate (300 mL), and the resulting suspension was filtered though celite. Concentration of the filtrate in vacuo provided crude product, which was purified by flash column chromatography (petroleum ether→ethyl acetate) to give product (300 mg, 44% yield). LCMS (ESI) m/z: 421.

N-(4-(4-methylpiperazin-1-yl)phenyl)-5-(4-(morpholinomethyl)phenyl)-[1,2,4]-triazolo[1,5-a]pyridin-2-amine A suspension of N-(4-chlorophenyl)-5-(4-(morpholinomethyl)phenyl)-[1,2,4]triazolo[1,5-a]pyridin-2-amine (300 mg, 0.7 mmol), 1-methylpiperazine (356 mg, 3.6 mmol), tris(dibenzylideneacetone)dipalladium (0) (65 mg, 0.07 mmol), cesium carbonate (456 mg, 1.4 mmol), and 4,5-bis(diphenylphosphino)-9,9-dimethylxanthene (410 mg, 0.07 mmol) in 1,4-dioxane (2 mL) was irradiated by microwave heating to 160° C. for 20 min. The reaction mixture was diluted with EtOAc (300 mL), and filtered though celite. The filtrate was concentrated to give a black residue, which was purified by preparative thin layer chromatography (10% methanol in dichloromethane) to afford product (38.9 mg 11% yield). $^{1}$H NMR (400 MHz, CDCl$_{3}$), δ: 7.96 (d, J=8 Hz, 2H), 7.52-7.42 (m, 6H), 6.92-6.87 (m, 3H), 6.68 (m, 1H), 3.79-3.72 (m, 4H), 3.59 (s, 2H), 3.18-3.12 (m, 4H), 2.6-2.55 (m 4H), 2.55-2.48 (m, 4H), 2.33 (s, 3H). LCMS (ESI) m/z: 484.1.

Example 232

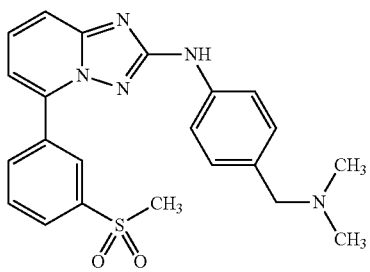 [SMILES: CN(C)Cc1ccc(Nc2nc3cccc(-c4cccc(S(C)(=O)=O)c4)n3n2)cc1]

N-(4-((Dimethylamino)methyl)phenyl)-5-(3-(methylsulfonyl)phenyl)-[1,2,4]triazolo[1,5-a]pyridin-2-amine

212

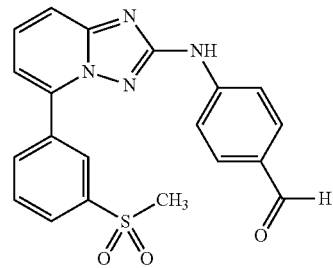 [SMILES: CS(=O)(=O)c1cccc(-c2cccc3nc(Nc4ccc(C=O)cc4)nn23)c1]

5-(3-(methylsulfonyl)phenyl)-[1,2,4]triazolo[1,5-a]pyridin-2-amine

Made by following the procedure described for the preparation of 5-[3-(propan-2-yl)phenyl][1,2,4]triazolo[1,5-a]pyridine-2-amine and making non-critical variations.

4-(5-(3-(methylsulfonyl)phenyl)-[1,2,4]triazolo[1,5-a]pyridin-2-ylamino)benzaldehyde Made by following the procedure described for the preparation of methyl 4-{[5-(3-chlorophenyl)[1,2,4]triazolo[1,5-a]pyridin-2-yl]amino}benzoate and making non-critical variations.

N-(4-((dimethylamino)methyl)phenyl)-5-(3-(methylsulfonyl)phenyl)-[1,2,4]triazolo[1,5-a]pyridin-2-amine To a solution of 4-(5-(3-(methylsulfonyl)phenyl)-[1,2,4]triazolo[1,5-a]pyridin-2-ylamino)benzaldehyde (150 mg, 0.38 mmol) in dichloromethane (50 mL) was added dimethylamine (1 M in THF) (3.6 g, 28 mmol). The resulting mixture was stirred at 24° C. for 1 h. Sodium triacetoxyborohydride was then added to the reaction mixture. After 16 h, the mixture was quenched with saturated aqueous sodium bicarbonate solution. The collected organic layer was dried over anhydrous sodium sulfate, filtered, and concentrated. Purification by preparative thin layer chromatography afforded the desired product (61 mg, 37% yield). LCMS (ESI) m/z: 421.9.

Example 233

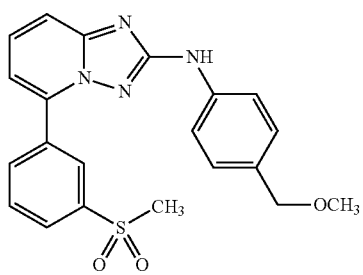 [SMILES: COCc1ccc(Nc2nc3cccc(-c4cccc(S(C)(=O)=O)c4)n3n2)cc1]

N-(4-(Methoxymethyl)phenyl)-5-(3-(methylsulfonyl)phenyl)-[1,2,4]triazolo[1,5-a]pyridin-2-amine

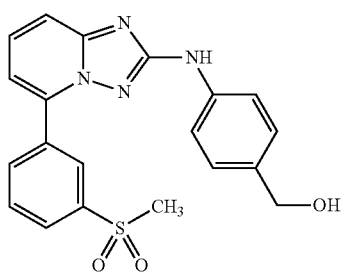 [SMILES: CS(=O)(=O)c1cccc(-c2cccc3nc(Nc4ccc(CO)cc4)nn23)c1]

(4-(5-(3-(methylsulfonyl)phenyl)-[1,2,4]triazolo[1,5-a]pyridin-2-ylamino)phenyl)methanol To a solution of 4-(5-(3-(methylsulfonyl)phenyl)-[1,2,4]triazolo[1,5-a]pyridin-2-ylamino)benzaldehyde (450 mg, 1.15 mmol) in tetrahydrofuran was added sodium borohydride (22 mg, 0.57 mmol) at 24° C. After 3 hr, the reaction mixture filtered through Celite. The solvent was removed in vacuo to provided the crude product which was purified by preparative thin layer chromatography to afford the desired product (300 mg, 67% yield). LCMS (ESI) m/z: 395.1.

N-(4-(Methoxymethyl)phenyl)-5-(3-(methylsulfonyl)phenyl)-[1,2,4]triazolo[1,5-a]pyridin-2-amine To the solution of (4-(5-(3-(methylsulfonyl)phenyl)-[1,2,4]triazolo[1,5-a]pyridin-2-ylamino)phenyl)methanol (200 mg, 0.51 mmol) in dimethyl sulfoxide (2 mL) was sequentially added potassium hydroxide (28 mg, 0.51 mmol) and iodomethane. After 3 hr, the reaction mixture was partitioned between water and dichloromethane. The collected organic layer was dried over anhydrous sodium sulfate, filtered, and concentrated. Purification by preparative thin layer chromatography afforded the desired product (45 mg, 12%). LCMS (ESI) m/z: 409.0.

Example 234

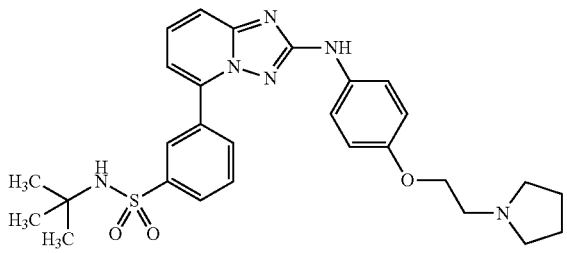 [SMILES: CC(C)(C)NS(=O)(=O)c1cccc(-c2cccc3nc(Nc4ccc(OCCN5CCCC5)cc4)nn23)c1]

N-tert-Butyl-3-(2-(4-(2-(pyrrolidin-1-yl)ethoxy)phenylamino)[1,2,4]triazolo[1,5-a]pyridin-5-yl)benzenesulfonamide

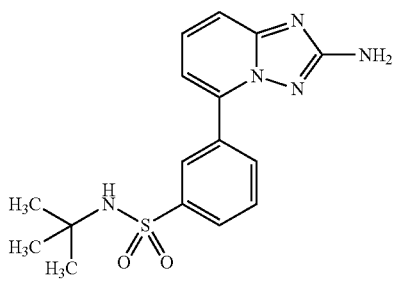 [SMILES: CC(C)(C)NS(=O)(=O)c1cccc(-c2cccc3nc(N)nn23)c1]

3-(2-amino-[1,2,4]triazolo[1,5-a]pyridin-5-yl)-N-tert-butylbenzenesulfonamide

Made by following the procedure described for the preparation of 5-[3-(propan-2-yl)phenyl][1,2,4]triazolo[1,5-a]pyridine-2-amine and making non-critical variations.

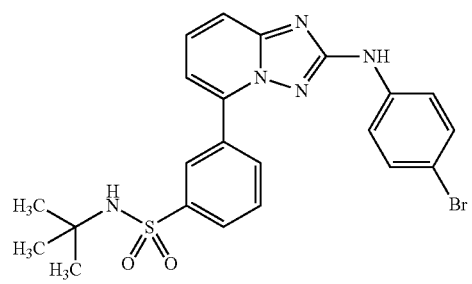 [SMILES: CC(C)(C)NS(=O)(=O)c1cccc(-c2cccc3nc(Nc4ccc(Br)cc4)nn23)c1]

3-(2-(4-bromophenylamino)-[1,2,4]triazolo[1,5-a]pyridin-5-yl)-N-tert-butylbenzenesulfonamide Made by following the procedure described for the preparation of 5 N-(4-chlorophenyl)-5-(4-(morpholinomethyl)phenyl)-[1,2,4]triazolo[1,5-a]pyridin-2-amine and making non-critical variations.

N-tert-butyl-3-(2-(4-(2-(pyrrolidin-1-yl)ethoxy)phenylamino)-[1,2,4]triazolo[1,5-a]pyridin-5-yl)benzenesulfonamide A solution of 3-(2-(4-bromophenylamino)-[1,2,4]triazolo[1,5-a]pyridin-5-yl)-N-tert-butylbenzenesulfonamide (150 mg, 0.3 mmol) and copper (I) iodide (57 mg, 0.3 mmol) in 2-(pyrrolidin-1-yl)ethanol (2 mL) was heated at 140° C. under a nitrogen atmosphere. After 18 hr, the reaction mixture was cooled to 20° C. and diluted with ethyl acetate (100 mL). The solution was washed with water. The collected organic was dried over anhydrous sodium sulfate, filtered, and concentrated. Purification by preparative thin layer chromatography afforded the desired product (58.5 mg, 36% yield). LCMS (ESI) m/z: 535.3. $^1$H NMR (400 MHz, DMSO-$d_6$), δ: 9.44 (s, 1H), 8.64 (s, 1H), 8.21-8.19 (d, J=8 Hz, 1H), 8.10-7.99 (d, J=8 Hz, 1H), 7.78 (m, 1H), 7.66-7.57 (m, 5H), 7.24-7.22 (d, J=8 Hz, 1H), 6.90-6.88 (d, J=8 Hz, 2H), 4.15-4.10 (m, 2H), 3.20-3.10 (m, 3H), 2.89-3.05 (m, 3H), 1.83-1.79 (m, 4H), 1.11 (s, 9H).

Example 235

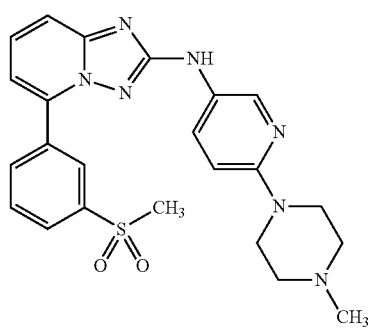 [SMILES: CN1CCN(c2ccc(Nc3nc4cccc(-c5cccc(S(C)(=O)=O)c5)n4n3)cn2)CC1]

N-(6-(4-Methylpiperazin-1-yl)pyridin-3-yl)-5-(3-(methylsulfonyl)phenyl)-[1,2,4]triazolo[1,5-a]pyridin-2-amine

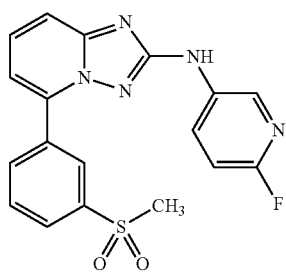 [SMILES: CS(=O)(=O)c1cccc(-c2cccc3nc(Nc4ccc(F)nc4)nn23)c1]

N-(6-fluoropyridin-3-yl)-5-(3-(methylsulfonyl)phenyl)-[1,2,4]triazolo[1,5-a]pyridin-2-amine Made by following the procedure described for the preparation of 5 N-(4-chlorophenyl)-5-(4-(morpholinomethyl)phenyl)-[1,2,4]triazolo[1,5-a]pyridin-2-amine and making non-critical variations.

N-(6-(4-Methylpiperazin-1-yl)pyridin-3-yl)-5-(3-(methylsulfonyl)phenyl)-[1,2,4]triazolo[1,5-a]pyridin-2-amine A solution of N-(6-fluoropyridin-3-yl)-5-(3-(methylsulfonyl)phenyl)-[1,2,4]triazolo[1,5-a]pyridin-2-amine (250 mg, 0.65 mmol) in 1-methylpiperazine (500 mg, 5 mmol) was heated at 140° C. After 16 h, the reaction mixture was diluted with ethyl acetate (100 mL). The resulting solution was washed with water, and the collected organic was concentrated. Purification by preparative thin layer chromatography afforded the desired product (101 mg). LCMS (ESI) m/z: 464.2. $^1$H NMR (400 MHz, CDCl$_3$), δ: 8.69 (s, 1H), 8.30 (s, 1H), 8.16-8.14 (d, J=8 Hz, 1H), 8.03-8.01 (d, J=8 Hz, 1H), 7.81-7.67 (m, 2H), 7.50-7.45 (m, 2H), 6.97 (s, 1H), 6.68-6.64 (m 2H), 3.42-3.34 (m, 4H), 3.10 (s, 3H), 2.48-2.45 (m, 4H), 2.47 (s, 3H).

Example 236

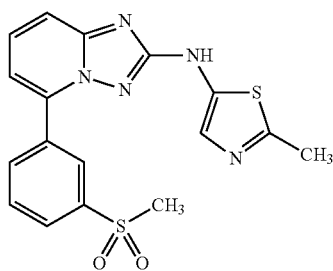 [SMILES: Cc1ncc(Nc2nc3cccc(-c4cccc(S(C)(=O)=O)c4)n3n2)s1]

2-Methyl-N-(5-(3-(methylsulfonyl)phenyl)-[1,2,4]triazolo[1,5-a]pyridin-2-yl)thiazol-5-amine

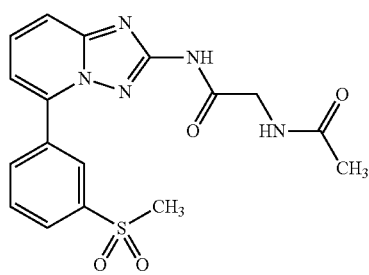 [SMILES: CC(=O)NCC(=O)Nc1nc2cccc(-c3cccc(S(C)(=O)=O)c3)n2n1]

2-acetamido-N-(5-(3-(methylsulfonyl)phenyl)-[1,2,4]triazolo[1,5-a]pyridin-2-yl)acetamide To a solution of N-Acetylglycine (406 mg, 3.47 mmol, 5.00 equiv) in pyridine (10 mL) was added triphenylphosphine (910 mg, 3.47 mmol, 5.00 equiv) at 0° C. After 5 min, carbon tetrabromide (1.15 g, 3.47 mmol, 5.0 equiv) was added, and the resulting yellow solution was maintained at 0° C. for 1.5 h. 5-(3-(Methylsulfonyl)phenyl)-[1,2,4]triazolo[1,5-a]pyridin-2-amine (0.200 g, 0.693 mmol, 1 equiv) was then added to the reaction mixture at 0° C. After 5 min, the reaction mixture was warmed to 24° C. and stirred overnight. Saturated aqueous sodium bicarbonate solution (20 mL), chloroform, and methanol were sequentially added to the reaction mixture. The solution was concentrated, and the resulting residue was purified by flash column chromatography (10% methanol, 1% ammonium hydroxide in dichloromethane) to afford product as white solid (220 mg, 78% yield). $^1$H NMR (400 MHz, CD$_3$OD) δ 8.65 (s, 1H), 8.29 (dd, J=7.9, 1.1 Hz, 1H), 8.08 (dd, J=7.9, 1.0 Hz, 1H), 7.85-7.70 (m, 2H), 7.66 (dd, J=8.9, 1.2 Hz, 1H), 7.36 (dd, J=7.2, 1.2 Hz, 1H), 4.17 (s, 2H), 3.22 (s, 3H), 2.04 (s, 3H).

2-Methyl-N-(5-(3-(methylsulfonyl)phenyl)-[1,2,4]triazolo[1,5-a]pyridin-2-yl)thiazol-5-amine A solution of 2-acetamido-N-(5-(3-(methylsulfonyl)phenyl)-[1,2,4]triazolo[1,5-a]pyridin-2-yl)acetamide (46 mg, 0.12 mmol, 1 equiv) and Lawesson's reagent (190 mg, 0.48 mmol, 4.0 equiv) was heated under reflux for 6 hr. The reaction mixture was concentrated in vacuo, and the resulting residue was diluted with water and ethyl acetate. The product was collected by filtration and purified by preparative HPLC to afford product (20 mg, 40% yield). $^1$H NMR (400 MHz, DMSO-d$_6$) δ 10.41 (s, 1H), 8.71 (t, J=1.6 Hz, 1H), 8.35 (s, 1H), 8.11 (s, 1H), 7.90 (d, J=7.9 Hz, 1H), 7.71 (d, J=7.2 Hz, 1H), 7.60 (m, 1H), 7.37 (dd, J=7.2, 1.3 Hz, 1H), 7.28 (s, 1H), 3.33 (s, 3H), 2.52 (s, 3H).

Example 237

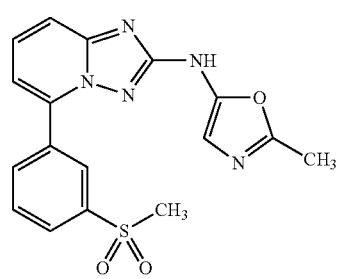 [SMILES: Cc1ncc(Nc2nc3cccc(-c4cccc(S(C)(=O)=O)c4)n3n2)o1]

2-Methyl-N-(5-(3-(methylsulfonyl)phenyl)-[1,2,4]triazolo[1,5-a]pyridin-2-yl)oxazol-5-amine To an ice-cooled solution of triphenylphosphine (101 mg, 0.387 mmol, 5.00 equiv) in pyridine (0.5 ml) was added iodine (0.980 g, 0.387 mmol, 5.00 equiv). After 30 min, a solution of 2-methyl-N-(5-(3-(methylsulfonyl)phenyl)-[1,2,4]triazolo[1,5-a]pyridin-2-yl)thiazol-5-amine (0.030 g, 0.08 mmol, 1 equiv) in pyridine (0.5 mL) was added to the reaction mixture. The reaction mixture was maintained at 0° C. for 1 h before warming to 24° C. After 2 h, the reaction mixture was concentrated in vacuo. The resulting residue was partitioned between saturated aqueous sodium bicarbonate and ethyl acetate. The organic was collected, dried over anhydrous sodium sulfate, filtered, and concentrated. Purification by flash column chromatography (10% methanol, 1% ammonium hydroxide in dichloromethane) yielded a yellow oil (6.0 mg, 20% yield). $^1$H NMR (400 MHz, CD$_3$OD) δ 8.76 (m, 1H), 8.30 (dd, J=14.9, 7.9 Hz, 1H), 8.11 (t, J=10.1 Hz, 1H), 7.84 (m, 2H), 7.70 (m, 1H), 7.63-7.45 (m, 2H), 7.29 (dd, J=21.1, 7.3 Hz, 1H), 3.21 (s, 3H), 2.39 (s, 3H).

Example 238

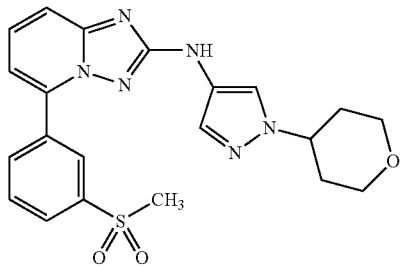 [SMILES: CS(=O)(=O)c1cccc(-c2cccc3nc(Nc4cnn(C5CCOCC5)c4)nn23)c1]

5-(3-(Methylsulfonyl)phenyl)-N-(1-(tetrahydro-2H-pyran-4-yl)-1H-pyrazol-4-yl)-[1,2,4]triazolo[1,5-a]pyridin-2-amine

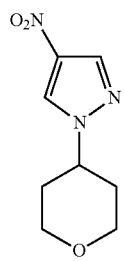 [SMILES: O=[N+]([O-])c1cnn(C2CCOCC2)c1]

4-nitro-1-(tetrahydro-2H-pyran-4-yl)-1H-pyrazole

Procedure adapted from Zabierek, A. A.; Konrad, K. M.; Haidle, A. M. *Tetrahedron Lett.* 2008, 49, 2996.

To a solution of 4-nitro-1H-pyrazole (0.40 mg, 3.5 mmol, 1 equiv), 4-hydroxy-tetrahydropyran (0.36 g, 3.6 mmol, 1.0 equiv) and triphenylphosphine (1.1 g, 4.2 mmol, 1.3 equiv) in tetrahydrofuran (10 mL) at 20° C. was added dibenzylazodicarboxylate (1.1 g, 4.6 mmol, 1.3 equiv) in tetrahydrofuran (2 mL) over 5 min. After 3 hr, the reaction mixture was concentrated in vacuo, and the resulting residue was purified by flash column chromatography (40% ethyl acetate in hexanes) to afford product as white solid (568 mg, 81% yield). $^1$H NMR (400 MHz, CD$_3$OD) δ 8.64 (s, 1H), 8.13 (s, 1H), 4.49 (s, 1H), 4.15-3.94 (m, 2H), 3.72-3.45 (m, 2H), 2.24-1.95 (m, 4H).

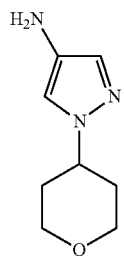

1-(tetrahydro-2H-pyran-4-yl)-1H-pyrazol-4-amine

A solution of 4-nitro-1-(tetrahydro-2H-pyran-4-yl)-1H-pyrazole (568 mg, 2.88 mmol, 1 equiv) in methanol was circulated through a H-Cube® Continuous-flow hydrogenation reactor (ThalesNano) fitted with a palladium on carbon catalyst cartridge at 50° C. The collected solution was concentrated in vacuo to afford product, which was used without further purification (458 mg, 95% yield). LCMS (ESI) m/z: 168.0.

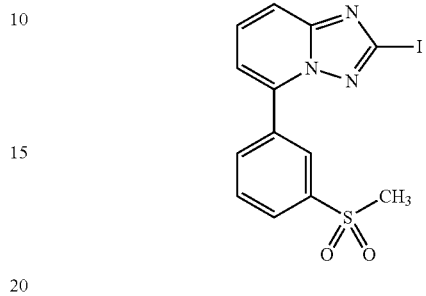

2-iodo-5-(3-(methylsulfonyl)phenyl)-[1,2,4]triazolo[1,5-a]pyridine

Made by following the procedure described for the preparation of 2-iodo-5-(4-methoxyphenyl)-[1,2,4]triazolo[1,5-a]pyridine and making non-critical variations.

5-(3-(Methylsulfonyl)phenyl)-N-(1-(tetrahydro-2H-pyran-4-yl)-1H-pyrazol-4-yl)-[1,2,4]triazolo[1,5-a]pyridin-2-amine A suspension of 1-(tetrahydro-2H-pyran-4-yl)-1H-pyrazol-4-amine (50.0 mg, 0.299 mmol, 1.2 equiv), 2-iodo-5-(3-(methylsulfonyl)phenyl)-[1,2,4]triazolo[1,5-a]pyridine (0.100 g, 0.249 mmol, 1 equiv), tris(dibenzylideneacetone)dipalladium (0) (17.0 mg, 0.019 mmol, 0.075 equiv), 4,5-bis(diphenylphosphino)-9,9-dimethylxanthene (21.6 mg, 0.037 mmol, 0.150 equiv), and sodium tert-butoxide in dioxane (2 mL) was heated at 160° C. for 15 min under microwave radiation. The reaction mixture was partitioned between half saturated aqueous sodium chloride solution and ethyl acetate. The aqueous layer was extracted with ethyl acetate (2×). The combined organic extracts were dried over anhydrous sodium sulfate, filtered, and concentrated. Purification by preparative HPLC provided product (11.5 mg, 11% yield). $^1$H NMR (400 MHz, DMSO-d$_6$), δ: 9.28 (s, 1H), 8.79 (s, 1H), 8.35 (d, J=7.9 Hz, 1H), 8.13 (d, J=8.0 Hz, 1H), 7.87 (dd, J=16.6, 8.8 Hz, 2H), 7.66 (dd, J=8.7, 7.3 Hz, 1H), 7.55 (m, 1H), 7.40 (m, 1H), 7.21 (m, 1H), 4.31 (m, 1H), 3.95 (d, J=11.1 Hz, 2H), 3.52-3.39 (m, 2H), 2.07 (s, 3H), 1.89 (m, 4H).

Examples 239-438 shown in Table 2 were prepared generally following the above-described Examples. For each compound shown in Table 2, the Example number followed is given in the Method column.

TABLE 2

| Ex | Structure | Name | Mthd | LCMS (ESI) m/z |
|---|---|---|---|---|
| 239 | 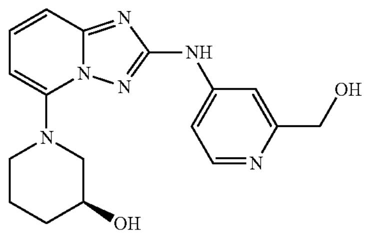 [SMILES: OCc1cc(Nc2nc3cccc(N4CCC[C@H](O)C4)n3n2)ccn1] | (S)-1-(2-(2-(hydroxymethyl)pyridin-4-ylamino)-[1,2,4]triazolo[1,5-a]pyridin-5-yl)piperidin-3-ol | 5 | 341.2 |
| 240 | 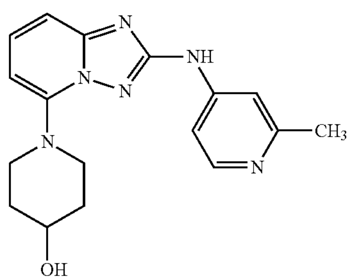 [SMILES: Cc1cc(Nc2nc3cccc(N4CCC(O)CC4)n3n2)ccn1] | 1-(2-(2-methylpyridin-4-ylamino)-[1,2,4]triazolo[1,5-a]pyridin-5-yl)piperidin-4-ol | 5 | 325.2 |
| 241 | 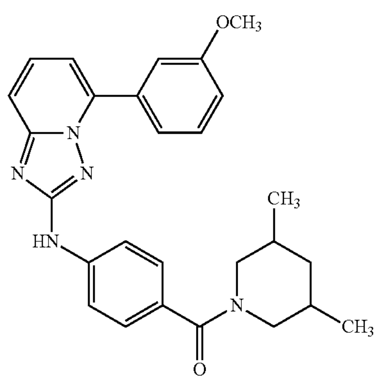 [SMILES: COc1cccc(-c2cccc3nc(Nc4ccc(C(=O)N5CC(C)CC(C)C5)cc4)nn23)c1] | (3,5-dimethylpiperidin-1-yl)(4-(5-(3-methoxyphenyl)-[1,2,4]triazolo[1,5-a]pyridin-2-ylamino)phenyl)methanone | 2 | 455.2 |
| 242 | 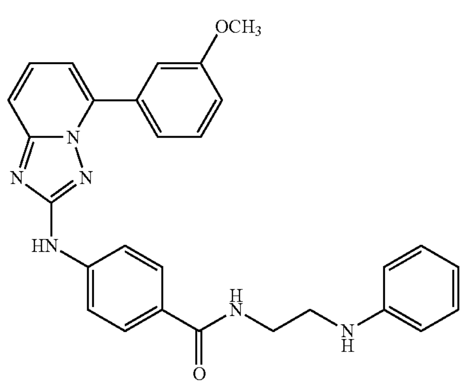 [SMILES: COc1cccc(-c2cccc3nc(Nc4ccc(C(=O)NCCNc5ccccc5)cc4)nn23)c1] | 4-(5-(3-methoxyphenyl)-[1,2,4]triazolo[1,5-a]pyridin-2-ylamino)-N-(2-(phenylamino)ethyl)benzamide | 2 | 479.2 |

TABLE 2-continued

| Ex | Structure | Name | Mthd | LCMS (ESI) m/z |
|---|---|---|---|---|
| 243 | 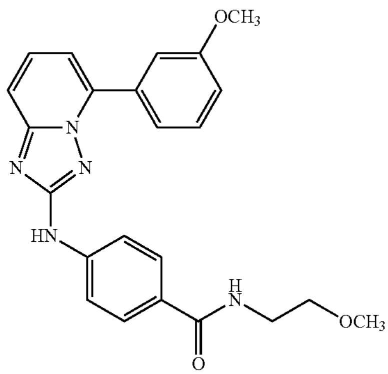 [SMILES: COCCNC(=O)c1ccc(Nc2nc3cccc(-c4cccc(OC)c4)n3n2)cc1] | N-(2-methoxyethyl)-4-(5-(3-methoxyphenyl)-[1,2,4]triazolo[1,5-a]pyridin-2-ylamino)benzamide | 2 | 418.0 |
| 244 | 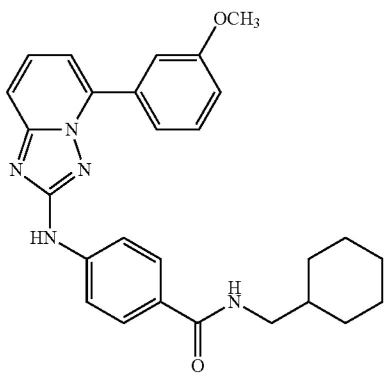 [SMILES: COc1cccc(-c2cccc3nc(Nc4ccc(C(=O)NCC5CCCCC5)cc4)nn23)c1] | N-(cyclohexylmethyl)-4-(5-(3-methoxyphenyl)-[1,2,4]triazolo[1,5-a]pyridin-2-ylamino)benzamide | 2 | 456.2 |
| 245 | 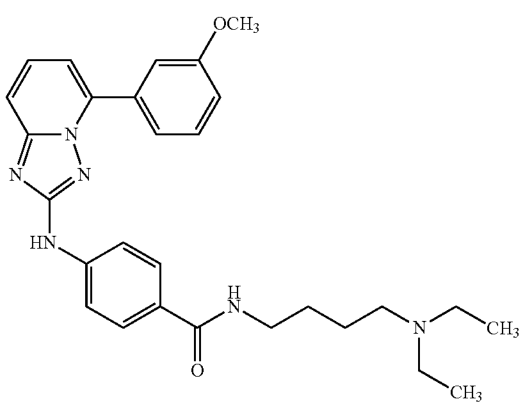 [SMILES: CCN(CC)CCCCNC(=O)c1ccc(Nc2nc3cccc(-c4cccc(OC)c4)n3n2)cc1] | N-(4-(diethylamino)butyl)-4-(5-(3-methoxyphenyl)-[1,2,4]triazolo[1,5-a]pyridin-2-ylamino)benzamide | 2 | 487.3 |
| 246 | 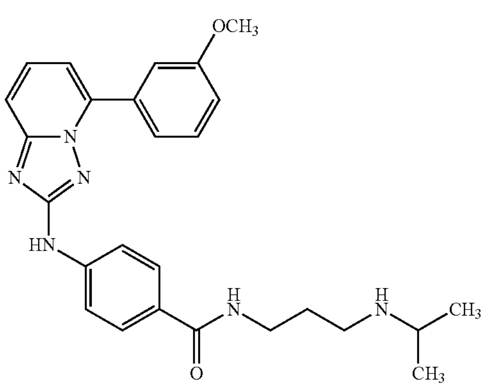 [SMILES: COc1cccc(-c2cccc3nc(Nc4ccc(C(=O)NCCCNC(C)C)cc4)nn23)c1] | N-(3-(isopropylamino)propyl)-4-(5-(3-methoxyphenyl)-[1,2,4]triazolo[1,5-a]pyridin-2-ylamino)benzamide | 2 | 459.2 |

TABLE 2-continued
| Ex | Structure | Name | Mthd | LCMS (ESI) m/z |
|---|---|---|---|---|
| 247 | 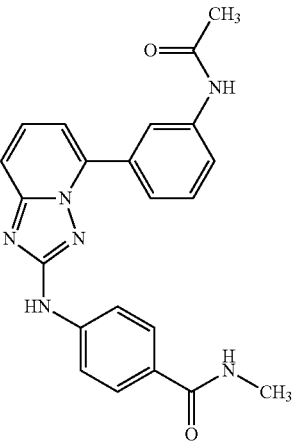 [SMILES: CNC(=O)c1ccc(Nc2nc3cccc(-c4cccc(NC(C)=O)c4)n3n2)cc1] | 4-(5-(3-acetamidophenyl)-[1,2,4]triazolo[1,5-a]pyridin-2-ylamino)-N-methylbenzamide | 2 | 401.2 |
| 248 | 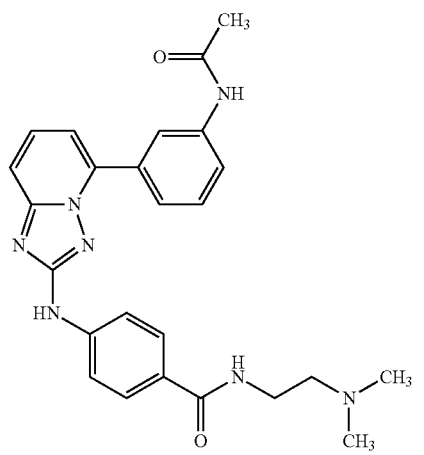 [SMILES: CC(=O)Nc1cccc(-c2cccc3nc(Nc4ccc(C(=O)NCCN(C)C)cc4)nn23)c1] | 4-(5-(3-acetamidophenyl)-[1,2,4]triazolo[1,5-a]pyridin-2-ylamino)-N-(2-(dimethylamino)ethyl)benzamide | 2 | 458.2 |
| 249 | 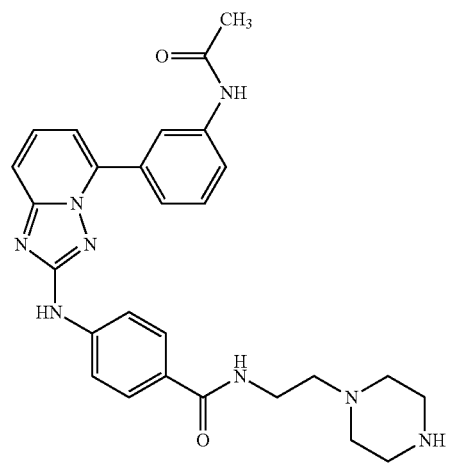 [SMILES: CC(=O)Nc1cccc(-c2cccc3nc(Nc4ccc(C(=O)NCCN5CCNCC5)cc4)nn23)c1] | 4-(5-(3-acetamidophenyl)-[1,2,4]triazolo[1,5-a]pyridin-2-ylamino)-N-(2-(piperazin-1-yl)ethyl)benzamide | 2 | 499.3 |

TABLE 2-continued

| Ex | Structure | Name | Mthd | LCMS (ESI) m/z |
|---|---|---|---|---|
| 250 | 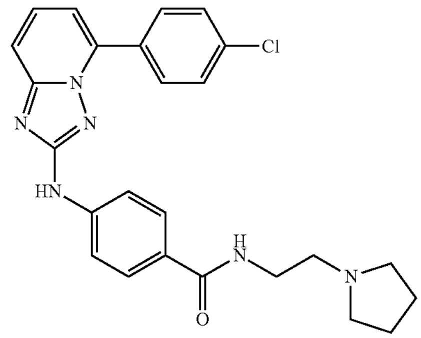 [SMILES: O=C(NCCN1CCCC1)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)-N-(2-(pyrrolidin-1-yl)ethyl)benzamide | 2 | 461.2 |
| 251 | 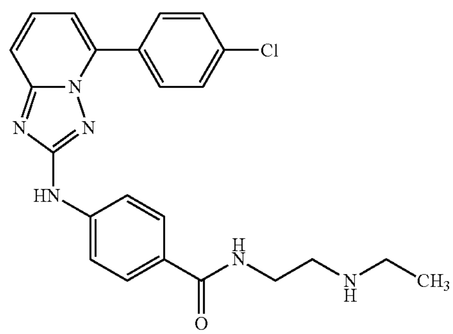 [SMILES: CCNCCNC(=O)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)-N-(2-(ethylamino)ethyl)benzamide | 2 | 435.2 |
| 252 | 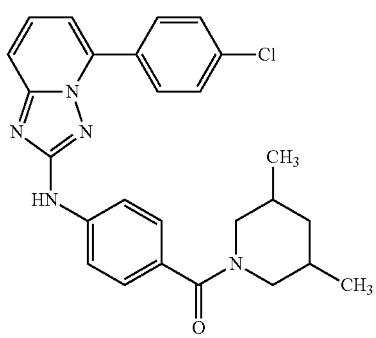 [SMILES: CC1CC(C)CN(C(=O)c2ccc(Nc3nc4cccc(-c5ccc(Cl)cc5)n4n3)cc2)C1] | (4-(5-(4-chlorophenyl)-[1,2,4]triazolo[1,5-a]pyridin-2-ylamino)phenyl)(3,5-dimethylpiperidin-1-yl)methanone | 2 | 460.2 |
| 253 | 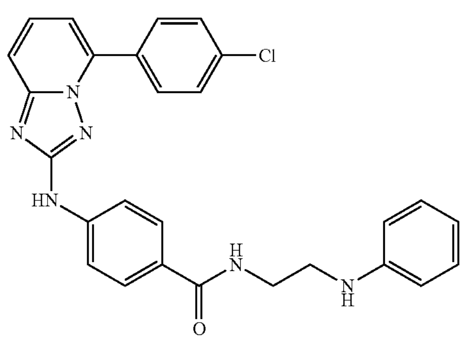 [SMILES: O=C(NCCNc1ccccc1)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)-N-(2-(phenylamino)ethyl)benzamide | 2 | 483.2 |

TABLE 2-continued

| Ex | Structure | Name | Mthd | LCMS (ESI) m/z |
|---|---|---|---|---|
| 254 | 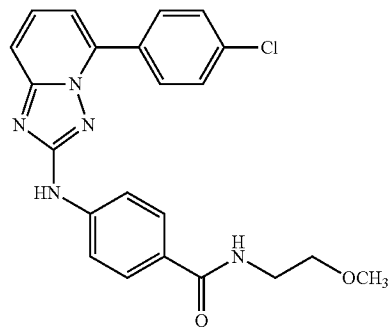 [SMILES: COCCNC(=O)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)-N-(2-methoxyethyl)benzamide | 2 | 422.1 |
| 255 | 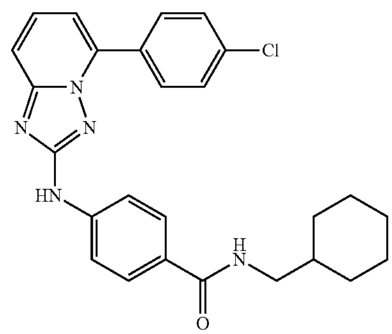 [SMILES: O=C(NCC1CCCCC1)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)-N-(cyclohexylmethyl)benzamide | 2 | 460.2 |
| 256 | 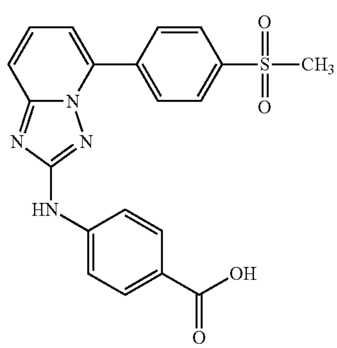 [SMILES: CS(=O)(=O)c1ccc(-c2cccc3nc(Nc4ccc(C(=O)O)cc4)nn23)cc1] | 4-(5-(4-(methylsulfonyl)phenyl)-[1,2,4]triazolo[1,5-a]pyridin-2-ylamino)benzoic acid | 2 | 408.9 |
| 257 | 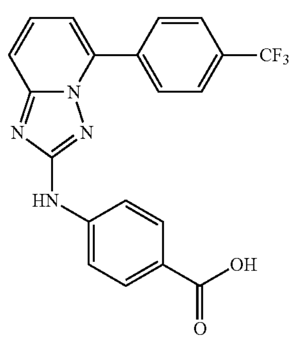 [SMILES: O=C(O)c1ccc(Nc2nc3cccc(-c4ccc(C(F)(F)F)cc4)n3n2)cc1] | 4-(5-(4-(trifluoromethyl)phenyl)-[1,2,4]triazolo[1,5-a]pyridin-2-ylamino)benzoic acid | 2 | 399.0 |

TABLE 2-continued

| Ex | Structure | Name | Mthd | LCMS (ESI) m/z |
|---|---|---|---|---|
| 258 | 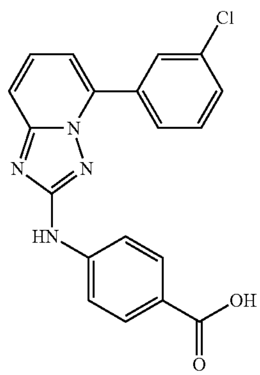 [SMILES: O=C(O)c1ccc(Nc2nc3cccc(-c4cccc(Cl)c4)n3n2)cc1] | 4-(5-(3-chlorophenyl)-[1,2,4]triazolo[1,5-a]pyridin-2-ylamino)benzoic acid | 2 | 365.0 |
| 259 | 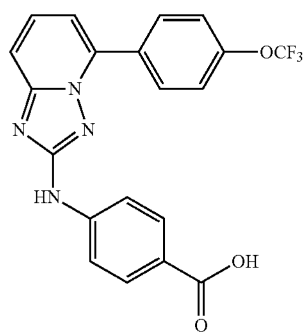 [SMILES: O=C(O)c1ccc(Nc2nc3cccc(-c4ccc(OC(F)(F)F)cc4)n3n2)cc1] | 4-(5-(4-(trifluoromethoxy)phenyl)-[1,2,4]triazolo[1,5-a]pyridin-2-ylamino)benzoic acid | 2 | 415.1 |
| 260 | 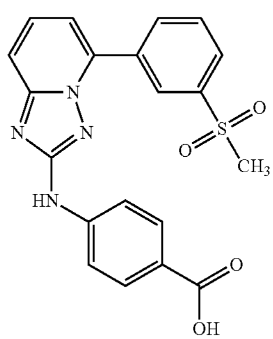 [SMILES: CS(=O)(=O)c1cccc(-c2cccc3nc(Nc4ccc(C(=O)O)cc4)nn23)c1] | 4-(5-(3-(methylsulfonyl)phenyl)-[1,2,4]triazolo[1,5-a]pyridin-2-ylamino)benzoic acid | 2 | 409.1 |
| 261 | 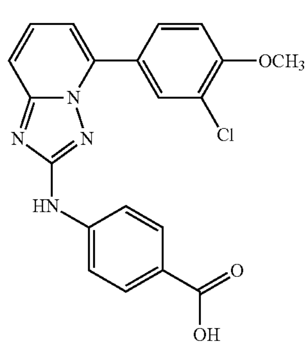 [SMILES: COc1ccc(-c2cccc3nc(Nc4ccc(C(=O)O)cc4)nn23)cc1Cl] | 4-(5-(3-chloro-4-methoxyphenyl)-[1,2,4]triazolo[1,5-a]pyridin-2-ylamino)benzoic acid | 2 | 395.1 |

TABLE 2-continued

| Ex | Structure | Name | Mthd | LCMS (ESI) m/z |
|---|---|---|---|---|
| 262 | 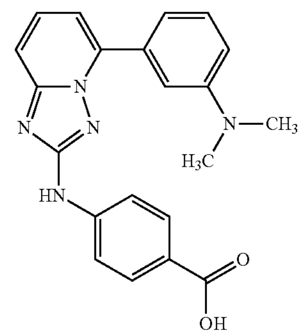 [SMILES: CN(C)c1cccc(-c2cccc3nc(Nc4ccc(C(=O)O)cc4)nn23)c1] | 4-(5-(3-(dimethylamino)phenyl)-[1,2,4]triazolo[1,5-a]pyridin-2-ylamino)benzoic acid | 2 | 373.9 |
| 263 | 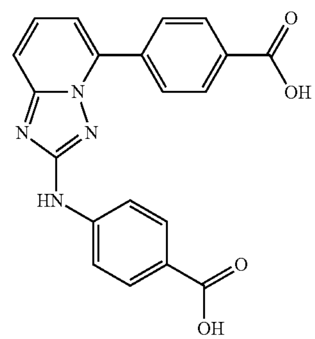 [SMILES: O=C(O)c1ccc(Nc2nc3cccc(-c4ccc(C(=O)O)cc4)n3n2)cc1] | 4-(5-(4-carboxyphenyl)-[1,2,4]triazolo[1,5-a]pyridin-2-ylamino)benzoic acid | 2 | 375.0 |
| 264 | 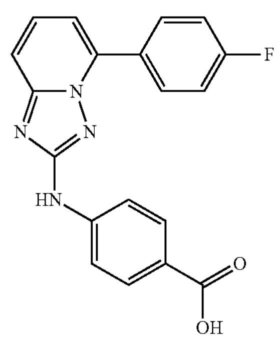 [SMILES: O=C(O)c1ccc(Nc2nc3cccc(-c4ccc(F)cc4)n3n2)cc1] | 4-(5-(4-fluorophenyl)-[1,2,4]triazolo[1,5-a]pyridin-2-ylamino)benzoic acid | 2 | 348.8 |
| 265 | 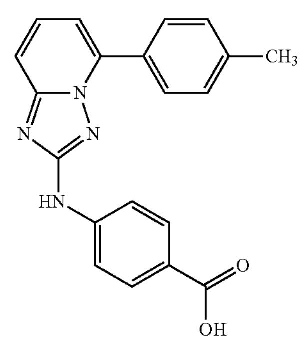 [SMILES: Cc1ccc(-c2cccc3nc(Nc4ccc(C(=O)O)cc4)nn23)cc1] | 4-(5-p-tolyl-[1,2,4]triazolo[1,5-a]pyridin-2-ylamino)benzoic acid | 2 | 344.9 |

TABLE 2-continued

| Ex | Structure | Name | Mthd | LCMS (ESI) m/z |
|---|---|---|---|---|
| 266 | 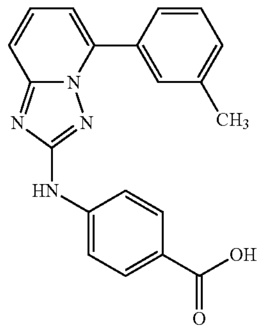 [SMILES: Cc1cccc(-c2cccc3nc(Nc4ccc(C(=O)O)cc4)nn23)c1] | 4-(5-m-tolyl-[1,2,4]triazolo[1,5-a]pyridin-2-ylamino)benzoic acid | 2 | 344.8 |
| 267 | 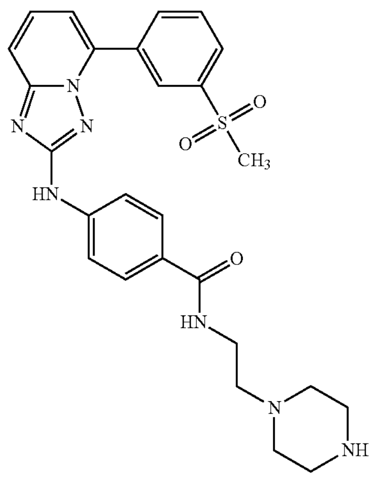 [SMILES: CS(=O)(=O)c1cccc(-c2cccc3nc(Nc4ccc(C(=O)NCCN5CCNCC5)cc4)nn23)c1] | 4-(5-(3-(methylsulfonyl)phenyl)-[1,2,4]triazolo[1,5-a]pyridin-2-ylamino)-N-(2-(piperazin-1-yl)ethyl)benzamide | 2 | 519.9 |
| 268 | 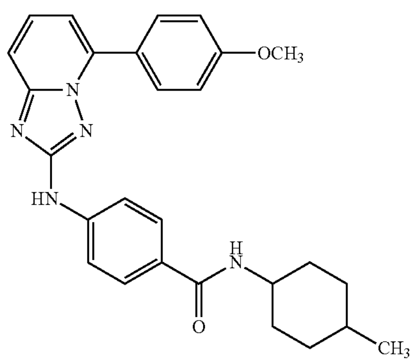 [SMILES: COc1ccc(-c2cccc3nc(Nc4ccc(C(=O)NC5CCC(C)CC5)cc4)nn23)cc1] | 4-(5-(4-methoxyphenyl)-[1,2,4]triazolo[1,5-a]pyridin-2-ylamino)-N-(4-methylcyclohexyl)benzamide | 2 | 456.2 |
| 269 | 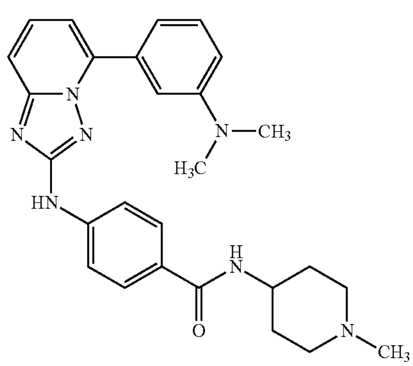 [SMILES: CN1CCC(NC(=O)c2ccc(Nc3nc4cccc(-c5cccc(N(C)C)c5)n4n3)cc2)CC1] | 4-(5-(3-(dimethylamino)phenyl)-[1,2,4]triazolo[1,5-a]pyridin-2-ylamino)-N-(1-methylpiperidin-4-yl)benzamide | 2 | 470.1 |

TABLE 2-continued

| Ex | Structure | Name | Mthd | LCMS (ESI) m/z |
|---|---|---|---|---|
| 270 | 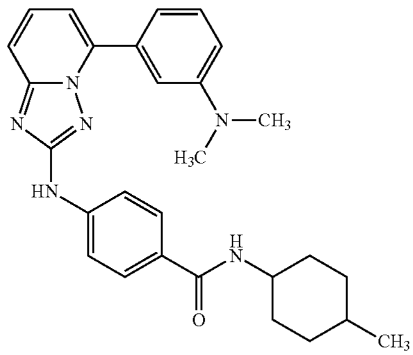 [SMILES: CC1CCC(NC(=O)c2ccc(Nc3nc4cccc(-c5cccc(N(C)C)c5)n4n3)cc2)CC1] | 4-(5-(3-(dimethylamino)phenyl)-[1,2,4]triazolo[1,5-a]pyridin-2-ylamino)-N-(4-methylcyclohexyl)benzamide | 2 | 469.1 |
| 271 | 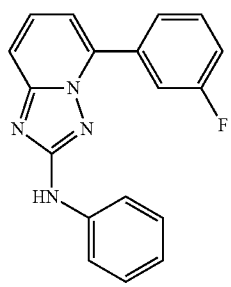 [SMILES: Fc1cccc(-c2cccc3nc(Nc4ccccc4)nn23)c1] | 5-(3-fluorophenyl)-N-phenyl-[1,2,4]triazolo[1,5-a]pyridin-2-amine | 1 | 305.3 |
| 272 | 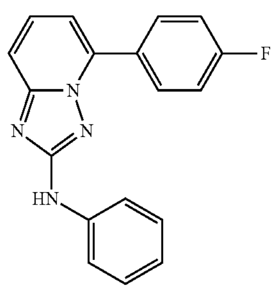 [SMILES: Fc1ccc(-c2cccc3nc(Nc4ccccc4)nn23)cc1] | 5-(4-fluorophenyl)-N-phenyl-[1,2,4]triazolo[1,5-a]pyridin-2-amine | 1 | 304.8 |
| 273 | 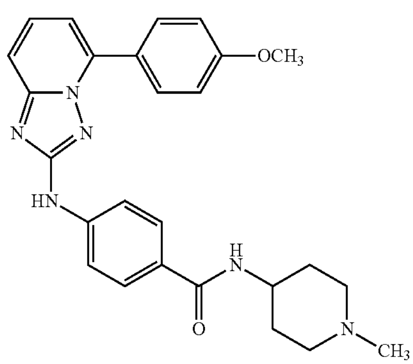 | 4-(5-(4-methoxyphenyl)-[1,2,4]triazolo[1,5-a]pyridin-2-ylamino)-N-(1-methylpiperidin-4-yl)benzamide | 2 | 457.0 |

TABLE 2-continued
| Ex | Structure | Name | Mthd | LCMS (ESI) m/z |
|---|---|---|---|---|
| 274 | 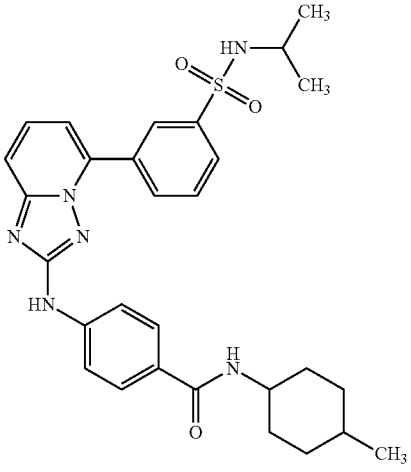 [SMILES: CC1CCC(NC(=O)c2ccc(Nc3nc4cccc(-c5cccc(S(=O)(=O)NC(C)C)c5)n4n3)cc2)CC1] | 4-(5-(3-(N-isopropylsulfamoyl)phenyl)-[1,2,4]triazolo[1,5-a]pyridin-2-ylamino)-N-(4-methylcyclohexyl)benzamide | 2 | 547.3 |
| 275 | 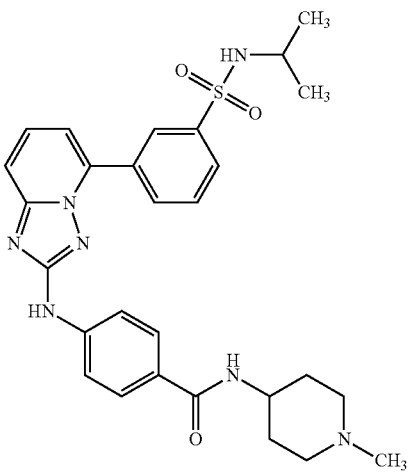 [SMILES: CC(C)NS(=O)(=O)c1cccc(-c2cccc3nc(Nc4ccc(C(=O)NC5CCN(C)CC5)cc4)nn23)c1] | 4-(5-(3-(N-isopropylsulfamoyl)phenyl)-[1,2,4]triazolo[1,5-a]pyridin-2-ylamino)-N-(1-methylpiperidin-4-yl)benzamide | 2 | 548.2 |
| 276 | 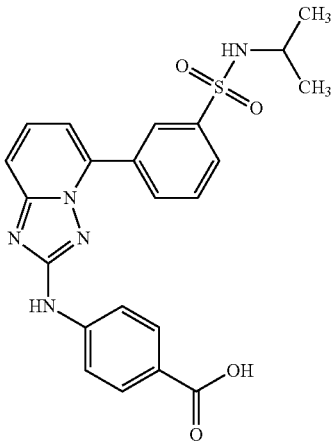 [SMILES: CC(C)NS(=O)(=O)c1cccc(-c2cccc3nc(Nc4ccc(C(=O)O)cc4)nn23)c1] | 4-(5-(3-(N-isopropylsulfamoyl)phenyl)-[1,2,4]triazolo[1,5-a]pyridin-2-ylamino)benzoic acid | 2 | 452.2 |

TABLE 2-continued

| Ex | Structure | Name | Mthd | LCMS (ESI) m/z |
|---|---|---|---|---|
| 277 | 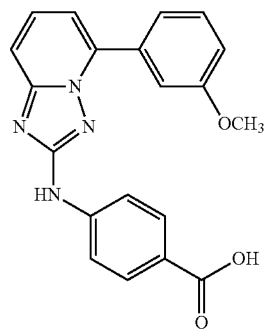 [SMILES: COc1cccc(-c2cccc3nc(Nc4ccc(C(=O)O)cc4)nn23)c1] | 4-(5-(3-methoxyphenyl)-[1,2,4]triazolo[1,5-a]pyridin-2-ylamino)benzoic acid | 2 | 360.9 |
| 278 | 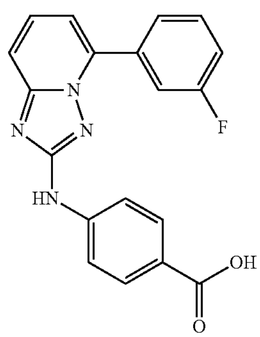 [SMILES: O=C(O)c1ccc(Nc2nc3cccc(-c4cccc(F)c4)n3n2)cc1] | 4-(5-(3-fluorophenyl)-[1,2,4]triazolo[1,5-a]pyridin-2-ylamino)benzoic acid | 2 | 348.9 |
| 279 | 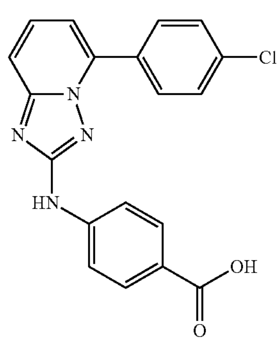 [SMILES: O=C(O)c1ccc(Nc2nc3cccc(-c4ccc(Cl)cc4)n3n2)cc1] | 4-(5-(4-chlorophenyl)-[1,2,4]triazolo[1,5-a]pyridin-2-ylamino)benzoic acid | 2 | 364.8 |
| 280 | 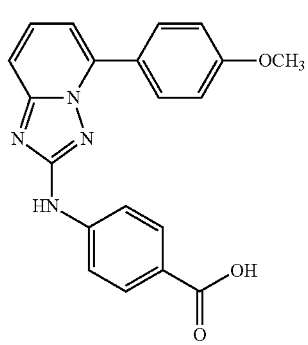 [SMILES: COc1ccc(-c2cccc3nc(Nc4ccc(C(=O)O)cc4)nn23)cc1] | 4-(5-(4-methoxyphenyl)-[1,2,4]triazolo[1,5-a]pyridin-2-ylamino)benzoic acid | 2 | 3600.9 |

TABLE 2-continued

| Ex | Structure | Name | Mthd | LCMS (ESI) m/z |
|---|---|---|---|---|
| 281 | 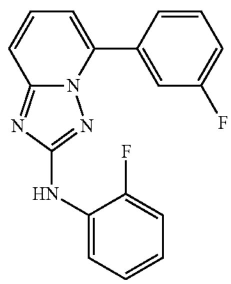 [SMILES: Fc1cccc(-c2cccc3nc(Nc4ccccc4F)nn23)c1] | N-(2-fluorophenyl)-5-(3-fluorophenyl)-[1,2,4]triazolo[1,5-a]pyridin-2-amine | 1 | 323.0 |
| 282 | 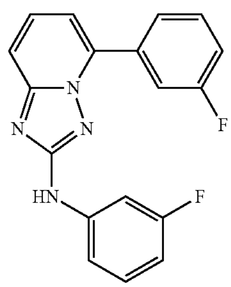 [SMILES: Fc1cccc(Nc2nc3cccc(-c4cccc(F)c4)n3n2)c1] | N,5-bis(3-fluorophenyl)-[1,2,4]triazolo[1,5-a]pyridin-2-amine | 1 | 323.2 |
| 283 | 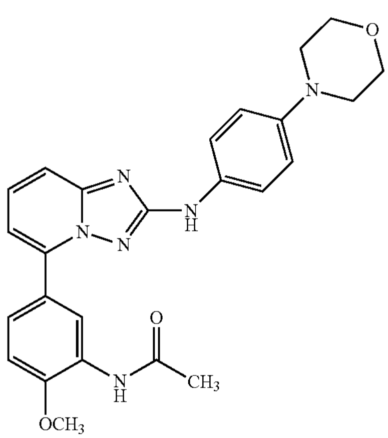 [SMILES: COc1ccc(-c2cccc3nc(Nc4ccc(N5CCOCC5)cc4)nn23)cc1NC(C)=O] | N-(2-methoxy-5-(2-(4-morpholinophenyl-amino)-[1,2,4]triazolo[1,5-a]pyridin-5-yl)phenyl)acetamide | 3 | 459.2 |
| 284 | 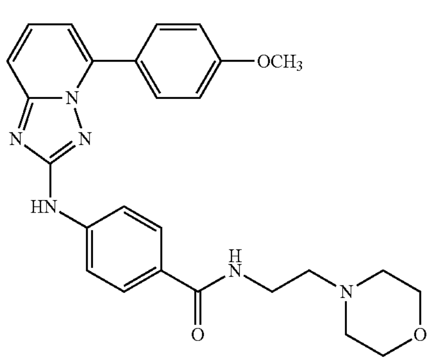 [SMILES: COc1ccc(-c2cccc3nc(Nc4ccc(C(=O)NCCN5CCOCC5)cc4)nn23)cc1] | 4-(5-(4-methoxyphenyl)-[1,2,4]triazolo[1,5-a]pyridin-2-ylamino)-N-(2-morpholinoethyl)benzamide | 2 | 473.0 |

TABLE 2-continued

| Ex | Structure | Name | Mthd | LCMS (ESI) m/z |
|---|---|---|---|---|
| 285 | 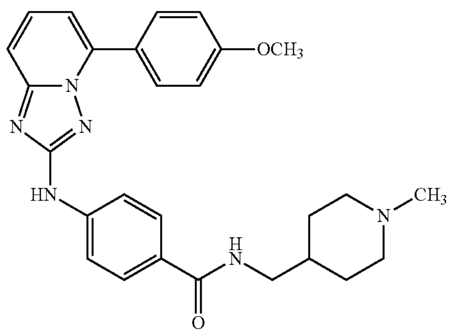 [SMILES: COc1ccc(-c2cccc3nc(Nc4ccc(C(=O)NCC5CCN(C)CC5)cc4)nn23)cc1] | 4-(5-(4-methoxyphenyl)-[1,2,4]triazolo[1,5-a]pyridin-2-ylamino)-N-((1-methylpiperidin-4-yl)methyl)benzamide | 2 | 471.0 |
| 286 | 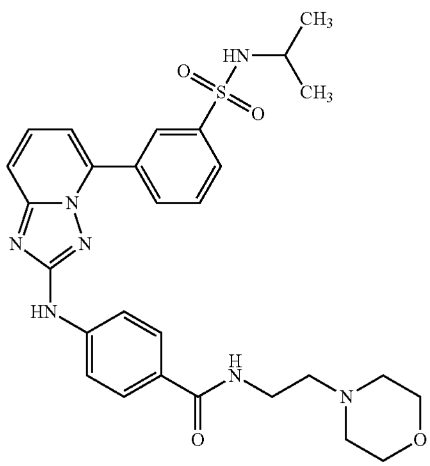 [SMILES: CC(C)NS(=O)(=O)c1cccc(-c2cccc3nc(Nc4ccc(C(=O)NCCN5CCOCC5)cc4)nn23)c1] | 4-(5-(3-(N-isopropylsulfamoyl)phenyl)-[1,2,4]triazolo[1,5-a]pyridin-2-ylamino)-N-(2-morpholinoethyl)benzamide | 2 | 564.2 |
| 287 | 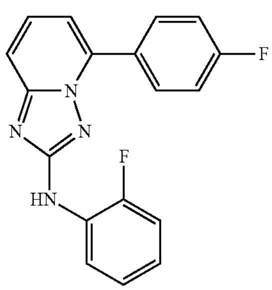 [SMILES: Fc1ccc(-c2cccc3nc(Nc4ccccc4F)nn23)cc1] | N-(2-fluorophenyl)-5-(4-fluorophenyl)-[1,2,4]triazolo[1,5-a]pyridin-2-amine | 1 | 322.8 |
| 288 | 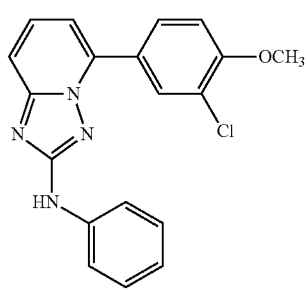 [SMILES: COc1ccc(-c2cccc3nc(Nc4ccccc4)nn23)cc1Cl] | 5-(3-chloro-4-methoxyphenyl)-N-phenyl-[1,2,4]triazolo[1,5-a]pyridin-2-amine | 1 | 351.1 |

TABLE 2-continued

| Ex | Structure | Name | Mthd | LCMS (ESI) m/z |
|---|---|---|---|---|
| 289 | 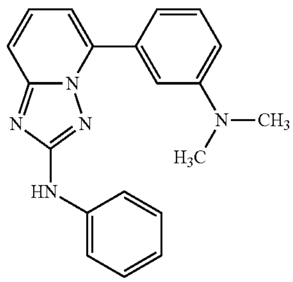 [SMILES: CN(C)c1cccc(-c2cccc3nc(Nc4ccccc4)nn23)c1] | 5-(3-(dimethylamino)phenyl)-N-phenyl-[1,2,4]triazolo[1,5-a]pyridin-2-amine | 1 | 330.1 |
| 290 | 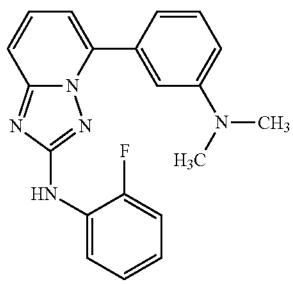 [SMILES: CN(C)c1cccc(-c2cccc3nc(Nc4ccccc4F)nn23)c1] | 5-(3-(dimethylamino)phenyl)-N-(2-fluorophenyl)-[1,2,4]triazolo[1,5-a]pyridin-2-amine | 1 | 348.1 |
| 291 | 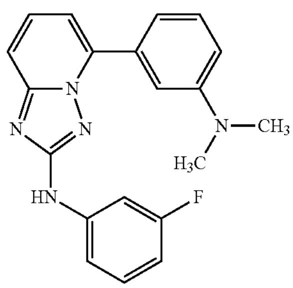 [SMILES: CN(C)c1cccc(-c2cccc3nc(Nc4cccc(F)c4)nn23)c1] | 5-(3-(dimethylamino)phenyl)-N-(3-fluorophenyl)-[1,2,4]triazolo[1,5-a]pyridin-2-amine | 1 | 348.1 |
| 292 | 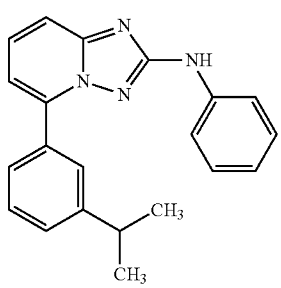 | 5-(3-isopropylphenyl)-N-phenyl-[1,2,4]triazolo[1,5-a]pyridin-2-amine | 1 | 329.2 |
| 293 | 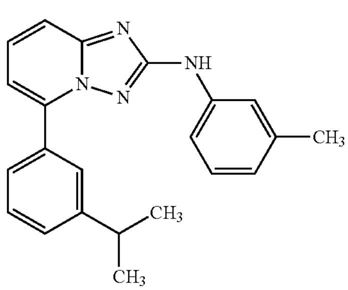 | 5-(3-isopropylphenyl)-N-m-tolyl-[1,2,4]triazolo[1,5-a]pyridin-2-amine | 1 | 343.2 |

TABLE 2-continued

| Ex | Structure | Name | Mthd | LCMS (ESI) m/z |
|---|---|---|---|---|
| 294 | 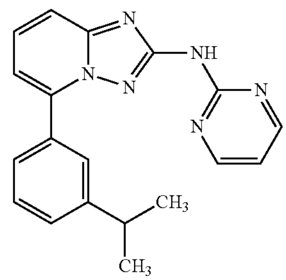 [SMILES: CC(C)c1cccc(-c2cccc3nc(Nc4ncccn4)nn23)c1] | 5-(3-isopropylphenyl)-N-(pyrimidin-2-yl)-[1,2,4]triazolo[1,5-a]pyridin-2-amine | 1 | 331.2 |
| 295 | 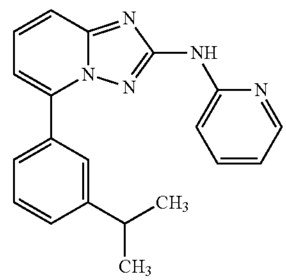 | 5-(3-isopropylphenyl)-N-(pyridin-2-yl)-[1,2,4]triazolo[1,5-a]pyridin-2-amine | 1 | 330.2 |
| 296 | 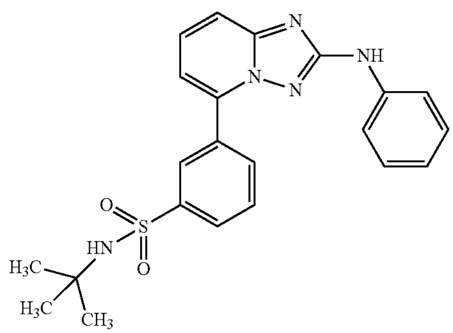 [SMILES: CC(C)(C)NS(=O)(=O)c1cccc(-c2cccc3nc(Nc4ccccc4)nn23)c1] | N-tert-butyl-3-(2-(phenylamino)-[1,2,4]triazolo[1,5-a]pyridin-5-yl)benzene-sulfonamide | 1 | 422.2 |
| 297 | 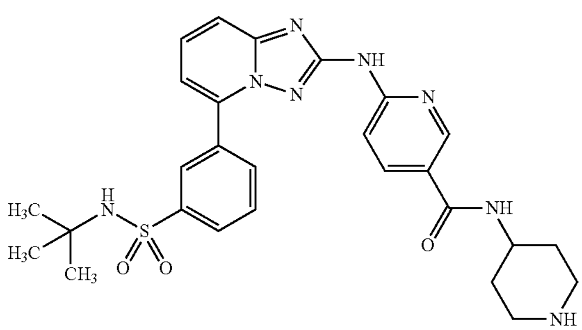 [SMILES: CC(C)(C)NS(=O)(=O)c1cccc(-c2cccc3nc(Nc4ccc(C(=O)NC5CCNCC5)cn4)nn23)c1] | 6-(5-(3-(N-tert-butylsulfamoyl)phenyl)-[1,2,4]triazolo[1,5-a]pyridin-2-ylamino)-N-(piperidin-4-yl)nicotinamide | 1 | 549.2 |
| 298 | 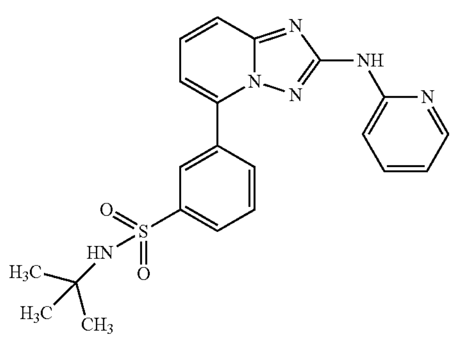 [SMILES: CC(C)(C)NS(=O)(=O)c1cccc(-c2cccc3nc(Nc4ccccn4)nn23)c1] | N-tert-butyl-3-(2-(pyridin-2-ylamino)-[1,2,4]triazolo[1,5-a]pyridin-5-yl)benzene-sulfonamide | 1 | 423.2 |

TABLE 2-continued

| Ex | Structure | Name | Mthd | LCMS (ESI) m/z |
|---|---|---|---|---|
| 299 | 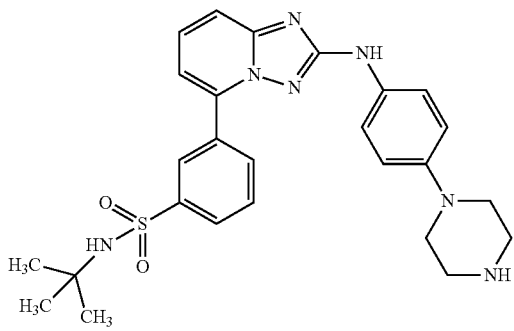 [SMILES: CC(C)(C)NS(=O)(=O)c1cccc(-c2cccc3nc(Nc4ccc(N5CCNCC5)cc4)nn23)c1] | N-tert-butyl-3-(2-(4-(piperazin-1-yl)phenylamino)-[1,2,4]triazolo[1,5-a]pyridin-5-yl)benzenesulfonamide | 1 | 506.2 |
| 300 | 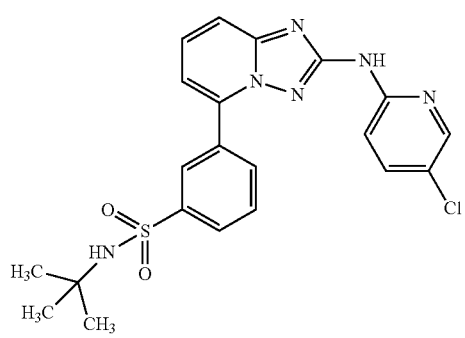 [SMILES: CC(C)(C)NS(=O)(=O)c1cccc(-c2cccc3nc(Nc4ccc(Cl)cn4)nn23)c1] | N-tert-butyl-3-(2-(5-chloropyridin-2-ylamino)-[1,2,4]triazolo[1,5-a]pyridin-5-yl)benzenesulfonamide | 1 | 457.1 |
| 301 | 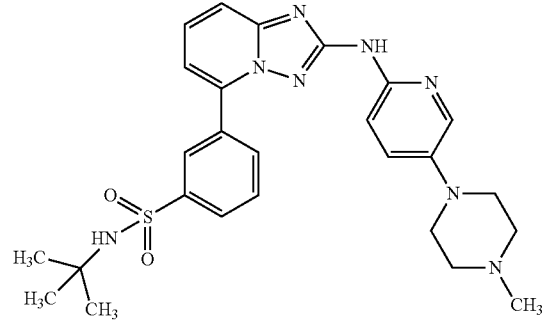 [SMILES: CN1CCN(c2ccc(Nc3nc4cccc(-c5cccc(S(=O)(=O)NC(C)(C)C)c5)n4n3)nc2)CC1] | N-tert-butyl-3-(2-(5-(4-methylpiperazin-1-yl)pyridin-2-ylamino)-[1,2,4]triazolo[1,5-a]pyridin-5-yl)benzenesulfonamide | 1 | 521.3 |
| 302 | 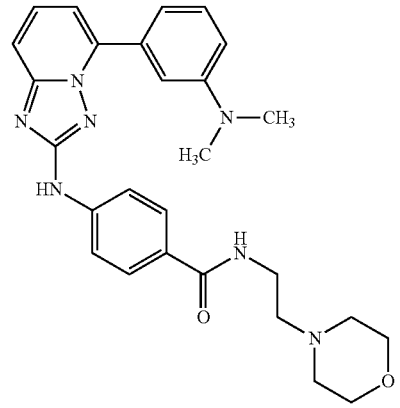 [SMILES: CN(C)c1cccc(-c2cccc3nc(Nc4ccc(C(=O)NCCN5CCOCC5)cc4)nn23)c1] | 4-(5-(3-(dimethylamino)phenyl)-[1,2,4]triazolo[1,5-a]pyridin-2-ylamino)-N-(2-morpholinoethyl)benzamide | 2 | 486.1 |

TABLE 2-continued

| Ex | Structure | Name | Mthd | LCMS (ESI) m/z |
|---|---|---|---|---|
| 303 | 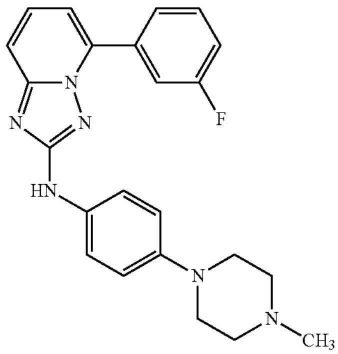 [SMILES: CN1CCN(c2ccc(Nc3nc4cccc(-c5cccc(F)c5)n4n3)cc2)CC1] | 5-(3-fluorophenyl)-N-(4-(4-methylpiperazin-1-yl)phenyl)-[1,2,4]triazolo[1,5-a]pyridin-2-amine | 231 | 403.2 |
| 304 | 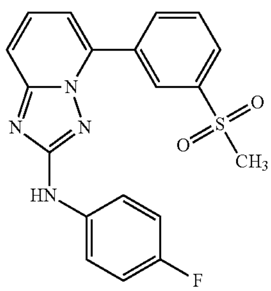 [SMILES: CS(=O)(=O)c1cccc(-c2cccc3nc(Nc4ccc(F)cc4)nn23)c1] | N-(4-fluorophenyl)-5-(3-(methylsulfonyl)phenyl)-[1,2,4]triazolo[1,5-a]pyridin-2-amine | 1 | 383.0 |
| 305 | 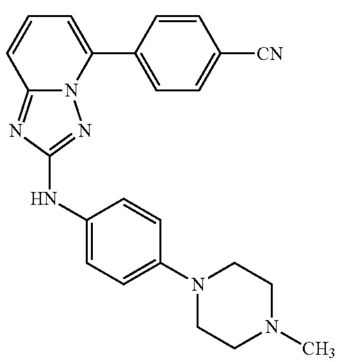 [SMILES: CN1CCN(c2ccc(Nc3nc4cccc(-c5ccc(C#N)cc5)n4n3)cc2)CC1] | 4-(2-(4-(4-methylpiperazin-1-yl)phenylamino)-[1,2,4]triazolo[1,5-a]pyridin-5-yl)benzonitrile | 231 | 410.1 |
| 306 | 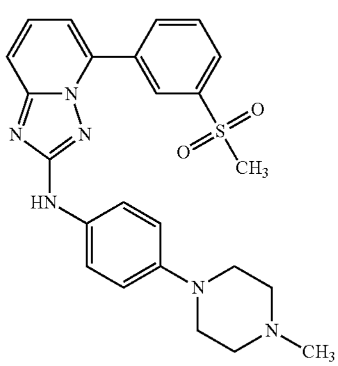 [SMILES: CN1CCN(c2ccc(Nc3nc4cccc(-c5cccc(S(C)(=O)=O)c5)n4n3)cc2)CC1] | N-(4-(4-methylpiperazin-1-yl)phenyl)-5-(3-(methylsulfonyl)phenyl)-[1,2,4]triazolo[1,5-a]pyridin-2-amine | 231 | 463.2 |

TABLE 2-continued

| Ex | Name | Mthd | LCMS (ESI) m/z |
|---|---|---|---|
| 307 | N-(4-(4-methylpiperazin-1-yl)phenyl)-5-(3-(trifluoromethoxy)phenyl)-[1,2,4]triazolo[1,5-a]pyridin-2-amine | 231 | 469.1 |
| 308 | 4-(2-(o-tolylamino)-[1,2,4]triazolo[1,5-a]pyridin-5-yl)benzonitrile | 1 | 326.0 |
| 309 | N-tert-butyl-3-(2-(5-(piperazin-1-yl)pyridin-2-ylamino)-[1,2,4]triazolo[1,5-a]pyridin-5-yl)benzenesulfonamide | 1 | 507.2 |
| 310 | 5-(4-fluorophenyl)-N-(4-(4-methylpiperazin-1-yl)phenyl)-[1,2,4]triazolo[1,5-a]pyridin-2-amine | 231 | 403.2 |

TABLE 2-continued

| Ex | Name | Mthd | LCMS (ESI) m/z |
|---|---|---|---|
| 311 | 5-(1H-indazol-4-yl)-N-(4-(4-methylpiperazin-1-yl)phenyl)-[1,2,4]triazolo[1,5-a]pyridin-2-amine | 231 | 425.2 |
| 312 | N-(4-(4-methylpiperazin-1-yl)phenyl)-5-(4-(morpholinomethyl)phenyl)-[1,2,4]triazolo[1,5-a]pyridin-2-amine | 231 | 484.3 |
| 313 | N-(4-(4-methylpiperazin-1-yl)phenyl)-5-(3-(trifluoromethyl)phenyl)-[1,2,4]triazolo[1,5-a]pyridin-2-amine | 231 | 453.2 |
| 314 | 5-(3-methoxyphenyl)-N-(4-(4-methylpiperazin-1-yl)phenyl)-[1,2,4]triazolo[1,5-a]pyridin-2-amine | 231 | 415.3 |

TABLE 2-continued
| Ex | Structure | Name | Mthd | LCMS (ESI) m/z |
|----|-----------|------|------|----------------|
| 315 | 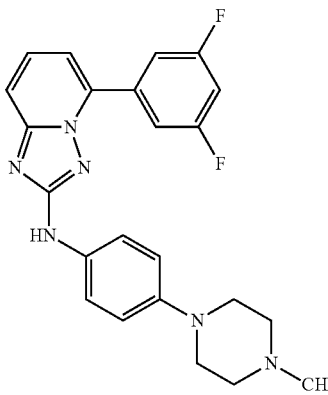 | 5-(3,5-difluorophenyl)-N-(4-(4-methylpiperazin-1-yl)phenyl)-[1,2,4]triazolo[1,5-a]pyridin-2-amine | 231 | 421.2 |
| 316 | 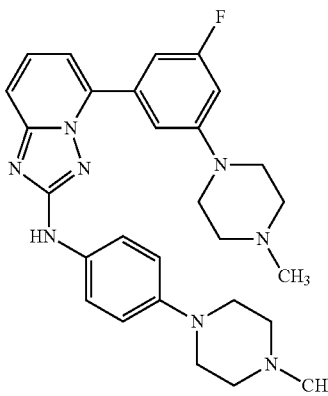 | 5-(3-fluoro-5-(4-methylpiperazin-1-yl)phenyl)-N-(4-(4-methylpiperazin-1-yl)phenyl)-[1,2,4]triazolo[1,5-a]pyridin-2-amine | 231 | 501.0 |
| 317 | 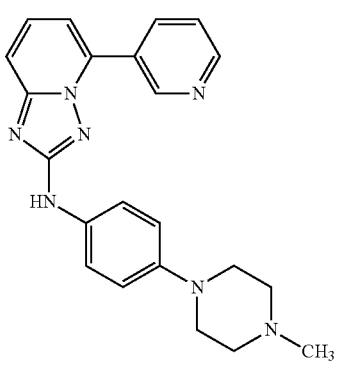 [SMILES: CN1CCN(c2ccc(Nc3nc4cccc(-c5cccnc5)n4n3)cc2)CC1] | N-(4-(4-methylpiperazin-1-yl)phenyl)-5-(pyridin-3-yl)-[1,2,4]triazolo[1,5-a]pyridin-2-amine | 231 | 386.1 |
| 318 | 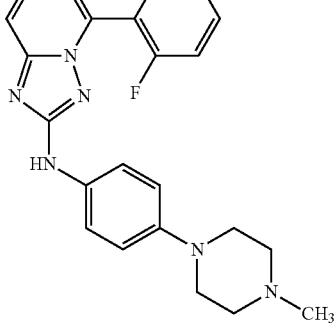 | 5-(2-fluorophenyl)-N-(4-(4-methylpiperazin-1-yl)phenyl)-[1,2,4]triazolo[1,5-a]pyridin-2-amine | 231 | 402.9 |

TABLE 2-continued

| Ex | Structure | Name | Mthd | LCMS (ESI) m/z |
|---|---|---|---|---|
| 319 | 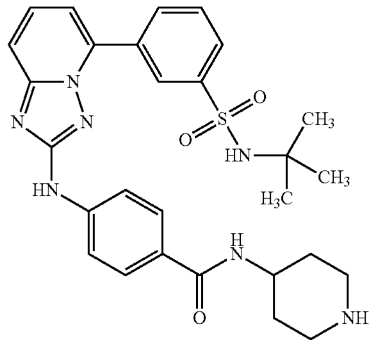 [SMILES: CC(C)(C)NS(=O)(=O)c1cccc(-c2cccc3nc(Nc4ccc(C(=O)NC5CCNCC5)cc4)nn23)c1] | 4-(5-(3-(N-tert-butylsulfamoyl)phenyl)-[1,2,4]triazolo[1,5-a]pyridin-2-ylamino)-N-(piperidin-4-yl)benzamide | 2 | 548.1 |
| 320 | 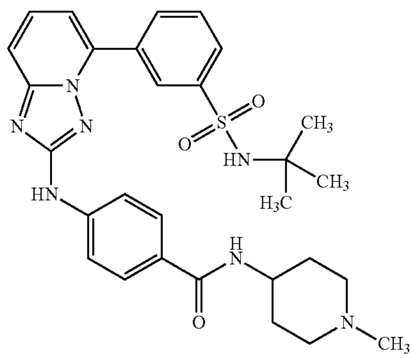 [SMILES: CN1CCC(NC(=O)c2ccc(Nc3nc4cccc(-c5cccc(S(=O)(=O)NC(C)(C)C)c5)n4n3)cc2)CC1] | 4-(5-(3-(N-tert-butylsulfamoyl)phenyl)-[1,2,4]triazolo[1,5-a]pyridin-2-ylamino)-N-(1-methylpiperidin-4-yl)benzamide | 2 | 562.2 |
| 321 | 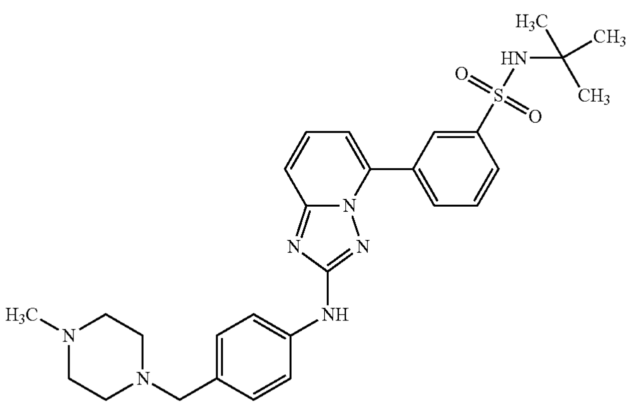 [SMILES: CN1CCN(Cc2ccc(Nc3nc4cccc(-c5cccc(S(=O)(=O)NC(C)(C)C)c5)n4n3)cc2)CC1] | N-tert-butyl-3-(2-(4-((4-methylpiperazin-1-yl)methyl)phenylamino)-[1,2,4]triazolo[1,5-a]pyridin-5-yl)benzenesulfonamide | 232 | 534.1 |
| 322 | 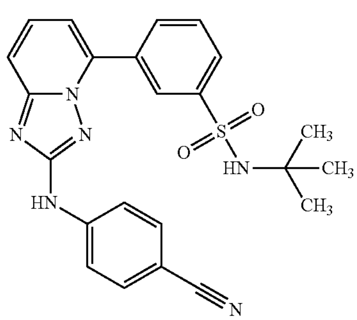 [SMILES: CC(C)(C)NS(=O)(=O)c1cccc(-c2cccc3nc(Nc4ccc(C#N)cc4)nn23)c1] | N-tert-butyl-3-(2-(4-cyanophenylamino)-[1,2,4]triazolo[1,5-a]pyridin-5-yl)benzenesulfonamide | 1 | 446.9 |

TABLE 2-continued

| Ex | Structure | Name | Mthd | LCMS (ESI) m/z |
|---|---|---|---|---|
| 323 | 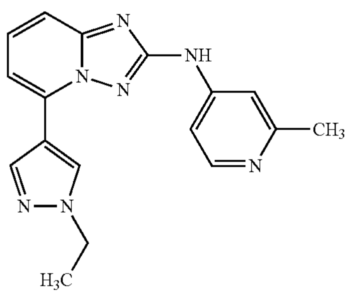 [SMILES: CCn1cc(-c2cccc3nc(Nc4ccnc(C)c4)nn23)cn1] | 5-(1-ethyl-1H-pyrazol-4-yl)-N-(2-methylpyridin-4-yl)-[1,2,4]triazolo[1,5-a]pyridin-2-amine | 1 | 320.2 |
| 324 | 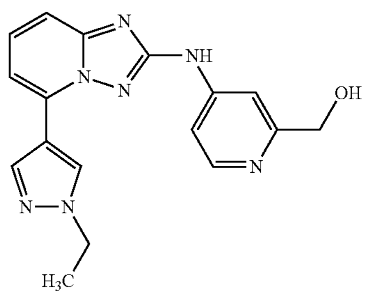 [SMILES: CCn1cc(-c2cccc3nc(Nc4ccnc(CO)c4)nn23)cn1] | (4-(5-(1-ethyl-1H-pyrazol-4-yl)-[1,2,4]triazolo[1,5-a]pyridin-2-ylamino)pyridin-2-yl)methanol | 1 | 336.2 |
| 325 | 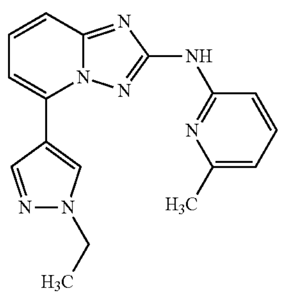 | 5-(1-ethyl-1H-pyrazol-4-yl)-N-(6-methylpyridin-2-yl)-[1,2,4]triazolo[1,5-a]pyridin-2-amine | 1 | 320.2 |
| 326 | 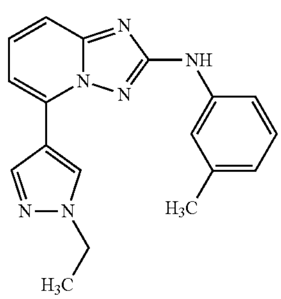 [SMILES: CCn1cc(-c2cccc3nc(Nc4cccc(C)c4)nn23)cn1] | 5-(1-ethyl-1H-pyrazol-4-yl)-N-m-tolyl-[1,2,4]triazolo[1,5-a]pyridin-2-amine | 1 | 319.2 |
| 327 | 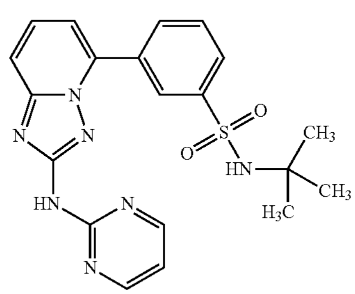 [SMILES: CC(C)(C)NS(=O)(=O)c1cccc(-c2cccc3nc(Nc4ncccn4)nn23)c1] | N-tert-butyl-3-(2-(pyrimidin-2-ylamino)-[1,2,4]triazolo[1,5-a]pyridin-5-yl)benzenesulfonamide | 1 | 424.0 |

TABLE 2-continued

| Ex | Structure | Name | Mthd | LCMS (ESI) m/z |
|---|---|---|---|---|
| 328 | 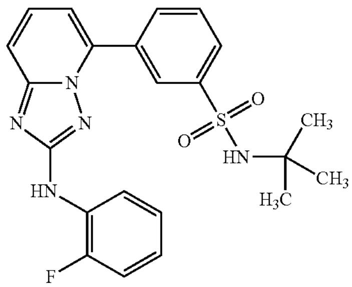 [SMILES: CC(C)(C)NS(=O)(=O)c1cccc(-c2cccc3nc(Nc4ccccc4F)nn23)c1] | N-tert-butyl-3-(2-(2-fluorophenylamino)-[1,2,4]triazolo[1,5-a]pyridin-5-yl)benzene-sulfonamide | 1 | 439.9 |
| 329 | 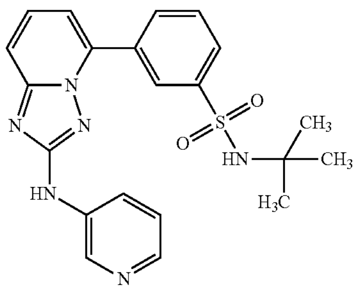 [SMILES: CC(C)(C)NS(=O)(=O)c1cccc(-c2cccc3nc(Nc4cccnc4)nn23)c1] | N-tert-butyl-3-(2-(pyridin-3-ylamino)-[1,2,4]triazolo[1,5-a]pyridin-5-yl)benzene-sulfonamide | 1 | 423.0 |
| 330 | 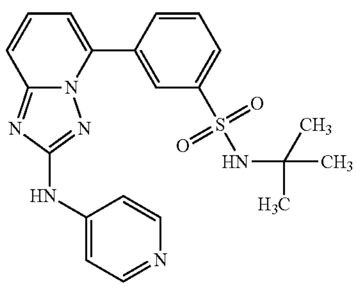 [SMILES: CC(C)(C)NS(=O)(=O)c1cccc(-c2cccc3nc(Nc4ccncc4)nn23)c1] | N-tert-butyl-3-(2-(pyridin-4-ylamino)-[1,2,4]triazolo[1,5-a]pyridin-5-yl)benzene-sulfonamide | 1 | 422.9 |
| 331 | 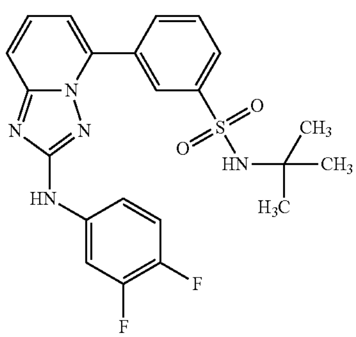 [SMILES: CC(C)(C)NS(=O)(=O)c1cccc(-c2cccc3nc(Nc4ccc(F)c(F)c4)nn23)c1] | N-tert-butyl-3-(2-(3,4-difluorophenyl-amino)-[1,2,4]triazolo[1,5-a]pyridin-5-yl)benzene-sulfonamide | 1 | 457.9 |
| 332 | 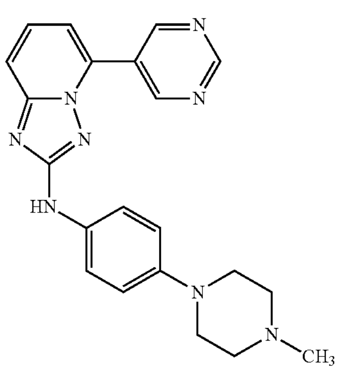 [SMILES: CN1CCN(c2ccc(Nc3nc4cccc(-c5cncnc5)n4n3)cc2)CC1] | N-(4-(4-methylpiperazin-1-yl)phenyl)-5-(pyrimidin-5-yl)-[1,2,4]triazolo[1,5-a]pyridin-2-amine | 231 | 387.2 |

TABLE 2-continued

| Ex | Structure | Name | Mthd | LCMS (ESI) m/z |
|---|---|---|---|---|
| 333 | 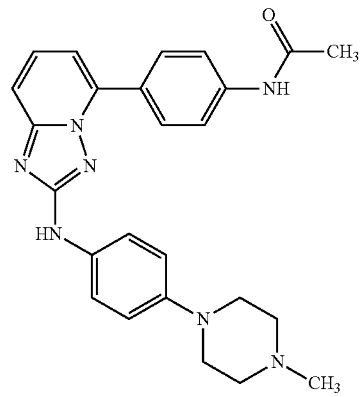 [SMILES: CC(=O)Nc1ccc(-c2cccc3nc(Nc4ccc(N5CCN(C)CC5)cc4)nn23)cc1] | N-(4-(2-(4-(4-methylpiperazin-1-yl)phenylamino)-[1,2,4]triazolo[1,5-a]pyridin-5-yl)phenyl)acetamide | 231 | 442.2 |
| 334 | 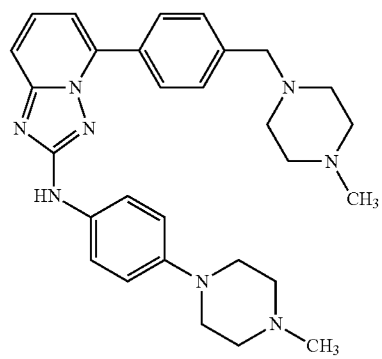 [SMILES: CN1CCN(Cc2ccc(-c3cccc4nc(Nc5ccc(N6CCN(C)CC6)cc5)nn34)cc2)CC1] | 5-(4-((4-methylpiperazin-1-yl)methyl)phenyl)-N-(4-(4-methylpiperazin-1-yl)phenyl)-[1,2,4]triazolo[1,5-a]pyridin-2-amine | 231 | 497.3 |
| 335 | 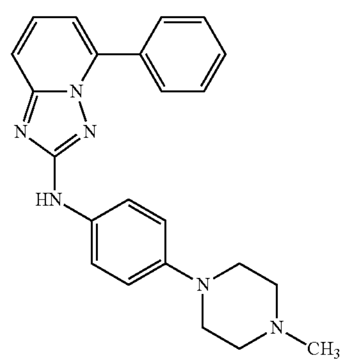 [SMILES: CN1CCN(c2ccc(Nc3nc4cccc(-c5ccccc5)n4n3)cc2)CC1] | N-(4-(4-methylpiperazin-1-yl)phenyl)-5-phenyl-[1,2,4]triazolo[1,5-a]pyridin-2-amine | 231 | 385.0 |
| 336 | 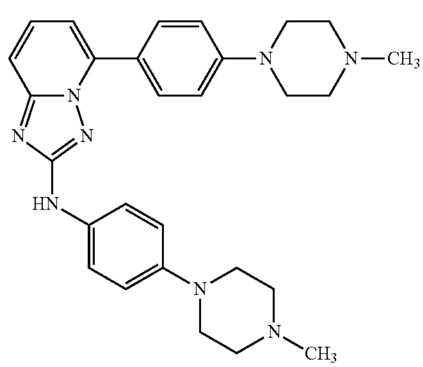 [SMILES: CN1CCN(c2ccc(Nc3nc4cccc(-c5ccc(N6CCN(C)CC6)cc5)n4n3)cc2)CC1] | N,5-bis(4-(4-methylpiperazin-1-yl)phenyl)-[1,2,4]triazolo[1,5-a]pyridin-2-amine | 231 | 483.1 |

TABLE 2-continued

| Ex | Name | Mthd | LCMS (ESI) m/z |
|---|---|---|---|
| 337 | N-tert-butyl-3-(2-(o-tolylamino)-[1,2,4]triazolo[1,5-a]pyridin-5-yl)benzenesulfonamide | 1 | 436.0 |
| 338 | 3-(5-(3-(N-tert-butylsulfamoyl)phenyl)-[1,2,4]triazolo[1,5-a]pyridin-2-ylamino)-N,N-dimethylbenzamide | 2 | 493.1 |
| 339 | 3-(5-(3-(N-tert-butylsulfamoyl)phenyl)-[1,2,4]triazolo[1,5-a]pyridin-2-ylamino)-N-(2-morpholinoethyl)benzamide | 2 | 578.1 |
| 340 | 3-(5-(3-(N-tert-butylsulfamoyl)phenyl)-[1,2,4]triazolo[1,5-a]pyridin-2-ylamino)-N-(piperidin-4-yl)benzamide | 2 | 548.1 |

TABLE 2-continued

| Ex | Structure | Name | Mthd | LCMS (ESI) m/z |
|---|---|---|---|---|
| 341 | 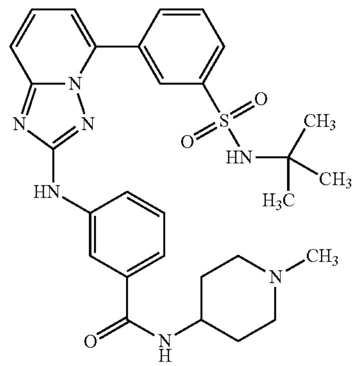 [SMILES: CN1CCC(NC(=O)c2cccc(Nc3nc4cccc(-c5cccc(S(=O)(=O)NC(C)(C)C)c5)n4n3)c2)CC1] | 3-(5-(3-(N-tert-butylsulfamoyl)phenyl)-[1,2,4]triazolo[1,5-a]pyridin-2-ylamino)-N-(1-methylpiperidin-4-yl)benzamide | 2 | 561.9 |
| 342 | 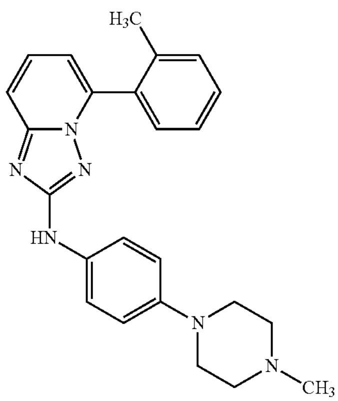 [SMILES: Cc1ccccc1-c1cccc2nc(Nc3ccc(N4CCN(C)CC4)cc3)nn12] | N-(4-(4-methylpiperazin-1-yl)phenyl)-5-o-tolyl-[1,2,4]triazolo[1,5-a]pyridin-2-amine | 231 | 399.0 |
| 343 | 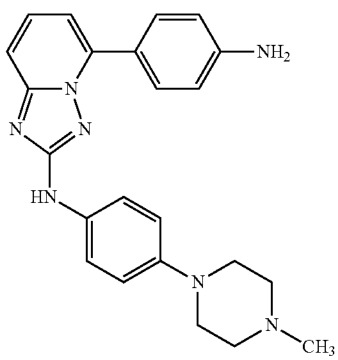 [SMILES: CN1CCN(c2ccc(Nc3nc4cccc(-c5ccc(N)cc5)n4n3)cc2)CC1] | 5-(4-aminophenyl)-N-(4-(4-methylpiperazin-1-yl)phenyl)-[1,2,4]triazolo[1,5-a]pyridin-2-amine | 231 | 400.0 |
| 344 | 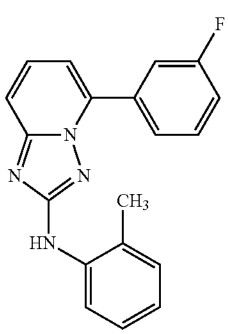 [SMILES: Cc1ccccc1Nc1nc2cccc(-c3cccc(F)c3)n2n1] | 5-(3-fluorophenyl)-N-o-tolyl-[1,2,4]triazolo[1,5-a]pyridin-2-amine | 1 | 319.3 |

TABLE 2-continued

| Ex | Structure | Name | Mthd | LCMS (ESI) m/z |
|---|---|---|---|---|
| 345 | 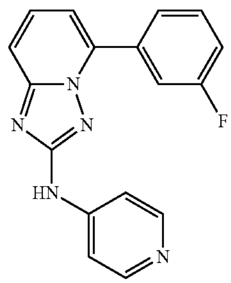 [SMILES: Fc1cccc(-c2cccc3nc(Nc4ccncc4)nn23)c1] | 5-(3-fluorophenyl)-N-(pyridin-4-yl)-[1,2,4]triazolo[1,5-a]pyridin-2-amine | 1 | 306.3 |
| 346 | 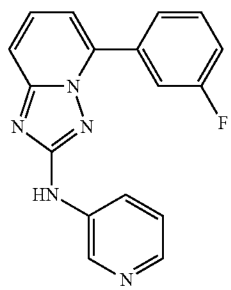 [SMILES: Fc1cccc(-c2cccc3nc(Nc4cccnc4)nn23)c1] | 5-(3-fluorophenyl)-N-(pyridin-3-yl)-[1,2,4]triazolo[1,5-a]pyridin-2-amine | 1 | 306.3 |
| 347 | 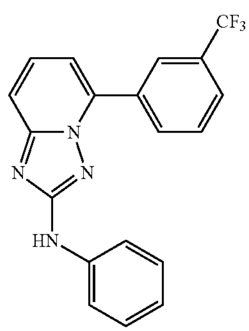 [SMILES: FC(F)(F)c1cccc(-c2cccc3nc(Nc4ccccc4)nn23)c1] | N-phenyl-5-(3-(trifluoromethyl)phenyl)-[1,2,4]triazolo[1,5-a]pyridin-2-amine | 1 | 355.3 |
| 348 | 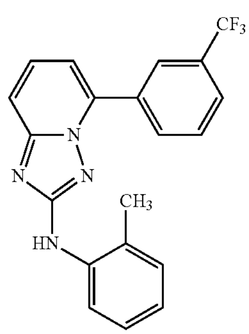 [SMILES: Cc1ccccc1Nc1nc2cccc(-c3cccc(C(F)(F)F)c3)n2n1] | N-o-tolyl-5-(3-(trifluoromethyl)phenyl)-[1,2,4]triazolo[1,5-a]pyridin-2-amine | 1 | 369.3 |
| 349 | 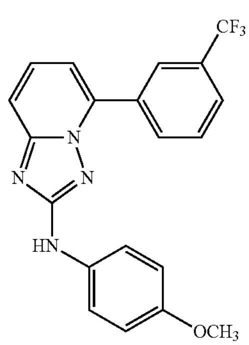 [SMILES: COc1ccc(Nc2nc3cccc(-c4cccc(C(F)(F)F)c4)n3n2)cc1] | N-(4-methoxyphenyl)-5-(3-(trifluoromethyl)phenyl)-[1,2,4]triazolo[1,5-a]pyridin-2-amine | 1 | 385.3 |

TABLE 2-continued

| Ex | Structure | Name | Mthd | LCMS (ESI) m/z |
|---|---|---|---|---|
| 350 | 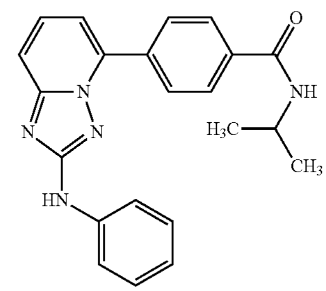 [SMILES: CC(C)NC(=O)c1ccc(-c2cccc3nc(Nc4ccccc4)nn23)cc1] | N-isopropyl-4-(2-(phenylamino)-[1,2,4]triazolo[1,5-a]pyridin-5-yl)benzamide | 1 | 372.3 |
| 351 | 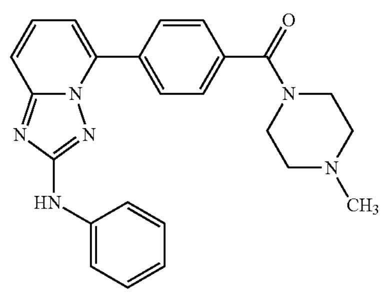 [SMILES: CN1CCN(C(=O)c2ccc(-c3cccc4nc(Nc5ccccc5)nn34)cc2)CC1] | (4-methylpiperazin-1-yl)(4-(2-(phenylamino)-[1,2,4]triazolo[1,5-a]pyridin-5-yl)phenyl)methanone | 1 | 413.3 |
| 352 | 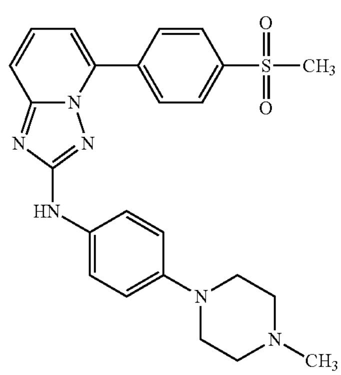 [SMILES: CN1CCN(c2ccc(Nc3nc4cccc(-c5ccc(S(C)(=O)=O)cc5)n4n3)cc2)CC1] | N-(4-(4-methylpiperazin-1-yl)phenyl)-5-(4-(methylsulfonyl)phenyl)-[1,2,4]triazolo[1,5-a]pyridin-2-amine | 231 | 462.9 |
| 353 | 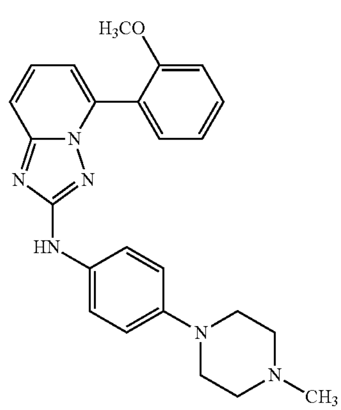 | 5-(2-methoxyphenyl)-N-(4-(4-methylpiperazin-1-yl)phenyl)-[1,2,4]triazolo[1,5-a]pyridin-2-amine | 231 | 415.0 |

TABLE 2-continued

| Ex | Structure | Name | Mthd | LCMS (ESI) m/z |
|---|---|---|---|---|
| 354 | 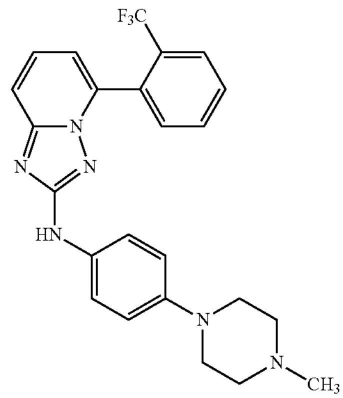 | N-(4-(4-methylpiperazin-1-yl)phenyl)-5-(2-(trifluoromethyl)phenyl)-[1,2,4]triazolo[1,5-a]pyridin-2-amine | 231 | 453.2 |
| 355 | 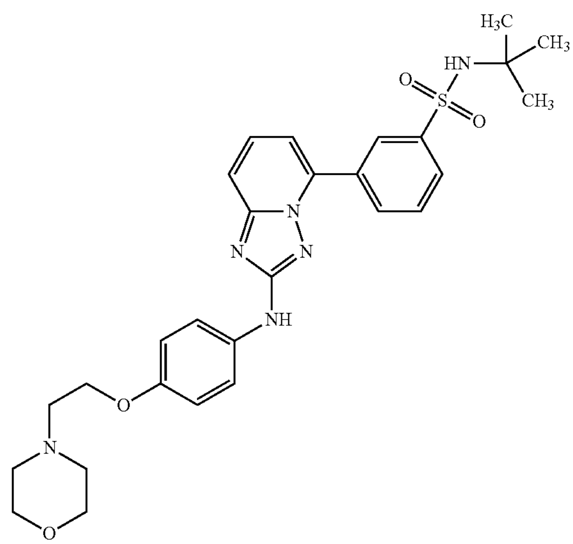 [SMILES: CC(C)(C)NS(=O)(=O)c1cccc(-c2cccc3nc(Nc4ccc(OCCN5CCOCC5)cc4)nn23)c1] | N-tert-butyl-3-(2-(4-(2-morpholinoethoxy)phenylamino)-[1,2,4]triazolo[1,5-a]pyridin-5-yl)benzene-sulfonamide | 234 | 551.0 |
| 356 | 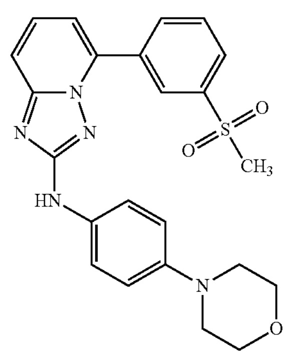 [SMILES: CS(=O)(=O)c1cccc(-c2cccc3nc(Nc4ccc(N5CCOCC5)cc4)nn23)c1] | 5-(3-(methylsulfonyl)phenyl)-N-(4-morpholinophenyl)-[1,2,4]triazolo[1,5-a]pyridin-2-amine | 231 | 450.2 |
| 357 | 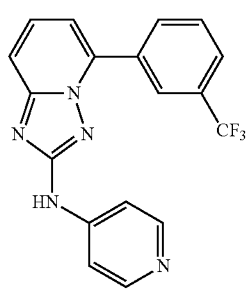 [SMILES: FC(F)(F)c1cccc(-c2cccc3nc(Nc4ccncc4)nn23)c1] | N-(pyridin-4-yl)-5-(3-(trifluoromethyl)phenyl)-[1,2,4]triazolo[1,5-a]pyridin-2-amine | 1 | 356.1 |

TABLE 2-continued

| Ex | Structure | Name | Mthd | LCMS (ESI) m/z |
|---|---|---|---|---|
| 358 | 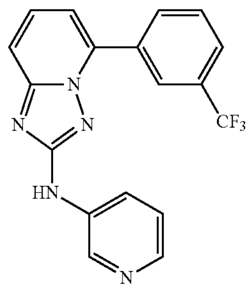 [SMILES: FC(F)(F)c1cccc(-c2cccc3nc(Nc4cccnc4)nn23)c1] | N-(pyridin-3-yl)-5-(3-(trifluoromethyl)phenyl)-[1,2,4]triazolo[1,5-a]pyridin-2-amine | 1 | 355.9 |
| 359 | 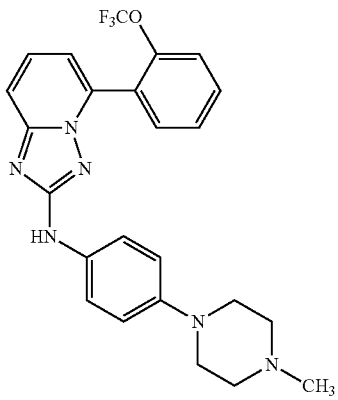 [SMILES: CN1CCN(c2ccc(Nc3nc4cccc(-c5ccccc5OC(F)(F)F)n4n3)cc2)CC1] | N-(4-(4-methylpiperazin-1-yl)phenyl)-5-(2-(trifluoromethoxy)phenyl)-[1,2,4]triazolo[1,5-a]pyridin-2-amine | 231 | 469.1 |
| 360 | 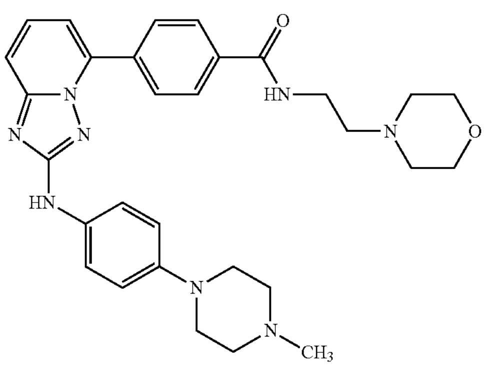 [SMILES: CN1CCN(c2ccc(Nc3nc4cccc(-c5ccc(C(=O)NCCN6CCOCC6)cc5)n4n3)cc2)CC1] | 4-(2-(4-(4-methylpiperazin-1-yl)phenylamino)-[1,2,4]triazolo[1,5-a]pyridin-5-yl)-N-(2-morpholinoethyl)benzamide | 231 | 541.1 |
| 361 | 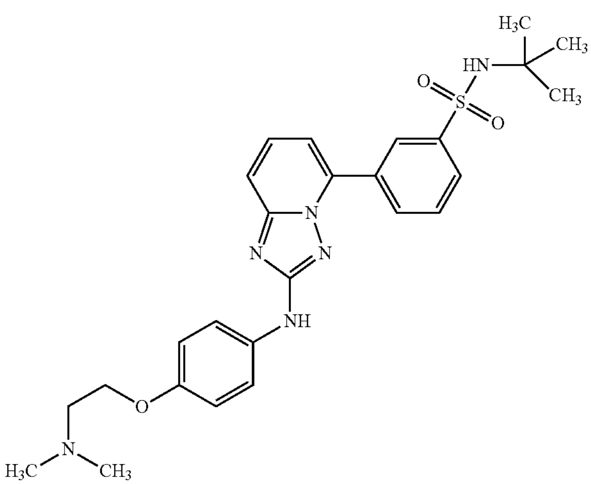 [SMILES: CN(C)CCOc1ccc(Nc2nc3cccc(-c4cccc(S(=O)(=O)NC(C)(C)C)c4)n3n2)cc1] | N-tert-butyl-3-(2-(4-(2-(dimethylamino)ethoxy)phenylamino)-[1,2,4]triazolo[1,5-a]pyridin-5-yl)benzenesulfonamide | 234 | 509.3 |

TABLE 2-continued

| Ex | Structure | Name | Mthd | LCMS (ESI) m/z |
|---|---|---|---|---|
| 362 | 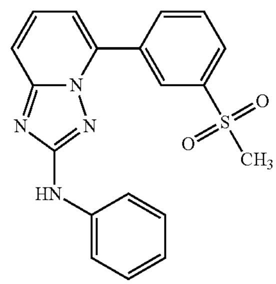 | 5-(3-(methylsulfonyl)phenyl)-N-phenyl-[1,2,4]triazolo[1,5-a]pyridin-2-amine | 1 | 365.0 |
| 363 | 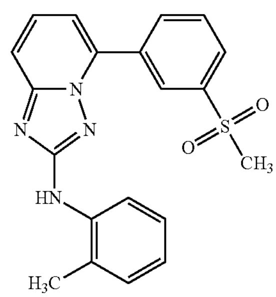 [SMILES: Cc1ccccc1Nc1nc2cccc(-c3cccc(S(C)(=O)=O)c3)n2n1] | 5-(3-(methylsulfonyl)phenyl)-N-o-tolyl-[1,2,4]triazolo[1,5-a]pyridin-2-amine | 1 | 379.1 |
| 364 | 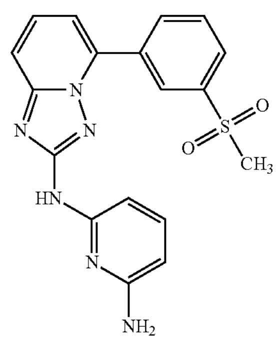 [SMILES: CS(=O)(=O)c1cccc(-c2cccc3nc(Nc4cccc(N)n4)nn23)c1] | N2-(5-(3-(methylsulfonyl)phenyl)-[1,2,4]triazolo[1,5-a]pyridin-2-yl)pyridine-2,6-diamine | 1 | 381.1 |
| 365 | 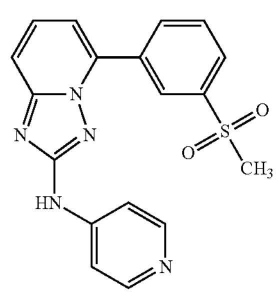 [SMILES: CS(=O)(=O)c1cccc(-c2cccc3nc(Nc4ccncc4)nn23)c1] | 5-(3-(methylsulfonyl)phenyl)-N-(pyridin-4-yl)-[1,2,4]triazolo[1,5-a]pyridin-2-amine | 1 | 366.1 |
| 366 | 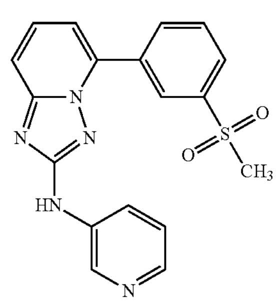 [SMILES: CS(=O)(=O)c1cccc(-c2cccc3nc(Nc4cccnc4)nn23)c1] | 5-(3-(methylsulfonyl)phenyl)-N-(pyridin-3-yl)-[1,2,4]triazolo[1,5-a]pyridin-2-amine | 1 | 366.2 |

TABLE 2-continued

| Ex | Structure | Name | Mthd | LCMS (ESI) m/z |
|---|---|---|---|---|
| 367 | 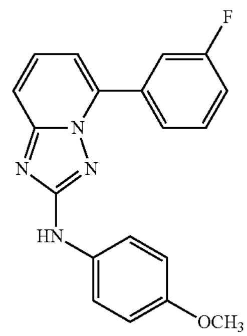 [SMILES: COc1ccc(Nc2nc3cccc(-c4cccc(F)c4)n3n2)cc1] | 5-(3-fluorophenyl)-N-(4-methoxyphenyl)-[1,2,4]triazolo[1,5-a]pyridin-2-amine | 1 | 335.2 |
| 368 | 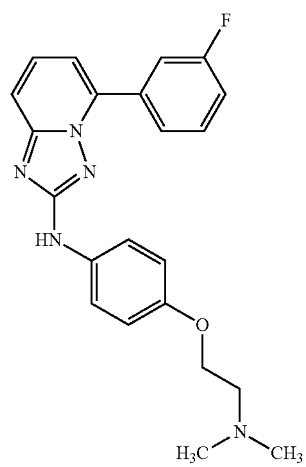 [SMILES: CN(C)CCOc1ccc(Nc2nc3cccc(-c4cccc(F)c4)n3n2)cc1] | N-(4-(2-(dimethylamino)ethoxy)phenyl)-5-(3-fluorophenyl)-[1,2,4]triazolo[1,5-a]pyridin-2-amine | 234 | 392.2 |
| 369 | 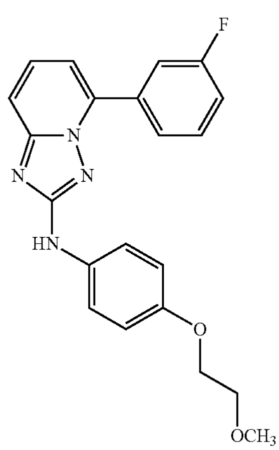 [SMILES: COCCOc1ccc(Nc2nc3cccc(-c4cccc(F)c4)n3n2)cc1] | 5-(3-fluorophenyl)-N-(4-(2-methoxyethoxy)phenyl)-[1,2,4]triazolo[1,5-a]pyridin-2-amine | 234 | 379.2 |

TABLE 2-continued

| Ex | Structure | Name | Mthd | LCMS (ESI) m/z |
|---|---|---|---|---|
| 370 | 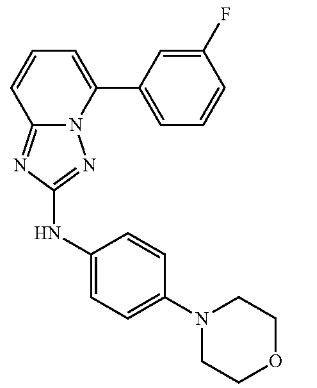 [SMILES: Fc1cccc(-c2cccc3nc(Nc4ccc(N5CCOCC5)cc4)nn23)c1] | 5-(3-fluorophenyl)-N-(4-morpholinophenyl)-[1,2,4]triazolo[1,5-a]pyridin-2-amine | 231 | 390.0 |
| 371 | 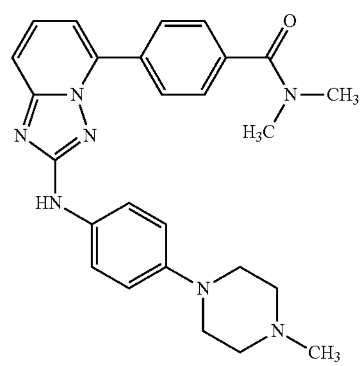 [SMILES: CN1CCN(c2ccc(Nc3nc4cccc(-c5ccc(C(=O)N(C)C)cc5)n4n3)cc2)CC1] | N,N-dimethyl-4-(2-(4-(4-methylpiperazin-1-yl)phenylamino)-[1,2,4]triazolo[1,5-a]pyridin-5-yl)benzamide | 231 | 456.1 |
| 372 | 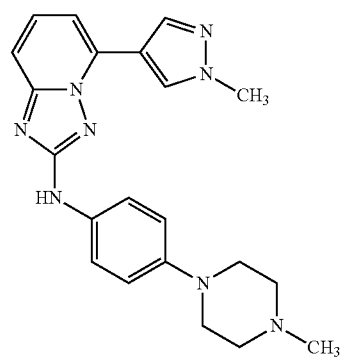 [SMILES: CN1CCN(c2ccc(Nc3nc4cccc(-c5cnn(C)c5)n4n3)cc2)CC1] | 5-(1-methyl-1H-pyrazol-4-yl)-N-(4-(4-methylpiperazin-1-yl)phenyl)-[1,2,4]triazolo[1,5-a]pyridin-2-amine | 231 | 389.2 |
| 373 | 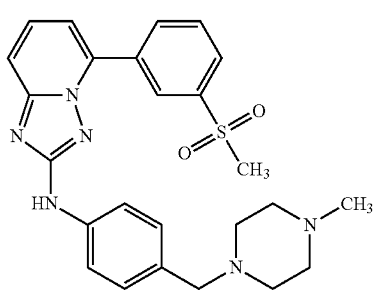 [SMILES: CN1CCN(Cc2ccc(Nc3nc4cccc(-c5cccc(S(C)(=O)=O)c5)n4n3)cc2)CC1] | N-(4-((4-methylpiperazin-1-yl)methyl)phenyl)-5-(3-(methylsulfonyl)phenyl)-[1,2,4]triazolo[1,5-a]pyridin-2-amine | 232 | 477.2 |

TABLE 2-continued

| Ex | Structure | Name | Mthd | LCMS (ESI) m/z |
|---|---|---|---|---|
| 374 | 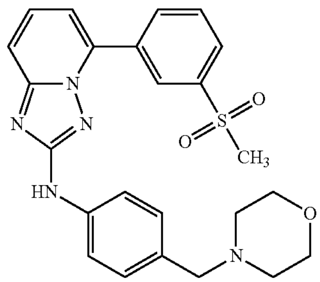 [SMILES: CS(=O)(=O)c1cccc(-c2cccc3nc(Nc4ccc(CN5CCOCC5)cc4)nn23)c1] | 5-(3-(methylsulfonyl)phenyl)-N-(4-(morpholinomethyl)phenyl)-[1,2,4]triazolo[1,5-a]pyridin-2-amine | 232 | 464.2 |
| 375 | 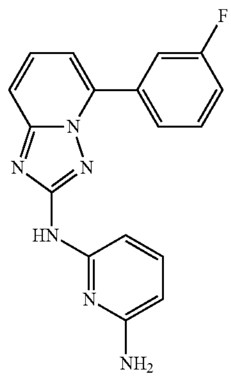 [SMILES: Nc1cccc(Nc2nc3cccc(-c4cccc(F)c4)n3n2)n1] | N2-(5-(3-fluorophenyl)-[1,2,4]triazolo[1,5-a]pyridin-2-yl)pyridine-2,6-diamine | 1 | 321.2 |
| 376 | 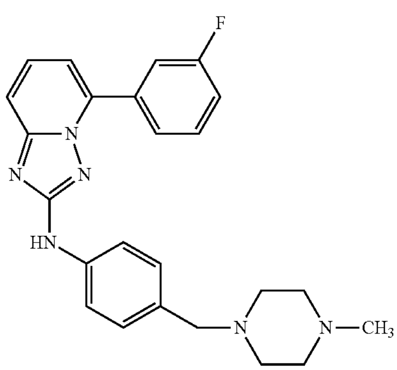 [SMILES: CN1CCN(Cc2ccc(Nc3nc4cccc(-c5cccc(F)c5)n4n3)cc2)CC1] | 5-(3-fluorophenyl)-N-(4-((4-methylpiperazin-1-yl)methyl)phenyl)-[1,2,4]triazolo[1,5-a]pyridin-2-amine | 232 | 416.9 |
| 377 | 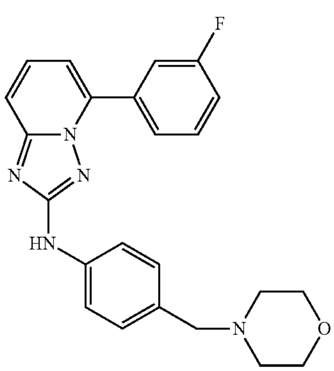 [SMILES: Fc1cccc(-c2cccc3nc(Nc4ccc(CN5CCOCC5)cc4)nn23)c1] | 5-(3-fluorophenyl)-N-(4-(morpholinomethyl)phenyl)-[1,2,4]triazolo[1,5-a]pyridin-2-amine | 232 | 403.8 |

TABLE 2-continued

| Ex | Structure | Name | Mthd | LCMS (ESI) m/z |
|---|---|---|---|---|
| 378 | 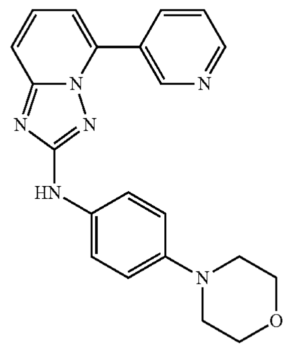 [SMILES: c1cncc(-c2cccc3nc(Nc4ccc(N5CCOCC5)cc4)nn23)c1] | N-(4-morpholinophenyl)-5-(pyridin-3-yl)-[1,2,4]triazolo[1,5-a]pyridin-2-amine | 231 | 373.2 |
| 379 | 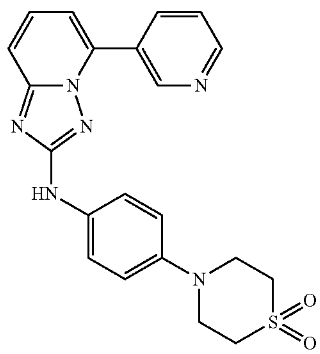 [SMILES: O=S1(=O)CCN(c2ccc(Nc3nc4cccc(-c5cccnc5)n4n3)cc2)CC1] | N-[4-(1,1-dioxidothiomorpholin-4-yl)phenyl]-5-(pyridin-3-yl)[1,2,4]triazolo[1,5-a]pyridin-2-amine | 231 | 421.1 |
| 380 | 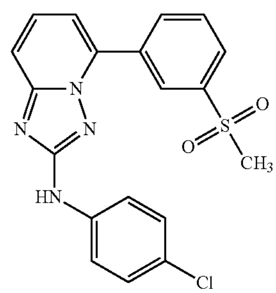 | N-(4-chlorophenyl)-5-(3-(methylsulfonyl)phenyl)-[1,2,4]triazolo[1,5-a]pyridin-2-amine | 1 | 399.2 |
| 381 | 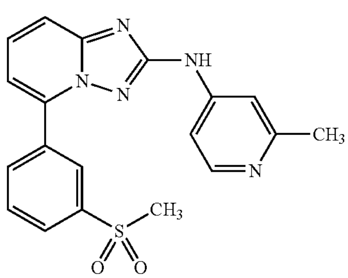 [SMILES: Cc1cc(Nc2nc3cccc(-c4cccc(S(C)(=O)=O)c4)n3n2)ccn1] | N-(2-methylpyridin-4-yl)-5-(3-(methylsulfonyl)phenyl)-[1,2,4]triazolo[1,5-a]pyridin-2-amine | 1 | 380.1 |
| 382 | 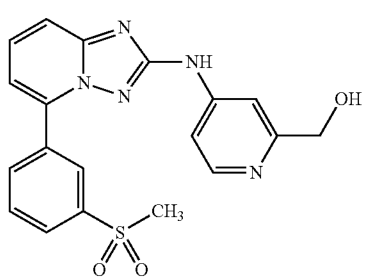 [SMILES: CS(=O)(=O)c1cccc(-c2cccc3nc(Nc4ccnc(CO)c4)nn23)c1] | (4-(5-(3-(methylsulfonyl)phenyl)-[1,2,4]triazolo[1,5-a]pyridin-2-ylamino)pyridin-2-yl)methanol | 1 | 396.1 |

TABLE 2-continued

| Ex | Name | Mthd | LCMS (ESI) m/z |
|---|---|---|---|
| 383 | 4-(5-(3-(methylsulfonyl)phenyl)-[1,2,4]triazolo[1,5-a]pyridin-2-ylamino)benzonitrile | 1 | 390.1 |
| 384 | 5-(3-(methylsulfonyl)phenyl)-N-(4-(methylsulfonyl)phenyl)-[1,2,4]triazolo[1,5-a]pyridin-2-amine | 1 | 443.0 |
| 385 | 5-(3-(methylsulfonyl)phenyl)-N-(pyrimidin-5-yl)-[1,2,4]triazolo[1,5-a]pyridin-2-amine | 1 | 367.0 |
| 386 | N-methyl-4-(5-(4-(methylsulfonyl)phenyl)-[1,2,4]triazolo[1,5-a]pyridin-2-ylamino)benzamide | 2 | 422.1 |
| 387 | N-(6-methylpyridin-3-yl)-5-(3-(methylsulfonyl)phenyl)-[1,2,4]triazolo[1,5-a]pyridin-2-amine | 1 | 380.1 |

TABLE 2-continued

| Ex | Structure | Name | Mthd | LCMS (ESI) m/z |
|---|---|---|---|---|
| 388 | 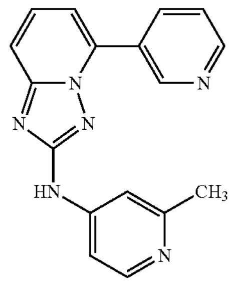 | N-(2-methylpyridin-4-yl)-5-(pyridin-3-yl)-[1,2,4]triazolo[1,5-a]pyridin-2-amine | 1 | 303.3 |
| 389 | 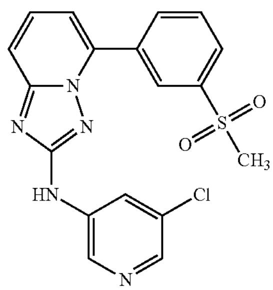 [SMILES: CS(=O)(=O)c1cccc(-c2cccc3nc(Nc4cncnc4)nn23)c1] | N-(5-chloropyridin-3-yl)-5-(3-(methylsulfonyl)phenyl)-[1,2,4]triazolo[1,5-a]pyridin-2-amine | 1 | 400.2 |
| 390 | 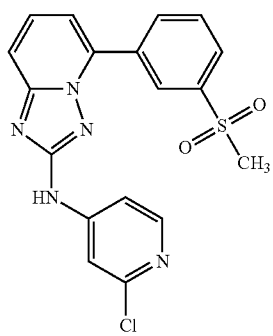 [SMILES: CS(=O)(=O)c1cccc(-c2cccc3nc(Nc4ccnc(Cl)c4)nn23)c1] | N-(2-chloropyridin-4-yl)-5-(3-(methylsulfonyl)phenyl)-[1,2,4]triazolo[1,5-a]pyridin-2-amine | 1 | 400.2 |
| 391 | 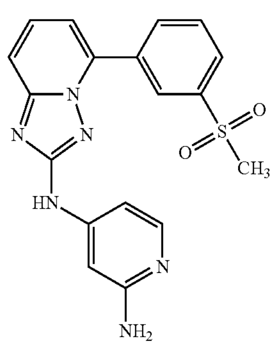 [SMILES: CS(=O)(=O)c1cccc(-c2cccc3nc(Nc4ccnc(N)c4)nn23)c1] | N4-(5-(3-(methylsulfonyl)phenyl)-[1,2,4]triazolo[1,5-a]pyridin-2-yl)pyridine-2,4-diamine | 1 | 381.2 |

TABLE 2-continued

| Ex | Structure | Name | Mthd | LCMS (ESI) m/z |
|---|---|---|---|---|
| 392 | 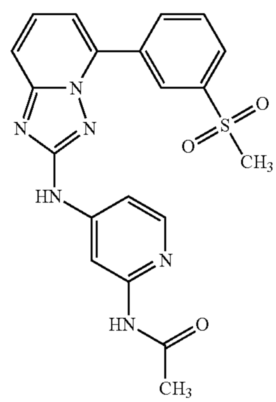 [SMILES: CC(=O)Nc1cc(Nc2nc3cccc(-c4cccc(S(C)(=O)=O)c4)n3n2)ccn1] | N-(4-(5-(3-(methylsulfonyl)phenyl)-[1,2,4]triazolo[1,5-a]pyridin-2-ylamino)pyridin-2-yl)acetamide | 1 | 423.2 |
| 393 | 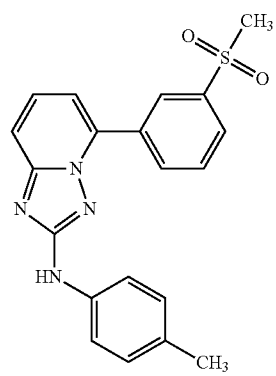 [SMILES: Cc1ccc(Nc2nc3cccc(-c4cccc(S(C)(=O)=O)c4)n3n2)cc1] | 5-(3-(methylsulfonyl)phenyl)-N-p-tolyl-[1,2,4]triazolo[1,5-a]pyridin-2-amine | 1 | 379.2 |
| 394 | 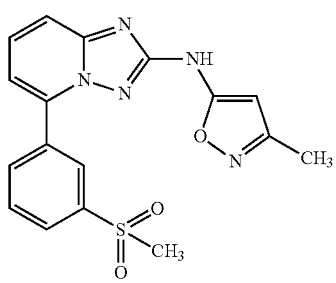 [SMILES: Cc1cc(Nc2nc3cccc(-c4cccc(S(C)(=O)=O)c4)n3n2)on1] | 3-methyl-N-(5-(3-(methylsulfonyl)phenyl)-[1,2,4]triazolo[1,5-a]pyridin-2-yl)isoxazol-5-amine | 3 | 370.1 |
| 395 | 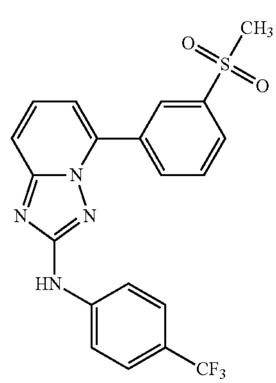 | 5-(3-(methylsulfonyl)phenyl)-N-(4-(trifluoromethyl)phenyl)-[1,2,4]triazolo[1,5-a]pyridin-2-amine | 1 | 433.2 |

TABLE 2-continued

| Ex | Structure | Name | Mthd | LCMS (ESI) m/z |
|---|---|---|---|---|
| 396 | 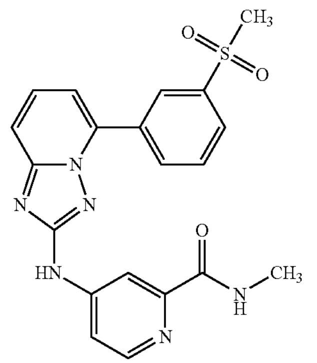 [SMILES: CNC(=O)c1cc(Nc2nc3cccc(-c4cccc(S(C)(=O)=O)c4)n3n2)ccn1] | N-methyl-4-(5-(3-(methylsulfonyl)phenyl)-[1,2,4]triazolo[1,5-a]pyridin-2-ylamino)picolinamide | 2 | 423.1 |
| 397 | 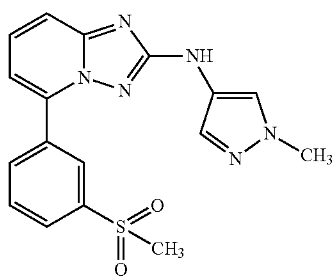 [SMILES: Cn1cc(Nc2nc3cccc(-c4cccc(S(C)(=O)=O)c4)n3n2)cn1] | N-(1-methyl-1H-pyrazol-4-yl)-5-(3-(methylsulfonyl)phenyl)-[1,2,4]triazolo[1,5-a]pyridin-2-amine | 3 | 369.1 |
| 398 | 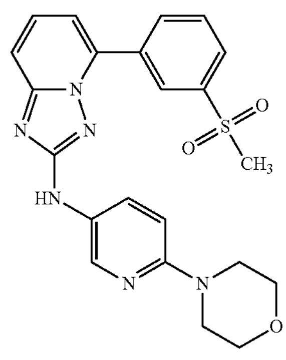 [SMILES: CS(=O)(=O)c1cccc(-c2cccc3nc(Nc4ccc(N5CCOCC5)nc4)nn23)c1] | 5-(3-(methylsulfonyl)phenyl)-N-(6-morpholinopyridin-3-yl)-[1,2,4]triazolo[1,5-a]pyridin-2-amine | 235 | 451.3 |
| 399 | 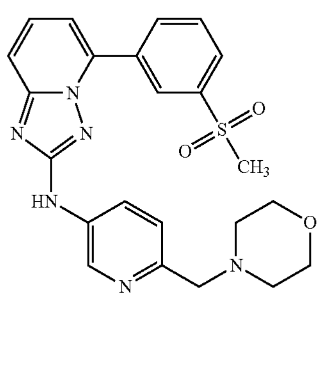 [SMILES: CS(=O)(=O)c1cccc(-c2cccc3nc(Nc4ccc(CN5CCOCC5)nc4)nn23)c1] | 5-(3-(methylsulfonyl)phenyl)-N-(6-(morpholinomethyl)pyridin-3-yl)-[1,2,4]triazolo[1,5-a]pyridin-2-amine | 232 | 465.1 |

TABLE 2-continued

| Ex | Structure | Name | Mthd | LCMS (ESI) m/z |
|---|---|---|---|---|
| 400 | 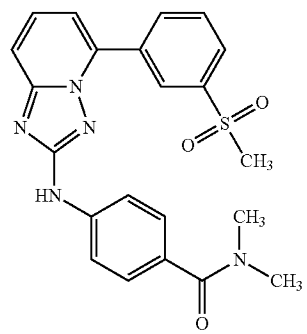 [SMILES: CN(C)C(=O)c1ccc(Nc2nc3cccc(-c4cccc(S(C)(=O)=O)c4)n3n2)cc1] | N,N-dimethyl-4-(5-(3-(methylsulfonyl)phenyl)-[1,2,4]triazolo[1,5-a]pyridin-2-ylamino)benzamide | 2 | 436.1 |
| 401 | 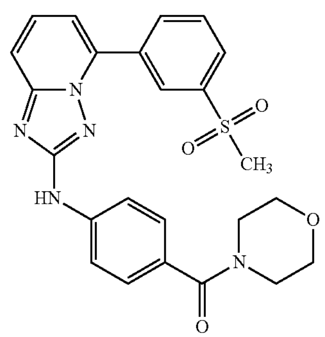 [SMILES: CS(=O)(=O)c1cccc(-c2cccc3nc(Nc4ccc(C(=O)N5CCOCC5)cc4)nn23)c1] | (4-(5-(3-(methylsulfonyl)phenyl)-[1,2,4]triazolo[1,5-a]pyridin-2-ylamino)phenyl)(morpholino)methanone | 2 | 478.1 |
| 412 | 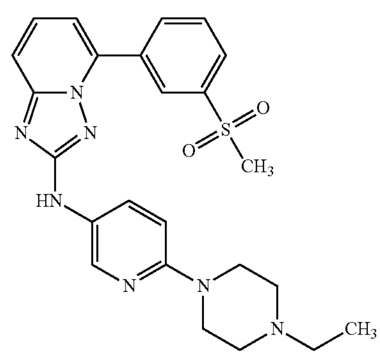 [SMILES: CCN1CCN(c2ccc(Nc3nc4cccc(-c5cccc(S(C)(=O)=O)c5)n4n3)cn2)CC1] | N-(6-(4-ethylpiperazin-1-yl)pyridin-3-yl)-5-(3-(methylsulfonyl)phenyl)-[1,2,4]triazolo[1,5-a]pyridin-2-amine | 231 | 478.2 |
| 403 | 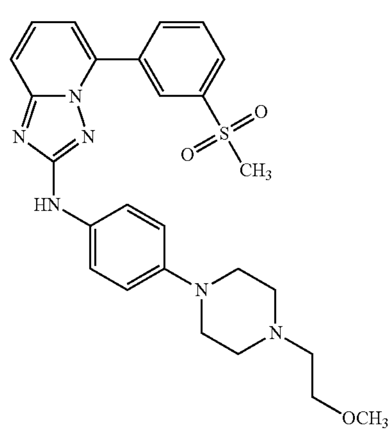 [SMILES: COCCN1CCN(c2ccc(Nc3nc4cccc(-c5cccc(S(C)(=O)=O)c5)n4n3)cc2)CC1] | N-(4-(4-(2-methoxyethyl)piperazin-1-yl)phenyl)-5-(3-(methylsulfonyl)phenyl)-[1,24]triazolo[1,5-a]pyridin-2-amine | 231 | 507.4 |

TABLE 2-continued

| Ex | Structure | Name | Mthd | LCMS (ESI) m/z |
|---|---|---|---|---|
| 404 | 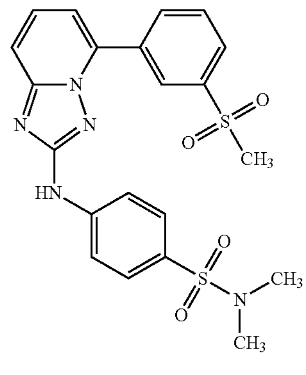 [SMILES: CN(C)S(=O)(=O)c1ccc(Nc2nc3cccc(-c4cccc(S(C)(=O)=O)c4)n3n2)cc1] | N,N-dimethyl-4-(5-(3-(methylsulfonyl)phenyl)-[1,2,4]triazolo[1,5-a]pyridin-2-ylamino)benzene-sulfonamide | 1 | 472.4 |
| 405 | 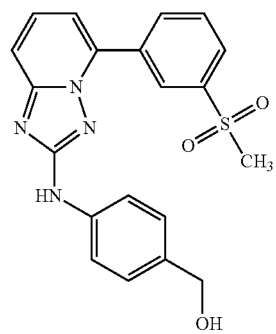 [SMILES: CS(=O)(=O)c1cccc(-c2cccc3nc(Nc4ccc(CO)cc4)nn23)c1] | (4-(5-(3-(methylsulfonyl)phenyl)-[1,2,4]triazolo[1,5-a]pyridin-2-ylamino)phenyl)methanol | 232 | 395.1 |
| 406 | 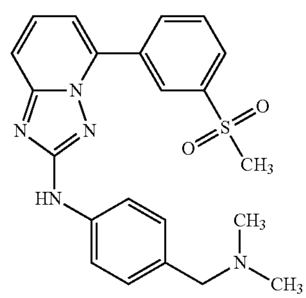 [SMILES: CN(C)Cc1ccc(Nc2nc3cccc(-c4cccc(S(C)(=O)=O)c4)n3n2)cc1] | N-(4-((dimethylamino)methyl)phenyl)-5-(3-(methylsulfonyl)phenyl)-[1,2,4]triazolo[1,5-a]pyridin-2-amine | 232 | 421.9 |
| 407 | 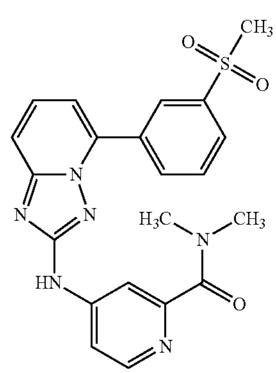 [SMILES: CN(C)C(=O)c1cc(Nc2nc3cccc(-c4cccc(S(C)(=O)=O)c4)n3n2)ccn1] | N,N-dimethyl-4-(5-(3-(methylsulfonyl)phenyl)-[1,2,4]triazolo[1,5-a]pyridin-2-ylamino)picolinamide | 2 | 437.0 |

TABLE 2-continued

| Ex | Structure | Name | Mthd | LCMS (ESI) m/z |
|---|---|---|---|---|
| 408 | 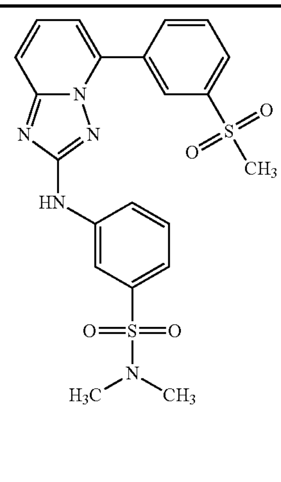 | N,N-dimethyl-3-(5-(3-(methylsulfonyl)phenyl)-[1,2,4]triazolo[1,5-a]pyridin-2-ylamino)benzenesulfonamide | 1 | 472.2 |
| 409 | 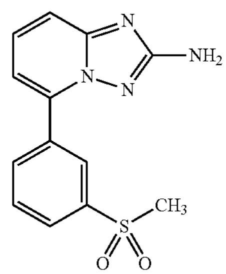 [SMILES: CS(=O)(=O)c1cccc(-c2cccc3nc(N)nn23)c1] | 5-(3-(methylsulfonyl)phenyl)-[1,2,4]triazolo[1,5-a]pyridin-2-amine | 1 | 289.1 |
| 410 | 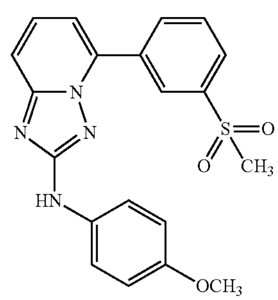 [SMILES: COc1ccc(Nc2nc3cccc(-c4cccc(S(C)(=O)=O)c4)n3n2)cc1] | N-(4-methoxyphenyl)-5-(3-(methylsulfonyl)phenyl)-[1,2,4]triazolo[1,5-a]pyridin-2-amine | 1 | 395.1 |
| 411 | 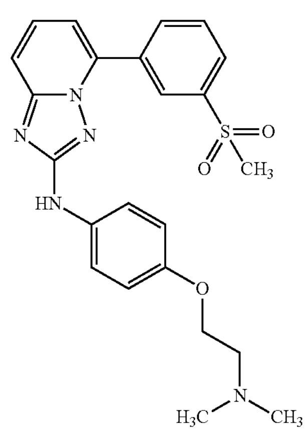 [SMILES: CN(C)CCOc1ccc(Nc2nc3cccc(-c4cccc(S(C)(=O)=O)c4)n3n2)cc1] | N-(4-(2-(dimethylamino)ethoxy)phenyl)-5-(3-(methylsulfonyl)phenyl)-[1,2,4]triazolo[1,5-a]pyridin-2-amine | 3 | 452.2 |

TABLE 2-continued

| Ex | Structure | Name | Mthd | LCMS (ESI) m/z |
|---|---|---|---|---|
| 412 | 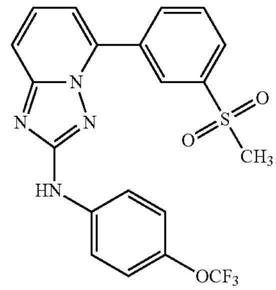 [SMILES: CS(=O)(=O)c1cccc(-c2cccc3nc(Nc4ccc(OC(F)(F)F)cc4)nn23)c1] | 5-(3-(methylsulfonyl)phenyl)-N-(4-(trifluoromethoxy)phenyl)-[1,2,4]triazolo[1,5-a]pyridin-2-amine | 1 | 449.0 |
| 413 | 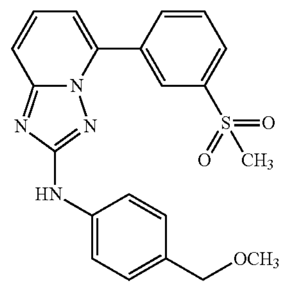 [SMILES: COCc1ccc(Nc2nc3cccc(-c4cccc(S(C)(=O)=O)c4)n3n2)cc1] | N-(4-(methoxymethyl)phenyl)-5-(3-(methylsulfonyl)phenyl)-[1,2,4]triazolo[1,5-a]pyridin-2-amine | 1 | 409.0 |
| 414 | 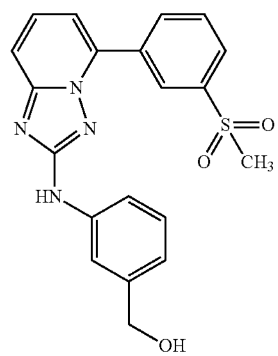 [SMILES: CS(=O)(=O)c1cccc(-c2cccc3nc(Nc4cccc(CO)c4)nn23)c1] | (3-(5-(3-(methylsulfonyl)phenyl)-[1,2,4]triazolo[1,5-a]pyridin-2-ylamino)phenyl)methanol | 232 | 395.1 |
| 415 | 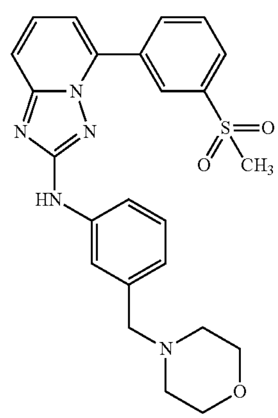 [SMILES: CS(=O)(=O)c1cccc(-c2cccc3nc(Nc4cccc(CN5CCOCC5)c4)nn23)c1] | 5-(3-(methylsulfonyl)phenyl)-N-(3-(morpholinomethyl)phenyl)-[1,2,4]triazolo[1,5-a]pyridin-2-amine | 232 | 464.2 |

TABLE 2-continued

| Ex | Structure | Name | Mthd | LCMS (ESI) m/z |
|---|---|---|---|---|
| 416 | 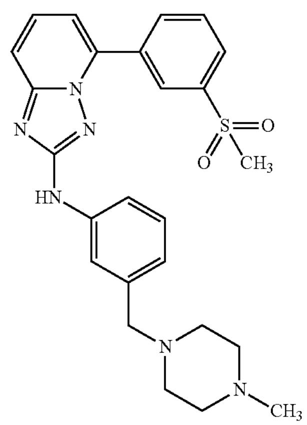 [SMILES: CN1CCN(Cc2cccc(Nc3nc4cccc(-c5cccc(S(C)(=O)=O)c5)n4n3)c2)CC1] | N-(3-((4-methylpiperazin-1-yl)methyl)phenyl)-5-(3-(methylsulfonyl)phenyl)-[1,2,4]triazolo[1,5-a]pyridin-2-amine | 232 | 477.2 |
| 417 | 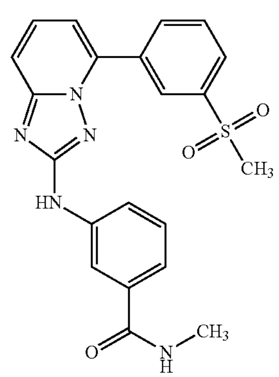 [SMILES: CNC(=O)c1cccc(Nc2nc3cccc(-c4cccc(S(C)(=O)=O)c4)n3n2)c1] | N-methyl-3-(5-(3-(methylsulfonyl)phenyl)-[1,2,4]triazolo[1,5-a]pyridin-2-ylamino)benzamide | 2 | 422.1 |
| 418 | 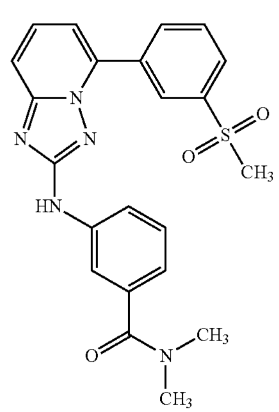 [SMILES: CN(C)C(=O)c1cccc(Nc2nc3cccc(-c4cccc(S(C)(=O)=O)c4)n3n2)c1] | N,N-dimethyl-3-(5-(3-(methylsulfonyl)phenyl)-[1,2,4]triazolo[1,5-a]pyridin-2-ylamino)benzamide | 2 | 436.2 |

TABLE 2-continued

| Ex | Structure | Name | Mthd | LCMS (ESI) m/z |
|---|---|---|---|---|
| 419 | 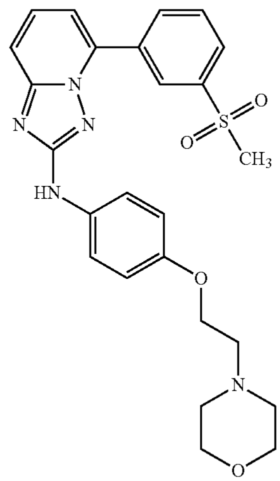 [SMILES: CS(=O)(=O)c1cccc(-c2cccc3nc(Nc4ccc(OCCN5CCOCC5)cc4)nn23)c1] | 5-(3-(methylsulfonyl)phenyl)-N-(4-(2-morpholinoethoxy)phenyl)-[1,2,4]triazolo[1,5-a]pyridin-2-amine | 3 | 494.0 |
| 420 | 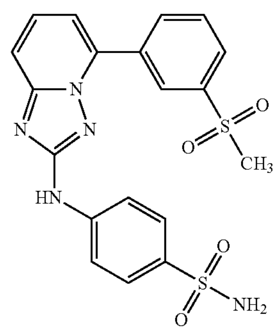 [SMILES: CS(=O)(=O)c1cccc(-c2cccc3nc(Nc4ccc(S(N)(=O)=O)cc4)nn23)c1] | 4-(5-(3-(methylsulfonyl)phenyl)-[1,2,4]triazolo[1,5-a]pyridin-2-ylamino)benzenesulfonamide | 1 | 443.9 |
| 421 | 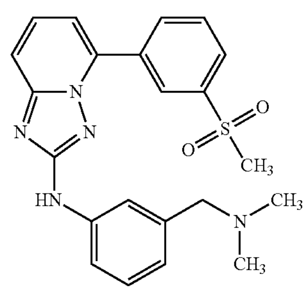 [SMILES: CN(C)Cc1cccc(Nc2nc3cccc(-c4cccc(S(C)(=O)=O)c4)n3n2)c1] | N-(3-((dimethylamino)methyl)phenyl)-5-(3-(methylsulfonyl)phenyl)-[1,2,4]triazolo[1,5-a]pyridin-2-amine | 232 | 422.1 |
| 422 | 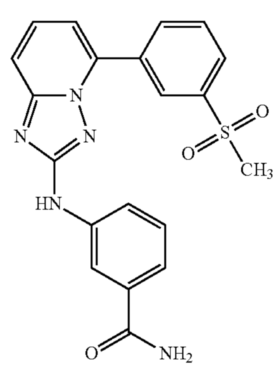 [SMILES: CS(=O)(=O)c1cccc(-c2cccc3nc(Nc4cccc(C(N)=O)c4)nn23)c1] | 3-(5-(3-(methylsulfonyl)phenyl)-[1,2,4]triazolo[1,5-a]pyridin-2-ylamino)benzamide | 2 | 40232.0 |

TABLE 2-continued

| Ex | Structure | Name | Mthd | LCMS (ESI) m/z |
|---|---|---|---|---|
| 423 | 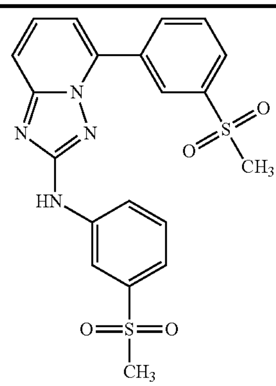 | N,5-bis(3-(methylsulfonyl)phenyl)-[1,2,4]triazolo[1,5-a]pyridin-2-amine | 1 | 442.9 |
| 424 | 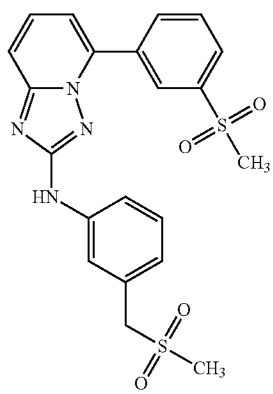 [SMILES: CS(=O)(=O)Cc1cccc(Nc2nc3cccc(-c4cccc(S(C)(=O)=O)c4)n3n2)c1] | 5-(3-(methylsulfonyl)phenyl)-N-(3-(methylsulfonyl-methyl)phenyl)-[1,2,4]triazolo[1,5-a]pyridin-2-amine | 1 | 457.1 |
| 425 | 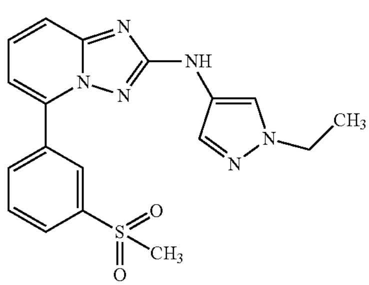 [SMILES: CCn1cc(Nc2nc3cccc(-c4cccc(S(C)(=O)=O)c4)n3n2)cn1] | N-(1-ethyl-1H-pyrazol-4-yl)-5-(3-(methylsulfonyl)phenyl)-[1,2,4]triazolo[1,5-a]pyridin-2-amine | 3 | 32323.1 |
| 426 | 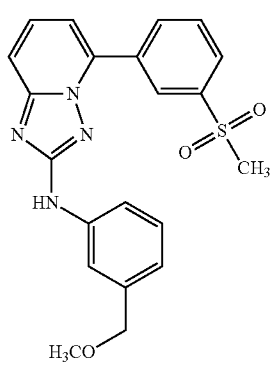 [SMILES: COCc1cccc(Nc2nc3cccc(-c4cccc(S(C)(=O)=O)c4)n3n2)c1] | N-(3-(methoxymethyl)phenyl)-5-(3-(methylsulfonyl)phenyl)-[1,2,4]triazolo[1,5-a]pyridin-2-amine | 232 | 409.1 |

TABLE 2-continued

| Ex | Structure | Name | Mthd | LCMS (ESI) m/z |
|---|---|---|---|---|
| 427 | 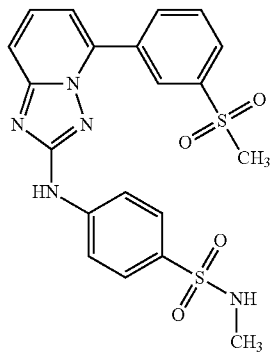 [SMILES: CNS(=O)(=O)c1ccc(Nc2nc3cccc(-c4cccc(S(C)(=O)=O)c4)n3n2)cc1] | N-methyl-4-(5-(3-(methylsulfonyl)phenyl)-[1,2,4]triazolo[1,5-a]pyridin-2-ylamino)benzenesulfonamide | 1 | 45232.1 |
| 42232 | 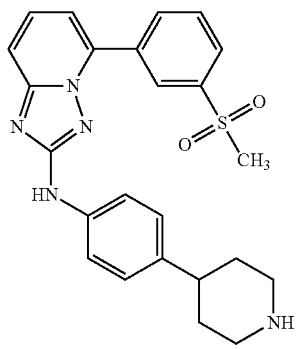 [SMILES: CS(=O)(=O)c1cccc(-c2cccc3nc(Nc4ccc(C5CCNCC5)cc4)nn23)c1] | 5-(3-(methylsulfonyl)phenyl)-N-(4-(piperidin-4-yl)phenyl)-[1,2,4]triazolo[1,5-a]pyridin-2-amine | 3 | 44232.3 |
| 429 | 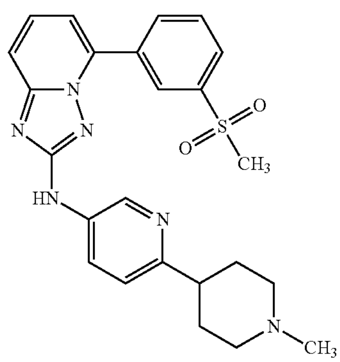 [SMILES: CN1CCC(c2ccc(Nc3nc4cccc(-c5cccc(S(C)(=O)=O)c5)n4n3)cn2)CC1] | N-(6-(1-methylpiperidin-4-yl)pyridin-3-yl)-5-(3-(methylsulfonyl)phenyl)-[1,2,4]triazolo[1,5-a]pyridin-2-amine | 3 | 463.3 |
| 430 | 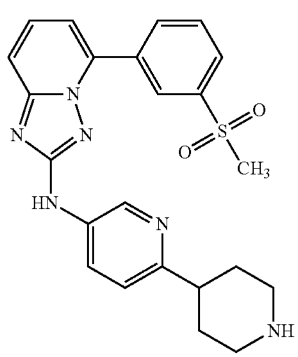 [SMILES: CS(=O)(=O)c1cccc(-c2cccc3nc(Nc4ccc(C5CCNCC5)nc4)nn23)c1] | 5-(3-(methylsulfonyl)phenyl)-N-(6-(piperidin-4-yl)pyridin-3-yl)-[1,2,4]triazolo[1,5-a]pyridin-2-amine | 3 | 449.2 |

TABLE 2-continued

| Ex | Structure | Name | Mthd | LCMS (ESI) m/z |
|---|---|---|---|---|
| 431 | 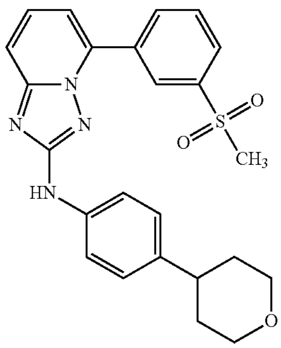 [SMILES: CS(=O)(=O)c1cccc(-c2cccc3nc(Nc4ccc(C5CCOCC5)cc4)nn23)c1] | 5-(3-(methylsulfonyl)phenyl)-N-(4-(tetrahydro-2H-pyran-4-yl)phenyl)-[1,2,4]triazolo[1,5-a]pyridin-2-amine | 3 | 449.1 |
| 432 | 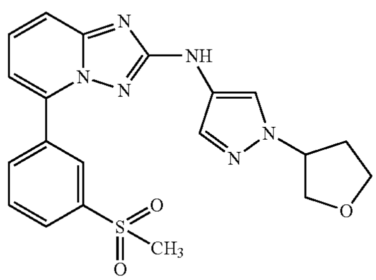 [SMILES: CS(=O)(=O)c1cccc(-c2cccc3nc(Nc4cnn(C5CCOC5)c4)nn23)c1] | 5-(3-(methylsulfonyl)phenyl)-N-(1-(tetrahydrofuran-3-yl)-1H-pyrazol-4-yl)-[1,2,4]triazolo[1,5-a]pyridin-2-amine | 238 | 425.1 |
| 433 | 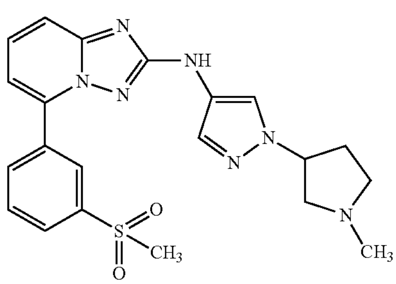 [SMILES: CN1CCC(n2cc(Nc3nc4cccc(-c5cccc(S(C)(=O)=O)c5)n4n3)cn2)C1] | N-(1-(1-methylpyrrolidin-3-yl)-1H-pyrazol-4-yl)-5-(3-(methylsulfonyl)phenyl)-[1,2,4]triazolo[1,5-a]pyridin-2-amine | 238 | 43232.1 |
| 434 | 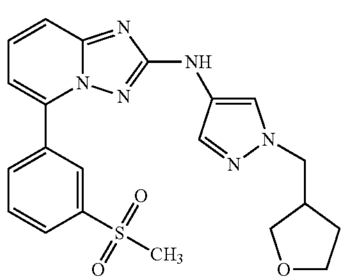 [SMILES: CS(=O)(=O)c1cccc(-c2cccc3nc(Nc4cnn(CC5CCOC5)c4)nn23)c1] | 5-(3-(methylsulfonyl)phenyl)-N-(1-((tetrahydrofuran-3-yl)methyl)-1H-pyrazol-4-yl)-[1,2,4]triazolo[1,5-a]pyridin-2-amine | 238 | 439.1 |

TABLE 2-continued

| Ex | Structure | Name | Mthd | LCMS (ESI) m/z |
|---|---|---|---|---|
| 435 | 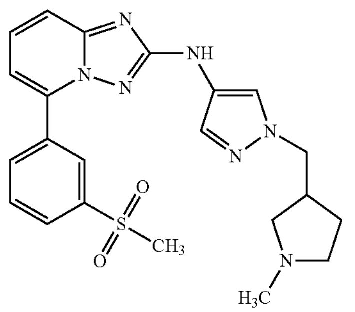 [SMILES: CN1CCC(Cn2cc(Nc3nc4cccc(-c5cccc(S(C)(=O)=O)c5)n4n3)cn2)C1] | N-(1-((1-methylpyrrolidin-3-yl)methyl)-1H-pyrazol-4-yl)-5-(3-(methylsulfonyl)phenyl)-[1,2,4]triazolo[1,5-a]pyridin-2-amine | 238 | 452.1 |
| 436 | 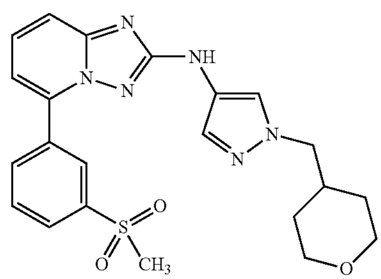 [SMILES: CS(=O)(=O)c1cccc(-c2cccc3nc(Nc4cnn(CC5CCOCC5)c4)nn23)c1] | 5-(3-(methylsulfonyl)phenyl)-N-(1-((tetrahydro-2H-pyran-4-yl)methyl)-1H-pyrazol-4-yl)-[1,2,4]triazolo[1,5-a]pyridin-2-amine | 238 | 453.1 |
| 437 | 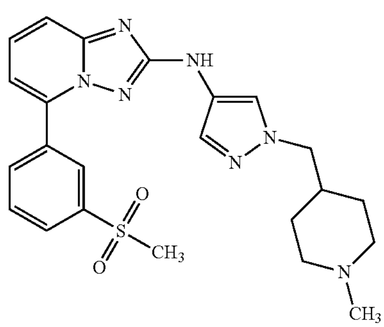 [SMILES: CN1CCC(Cn2cc(Nc3nc4cccc(-c5cccc(S(C)(=O)=O)c5)n4n3)cn2)CC1] | N-(1-((1-methylpiperidin-4-yl)methyl)-1H-pyrazol-4-yl)-5-(3-(methylsulfonyl)phenyl)-[1,2,4]triazolo[1,5-a]pyridin-2-amine | 238 | 466.2 |
| 438 | 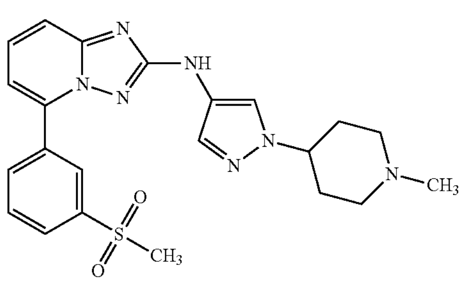 [SMILES: CN1CCC(n2cc(Nc3nc4cccc(-c5cccc(S(C)(=O)=O)c5)n4n3)cn2)CC1] | N-(1-(1-methylpiperidin-4-yl)-1H-pyrazol-4-yl)-5-(3-(methylsulfonyl)phenyl)-[1,2,4]triazolo[1,5-a]pyridin-2-amine | 238 | 452.1 |

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:

1. A compound selected from the group consisting of:

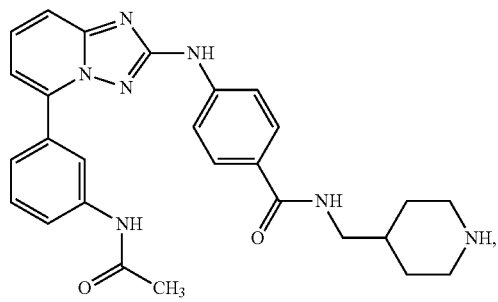

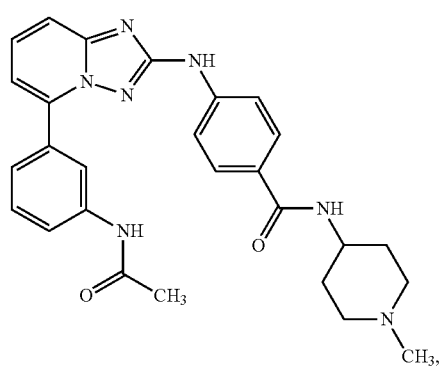

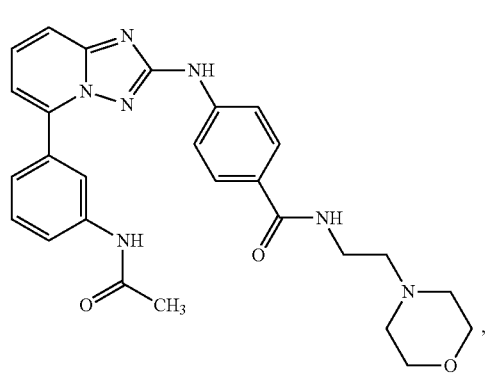

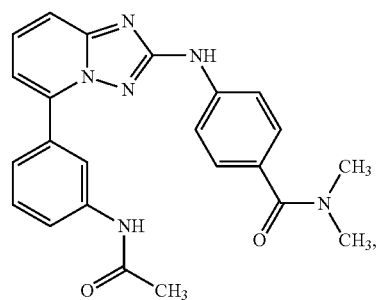

-continued

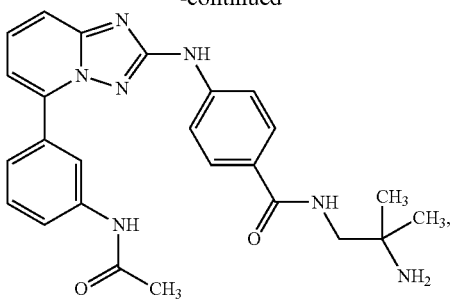

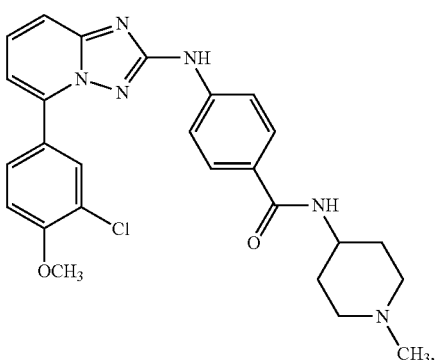

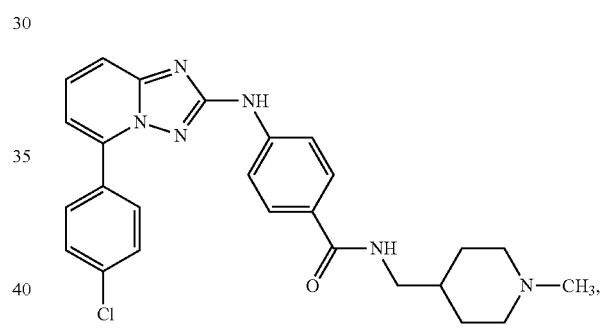

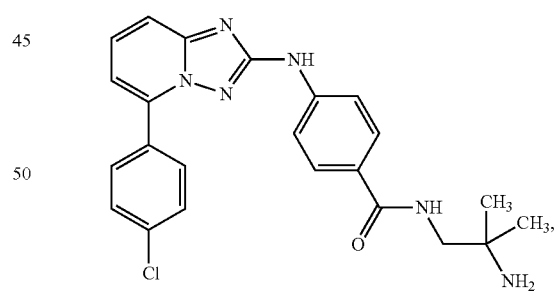

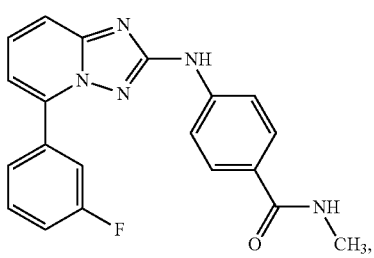

319
-continued
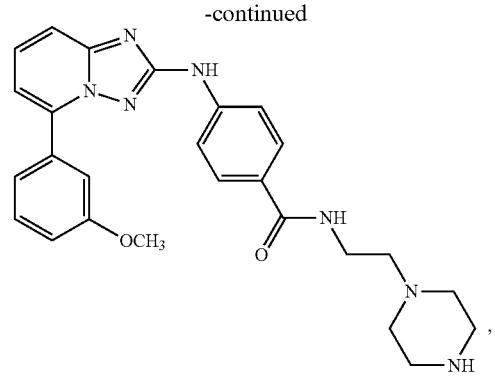
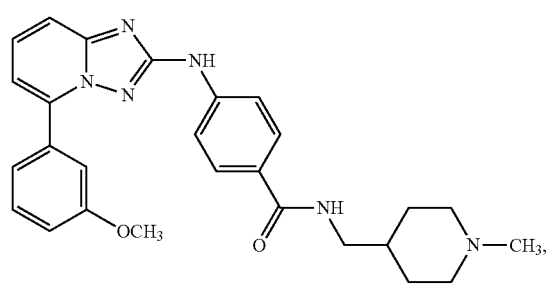
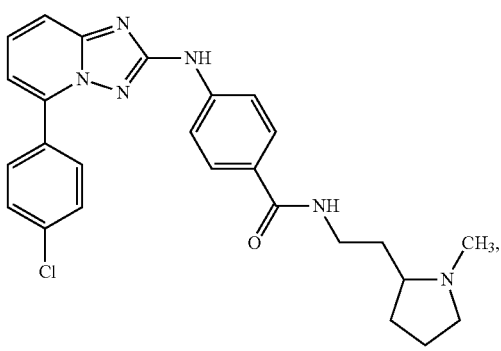
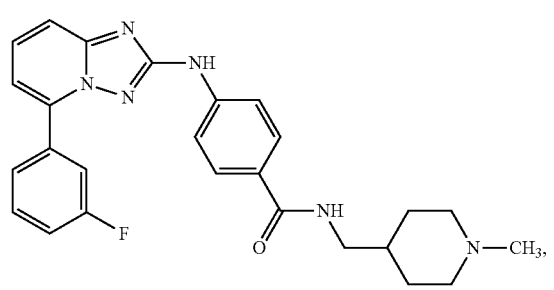
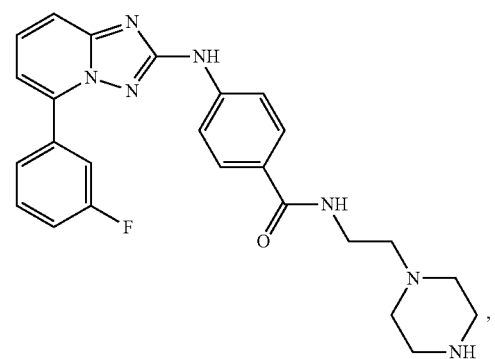
320
-continued
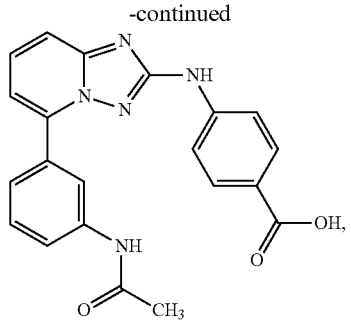
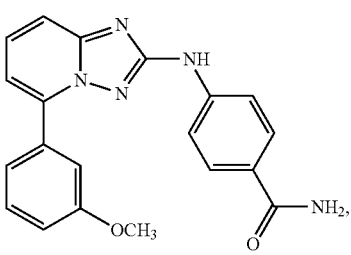
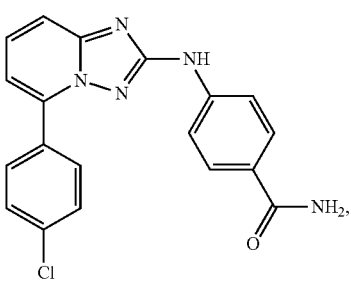
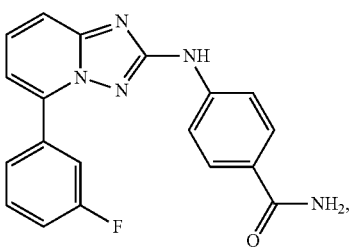
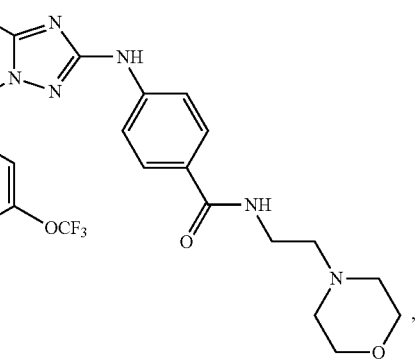

321
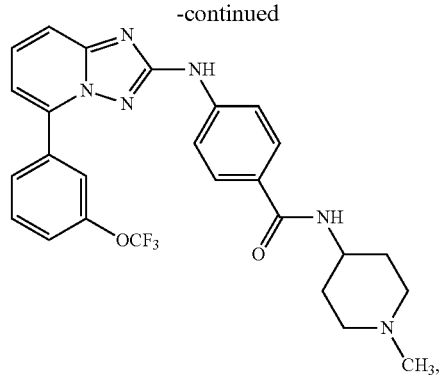
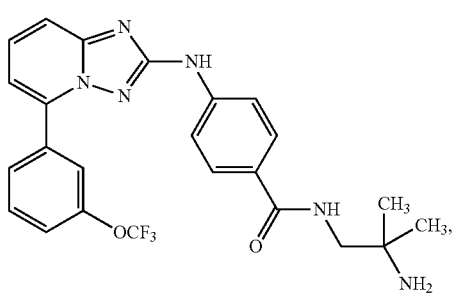
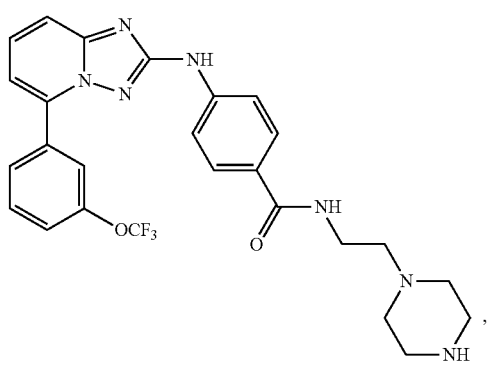
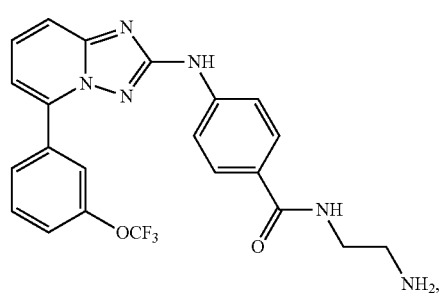
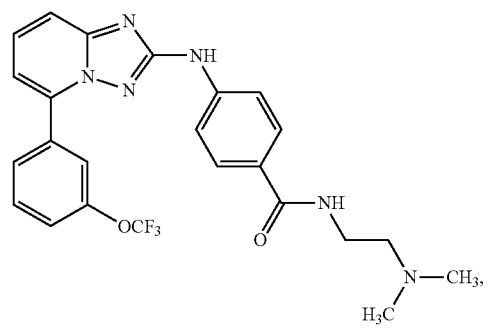
322
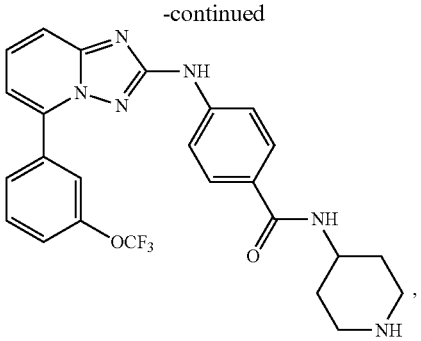
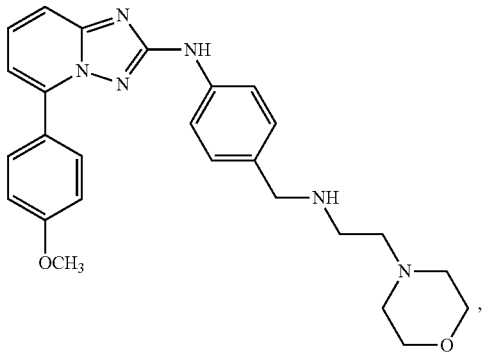
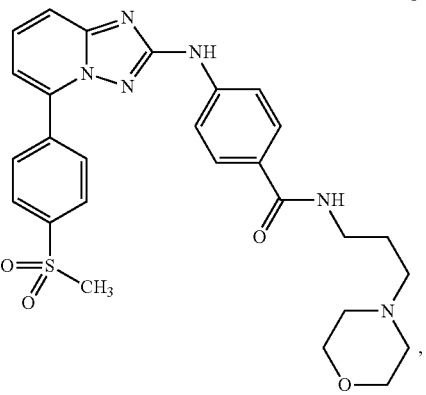
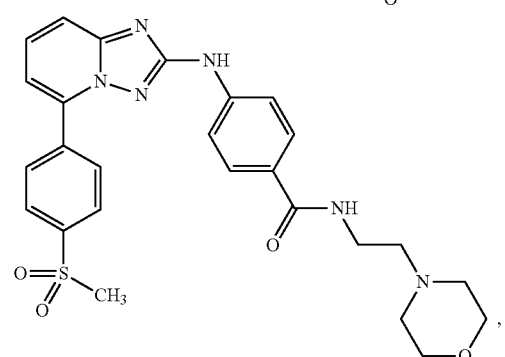
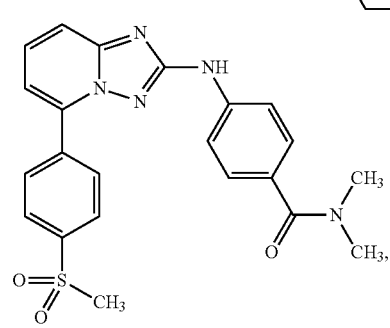

323
-continued
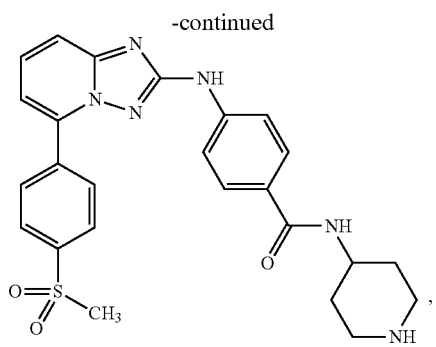
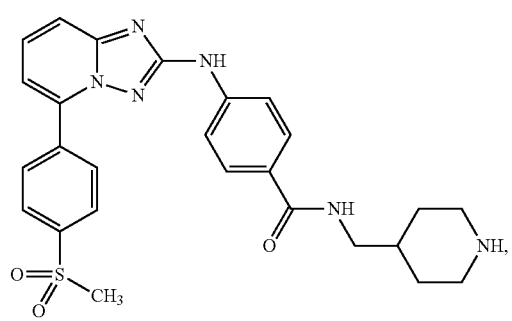
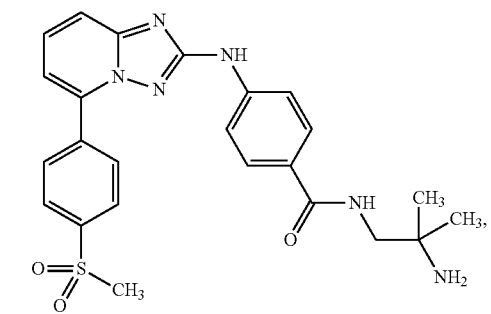
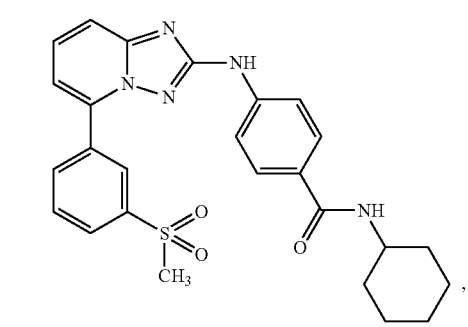
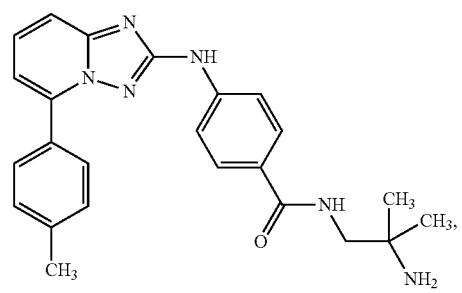
324
-continued
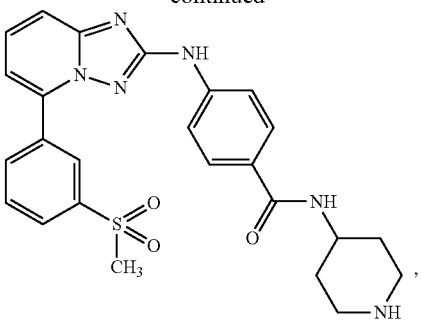
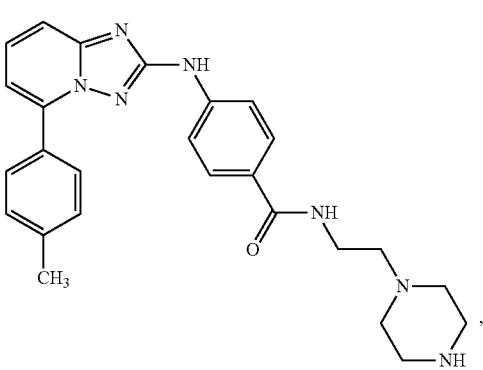
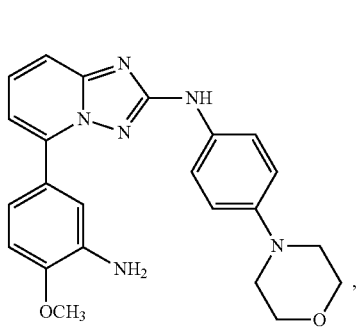
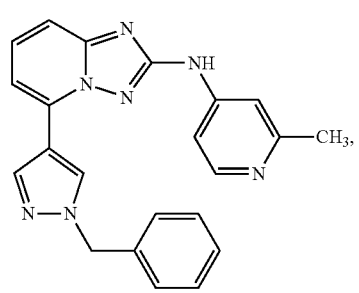

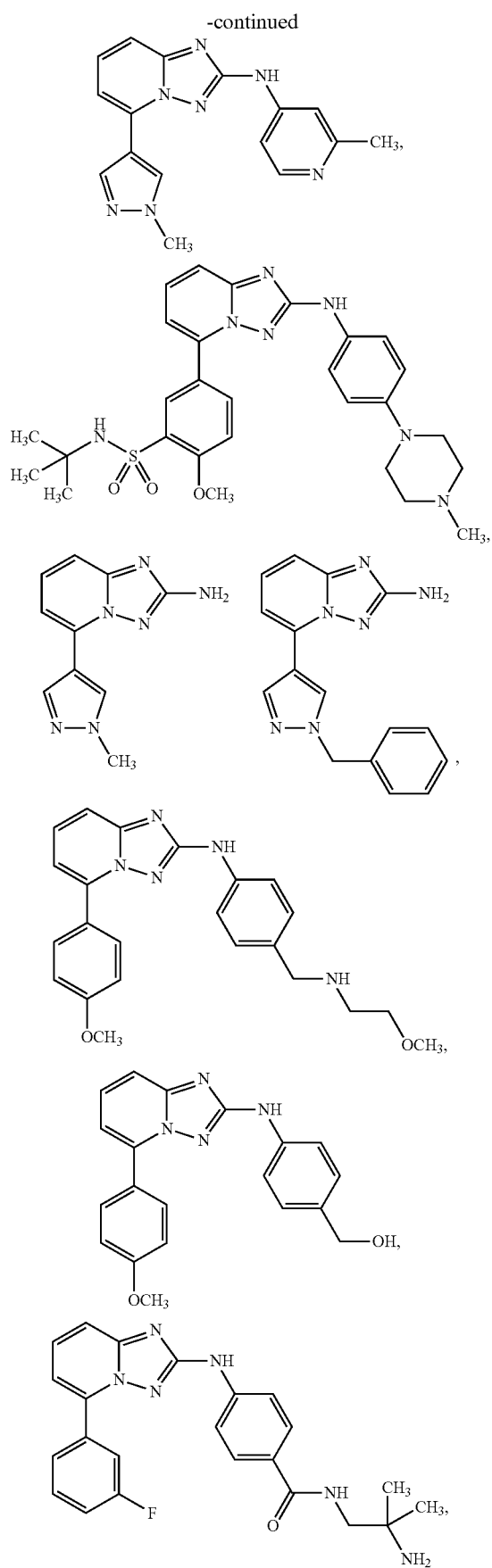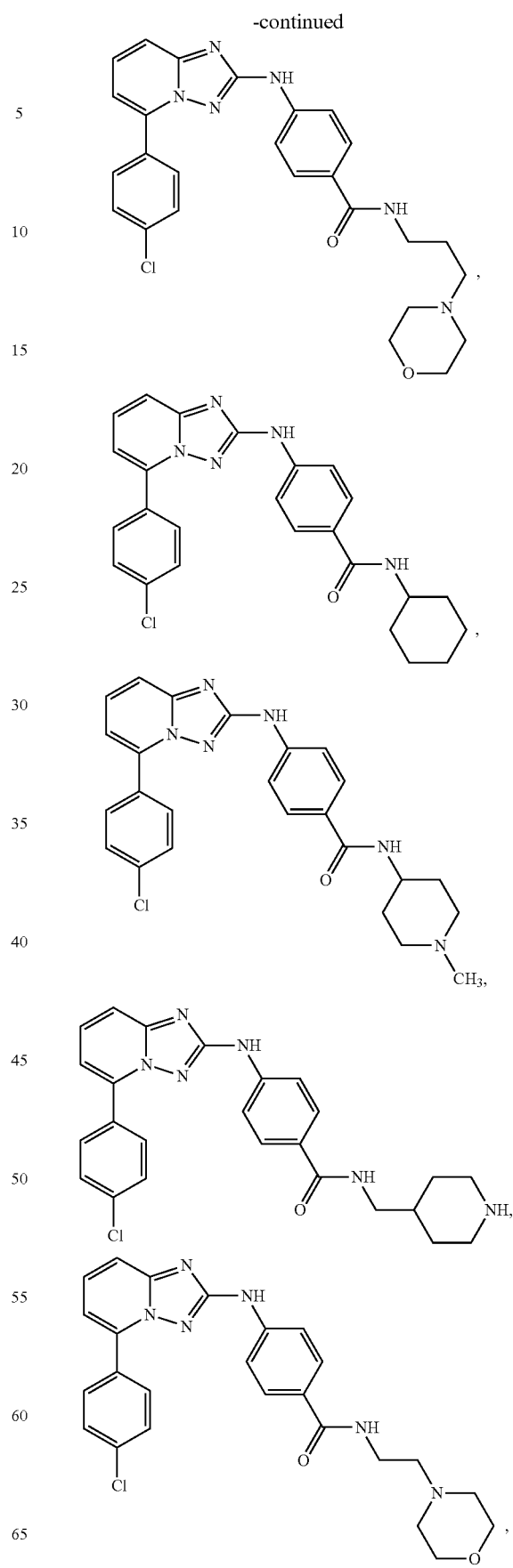

327
-continued
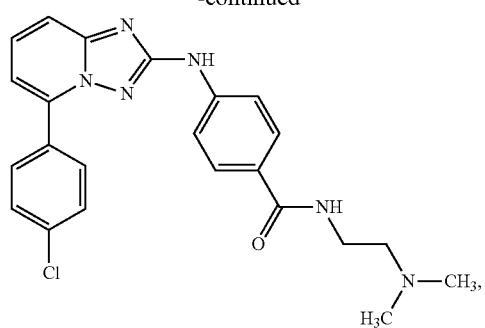
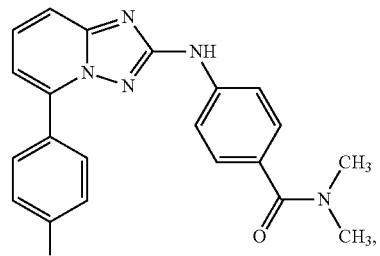
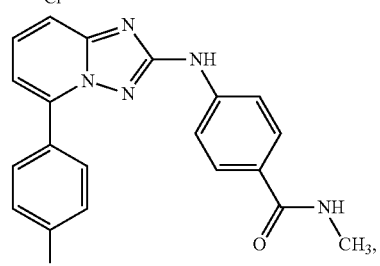
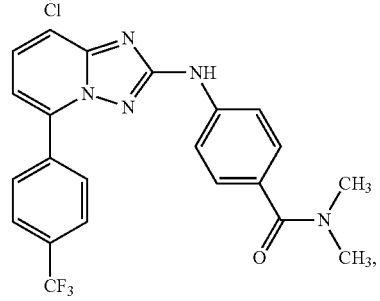
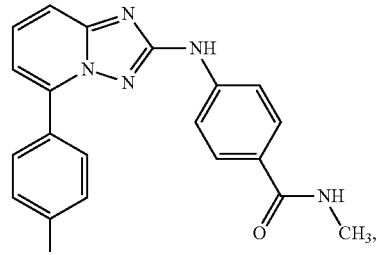
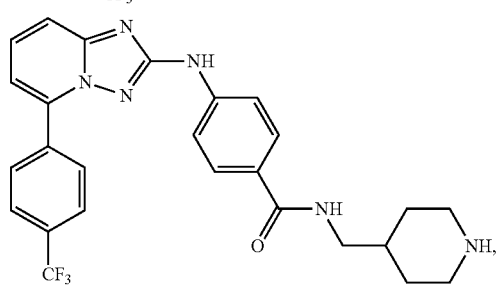
328
-continued
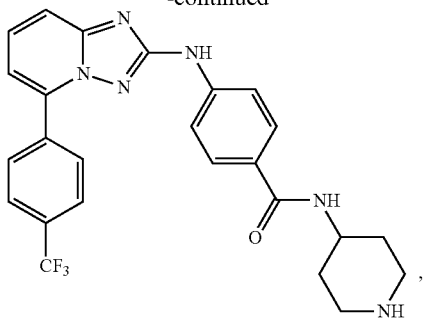
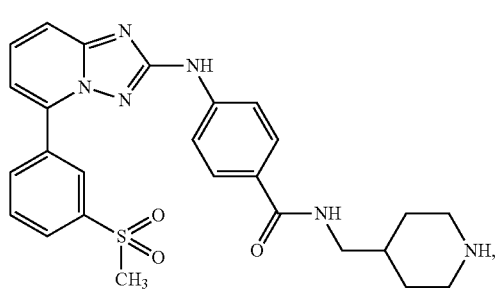
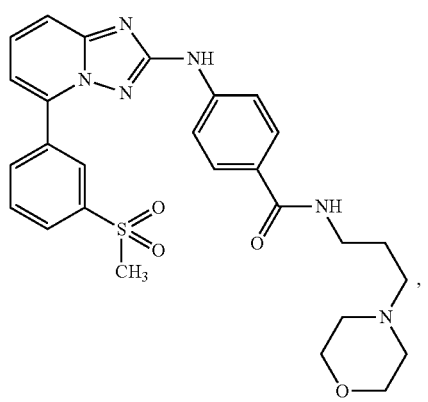
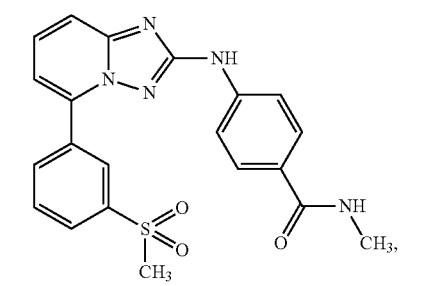
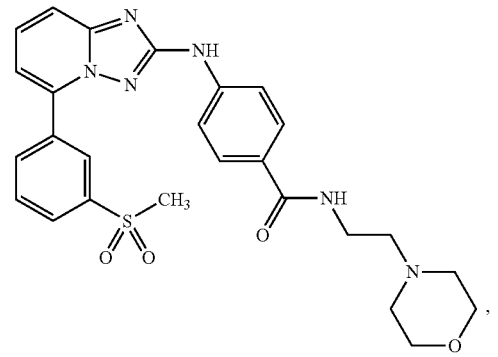

329
-continued
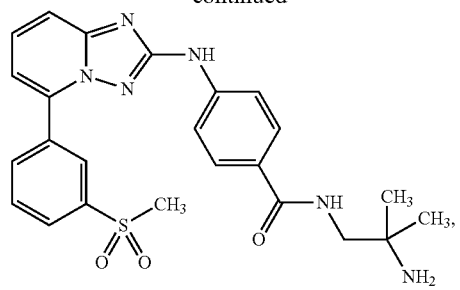
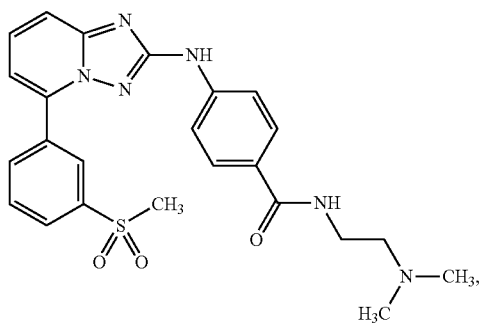
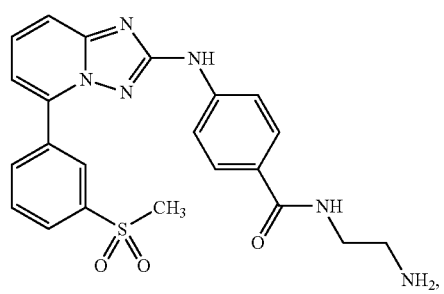
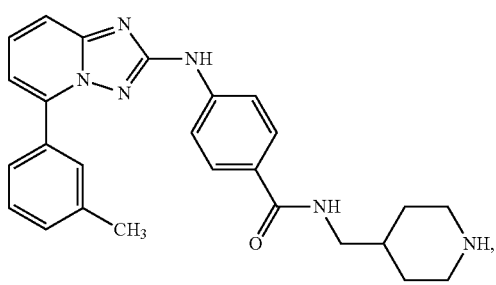
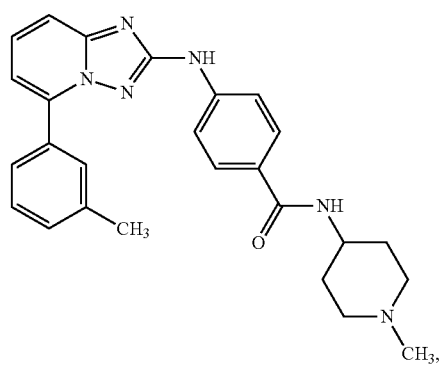
330
-continued
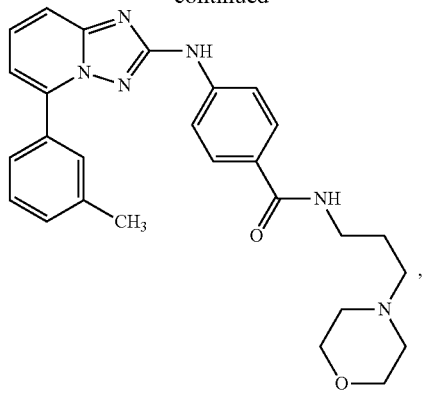
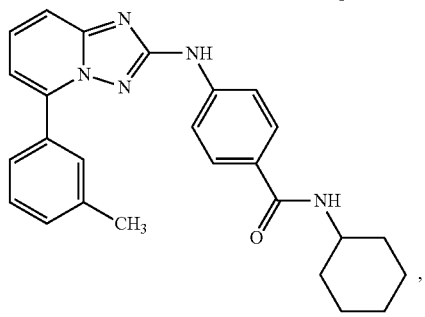
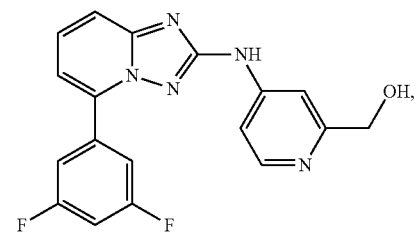
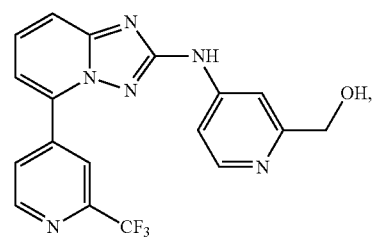
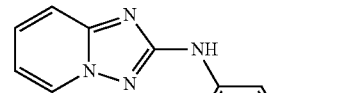
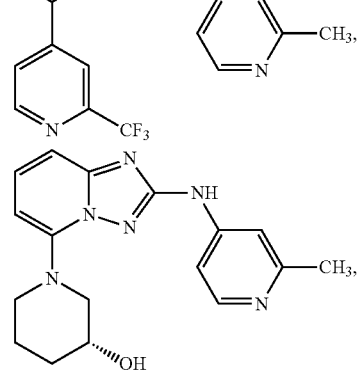

331
-continued
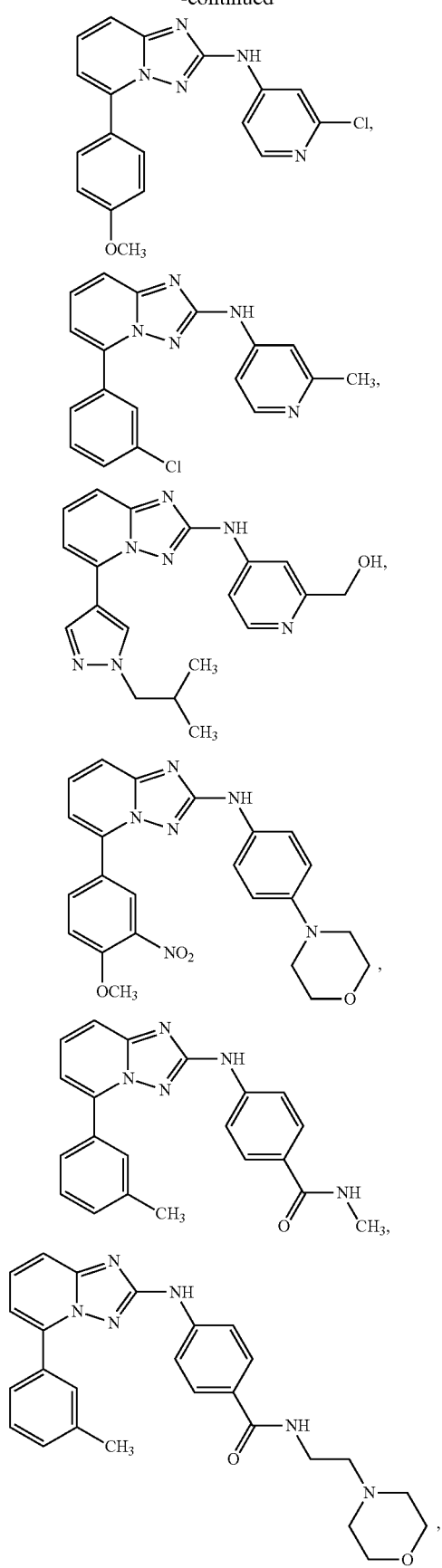
332
-continued
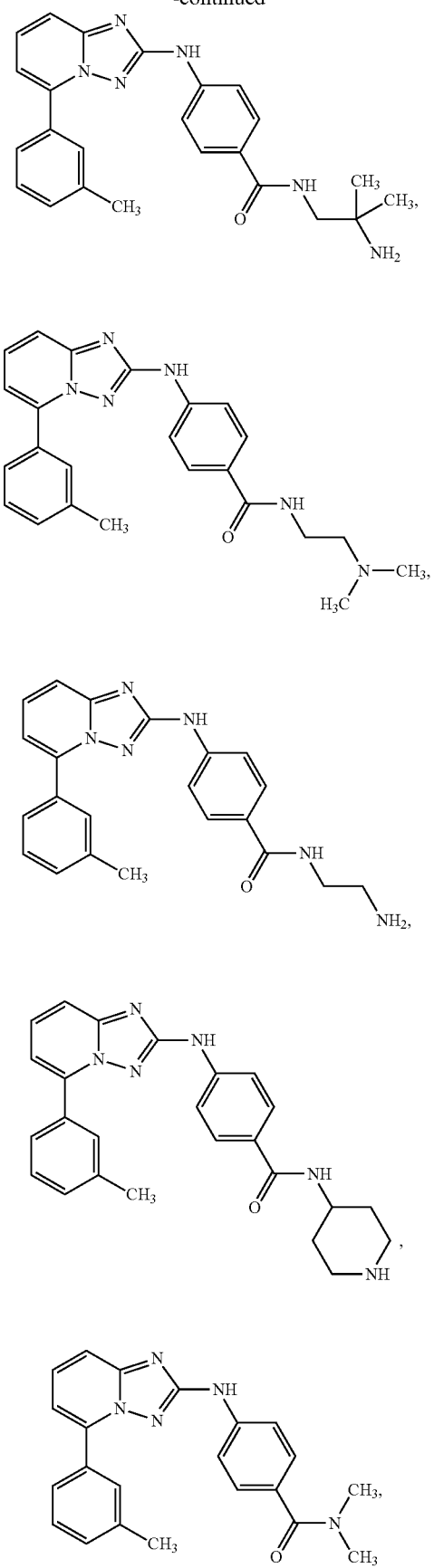

333
-continued
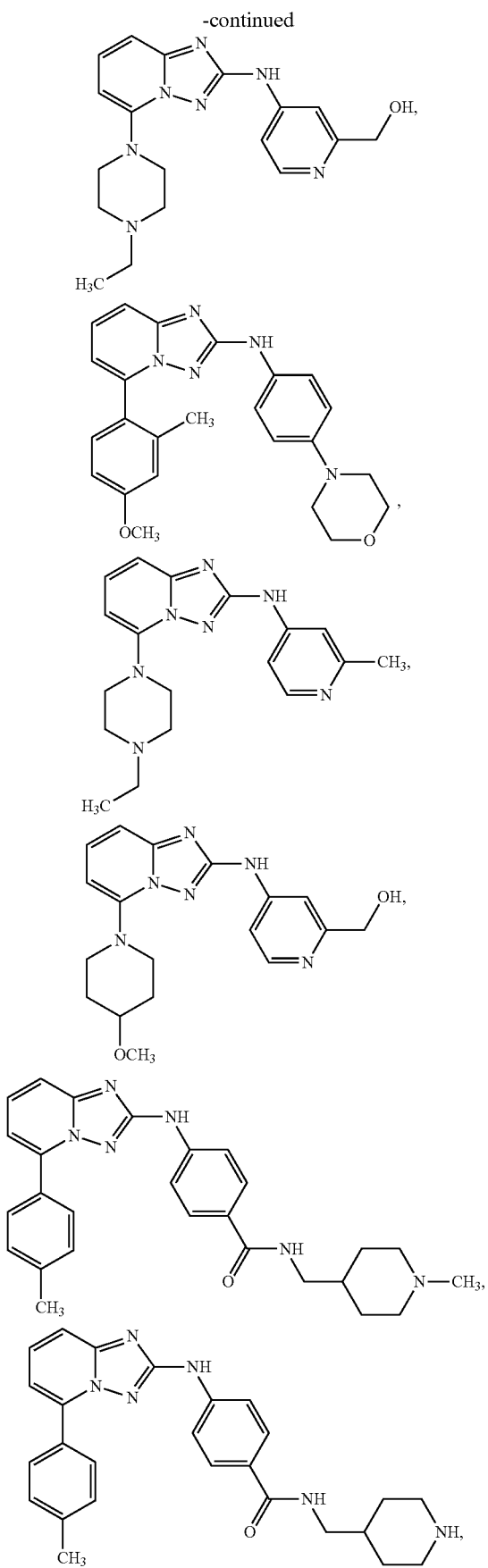
334
-continued
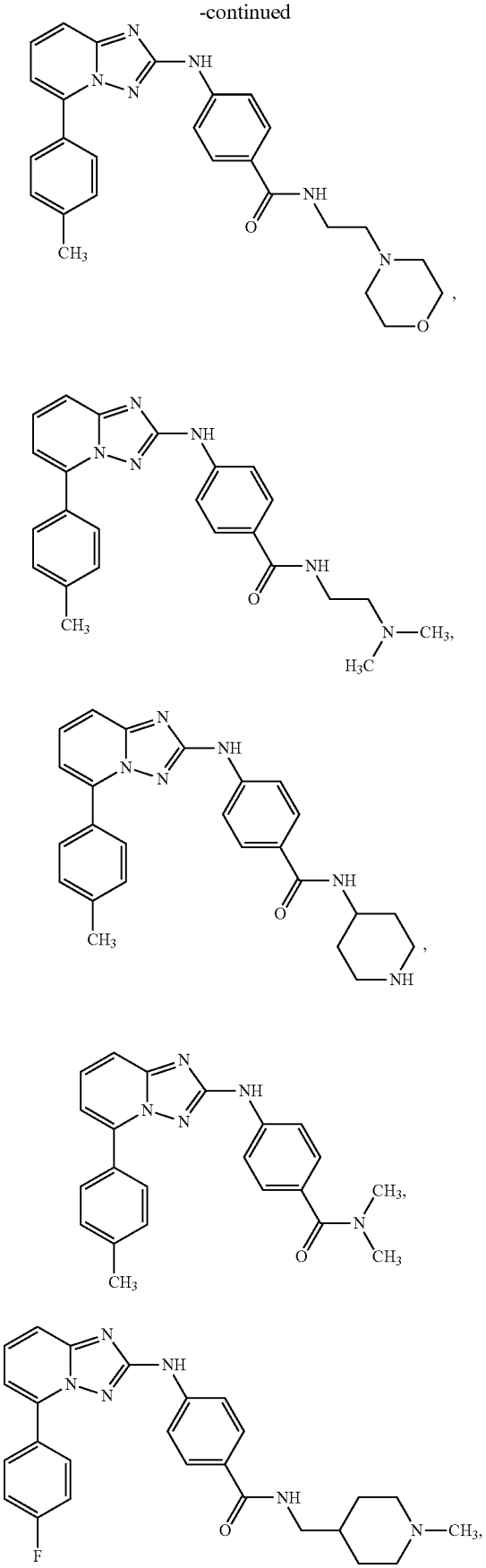

-continued
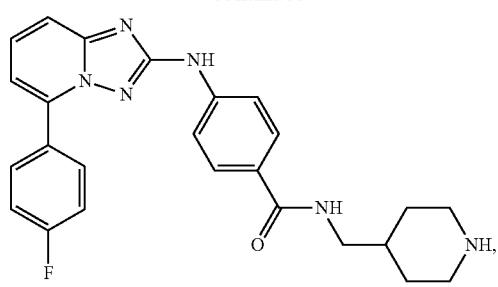
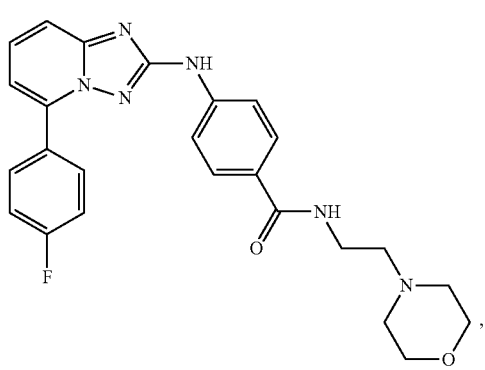
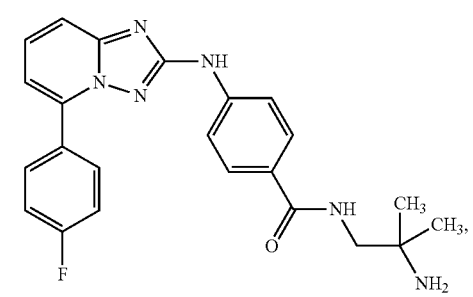
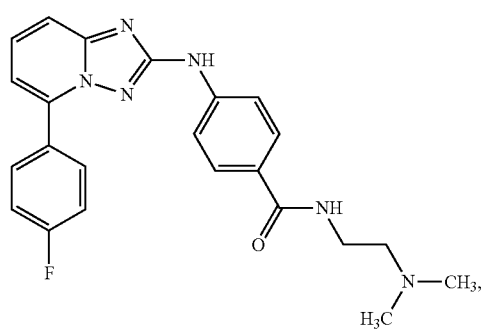
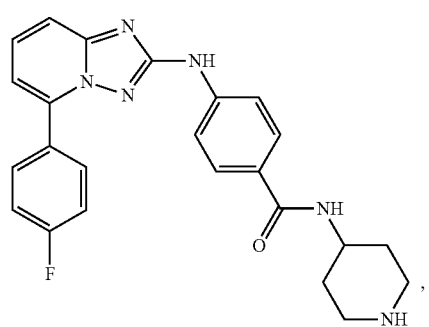
-continued
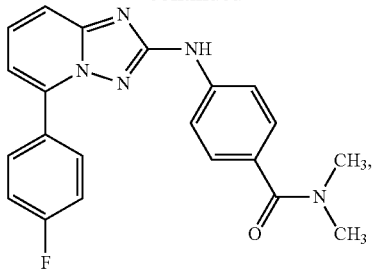
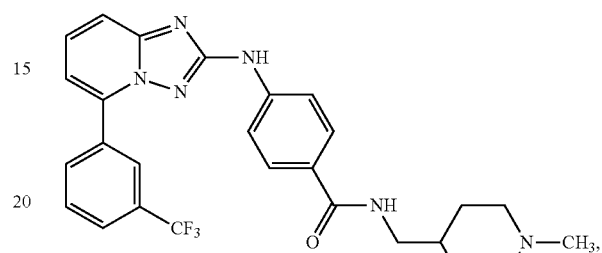
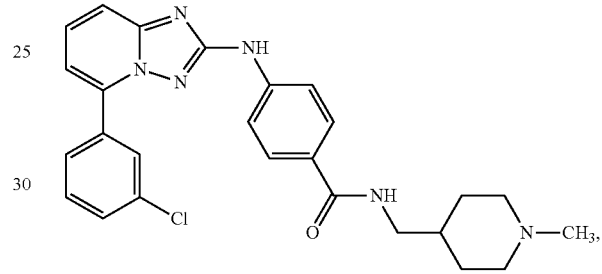
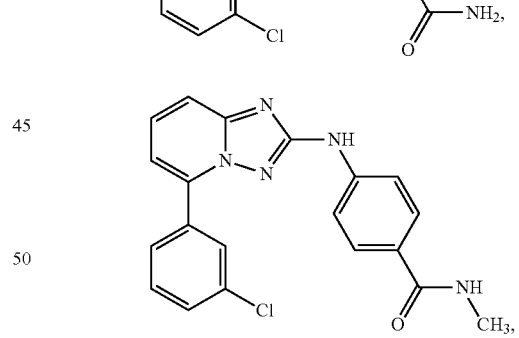
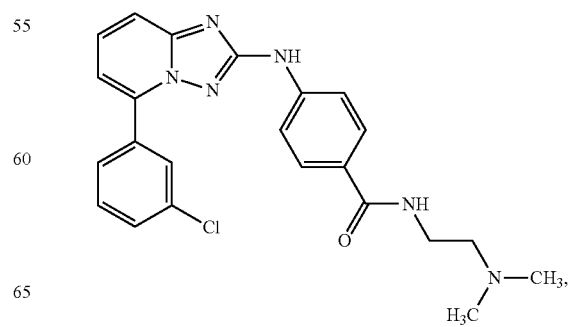

337
-continued
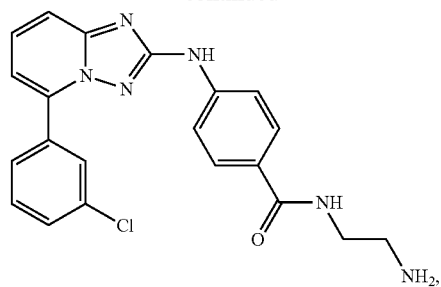
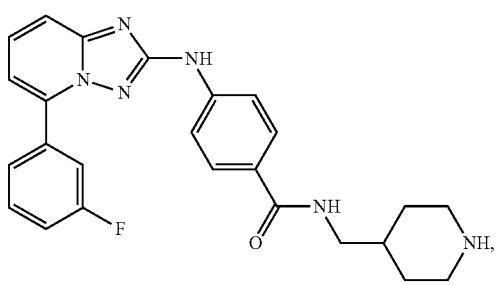
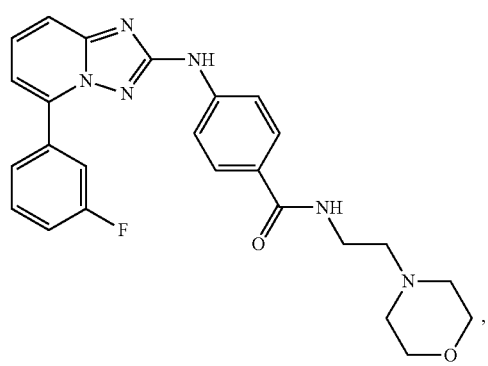
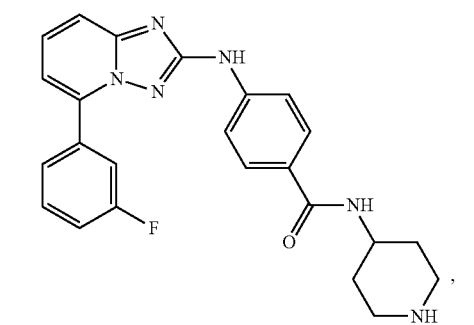
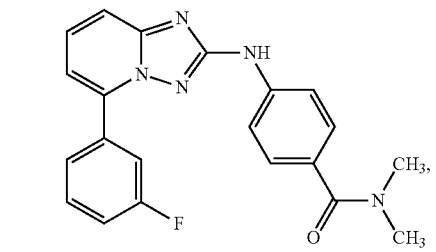
338
-continued
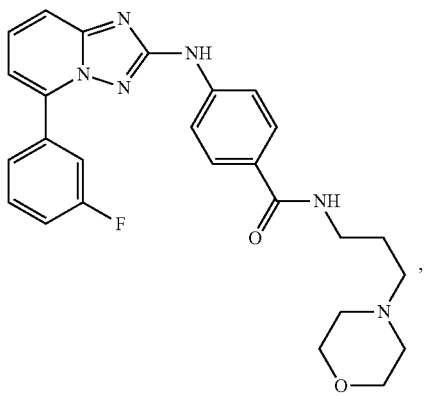
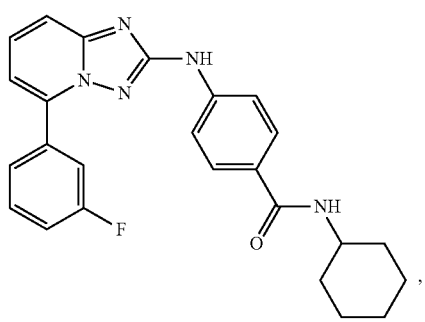
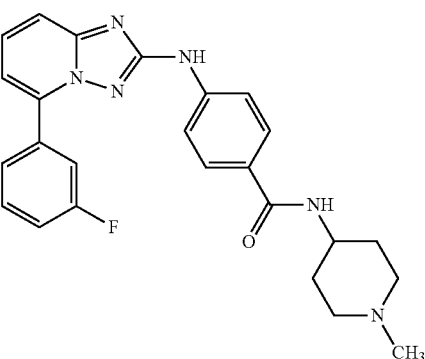
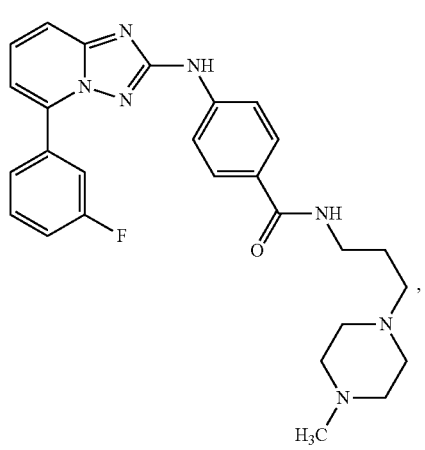

339
-continued
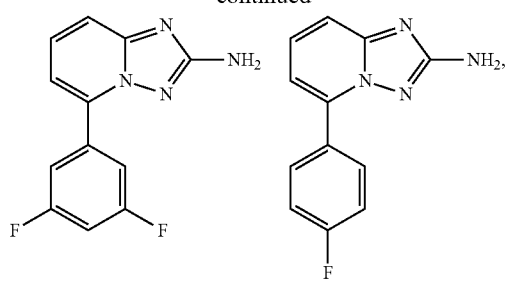
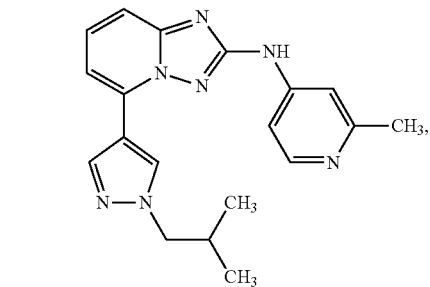
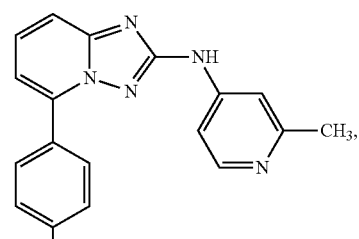
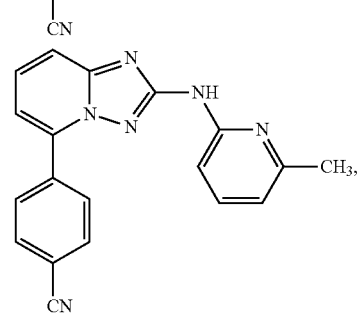
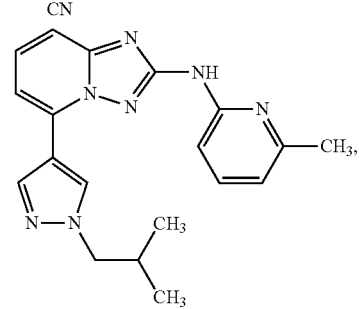
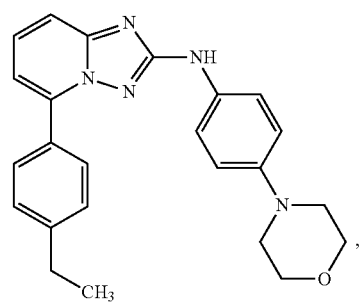
340
-continued
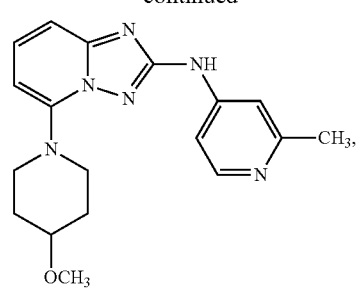
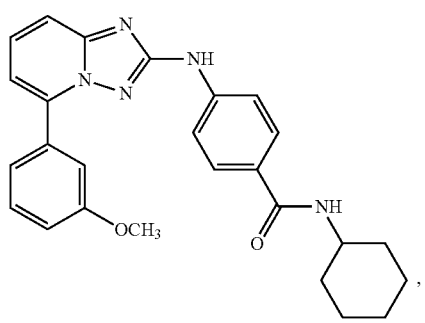
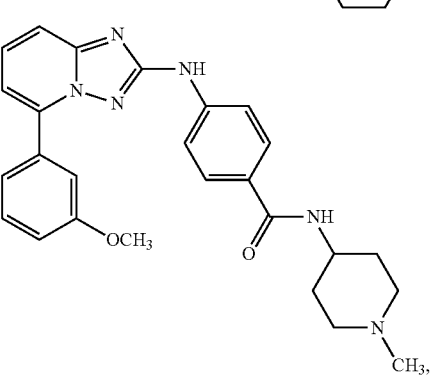
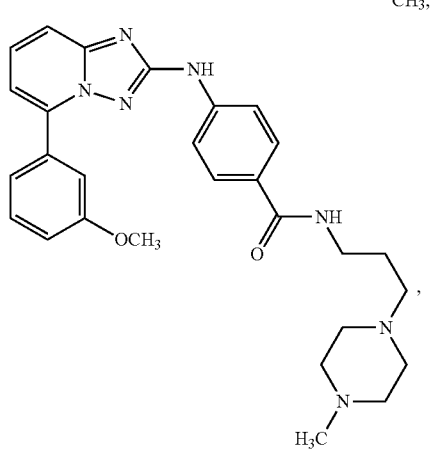
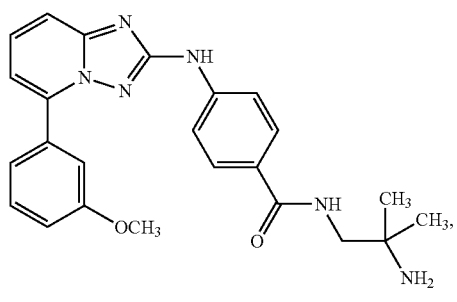

341
-continued
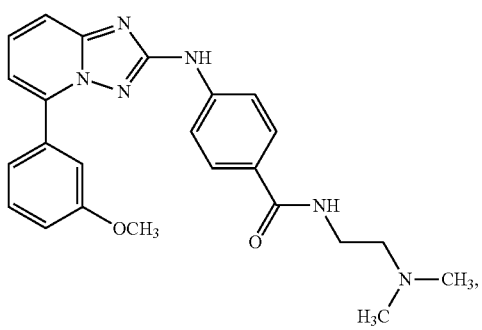
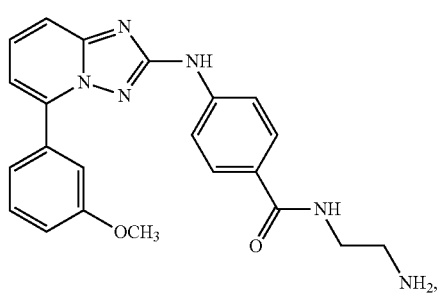
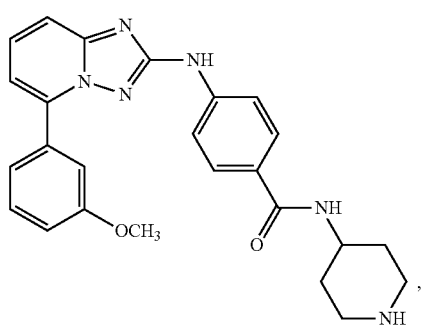
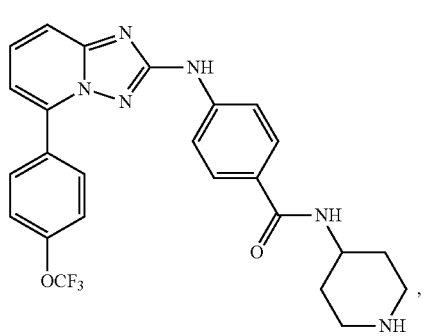
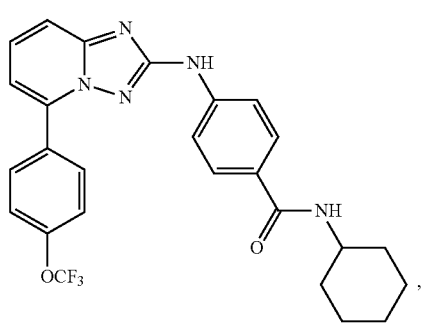
342
-continued
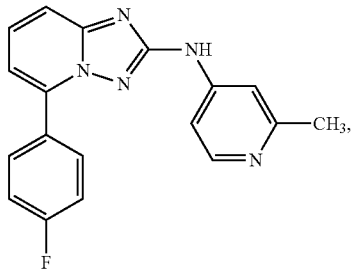
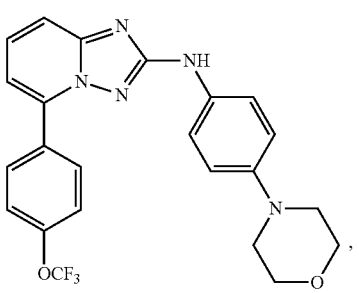
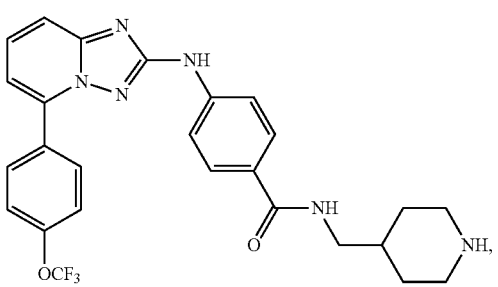
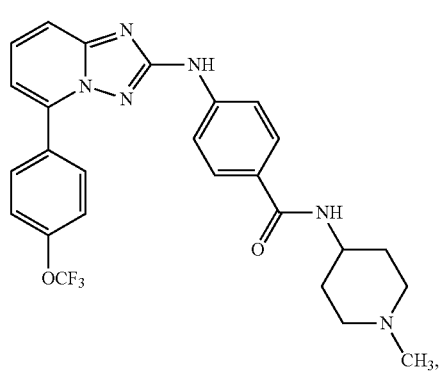
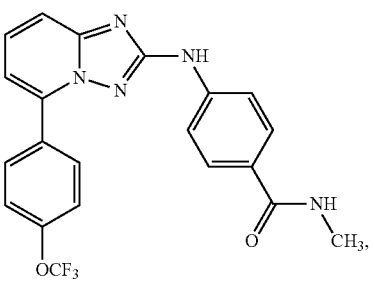

343
-continued
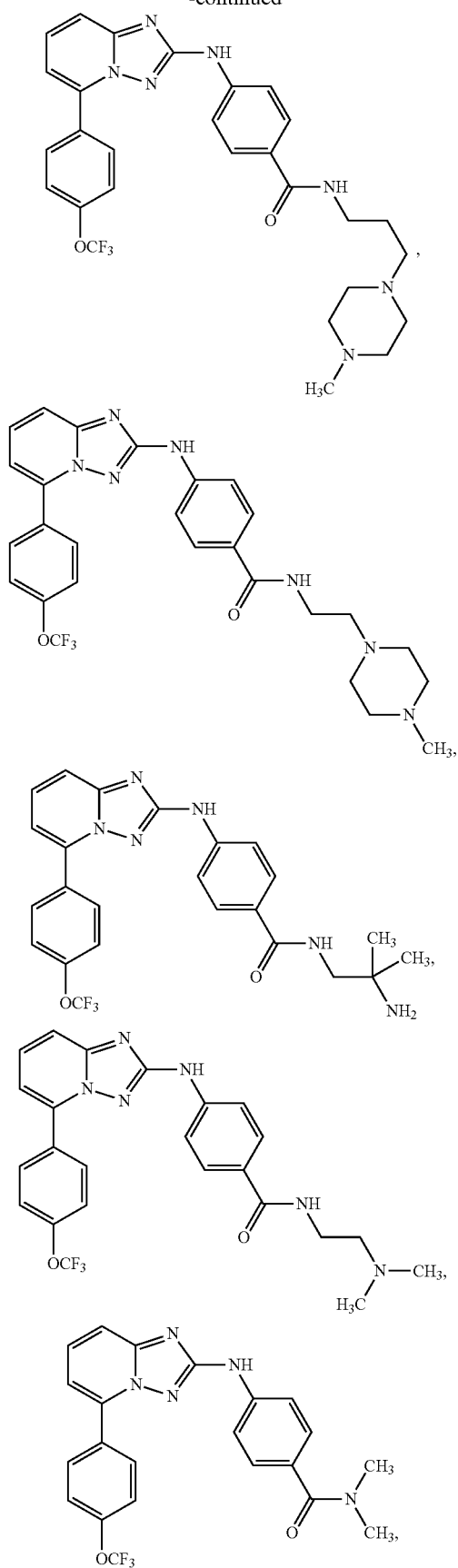
344
-continued
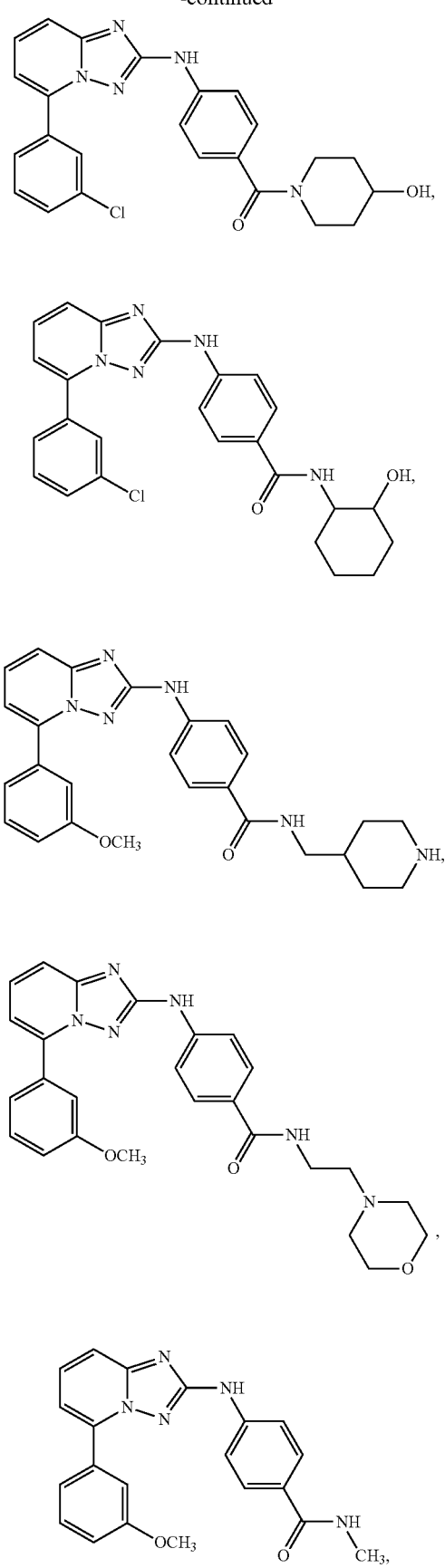

345
-continued
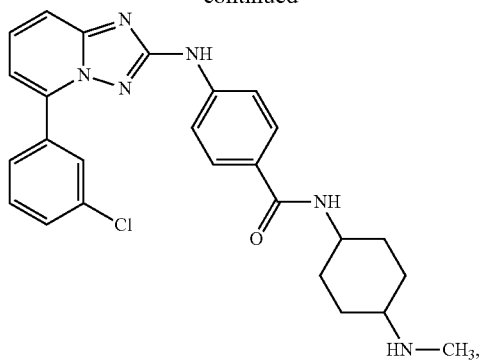
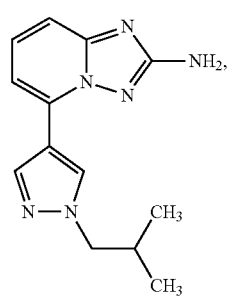
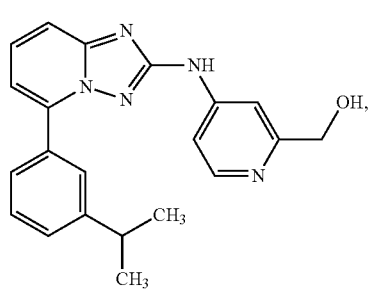
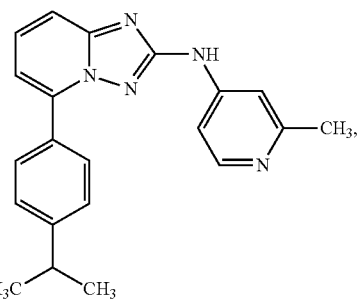
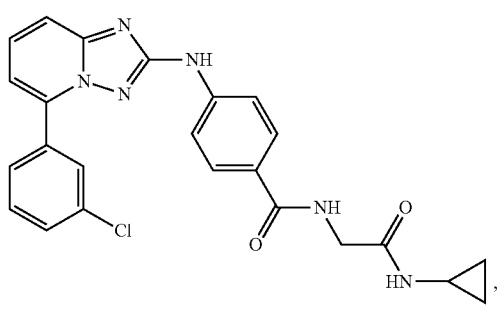
346
-continued
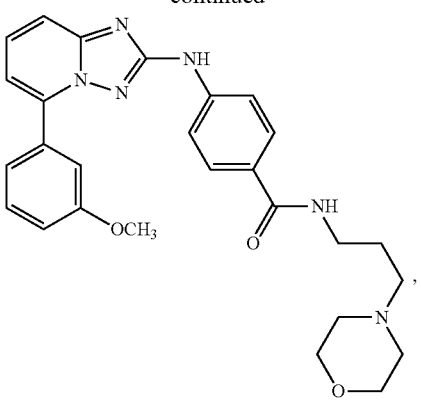
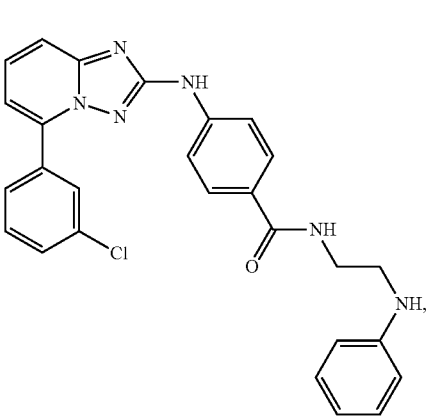
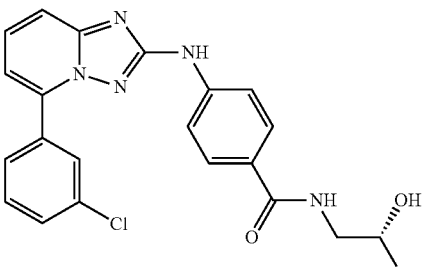
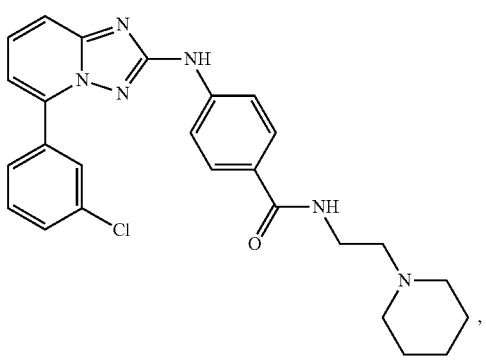

347
-continued
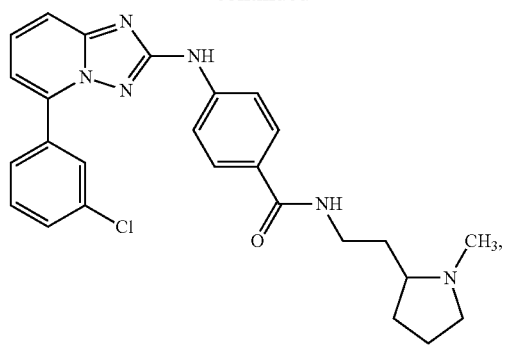
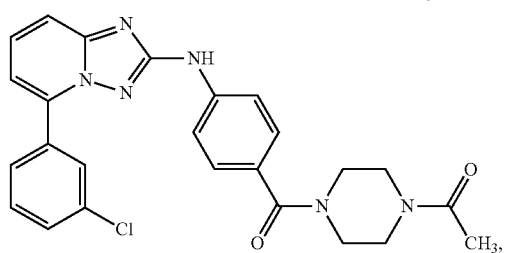
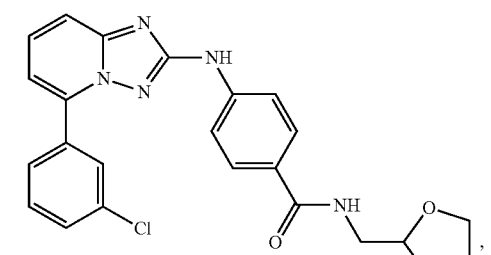
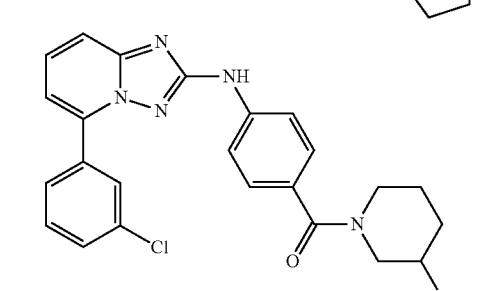
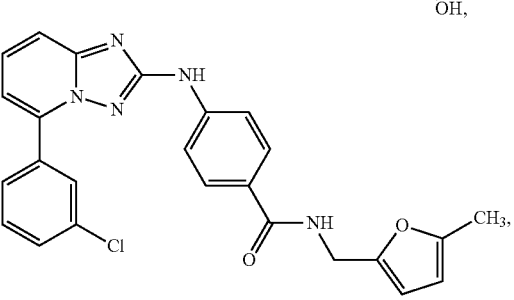
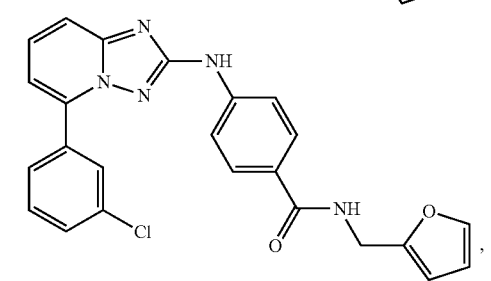
348
-continued
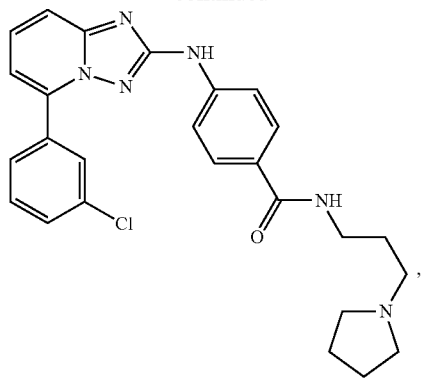
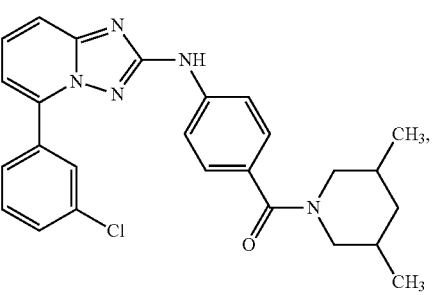
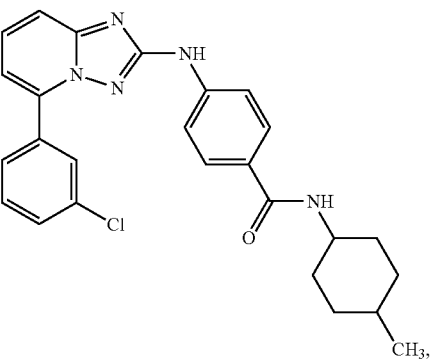
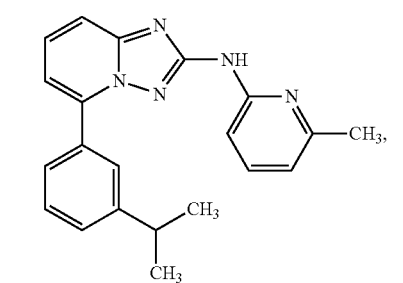
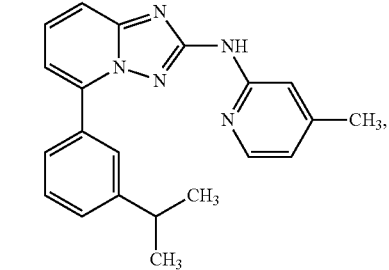

349
-continued
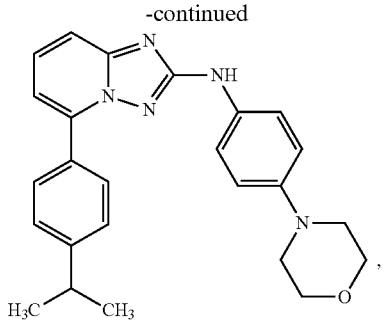
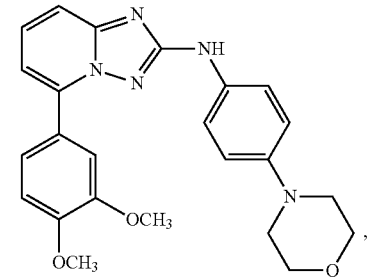
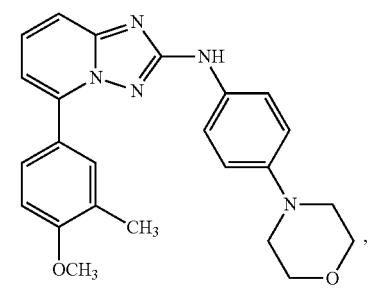
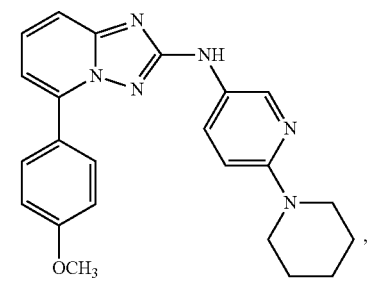
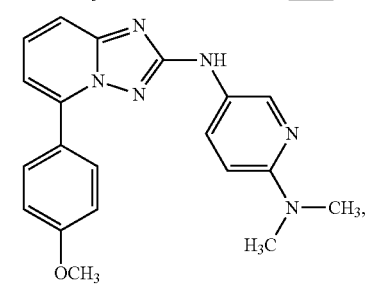
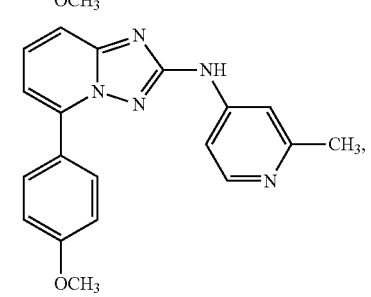
350
-continued
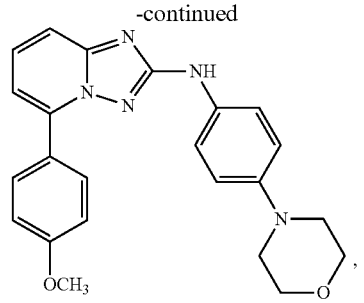
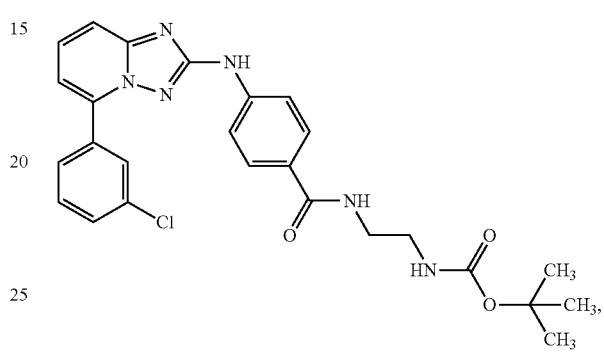
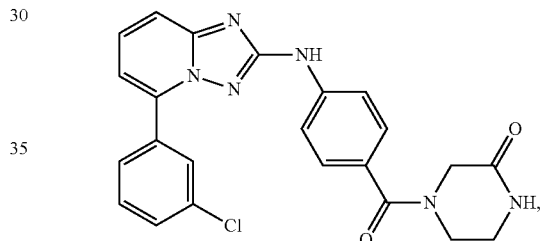
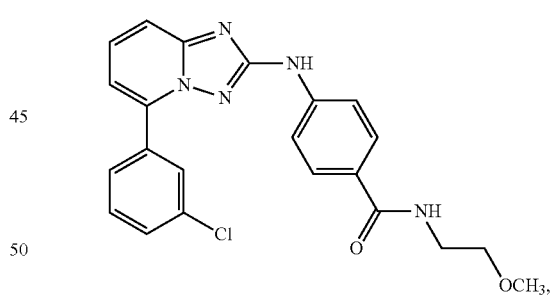
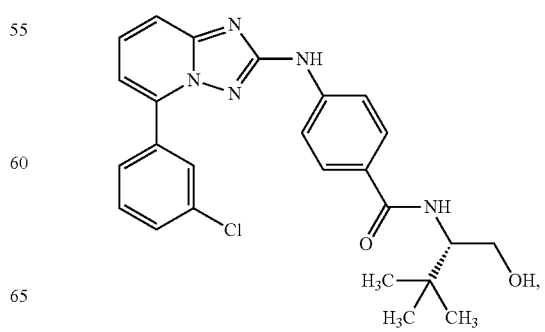

351
-continued
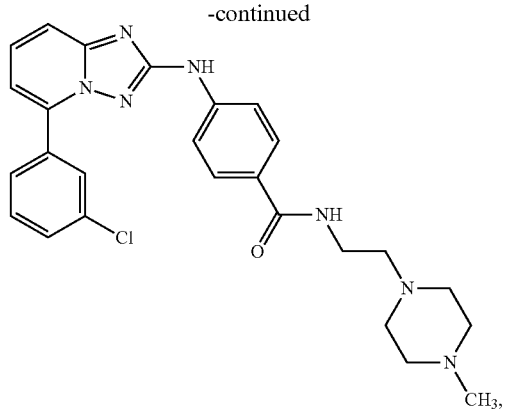
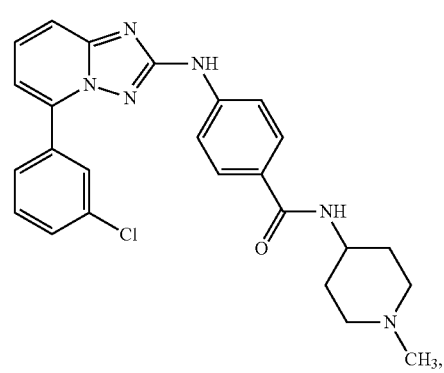
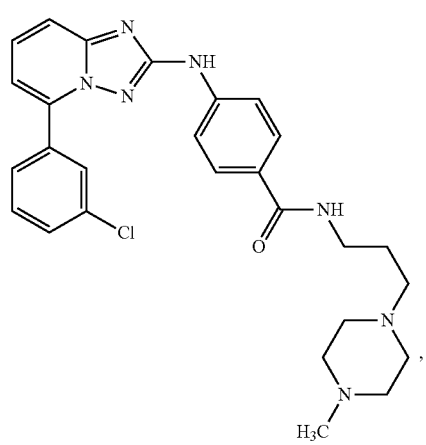
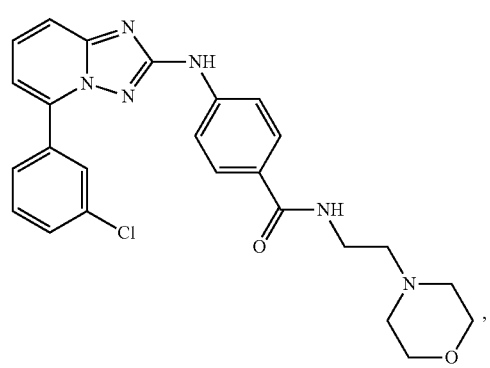
352
-continued
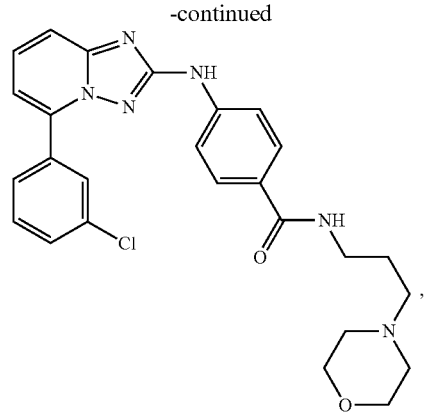
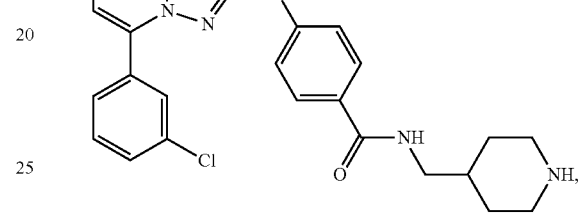
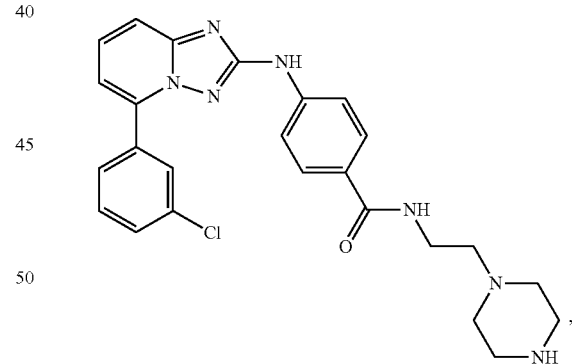
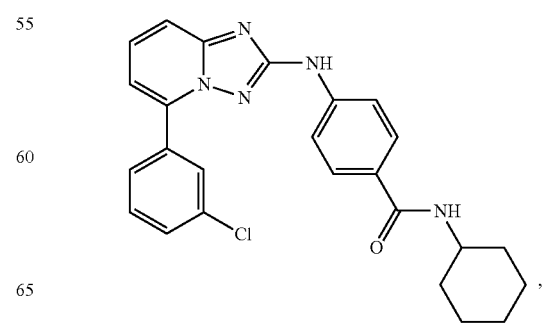

353
-continued
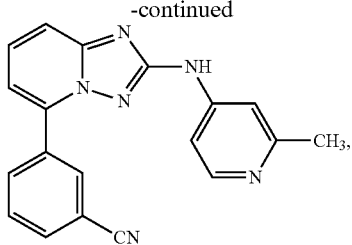
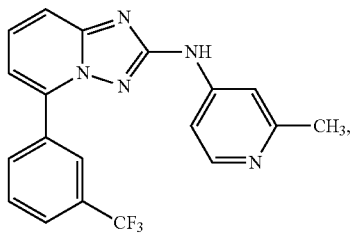
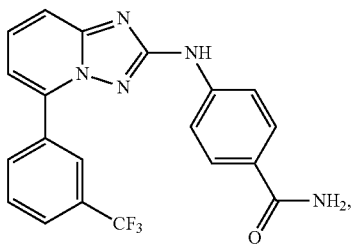
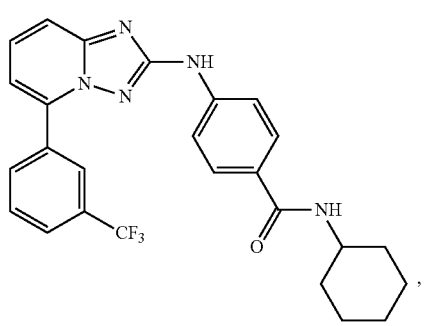
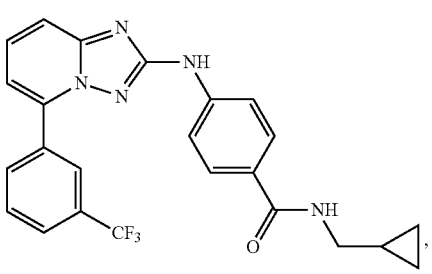
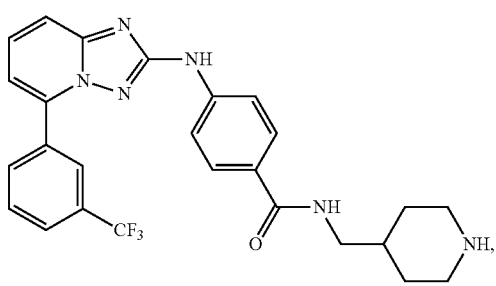
354
-continued
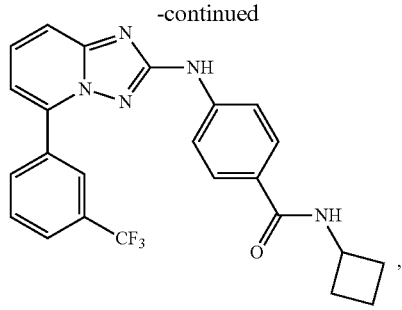
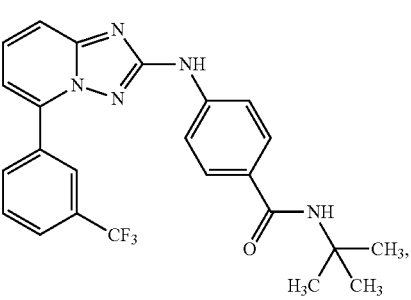
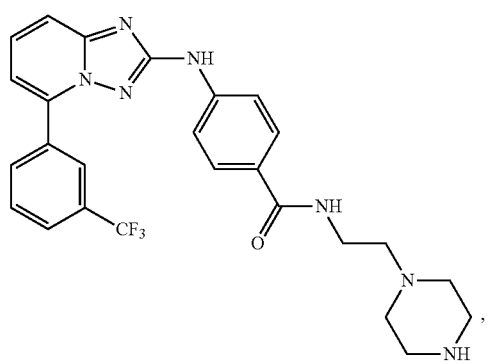
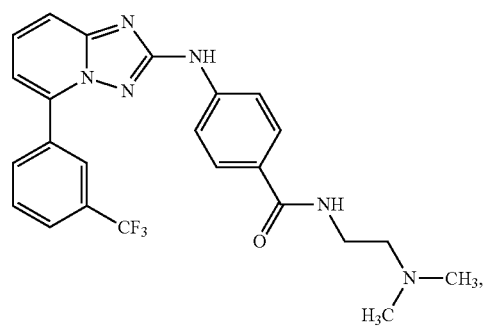
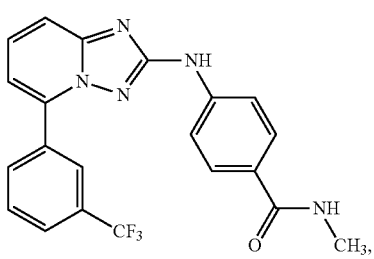

355
-continued
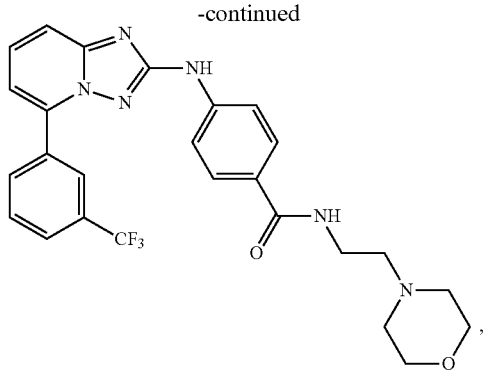
356
-continued
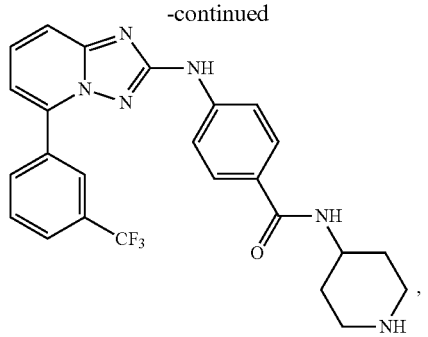
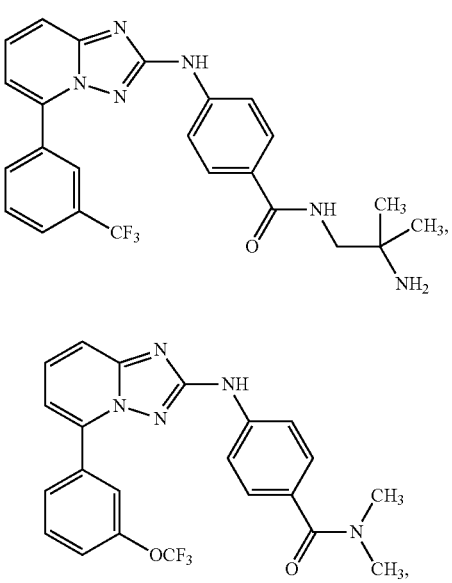
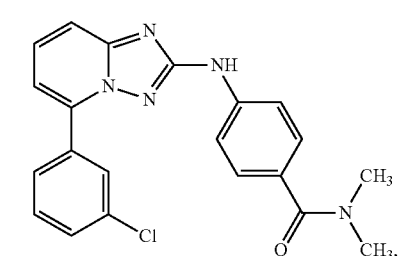
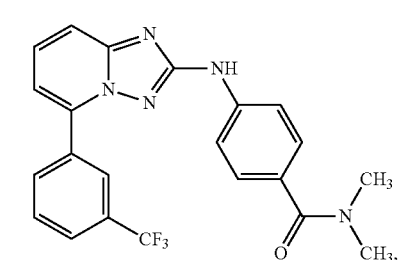
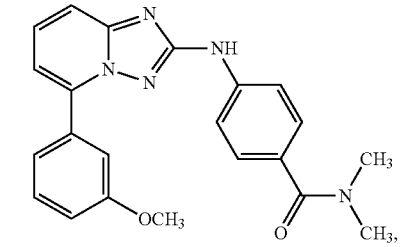

357
-continued
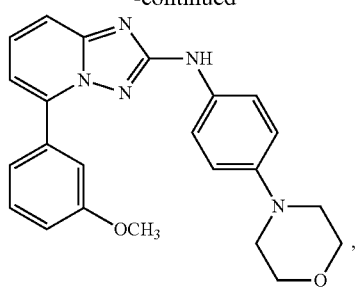
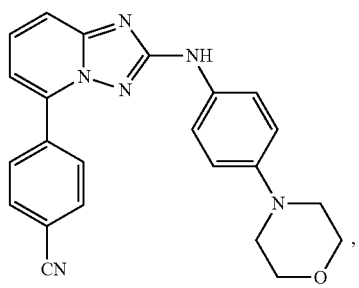
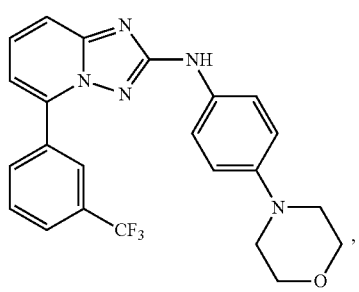
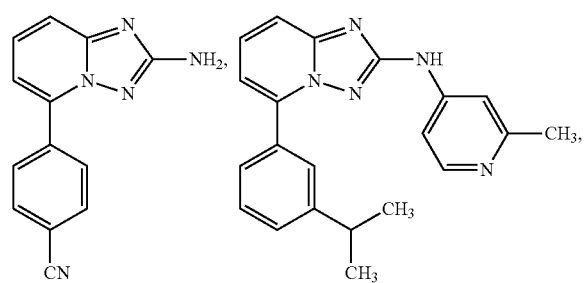
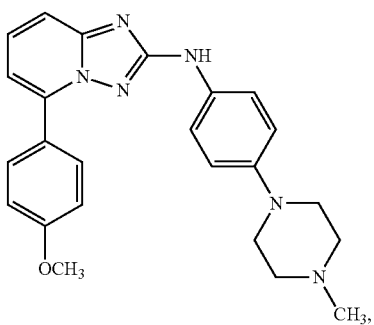
358
-continued
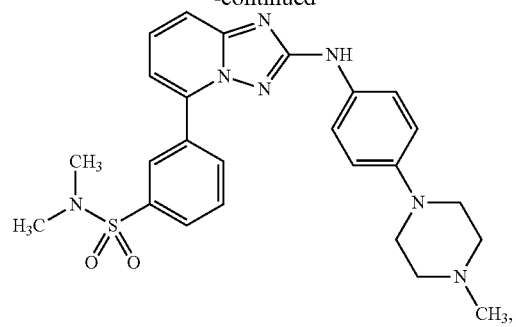
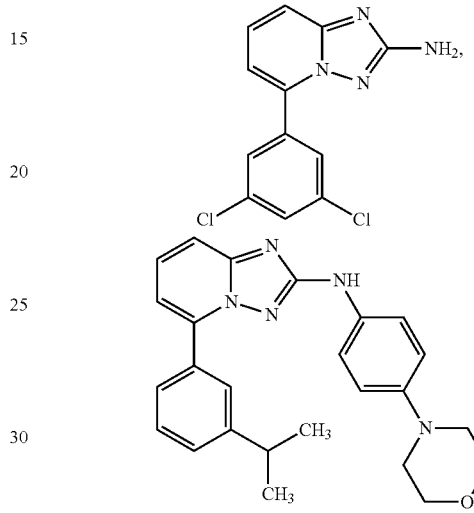
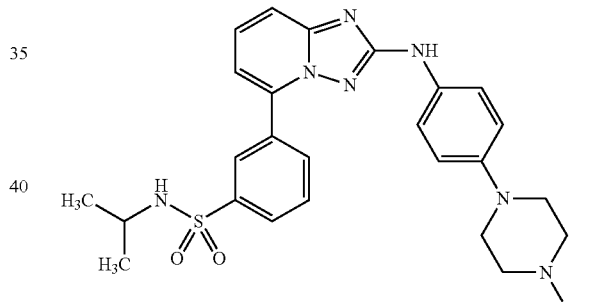
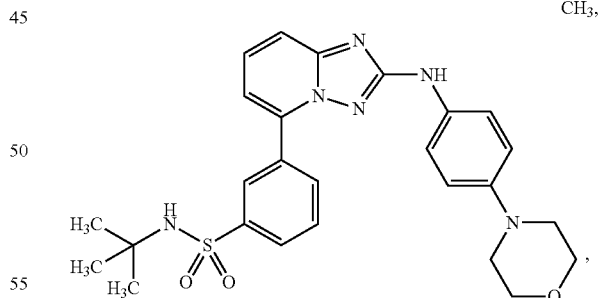
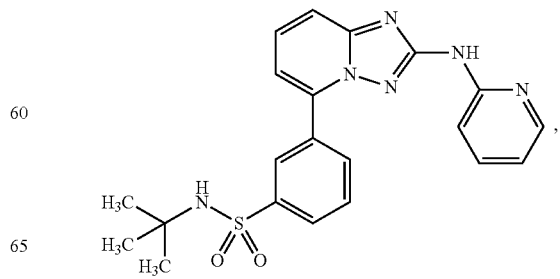

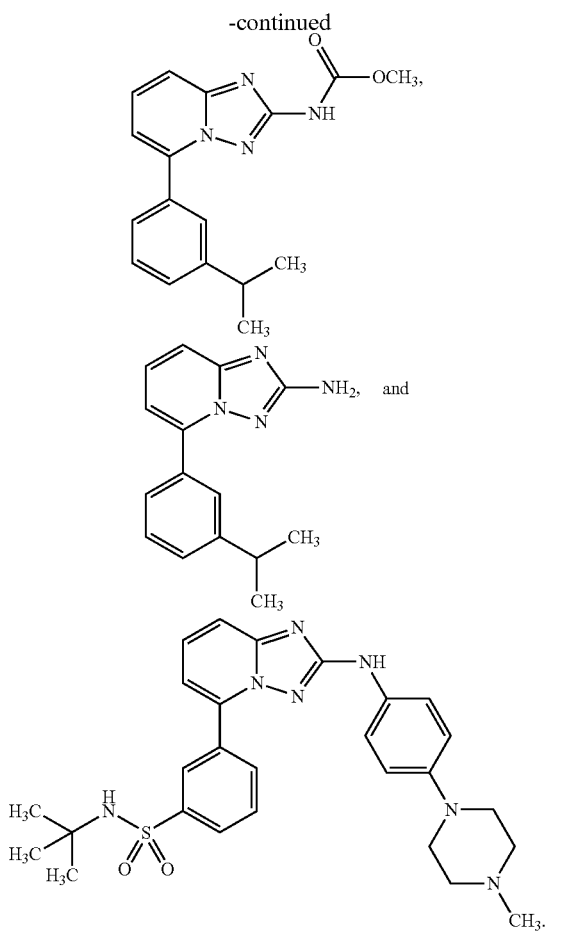

2. A pharmaceutical composition comprising a compound of claim 1 and a pharmaceutically acceptable carrier, adjuvant or vehicle.

3. The composition of claim 2, further comprising a therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

4. A pharmaceutical composition comprising a compound of claim 1 in an amount to detectably inhibit JAK2 kinase activity and a pharmaceutically acceptable carrier, adjuvant or vehicle.

5. The composition of claim 4, wherein said compound of claim 1 is in an amount to detectably inhibit JAK2 kinase activity and is at least 10 fold or more selective in inhibiting JAK2 kinase activity over inhibiting each of JAK1, JAK3 and Tyk-2 activity.

6. A compound selected from:
5-[3-(propan-2-yl)phenyl]-N-(2-methylpyridin-4-yl)[1,2,4]triazolo[1,5-a]pyridin-2-amine;
4-(5-(3-chlorophenyl)-[1,2,4]triazolo[1,5-a]pyridin-2-ylamino)-N-(piperidin-4-yl)benzamide;
5-(4-methoxyphenyl)-N-(4-(4-methylpiperazin-1-yl)phenyl)-[1,2,4]triazolo[1,5-a]pyridin-2-amine;
N-(4-((2-methoxyethylamino)methyl)phenyl)-5-(4-methoxyphenyl)[1,2,4]triazolo[1,5-a]pyridin-2-amine;
5-(4-methoxypiperidin-1-yl)-N-(2-methylpyridin-4-yl)-[1,2,4]triazolo[1,5-a]pyridin-2-amine;
[5-(3-Isopropyl-phenyl)-[1,2,4]triazolo[1,5-a]pyridin-2-yl]-carbamic acid methyl ester;
4-[5-(3-Acetylamino-phenyl)-[1,2,4]triazolo[1,5-a]pyridin-2-ylamino]-N-piperidin-4-ylmethyl-benzamide;
4-[5-(3-Acetylamino-phenyl)-[1,2,4]triazolo[1,5-a]pyridin-2-ylamino]-N-(1-methyl-piperidin-4-yl)-benzamide;
4-[5-(3-Acetylamino-phenyl)-[1,2,4]triazolo[1,5-a]pyridin-2-ylamino]-N-(2-morpholin-4-yl-ethyl)-benzamide;
4-[5-(3-Acetylamino-phenyl)-[1,2,4]triazolo[1,5-a]pyridin-2-ylamino]-N,N-dimethylbenzamide;
4-[5-(3-Acetylamino-phenyl)-[1,2,4]triazolo[1,5-a]pyridin-2-ylamino]-N-(2-amino-2-methyl-propyl)-benzamide;
4-[5-(3-Chloro-4-methoxy-phenyl)-[1,2,4]triazolo[1,5-a]pyridin-2-ylamino]-N-(1-methyl-piperidin-4-yl)-benzamide;
4-[5-(4-Chloro-phenyl)-[1,2,4]triazolo[1,5-a]pyridin-2-ylamino]-N-(1-methyl-piperidin-4-ylmethyl)-benzamide;
N-(2-Amino-2-methyl-propyl)-4-[5-(4-chloro-phenyl)-[1,2,4]triazolo[1,5-a]pyridin-2-ylamino]-benzamide;
4-[5-(4-Chloro-phenyl)-[1,2,4]triazolo[1,5-a]pyridin-2-ylamino]-N-[2-(1-methylpyrrolidin-2-yl)-ethyl]-benzamide;
4-[5-(3-Methoxy-phenyl)-[1,2,4]triazolo[1,5-a]pyridin-2-ylamino]-N-(1-methyl-piperidin-4-ylmethyl)-benzamide;
4-[5-(3-Methoxy-phenyl)-[1,2,4]triazolo[1,5-a]pyridin-2-ylamino]-N-(2-piperazin-1-yl-ethyl)-benzamide;
4-[5-(3-Fluoro-phenyl)-[1,2,4]triazolo[1,5-a]pyridin-2-ylamino]-N-(1-methyl-piperidin-4-ylmethyl)-benzamide;
4-[5-(3-Fluoro-phenyl)-[1,2,4]triazolo[1,5-a]pyridin-2-ylamino]-N-(2-piperazin-1-yl-ethyl)-benzamide;
4-[5-(3-Fluoro-phenyl)-[1,2,4]triazolo[1,5-a]pyridin-2-ylamino]-N-methyl-benzamide;
4-[5-(3-Acetylamino-phenyl)-[1,2,4]triazolo[1,5-a]pyridin-2-ylamino]-benzoic acid;
4-[5-(3-Methoxy-phenyl)-[1,2,4]triazolo[1,5-a]pyridin-2-ylamino]-benzamide;
4-[5-(4-Chloro-phenyl)-[1,2,4]triazolo[1,5-a]pyridin-2-ylamino]-benzamide;
4-[5-(3-Fluoro-phenyl)-[1,2,4]triazolo[1,5-a]pyridin-2-ylamino]-benzamide;
N-(2-Morpholin-4-yl-ethyl)-4-[5-(3-trifluoromethoxy-phenyl)-[1,2,4]triazolo[1,5-a]pyridin-2-ylamino]-benzamide;
N-(1-Methyl-piperidin-4-yl)-4-[5-(3-trifluoromethoxy-phenyl)-[1,2,4]triazolo[1,5-a]pyridin-2-ylamino]-benzamide;
N-(2-Amino-2-methyl-propyl)-4-[5-(3-trifluoromethoxy-phenyl)-[1,2,4]triazolo[1,5-a]pyridin-2-ylamino]-benzamide;
N-(2-piperazin-1-yl-ethyl)-4-[5-(3-trifluoromethoxy-phenyl)-[1,2,4]triazolo[1,5-a]pyridin-2-ylamino]-benzamide;
N-(2-Amino-ethyl)-4-[5-(3-trifluoromethoxy-phenyl)-[1,2,4]triazolo[1,5-a]pyridin-2-ylamino]-benzamide;
N-(2-Dimethylamino-ethyl)-4-[5-(3-trifluoromethoxy-phenyl)-[1,2,4]triazolo[1,5-a]pyridin-2-ylamino]-benzamide;
N-Piperidin-4-yl-4-[5-(3-trifluoromethoxy-phenyl)-[1,2,4]triazolo[1,5-a]pyridin-2-ylamino]-benzamide;

[5-(4-Methoxy-phenyl)-[1,2,4]triazolo[1,5-a]pyridin-2-yl]-{4-[(2-morpholin-4-yl-ethylamino)-methyl]-phenyl}-amine;
4-[5-(4-Methanesulfonyl-phenyl)-[1,2,4]triazolo[1,5-a]pyridin-2-ylamino]-N-(3-morpholin-4-yl-propyl)-benzamide;
4-[5-(4-Methanesulfonyl-phenyl)-[1,2,4]triazolo[1,5-a]pyridin-2-ylamino]-N-(2-morpholin-4-yl-ethyl)-benzamide;
4-[5-(4-Methanesulfonyl-phenyl)-[1,2,4]triazolo[1,5-a]pyridin-2-ylamino]-N,N-dimethylbenzamide;
4-[5-(4-Methanesulfonyl-phenyl)-[1,2,4]triazolo[1,5-a]pyridin-2-ylamino]-N-piperidin-4-yl-benzamide;
4-[5-(4-Methanesulfonyl-phenyl)-[1,2,4]triazolo[1,5-a]pyridin-2-ylamino]-N-piperidin-4-ylmethyl-benzamide;
N-(2-Amino-2-methyl-propyl)-4-[5-(4-methanesulfonyl-phenyl)-[1,2,4]triazolo[1,5-a]pyridin-2-ylamino]-benzamide;
N-(2-Piperazin-1-yl-ethyl)-4-(5-p-tolyl-[1,2,4]triazolo[1,5-a]pyridin-2-ylamino)-benzamide;
N-(2-Amino-2-methyl-propyl)-4-(5-p-tolyl-[1,2,4]triazolo[1,5-a]pyridin-2-ylamino)-benzamide;
4-[5-(3-Methanesulfonyl-phenyl)-[1,2,4]triazolo[1,5-a]pyridin-2-ylamino]-N-piperidin-4-yl-benzamide;
N-Cyclohexyl-4-[5-(3-methanesulfonyl-phenyl)-[1,2,4]triazolo[1,5-a]pyridin-2-ylamino]-benzamide;
4-[2-(2-Hydroxymethyl-pyridin-4-ylamino)-[1,2,4]triazolo[1,5-a]pyridin-5-yl]-benzonitrile;
[5-(3-Amino-4-methoxy-phenyl)-[1,2,4]triazolo[1,5-a]pyridin-2-yl]-(4-morpholin-4-yl-phenyl)-amine;
[5-(1-Benzyl-1H-pyrazol-4-yl)-[1,2,4]triazolo[1,5-a]pyridin-2-yl]-(2-methyl-pyridin-4-yl)-amine;
[5-(1-Methyl-1H-pyrazol-4-yl)-[1,2,4]triazolo[1,5-a]pyridin-2-yl]-(2-methyl-pyridin-4-yl)-amine;
N-tert-Butyl-2-methoxy-5-{2-[4-(4-methyl-piperazin-1-yl)-phenylamino]-[1,2,4]triazolo[1,5-a]pyridin-5-yl}-benzenesulfonamide;
5-(1-Methyl-1H-pyrazol-4-yl)-[1,2,4]triazolo[1,5-a]pyridin-2-ylamine;
5-(1-Benzyl-1H-pyrazol-4-yl)-[1,2,4]triazolo[1,5-a]pyridin-2-ylamine;
{4-[(2-Methoxy-ethylamino)-methyl]-phenyl}-[1,5-(4-methoxy-phenyl)-[1,2,4]triazolo[1,5-a]pyridin-2-yl]-amine;
{4-[5-(4-Methoxy-phenyl)-[1,2,4]triazolo[1,5-a]pyridin-2-ylamino]-phenyl}-methanol;
N-(2-Amino-2-methyl-propyl)-4-[5-(3-fluoro-phenyl)-[1,2,4]triazolo[1,5-a]pyridin-2-ylamino]-benzamide;
4-[5-(4-Chloro-phenyl)[1,2,4]triazolo[1,5-a]pyridin-2-ylamino]-N-(3-morpholin-4-yl-propyl)-benzamide;
4-[5-(4-Chloro-phenyl)[1,2,4]triazolo[1,5-a]pyridin-2-ylamino]-N-cyclohexyl-benzamide;
4-[5-(4-Chloro-phenyl)[1,2,4]triazolo[1,5-a]pyridin-2-ylamino]-N-(1-methyl-piperidin-4-yl)-benzamide;
4-[5-(4-Chloro-phenyl)[1,2,4]triazolo[1,5-a]pyridin-2-ylamino]-N-piperidin-4-ylmethyl-benzamide;
4-[5-(4-Chloro-phenyl)[1,2,4]triazolo[1,5-a]pyridin-2-ylamino]-N-(2-morpholin-4-yl-ethyl)-benzamide;
4-[5-(4-Chloro-phenyl)[1,2,4]triazolo[1,5-a]pyridin-2-ylamino]-N-(2-dimethylamino-ethyl)-benzamide;
4-[5-(4-Chloro-phenyl)[1,2,4]triazolo[1,5-a]pyridin-2-ylamino]-N,N-dimethylbenzamide;
4-[5-(4-Chloro-phenyl)[1,2,4]triazolo[1,5-a]pyridin-2-ylamino]-N-methyl-benzamide;
N,N-Dimethyl-4-[5-(4-trifluoromethyl-phenyl)-[1,2,4]triazolo[1,5-a]pyridin-2-ylamino]-benzamide;
N-Methyl-4-[5-(4-trifluoromethyl-phenyl)-[1,2,4]triazolo[1,5-a]pyridin-2-ylamino]-benzamide;
N-Piperidin-4-ylmethyl-4-[5-(4-trifluoromethyl-phenyl)[1,2,4]triazolo[1,5-a]pyridin-2-ylamino]-benzamide;
N-Piperidin-4-yl-4-[5-(4-trifluoromethyl-phenyl)-[1,2,4]triazolo[1,5-a]pyridin-2-ylamino]-benzamide;
4-[5-(3-Methanesulfonyl-phenyl)[1,2,4]triazolo[1,5-a]pyridin-2-ylamino]-N-piperidin-4-ylmethyl-benzamide;
4-[5-(3-Methanesulfonyl-phenyl)[1,2,4]triazolo[1,5-a]pyridin-2-ylamino]-N-(3-morpholin-4-yl-propyl)-benzamide;
4-[5-(3-Methanesulfonyl-phenyl)-[1,2,4]triazolo[1,5-a]pyridin-2-ylamino]-N-methyl-benzamide;
4-[5-(3-Methanesulfonyl-phenyl)-[1,2,4]triazolo[1,5-a]pyridin-2-ylamino]-N-(2-morpholin-4-yl-ethyl)-benzamide;
N-(2-Amino-2-methyl-propyl)-4-[5-(3-methanesulfonyl-phenyl)-[1,2,4]triazolo[1,5-a]pyridin-2-ylamino]-benzamide;
N-(2-Dimethylamino-ethyl)-4-[5-(3-methanesulfonyl-phenyl)-[1,2,4]triazolo[1,5-a]pyridin-2-ylamino]-benzamide;
N-(2-Amino-ethyl)-4-[5-(3-methanesulfonyl-phenyl)-[1,2,4]triazolo[1,5-a]pyridin-2-ylamino]-benzamide;
N-Piperidin-4-ylmethyl-4-(5-m-tolyl-[1,2,4]triazolo[1,5-a]pyridin-2-ylamino)-benzamide;
N-(1-Methyl-piperidin-4-yl)-4-(5-m-tolyl-[1,2,4]triazolo[1,5-a]pyridin-2-ylamino)-benzamide;
N-(3-Morpholin-4-yl-propyl)-4-(5-m-tolyl-[1,2,4]triazolo[1,5-a]pyridin-2-ylamino)-benzamide;
N-Cyclohexyl-4-(5-m-tolyl-[1,2,4]triazolo[1,5-a]pyridin-2-ylamino)-benzamide;
{4-[5-(3,5-Difluoro-phenyl)-[1,2,4]triazolo[1,5-a]pyridin-2-ylamino]-pyridin-2-yl}-methanol;
{4-[5-(2-Trifluoromethyl-pyridin-4-yl)-[1,2,4]triazolo[1,5-a]pyridin-2-ylamino]-pyridin-2-yl}-methanol;
(2-Methyl-pyridin-4-yl)-[1,5-(2-trifluoromethyl-pyridin-4-yl)-[1,2,4]triazolo[1,5-a]pyridin-2-yl]-amine;
(R)-1-[2-(2-Methyl-pyridin-4-ylamino)-[1,2,4]triazolo[1,5-a]pyridin-5-yl]-piperidin-3-ol;
(2-Chloro-pyridin-4-yl)[5-(4-methoxy-phenyl)-[1,2,4]triazolo[1,5-a]pyridin-2-yl]-amine;
[5-(3-Chloro-phenyl)-[1,2,4]triazolo[1,5-a]pyridin-2-yl]-(2-methyl-pyridin-4-yl)-amine;
{4-[5-(1-Isobutyl-1H-pyrazol-4-yl)-[1,2,4]triazolo[1,5-a]pyridin-2-ylamino]-pyridin-2-yl}-methanol;
[5-(4-Methoxy-3-nitro-phenyl)-[1,2,4]triazolo[1,5-a]pyridin-2-yl]-(4-morpholin-4-yl-phenyl)-amine;
N-Methyl-4-(5-m-tolyl-[1,2,4]triazolo[1,5-a]pyridin-2-ylamino)-benzamide;
N-(2-Morpholin-4-yl-ethyl)-4-(5-m-tolyl-[1,2,4]triazolo[1,5-a]pyridin-2-ylamino)-benzamide;
N-(2-Amino-2-methyl-propyl)-4-(5-m-tolyl-[1,2,4]triazolo[1,5-a]pyridin-2-ylamino)-benzamide;
N-(2-Dimethylamino-ethyl)-4-(5-m-tolyl-[1,2,4]triazolo[1,5-a]pyridin-2-ylamino)-benzamide;
N-(2-Amino-ethyl)-4-(5-m-tolyl-[1,2,4]triazolo[1,5-a]pyridin-2-ylamino)-benzamide;
N-Piperidin-4-yl-4-(5-m-tolyl-[1,2,4]triazolo[1,5-a]pyridin-2-ylamino)-benzamide;
N,N-Dimethyl-4-(5-m-tolyl-[1,2,4]triazolo[1,5-a]pyridin-2-ylamino)-benzamide;
{4-[5-(4-Ethyl-piperazin-1-yl)-[1,2,4]triazolo[1,5-a]pyridin-2-ylamino]-pyridin-2-yl}-methanol;
[5-(4-Methoxy-2-methyl-phenyl)-[1,2,4]triazolo[1,5-a]pyridin-2-yl]-(4-morpholin-4-yl-phenyl)-amine;

[5-(4-Ethyl-piperazin-1-yl)-[1,2,4]triazolo[1,5-a]pyridin-2-yl]-(2-methyl-pyridin-4-yl)-amine;
{4-[5-(4-Methoxy-piperidin-1-yl)-[1,2,4]triazolo[1,5-a]pyridin-2-ylamino]-pyridin-2-yl}-methanol;
N-(1-Methyl-piperidin-4-ylmethyl)-4-(5-p-tolyl-[1,2,4]triazolo[1,5-a]pyridin-2-ylamino)-benzamide;
N-Piperidin-4-ylmethyl-4-(5-p-tolyl-[1,2,4]triazolo[1,5-a]pyridin-2-ylamino)-benzamide;
N-(2-Morpholin-4-yl-ethyl)-4-(5-p-tolyl-[1,2,4]triazolo[1,5-a]pyridin-2-ylamino)-benzamide;
N-(2-Dimethylamino-ethyl)-4-(5-p-tolyl-[1,2,4]triazolo[1,5-a]pyridin-2-ylamino)-benzamide;
N-Piperidin-4-yl-4-(5-p-tolyl-[1,2,4]triazolo[1,5-a]pyridin-2-ylamino)-benzamide;
N,N-Dimethyl-4-(5-p-tolyl-[1,2,4]triazolo[1,5-a]pyridin-2-ylamino)-benzamide;
4-[5-(4-Fluoro-phenyl)-[1,2,4]triazolo[1,5-a]pyridin-2-ylamino]-N-(1-methyl-piperidin-4-ylmethyl)-benzamide;
4-[5-(4-Fluoro-phenyl)-[1,2,4]triazolo[1,5-a]pyridin-2-ylamino]-N-piperidin-4-ylmethyl-benzamide;
4-[5-(4-Fluoro-phenyl)-[1,2,4]triazolo[1,5-a]pyridin-2-ylamino]-N-(2-morpholin-4-yl-ethyl)-benzamide;
N-(2-Amino-2-methyl-propyl)-4-[5-(4-fluoro-phenyl)-[1,2,4]triazolo[1,5-a]pyridin-2-ylamino]-benzamide;
N-(2-Dimethylamino-ethyl)-4-[5-(4-fluoro-phenyl)[1,2,4]triazolo[1,5-a]pyridin-2-ylamino]-benzamide;
4-[5-(4-Fluoro-phenyl)-[1,2,4]triazolo[1,5-a]pyridin-2-ylamino]-N-piperidin-4-yl-benzamide;
4-[5-(4-Fluoro-phenyl)-[1,2,4]triazolo[1,5-a]pyridin-2-ylamino]-N,N-dimethylbenzamide;
N-(1-Methyl-piperidin-4-ylmethyl)-4-[5-(3-trifluoromethyl-phenyl)-[1,2,4]triazolo[1,5-a]pyridin-2-ylamino]-benzamide;
4-[5-(3-Chloro-phenyl)[1,2,4]triazolo[1,5-a]pyridin-2-ylamino]-N-(1-methyl-piperidin-4-ylmethyl)-benzamide;
4-[5-(3-Chloro-phenyl)-[1,2,4]triazolo[1,5-a]pyridin-2-ylamino]-benzamide;
4-[5-(3-Chloro-phenyl)-[1,2,4]triazolo[1,5-a]pyridin-2-ylamino]-N-methyl-benzamide;
4-[5-(3-Chloro-phenyl)[1,2,4]triazolo[1,5-a]pyridin-2-ylamino]-N-(2-dimethylamino-ethyl)-benzamide;
N-(2-Amino-ethyl)-4-[5-(3-chloro-phenyl)[1,2,4]triazolo[1,5-a]pyridin-2-ylamino]-benzamide;
4-[5-(3-Fluoro-phenyl)-[1,2,4]triazolo[1,5-a]pyridin-2-ylamino]-N-piperidin-4-ylmethyl-benzamide;
4-[5-(3-Fluoro-phenyl)-[1,2,4]triazolo[1,5-a]pyridin-2-ylamino]-N-(2-morpholin-4-yl-ethyl)-benzamide;
4-[5-(3-Fluoro-phenyl)-[1,2,4]triazolo[1,5-a]pyridin-2-ylamino]-N-piperidin-4-yl-benzamide;
4-[5-(3-Fluoro-phenyl)-[1,2,4]triazolo[1,5-a]pyridin-2-ylamino]-N,N-dimethylbenzamide;
4-[5-(3-Fluoro-phenyl)-[1,2,4]triazolo[1,5-a]pyridin-2-ylamino]-N-(3-morpholin-4-yl-propyl)-benzamide;
N-Cyclohexyl-4-[5-(3-fluoro-phenyl)-[1,2,4]triazolo[1,5-a]pyridin-2-ylamino]-benzamide;
4-[5-(3-Fluoro-phenyl)-[1,2,4]triazolo[1,5-a]pyridin-2-ylamino]-N-(1-methyl-piperidin-4-yl)-benzamide;
4-[5-(3-Fluoro-phenyl)-[1,2,4]triazolo[1,5-a]pyridin-2-ylamino]-N-[3-(4-methyl-piperazin-1-yl)-propyl]-benzamide;
5-(3,5-Difluoro-phenyl)-[1,2,4]triazolo[1,5-a]pyridin-2-ylamine;
5-(4-Fluoro-phenyl)-[1,2,4]triazolo[1,5-a]pyridin-2-ylamine;
[5-(1-Isobutyl-1H-pyrazol-4-yl)-[1,2,4]triazolo[1,5-a]pyridin-2-yl]-(2-methyl-pyridin-4-yl)-amine;
4-[2-(2-Methyl-pyridin-4-ylamino)[1,2,4]triazolo[1,5-a]pyridin-5-yl]-benzonitrile;
4-[2-(6-Methyl-pyridin-2-ylamino)[1,2,4]triazolo[1,5-a]pyridin-5-yl]-benzonitrile;
[5-(1-Isobutyl-1H-pyrazol-4-yl)-[1,2,4]triazolo[1,5-a]pyridin-2-yl]-(6-methyl-pyridin-2-yl)-amine;
[5-(4-Ethyl-phenyl)-[1,2,4]triazolo[1,5-a]pyridin-2-yl]-(4-morpholin-4-yl-phenyl)-amine;
[5-(4-Methoxy-piperidin-1-yl)-[1,2,4]triazolo[1,5-a]pyridin-2-yl]-(2-methyl-pyridin-4-yl)-amine;
N-Cyclohexyl-4-[5-(3-methoxy-phenyl)-[1,2,4]triazolo[1,5-a]pyridin-2-ylamino]-benzamide;
4-[5-(3-Methoxy-phenyl)-[1,2,4]triazolo[1,5-a]pyridin-2-ylamino]-N-(1-methyl-piperidin-4-yl)-benzamide;
4-[5-(3-Methoxy-phenyl)-[1,2,4]triazolo[1,5-a]pyridin-2-ylamino]-N-[3-(4-methyl-piperazin-1-yl)-propyl]-benzamide;
N-(2-Amino-2-methyl-propyl)-4-[5-(3-methoxy-phenyl)-[1,2,4]triazolo[1,5-a]pyridin-2-ylamino]-benzamide;
N-(2-Dimethylamino-ethyl)-4-[5-(3-methoxy-phenyl)-[1,2,4]triazolo[1,5-a]pyridin-2-ylamino]-benzamide;
N-(2-Amino-ethyl)-4-[5-(3-methoxy-phenyl)-[1,2,4]triazolo[1,5-a]pyridin-2-ylamino]-benzamide;
4-[5-(3-Methoxy-phenyl)-[1,2,4]triazolo[1,5-a]pyridin-2-ylamino]-N-piperidin-4-yl-benzamide;
N-Piperidin-4-yl-4-[5-(4-trifluoromethoxy-phenyl)-[1,2,4]triazolo[1,5-a]pyridin-2-ylamino]-benzamide;
N-Cyclohexyl-4-[5-(4-trifluoromethoxy-phenyl)-[1,2,4]triazolo[1,5-a]pyridin-2-ylamino]-benzamide;
[5-(4-Fluoro-phenyl)-[1,2,4]triazolo[1,5-a]pyridin-2-yl]-(2-methyl-pyridin-4-yl)-amine;
(4-Morpholin-4-yl-phenyl)[5-(4-trifluoromethoxy-phenyl)-[1,2,4]triazolo[1,5-a]pyridin-2-yl]-amine;
N-Piperidin-4-ylmethyl-4-[5-(4-trifluoromethoxy-phenyl)-[1,2,4]triazolo[1,5-a]pyridin-2-ylamino]-benzamide;
N-(1-Methyl-piperidin-4-yl)-4-[5-(4-trifluoromethoxy-phenyl)-[1,2,4]triazolo[1,5-a]pyridin-2-ylamino]-benzamide;
N-Methyl-4-[5-(4-trifluoromethoxy-phenyl)-[1,2,4]triazolo[1,5-a]pyridin-2-ylamino]-benzamide;
N-[3-(4-Methyl-piperazin-1-yl)-propyl]-4-[5-(4-trifluoromethoxy-phenyl)-[1,2,4]triazolo[1,5-a]pyridin-2-ylamino]-benzamide;
N-[2-(4-Methyl-piperazin-1-yl)-ethyl]-4-[5-(4-trifluoromethoxy-phenyl)-[1,2,4]triazolo[1,5-a]pyridin-2-ylamino]-benzamide;
N-(2-Amino-2-methyl-propyl)-4-[5-(4-trifluoromethoxy-phenyl)-[1,2,4]triazolo[1,5-a]pyridin-2-ylamino]-benzamide;
N-(2-Dimethylamino-ethyl)-4-[5-(4-trifluoromethoxy-phenyl)-[1,2,4]triazolo[1,5-a]pyridin-2-ylamino]-benzamide;
N,N-Dimethyl-4-[5-(4-trifluoromethoxy-phenyl)-[1,2,4]triazolo[1,5-a]pyridin-2-ylamino]-benzamide;
{4-[5-(3-Chloro-phenyl)-[1,2,4]triazolo[1,5-a]pyridin-2-ylamino]-phenyl}-(4-hydroxy-piperidin-1-yl)-methanone;
4-[5-(3-Chloro-phenyl)-[1,2,4]triazolo[1,5-a]pyridin-2-ylamino]-N-(2-hydroxy-cyclohexyl)-benzamide;
4-[5-(3-Methoxy-phenyl)-[1,2,4]triazolo[1,5-a]pyridin-2-ylamino]-N-piperidin-4-ylmethyl-benzamide;
4-[5-(3-Methoxy-phenyl)-[1,2,4]triazolo[1,5-a]pyridin-2-ylamino]-N-(2-morpholin-4-yl-ethyl)-benzamide;

4-[5-(3-Methoxy-phenyl)-[1,2,4]triazolo[1,5-a]pyridin-2-ylamino]-N-methyl-benzamide;
4-[5-(3-Chloro-phenyl)-[1,2,4]triazolo[1,5-a]pyridin-2-ylamino]-N-(4-methylamino-cyclohexyl)-benzamide;
5-(1-Isobutyl-1H-pyrazol-4-yl)-[1,2,4]triazolo[1,5-a]pyridin-2-ylamine;
{4-[5-(3-Isopropyl-phenyl)-[1,2,4]triazolo[1,5-a]pyridin-2-ylamino]-pyridin-2-yl}-methanol;
[5-(4-Isopropyl-phenyl)-[1,2,4]triazolo[1,5-a]pyridin-2-yl]-(2-methyl-pyridin-4-yl)-amine;
4-[5-(3-Chloro-phenyl)-[1,2,4]triazolo[1,5-a]pyridin-2-ylamino]-N-cyclopropylcarbamoylmethyl-benzamide;
4-[5-(3-Methoxy-phenyl)-[1,2,4]triazolo[1,5-a]pyridin-2-ylamino]-N-(3-morpholin-4-yl-propyl)-benzamide;
4-[5-(3-Chloro-phenyl)-[1,2,4]triazolo[1,5-a]pyridin-2-ylamino]-N-(2-phenylamino-ethyl)-benzamide;
4-[5-(3-Chloro-phenyl)-[1,2,4]triazolo[1,5-a]pyridin-2-ylamino]-N—((R)-2-hydroxy-propyl)-benzamide;
4-[5-(3-Chloro-phenyl)-[1,2,4]triazolo[1,5-a]pyridin-2-ylamino]-N-(2-piperidin-1-yl-ethyl)-benzamide;
4-[5-(3-Chloro-phenyl)-[1,2,4]triazolo[1,5-a]pyridin-2-ylamino]-N-[2-(1-methylpyrrolidin-2-yl)-ethyl]-benzamide;
1-(4-{4-[5-(3-Chloro-phenyl)-[1,2,4]triazolo[1,5-a]pyridin-2-ylamino]-benzoyl}-piperazin-1-yl)-ethanone;
4-[5-(3-Chloro-phenyl)-[1,2,4]triazolo[1,5-a]pyridin-2-ylamino]-N-(tetrahydro-furan-2-ylmethyl)-benzamide;
{4-[5-(3-Chloro-phenyl)-[1,2,4]triazolo[1,5-a]pyridin-2-ylamino]-phenyl}-(3-hydroxy-piperidin-1-yl)-methanone;
4-[5-(3-Chloro-phenyl)-[1,2,4]triazolo[1,5-a]pyridin-2-ylamino]-N-(5-methyl-furan-2-ylmethyl)-benzamide;
4-[5-(3-Chloro-phenyl)-[1,2,4]triazolo[1,5-a]pyridin-2-ylamino]-N-furan-2-ylmethyl-benzamide;
4-[5-(3-Chloro-phenyl)-[1,2,4]triazolo[1,5-a]pyridin-2-ylamino]-N-(3-pyrrolidin-1-yl-propyl)-benzamide;
{4-[5-(3-Chloro-phenyl)-[1,2,4]triazolo[1,5-a]pyridin-2-ylamino]-phenyl}-(3,5-dimethylpiperidin-1-yl)-methanone;
4-[5-(3-Chloro-phenyl)[1,2,4]triazolo[1,5-a]pyridin-2-ylamino]-N-(4-methyl-cyclohexyl)-benzamide;
[5-(3-Isopropyl-phenyl)-[1,2,4]triazolo[1,5-a]pyridin-2-yl]-(6-methyl-pyridin-2-yl)-amine;
[5-(3-Isopropyl-phenyl)-[1,2,4]triazolo[1,5-a]pyridin-2-yl]-(4-methyl-pyridin-2-yl)-amine;
[5-(4-Isopropyl-phenyl)-[1,2,4]triazolo[1,5-a]pyridin-2-yl]-(4-morpholin-4-yl-phenyl)-amine;
[5-(3,4-Dimethoxy-phenyl)[1,2,4]triazolo[1,5-a]pyridin-2-yl]-(4-morpholin-4-yl-phenyl)-amine;
[5-(4-Methoxy-3-methyl-phenyl)-[1,2,4]triazolo[1,5-a]pyridin-2-yl]-(4-morpholin-4-yl-phenyl)-amine;
[5-(4-Methoxy-phenyl)[1,2,4]triazolo[1,5-a]pyridin-2-yl]-(3,4,5,6-tetrahydro-2H-[1,2]bipyridinyl-5'-yl)-amine;
N%5&-[5-(4-Methoxy-phenyl)[1,2,4]triazolo[1,5-a]pyridin-2-yl]-N%2&,N%2&-dimethyl-pyridine-2,5-diamine;
[5-(4-Methoxy-phenyl)[1,2,4]triazolo[1,5-a]pyridin-2-yl]-(2-methyl-pyridin-4-yl)-amine;
[5-(4-Methoxy-phenyl)[1,2,4]triazolo[1,5-a]pyridin-2-yl]-(4-morpholin-4-yl-phenyl)-amine;
(2-{4-[5-(3-Chloro-phenyl)-[1,2,4]triazolo[1,5-a]pyridin-2-ylamino]-benzoylamino}-ethyl)-carbamic acid tert-butyl ester;
4-{4-[5-(3-Chloro-phenyl)[1,2,4]triazolo[1,5-a]pyridin-2-ylamino]-benzoyl}-piperazin-2-one;
4-[5-(3-Chloro-phenyl)-[1,2,4]triazolo[1,5-a]pyridin-2-ylamino]-N-(2-methoxy-ethyl)-benzamide;
4-[5-(3-Chloro-phenyl)-[1,2,4]triazolo[1,5-a]pyridin-2-ylamino]-N—((S)-1-hydroxymethyl-2,2-dimethyl-propyl)-benzamide;
4-[5-(3-Chloro-phenyl)-[1,2,4]triazolo[1,5-a]pyridin-2-ylamino]-N-[2-(4-methyl-piperazin-1-yl)-ethyl]-benzamide;
4-[5-(3-Chloro-phenyl)-[1,2,4]triazolo[1,5-a]pyridin-2-ylamino]-N-(1-methyl-piperidin-4-yl)-benzamide;
4-[5-(3-Chloro-phenyl)-[1,2,4]triazolo[1,5-a]pyridin-2-ylamino]-N-[3-(4-methyl-piperazin-1-yl)-propyl]-benzamide;
4-[5-(3-Chloro-phenyl)-[1,2,4]triazolo[1,5-a]pyridin-2-ylamino]-N-(2-morpholin-4-yl-ethyl)-benzamide;
4-[5-(3-Chloro-phenyl)-[1,2,4]triazolo[1,5-a]pyridin-2-ylamino]-N-(3-morpholin-4-yl-propyl)-benzamide;
4-[5-(3-Chloro-phenyl)-[1,2,4]triazolo[1,5-a]pyridin-2-ylamino]-N-piperidin-4-ylmethyl-benzamide;
4-[5-(3-Chloro-phenyl)-[1,2,4]triazolo[1,5-a]pyridin-2-ylamino]-N-piperidin-4-yl-benzamide;
4-[5-(3-Chloro-phenyl)-[1,2,4]triazolo[1,5-a]pyridin-2-ylamino]-N-(2-piperazin-1-yl-ethyl)-benzamide;
4-[5-(3-Chloro-phenyl)-[1,2,4]triazolo[1,5-a]pyridin-2-ylamino]-N-cyclohexyl-benzamide;
3-[2-(2-Methyl-pyridin-4-ylamino)-[1,2,4]triazolo[1,5-a]pyridin-5-yl]-benzonitrile;
(2-Methyl-pyridin-4-yl)-[5-(3-trifluoromethyl-phenyl)-[1,2,4]triazolo[1,5-a]pyridin-2-yl]-amine;
4-[5-(3-Trifluoromethyl-phenyl)-[1,2,4]triazolo[1,5-a]pyridin-2-ylamino]-benzamide;
N-Cyclohexyl-4-[5-(3-trifluoromethyl-phenyl)[1,2,4]triazolo[1,5-a]pyridin-2-ylamino]-benzamide;
N-Cyclopropylmethyl-4-[5-(3-trifluoromethyl-phenyl)[1,2,4]triazolo[1,5-a]pyridin-2-ylamino]-benzamide;
N-Piperidin-4-ylmethyl-4-[5-(3-trifluoromethyl-phenyl)[1,2,4]triazolo[1,5-a]pyridin-2-ylamino]-benzamide;
N-Cyclobutyl-4-[5-(3-trifluoromethyl-phenyl)-[1,2,4]triazolo[1,5-a]pyridin-2-ylamino]-benzamide;
N-tert-Butyl-4-[5-(3-trifluoromethyl-phenyl)[1,2,4]triazolo[1,5-a]pyridin-2-ylamino]-benzamide;
N-(2-piperazin-1-yl-ethyl)-4-[5-(3-trifluoromethyl-phenyl)[1,2,4]triazolo[1,5-a]pyridin-2-ylamino]-benzamide;
N-(2-Dimethylamino-ethyl)-4-[5-(3-trifluoromethyl-phenyl)-[1,2,4]triazolo[1,5-a]pyridin-2-ylamino]-benzamide;
N-Methyl-4-[5-(3-trifluoromethyl-phenyl)-[1,2,4]triazolo[1,5-a]pyridin-2-ylamino]-benzamide;
N-(2-Morpholin-4-yl-ethyl)-4-[5-(3-trifluoromethyl-phenyl)[1,2,4]triazolo[1,5-a]pyridin-2-ylamino]-benzamide;
N-[2-(4-Methyl-piperazin-1-yl)-ethyl]-4-[5-(3-trifluoromethyl-phenyl)-[1,2,4]triazolo[1,5-a]pyridin-2-ylamino]-benzamide;
N-(1-Methyl-piperidin-4-yl)-4-[5-(3-trifluoromethyl-phenyl)[1,2,4]triazolo[1,5-a]pyridin-2-ylamino]-benzamide;
N-[3-(4-Methyl-piperazin-1-yl)-propyl]-4-[5-(3-trifluoromethyl-phenyl)-[1,2,4]triazolo[1,5-a]pyridin-2-ylamino]-benzamide;
N-Piperidin-4-yl-4-[5-(3-trifluoromethyl-phenyl)-[1,2,4]triazolo[1,5-a]pyridin-2-ylamino]-benzamide;
N-(2-Amino-2-methyl-propyl)-4-[5-(3-trifluoromethyl-phenyl)-[1,2,4]triazolo[1,5-a]pyridin-2-ylamino]-benzamide;

N,N-Dimethyl-4-[5-(3-trifluoromethoxy-phenyl)-[1,2,4]triazolo[1,5-a]pyridin-2-ylamino]-benzamide;
4-[5-(3-Chloro-phenyl)-[1,2,4]triazolo[1,5-a]pyridin-2-ylamino]-N,N-dimethylbenzamide;
N,N-Dimethyl-4-[5-(3-trifluoromethyl-phenyl)-[1,2,4]triazolo[1,5-a]pyridin-2-ylamino]-benzamide;
4-[5-(3-Methoxy-phenyl)-[1,2,4]triazolo[1,5-a]pyridin-2-ylamino]-N,N-dimethylbenzamide;
[5-(3-Methoxy-phenyl)-[1,2,4]triazolo[1,5-a]pyridin-2-yl]-(4-morpholin-4-yl-phenyl)-amine;
4-[2-(4-Morpholin-4-yl-phenylamino)-[1,2,4]triazolo[1,5-a]pyridin-5-yl]-benzonitrile;
(4-Morpholin-4-yl-phenyl)-[5-(3-trifluoromethyl-phenyl)-[1,2,4]triazolo[1,5-a]pyridin-2-yl]-amine;
4-(2-Amino-[1,2,4]triazolo[1,5-a]pyridin-5-yl)-benzonitrile;
[5-(3-Isopropyl-phenyl)-[1,2,4]triazolo[1,5-a]pyridin-2-yl]-(2-methyl-pyridin-4-yl)-amine;
[5-(4-Methoxy-phenyl)-[1,2,4]triazolo[1,5-a]pyridin-2-yl]-[4-(4-methyl-piperazin-1-yl)-phenyl]-amine;
N,N-Dimethyl-3-{2-[4-(4-methyl-piperazin-1-yl)-phenylamino]-[1,2,4]triazolo[1,5-a]pyridin-5-yl}-benzenesulfonamide;
5-(3,5-Dichloro-phenyl)-[1,2,4]triazolo[1,5-a]pyridin-2-ylamine;
[5-(3-Isopropyl-phenyl)-[1,2,4]triazolo[1,5-a]pyridin-2-yl]-(4-morpholin-4-yl-phenyl)-amine;
N-Isopropyl-3-{2-[4-(4-methyl-piperazin-1-yl)-phenylamino]-[1,2,4]triazolo[1,5-a]pyridin-5-yl}-benzenesulfonamide;
N-tert-Butyl-3-[2-(4-morpholin-4-yl-phenylamino)[1,2,4]triazolo[1,5-a]pyridin-5-yl]-benzenesulfonamide;
N-tert-Butyl-3-[2-(pyridin-2-ylamino)[1,2,4]triazolo[1,5-a]pyridin-5-yl]-benzenesulfonamide;
[5-(3-Isopropyl-phenyl)-[1,2,4]triazolo[1,5-a]pyridin-2-yl]-carbamic acid methyl ester;
5-(3-Isopropyl-phenyl)-[1,2,4]triazolo[1,5-a]pyridin-2-ylamine;
N-tert-Butyl-3-{2-[4-(4-methyl-piperazin-1-yl)-phenylamino]-[1,2,4]triazolo[1,5-a]pyridin-5-yl}-benzenesulfonamide;
N-(4-(4-Methylpiperazin-1-yl)phenyl)-5-(4-(morpholinomethyl)phenyl)-[1,2,4]triazolo[1,5-a]pyridin-2-amine;
N-(4-((Dimethylamino)methyl)phenyl)-5-(3-(methylsulfonyl)phenyl)-[1,2,4]triazolo[1,5-a]pyridin-2-amine;
N-(4-(Methoxymethyl)phenyl)-5-(3-(methylsulfonyl)phenyl)-[1,2,4]triazolo[1,5-a]pyridin-2-amine;
N-tert-Butyl-3-(2-(4-(2-(pyrrolidin-1-yl)ethoxy)phenylamino)-[1,2,4]triazolo[1,5-a]pyridin-5-yl)benzenesulfonamide;
N-(6-(4-Methylpiperazin-1-yl)pyridin-3-yl)-5-(3-(methylsulfonyl)phenyl)-[1,2,4]triazolo[1,5-a]pyridin-2-amine;
2-Methyl-N-(5-(3-(methylsulfonyl)phenyl)-[1,2,4]triazolo[1,5-a]pyridin-2-yl)thiazol-5-amine;
2-Methyl-N-(5-(3-(methylsulfonyl)phenyl)-[1,2,4]triazolo[1,5-a]pyridin-2-yl)oxazol-5-amine;
5-(3-(Methylsulfonyl)phenyl)-N-(1-(tetrahydro-2H-pyran-4-yl)-1H-pyrazol-4-yl)-[1,2,4]triazolo[1,5-a]pyridin-2-amine;
(S)-1-(2-(2-(hydroxymethyl)pyridin-4-ylamino)-[1,2,4]triazolo[1,5-a]pyridin-5-yl)piperidin-3-ol;
1-(2-(2-methylpyridin-4-ylamino)-[1,2,4]triazolo[1,5-a]pyridin-5-yl)piperidin-4-ol;
(3,5-dimethylpiperidin-1-yl)(4-(5-(3-methoxyphenyl)-[1,2,4]triazolo[1,5-a]pyridin-2-ylamino)phenyl)methanone;
4-(5-(3-methoxyphenyl)-[1,2,4]triazolo[1,5-a]pyridin-2-ylamino)-N-(2-(phenylamino)ethyl)benzamide;
N-(2-methoxyethyl)-4-(5-(3-methoxyphenyl)-[1,2,4]triazolo[1,5-a]pyridin-2-ylamino)benzamide;
N-(cyclohexylmethyl)-4-(5-(3-methoxyphenyl)-[1,2,4]triazolo[1,5-a]pyridin-2-ylamino)benzamide;
N-(4-(diethylamino)butyl)-4-(5-(3-methoxyphenyl)-[1,2,4]triazolo[1,5-a]pyridin-2-ylamino)benzamide;
N-(3-(isopropylamino)propyl)-4-(5-(3-methoxyphenyl)-[1,2,4]triazolo[1,5-a]pyridin-2-ylamino)benzamide;
4-(5-(3-acetamidophenyl)-[1,2,4]triazolo[1,5-a]pyridin-2-ylamino)-N-methylbenzamide;
4-(5-(3-acetamidophenyl)-[1,2,4]triazolo[1,5-a]pyridin-2-ylamino)-N-(2-(dimethylamino)ethyl)benzamide;
4-(5-(3-acetamidophenyl)-[1,2,4]triazolo[1,5-a]pyridin-2-ylamino)-N-(2-(piperazin-1-yl)ethyl)benzamide;
4-(5-(4-chlorophenyl)-[1,2,4]triazolo[1,5-a]pyridin-2-ylamino)-N-(2-(pyrrolidin-1-yl)ethyl)benzamide;
4-(5-(4-chlorophenyl)-[1,2,4]triazolo[1,5-a]pyridin-2-ylamino)-N-(2-(ethylamino)ethyl)benzamide;
(4-(5-(4-chlorophenyl)-[1,2,4]triazolo[1,5-a]pyridin-2-ylamino)phenyl)(3,5-dimethylpiperidin-1-yl)methanone;
4-(5-(4-chlorophenyl)-[1,2,4]triazolo[1,5-a]pyridin-2-ylamino)-N-(2-(phenylamino)ethyl)benzamide;
4-(5-(4-chlorophenyl)-[1,2,4]triazolo[1,5-a]pyridin-2-ylamino)-N-(2-methoxyethyl)benzamide;
4-(5-(4-chlorophenyl)-[1,2,4]triazolo[1,5-a]pyridin-2-ylamino)-N-(cyclohexylmethyl)benzamide;
4-(5-(4-(methylsulfonyl)phenyl)-[1,2,4]triazolo[1,5-a]pyridin-2-ylamino)benzoic acid;
4-(5-(4-(trifluoromethyl)phenyl)-[1,2,4]triazolo[1,5-a]pyridin-2-ylamino)benzoic acid;
4-(5-(3-chlorophenyl)-[1,2,4]triazolo[1,5-a]pyridin-2-ylamino)benzoic acid;
4-(5-(4-(trifluoromethoxy)phenyl)-[1,2,4]triazolo[1,5-a]pyridin-2-ylamino)benzoic acid;
4-(5-(3-(methylsulfonyl)phenyl)-[1,2,4]triazolo[1,5-a]pyridin-2-ylamino)benzoic acid;
4-(5-(3-chloro-4-methoxyphenyl)-[1,2,4]triazolo[1,5-a]pyridin-2-ylamino)benzoic acid;
4-(5-(3-(dimethylamino)phenyl)-[1,2,4]triazolo[1,5-a]pyridin-2-ylamino)benzoic acid;
4-(5-(4-carboxyphenyl)-[1,2,4]triazolo[1,5-a]pyridin-2-ylamino)benzoic acid;
4-(5-(4-fluorophenyl)-[1,2,4]triazolo[1,5-a]pyridin-2-ylamino)benzoic acid;
4-(5-p-tolyl-[1,2,4]triazolo[1,5-a]pyridin-2-ylamino)benzoic acid;
4-(5-m-tolyl-[1,2,4]triazolo[1,5-a]pyridin-2-ylamino)benzoic acid;
4-(5-(3-(methylsulfonyl)phenyl)-[1,2,4]triazolo[1,5-a]pyridin-2-ylamino)-N-(2-(piperazin-1-yl)ethyl)benzamide;
4-(5-(4-methoxyphenyl)-[1,2,4]triazolo[1,5-a]pyridin-2-ylamino)-N-(4-methylcyclohexyl)benzamide;
4-(5-(3-dimethylamino)phenyl)-[1,2,4]triazolo[1,5-a]pyridin-2-ylamino)-N-(1-methylpiperidin-4-yl)benzamide;
4-(5-(3-(dimethylamino)phenyl)-[1,2,4]triazolo[1,5-a]pyridin-2-ylamino)-N-(4-methylcyclohexyl)benzamide;
5-(3-fluorophenyl)-N-phenyl-[1,2,4]triazolo[1,5-a]pyridin-2-amine;

5-(4-fluorophenyl)-N-phenyl-[1,2,4]triazolo[1,5-a]pyridin-2-amine;
4-(5-(4-methoxyphenyl)-[1,2,4]triazolo[1,5-a]pyridin-2-ylamino)-N-(1-methylpiperidin-4-yl)benzamide;
4-(5-(3-(N-isopropylsulfamoyl)phenyl)-[1,2,4]triazolo[1,5-a]pyridin-2-ylamino)-N-(4-methylcyclohexyl)benzamide;
4-(5-(3-(N-isopropylsulfamoyl)phenyl)-[1,2,4]triazolo[1,5-a]pyridin-2-ylamino)-N-(1-methylpiperidin-4-yl)benzamide;
4-(5-(3-(N-isopropylsulfamoyl)phenyl)-[1,2,4]triazolo[1,5-a]pyridin-2-ylamino)benzoic acid;
4-(5-(3-methoxyphenyl)[1,2,4]triazolo[1,5-a]pyridin-2-ylamino)benzoic acid;
4-(5-(3-fluorophenyl)-[1,2,4]triazolo[1,5-a]pyridin-2-ylamino)benzoic acid;
4-(5-(4-chlorophenyl)-[1,2,4]triazolo[1,5-a]pyridin-2-ylamino)benzoic acid;
4-(5-(4-methoxyphenyl)-[1,2,4]triazolo[1,5-a]pyridin-2-ylamino)benzoic acid;
N-(2-fluorophenyl)-5-(3-fluorophenyl)[1,2,4]triazolo[1,5-a]pyridin-2-amine;
N,5-bis(3-fluorophenyl)[1,2,4]triazolo[1,5-a]pyridin-2-amine;
N-(2-methoxy-5-(2-(4-morpholinophenylamino)-[1,2,4]triazolo[1,5-a]pyridin-5-yl)phenyl)acetamide;
4-(5-(4-methoxyphenyl)-[1,2,4]triazolo[1,5-a]pyridin-2-ylamino)-N-(2-morpholinoethyl)benzamide;
4-(5-(4-methoxyphenyl)-[1,2,4]triazolo[1,5-a]pyridin-2-ylamino)-N-((1-methylpiperidin-4-yl)methyl)benzamide;
4-(5-(3-(N-isopropylsulfamoyl)phenyl)-[1,2,4]triazolo[1,5-a]pyridin-2-ylamino)-N-(2-morpholinoethyl)benzamide;
N-(2-fluorophenyl)-5-(4-fluorophenyl)[1,2,4]triazolo[1,5-a]pyridin-2-amine;
5-(3-chloro-4-methoxyphenyl)-N-phenyl-[1,2,4]triazolo[1,5-a]pyridin-2-amine;
5-(3-(dimethylamino)phenyl)-N-phenyl-[1,2,4]triazolo[1,5-a]pyridin-2-amine;
5-(3-(dimethylamino)phenyl)-N-(2-fluorophenyl)-[1,2,4]triazolo[1,5-a]pyridin-2-amine;
5-(3-(dimethylamino)phenyl)-N-(3-fluorophenyl)-[1,2,4]triazolo[1,5-a]pyridin-2-amine;
5-(3-isopropylphenyl)-N-phenyl-[1,2,4]triazolo[1,5-a]pyridin-2-amine;
5-(3-isopropylphenyl)-N-m-tolyl-[1,2,4]triazolo[1,5-a]pyridin-2-amine;
5-(3-isopropylphenyl)-N-(pyrimidin-2-yl)-[1,2,4]triazolo[1,5-a]pyridin-2-amine;
5-(3-isopropylphenyl)-N-(pyridin-2-yl)-[1,2,4]triazolo[1,5-a]pyridin-2-amine;
N-tert-butyl-3-(2-(phenylamino)[1,2,4]triazolo[1,5-a]pyridin-5-yl)benzenesulfonamide;
6-(5-(3-(N-tert-butylsulfamoyl)phenyl)-[1,2,4]triazolo[1,5-a]pyridin-2-ylamino)-N-(piperidin-4-yl)nicotinamide;
N-tert-butyl-3-(2-(pyridin-2-ylamino)-[1,2,4]triazolo[1,5-a]pyridin-5-yl)benzenesulfonamide;
N-tert-butyl-3-(2-(4-(piperazin-1-yl)phenylamino)-[1,2,4]triazolo[1,5-a]pyridin-5-yl)benzenesulfonamide;
N-tert-butyl-3-(2-(5-chloropyridin-2-ylamino)-[1,2,4]triazolo[1,5-a]pyridin-5-yl)benzenesulfonamide;
N-tert-butyl-3-(2-(5-(4-methylpiperazin-1-yl)pyridin-2-ylamino)-[1,2,4]triazolo[1,5-a]pyridin-5-yl)benzenesulfonamide;
4-(5-(3-(dimethylamino)phenyl)-[1,2,4]triazolo[1,5-a]pyridin-2-ylamino)-N-(2-morpholinoethyl)benzamide;
5-(3-fluorophenyl)-N-(4-(4-methylpiperazin-1-yl)phenyl)[1,2,4]triazolo[1,5-a]pyridin-2-amine;
N-(4-fluorophenyl)-5-(3-(methylsulfonyl)phenyl)-[1,2,4]triazolo[1,5-a]pyridin-2-amine;
4-(2-(4-(4-methylpiperazin-1-yl)phenylamino)-[1,2,4]triazolo[1,5-a]pyridin-5-yl)benzonitrile;
N-(4-(4-methylpiperazin-1-yl)phenyl)-5-(3-(methylsulfonyl)phenyl)-[1,2,4]triazolo[1,5-a]pyridin-2-amine;
N-(4-(4-methylpiperazin-1-yl)phenyl)-5-(3-(trifluoromethoxy)phenyl)-[1,2,4]triazolo[1,5-a]pyridin-2-amine;
4-(2-(o-tolylamino)-[1,2,4]triazolo[1,5-a]pyridin-5-yl)benzonitrile;
N-tert-butyl-3-(2-(5-(piperazin-1-yl)pyridin-2-ylamino)-[1,2,4]triazolo[1,5-a]pyridin-5-yl)benzenesulfonamide;
5-(4-fluorophenyl)-N-(4-(4-methylpiperazin-1-yl)phenyl)[1,2,4]triazolo[1,5-a]pyridin-2-amine;
5-(1H-indazol-4-yl)-N-(4-(4-methylpiperazin-1-yl)phenyl)-[1,2,4]triazolo[1,5-a]pyridin-2-amine;
N-(4-(4-methylpiperazin-1-yl)phenyl)-5-(4-(morpholinomethyl)phenyl)-[1,2,4]triazolo[1,5-a]pyridin-2-amine;
N-(4-(4-methylpiperazin-1-yl)phenyl)-5-(3-(trifluoromethyl)phenyl)-[1,2,4]triazolo[1,5-a]pyridin-2-amine;
5-(3-methoxyphenyl)-N-(4-(4-methylpiperazin-1-yl)phenyl)[1,2,4]triazolo[1,5-a]pyridin-2-amine;
5-(3,5-difluorophenyl)-N-(4-(4-methylpiperazin-1-yl)phenyl)-[1,2,4]triazolo[1,5-a]pyridin-2-amine;
5-(3-fluoro-5-(4-methylpiperazin-1-yl)phenyl)-N-(4-(4-methylpiperazin-1-yl)phenyl)-[1,2,4]triazolo[1,5-a]pyridin-2-amine;
N-(4-(4-methylpiperazin-1-yl)phenyl)-5-(pyridin-3-yl)-[1,2,4]triazolo[1,5-a]pyridin-2-amine;
5-(2-fluorophenyl)-N-(4-(4-methylpiperazin-1-yl)phenyl)[1,2,4]triazolo[1,5-a]pyridin-2-amine;
4-(5-(3-(N-tert-butylsulfamoyl)phenyl)[1,2,4]triazolo[1,5-a]pyridin-2-ylamino)-N-(piperidin-4-yl)benzamide;
4-(5-(3-(N-tert-butylsulfamoyl)phenyl)[1,2,4]triazolo[1,5-a]pyridin-2-ylamino)-N-(1-methylpiperidin-4-yl)benzamide;
N-tert-butyl-3-(2-(4-((4-methylpiperazin-1-yl)methyl)phenylamino)-[1,2,4]triazolo[1,5-a]pyridin-5-yl)benzenesulfonamide;
N-tert-butyl-3-(2-(4-cyanophenylamino)-[1,2,4]triazolo[1,5-a]pyridin-5-yl)benzenesulfonamide;
5-(1-ethyl-1H-pyrazol-4-yl)-N-(2-methylpyridin-4-yl)-[1,2,4]triazolo[1,5-a]pyridin-2-amine;
(4-(5-(1-ethyl-1H-pyrazol-4-yl)-[1,2,4]triazolo[1,5-a]pyridin-2-ylamino)pyridin-2-yl)methanol;
5-(1-ethyl-1H-pyrazol-4-yl)-N-(6-methylpyridin-2-yl)-[1,2,4]triazolo[1,5-a]pyridin-2-amine;
5-(1-ethyl-1H-pyrazol-4-yl)-N-m-tolyl-[1,2,4]triazolo[1,5-a]pyridin-2-amine;
N-tert-butyl-3-(2-(pyrimidin-2-ylamino)-[1,2,4]triazolo[1,5-a]pyridin-5-yl)benzenesulfonamide;
N-tert-butyl-3-(2-(2-fluorophenylamino)-[1,2,4]triazolo[1,5-a]pyridin-5-yl)benzenesulfonamide;
N-tert-butyl-3-(2-(pyridin-3-ylamino)-[1,2,4]triazolo[1,5-a]pyridin-5-yl)benzenesulfonamide;
N-tert-butyl-3-(2-(pyridin-4-ylamino)-[1,2,4]triazolo[1,5-a]pyridin-5-yl)benzenesulfonamide;
N-tert-butyl-3-(2-(3,4-difluorophenylamino)-[1,2,4]triazolo[1,5-a]pyridin-5-yl)benzenesulfonamide;

N-(4-(4-methylpiperazin-1-yl)phenyl)-5-(pyrimidin-5-yl)-[1,2,4]triazolo[1,5-a]pyridin-2-amine;
N-(4-(2-(4-(4-methylpiperazin-1-yl)phenylamino)-[1,2,4]triazolo[1,5-a]pyridin-5-yl)phenyl)acetamide;
5-(4-((4-methylpiperazin-1-yl)methyl)phenyl)-N-(4-(4-methylpiperazin-1-yl)phenyl)-[1,2,4]triazolo[1,5-a]pyridin-2-amine;
N-(4-(4-methylpiperazin-1-yl)phenyl)-5-phenyl-[1,2,4]triazolo[1,5-a]pyridin-2-amine;
N,5-bis(4-(4-methylpiperazin-1-yl)phenyl)-[1,2,4]triazolo[1,5-a]pyridin-2-amine;
N-tert-butyl-3-(2-(o-tolylamino)-[1,2,4]triazolo[1,5-a]pyridin-5-yl)benzenesulfonamide;
3-(5-(3-(N-tert-butylsulfamoyl)phenyl)-[1,2,4]triazolo[1,5-a]pyridin-2-ylamino)-N,N-dimethylbenzamide;
3-(5-(3-(N-tert-butylsulfamoyl)phenyl)-[1,2,4]triazolo[1,5-a]pyridin-2-ylamino)-N-(2-morpholinoethyl)benzamide;
3-(5-(3-(N-tert-butylsulfamoyl)phenyl)-[1,2,4]triazolo[1,5-a]pyridin-2-ylamino)-N-(piperidin-4-yl)benzamide;
3-(5-(3-(N-tert-butylsulfamoyl)phenyl)-[1,2,4]triazolo[1,5-a]pyridin-2-ylamino)-N-(1-methylpiperidin-4-yl)benzamide;
N-(4-(4-methylpiperazin-1-yl)phenyl)-5-o-tolyl-[1,2,4]triazolo[1,5-a]pyridin-2-amine;
5-(4-aminophenyl)-N-(4-(4-methylpiperazin-1-yl)phenyl)-[1,2,4]triazolo[1,5-a]pyridin-2-amine;
5-(3-fluorophenyl)-N-o-tolyl-[1,2,4]triazolo[1,5-a]pyridin-2-amine;
5-(3-fluorophenyl)-N-(pyridin-4-yl)-[1,2,4]triazolo[1,5-a]pyridin-2-amine;
5-(3-fluorophenyl)-N-(pyridin-3-yl)-[1,2,4]triazolo[1,5-a]pyridin-2-amine;
N-phenyl-5-(3-(trifluoromethyl)phenyl)-[1,2,4]triazolo[1,5-a]pyridin-2-amine;
N-o-tolyl-5-(3-(trifluoromethyl)phenyl)-[1,2,4]triazolo[1,5-a]pyridin-2-amine;
N-(4-methoxyphenyl)-5-(3-(trifluoromethyl)phenyl)-[1,2,4]triazolo[1,5-a]pyridin-2-amine;
N-isopropyl-4-(2-(phenylamino)-[1,2,4]triazolo[1,5-a]pyridin-5-yl)benzamide;
(4-methylpiperazin-1-yl)(4-(2-(phenylamino)-[1,2,4]triazolo[1,5-a]pyridin-5-yl)phenyl)methanone;
N-(4-(4-methylpiperazin-1-yl)phenyl)-5-(4-(methylsulfonyl)phenyl)-[1,2,4]triazolo[1,5-a]pyridin-2-amine;
5-(2-methoxyphenyl)-N-(4-(4-methylpiperazin-1-yl)phenyl)-[1,2,4]triazolo[1,5-a]pyridin-2-amine;
N-(4-(4-methylpiperazin-1-yl)phenyl)-5-(2-(trifluoromethyl)phenyl)-[1,2,4]triazolo[1,5-a]pyridin-2-amine;
N-tert-butyl-3-(2-(4-(2-morpholinoethoxy)phenylamino)-[1,2,4]triazolo[1,5-a]pyridin-5-yl)benzenesulfonamide;
5-(3-(methylsulfonyl)phenyl)-N-(4-morpholinophenyl)-[1,2,4]triazolo[1,5-a]pyridin-2-amine;
N-(pyridin-4-yl)-5-(3-(trifluoromethyl)phenyl)-[1,2,4]triazolo[1,5-a]pyridin-2-amine;
N-(pyridin-3-yl)-5-(3-(trifluoromethyl)phenyl)-[1,2,4]triazolo[1,5-a]pyridin-2-amine;
N-(4-(4-methylpiperazin-1-yl)phenyl)-5-(2-(trifluoromethoxy)phenyl)-[1,2,4]triazolo[1,5-a]pyridin-2-amine;
4-(2-(4-(4-methylpiperazin-1-yl)phenylamino)-[1,2,4]triazolo[1,5-a]pyridin-5-yl)-N-(2-morpholinoethyl)benzamide;
N-tert-butyl-3-(2-(4-(2-(dimethylamino)ethoxy)phenylamino)-[1,2,4]triazolo[1,5-a]pyridin-5-yl)benzenesulfonamide;
5-(3-(methylsulfonyl)phenyl)-N-phenyl-[1,2,4]triazolo[1,5-a]pyridin-2-amine;
5-(3-(methylsulfonyl)phenyl)-N-o-tolyl-[1,2,4]triazolo[1,5-a]pyridin-2-amine;
N2-(5-(3-(methylsulfonyl)phenyl)-[1,2,4]triazolo[1,5-a]pyridin-2-yl)pyridine-2,6-diamine;
5-(3-(methylsulfonyl)phenyl)-N-(pyridin-4-yl)-[1,2,4]triazolo[1,5-a]pyridin-2-amine;
5-(3-(methylsulfonyl)phenyl)-N-(pyridin-3-yl)-[1,2,4]triazolo[1,5-a]pyridin-2-amine;
5-(3-fluorophenyl)-N-(4-methoxyphenyl)-[1,2,4]triazolo[1,5-a]pyridin-2-amine;
N-(4-(2-(dimethylamino)ethoxy)phenyl)-5-(3-fluorophenyl)-[1,2,4]triazolo[1,5-a]pyridin-2-amine;
5-(3-fluorophenyl)-N-(4-(2-methoxyethoxy)phenyl)-[1,2,4]triazolo[1,5-a]pyridin-2-amine;
5-(3-fluorophenyl)-N-(4-morpholinophenyl)-[1,2,4]triazolo[1,5-a]pyridin-2-amine;
N,N-dimethyl-4-(2-(4-(4-methylpiperazin-1-yl)phenylamino)-[1,2,4]triazolo[1,5-a]pyridin-5-yl)benzamide;
5-(1-methyl-1H-pyrazol-4-yl)-N-(4-(4-methylpiperazin-1-yl)phenyl)-[1,2,4]triazolo[1,5-a]pyridin-2-amine;
N-(4-((4-methylpiperazin-1-yl)methyl)phenyl)-5-(3-(methylsulfonyl)phenyl)-[1,2,4]triazolo[1,5-a]pyridin-2-amine;
5-(3-(methylsulfonyl)phenyl)-N-(4-(morpholinomethyl)phenyl)-[1,2,4]triazolo[1,5-a]pyridin-2-amine;
N2-(5-(3-fluorophenyl)-[1,2,4]triazolo[1,5-a]pyridin-2-yl)pyridine-2,6-diamine;
5-(3-fluorophenyl)-N-(4-((4-methylpiperazin-1-yl)methyl)phenyl)-[1,2,4]triazolo[1,5-a]pyridin-2-amine;
5-(3-fluorophenyl)-N-(4-(morpholinomethyl)phenyl)-[1,2,4]triazolo [1,5-a]pyridin-2-amine;
N-(4-morpholinophenyl)-5-(pyridin-3-yl)-[1,2,4]triazolo[1,5-a]pyridin-2-amine;
N-[4-(1,1-dioxidothiomorpholin-4-yl)phenyl]-5-(pyridin-3-yl)[1,2,4]triazolo[1,5-a]pyridin-2-amine;
N-(4-chlorophenyl)-5-(3-(methylsulfonyl)phenyl)-[1,2,4]triazolo[1,5-a]pyridin-2-amine;
N-(2-methylpyridin-4-yl)-5-(3-(methylsulfonyl)phenyl)-[1,2,4]triazolo[1,5-a]pyridin-2-amine;
(4-(5-(3-(methylsulfonyl)phenyl)-[1,2,4]triazolo[1,5-a]pyridin-2-ylamino)pyridin-2-yl)methanol;
4-(5-(3-(methylsulfonyl)phenyl)-[1,2,4]triazolo[1,5-a]pyridin-2-ylamino)benzonitrile;
5-(3-(methylsulfonyl)phenyl)-N-(4-(methylsulfonyl)phenyl)-[1,2,4]triazolo [1,5-a]pyridin-2-amine;
5-(3-(methylsulfonyl)phenyl)-N-(pyrimidin-5-yl)-[1,2,4]triazolo[1,5-a]pyridin-2-amine;
N-methyl-4-(5-(4-(methylsulfonyl)phenyl)-[1,2,4]triazolo[1,5-a]pyridin-2-ylamino)benzamide;
N-(6-methylpyridin-3-yl)-5-(3-(methylsulfonyl)phenyl)-[1,2,4]triazolo[1,5-a]pyridin-2-amine;
N-(2-methylpyridin-4-yl)-5-(pyridin-3-yl)-[1,2,4]triazolo[1,5-a]pyridin-2-amine;
N-(5-chloropyridin-3-yl)-5-(3-(methylsulfonyl)phenyl)-[1,2,4]triazolo[1,5-a]pyridin-2-amine;
N-(2-chloropyridin-4-yl)-5-(3-(methylsulfonyl)phenyl)-[1,2,4]triazolo[1,5-a]pyridin-2-amine;
N4-(5-(3-(methylsulfonyl)phenyl)-[1,2,4]triazolo[1,5-a]pyridin-2-yl)pyridine-2,4-diamine;
N-(4-(5-(3-(methylsulfonyl)phenyl)-[1,2,4]triazolo[1,5-a]pyridin-2-ylamino)pyridin-2-yl)acetamide;
5-(3-(methylsulfonyl)phenyl)-N-p-tolyl-[1,2,4]triazolo[1,5-a]pyridin-2-amine;
3-methyl-N-(5-(3-(methylsulfonyl)phenyl)-[1,2,4]triazolo[1,5-a]pyridin-2-yl)isoxazol-5-amine;

5-(3-(methylsulfonyl)phenyl)-N-(4-(trifluoromethyl)phenyl)-[1,2,4]triazolo[1,5-a]pyridin-2-amine;
N-methyl-4-(5-(3-(methylsulfonyl)phenyl)-[1,2,4]triazolo[1,5-a]pyridin-2-ylamino)picolinamide;
N-(1-methyl-1H-pyrazol-4-yl)-5-(3-(methylsulfonyl)phenyl)-[1,2,4]triazolo[1,5-a]pyridin-2-amine;
5-(3-(methylsulfonyl)phenyl)-N-(6-morpholinopyridin-3-yl)-[1,2,4]triazolo[1,5-a]pyridin-2-amine;
5-(3-(methylsulfonyl)phenyl)-N-(6-(morpholinomethyl)pyridin-3-yl)-[1,2,4]triazolo[1,5-a]pyridin-2-amine;
N,N-dimethyl-4-(5-(3-(methylsulfonyl)phenyl)-[1,2,4]triazolo[1,5-a]pyridin-2-ylamino)benzamide;
(4-(5-(3-(methylsulfonyl)phenyl)-[1,2,4]triazolo[1,5-a]pyridin-2-ylamino)phenyl)(morpholino)methanone;
N-(6-(4-ethylpiperazin-1-yl)pyridin-3-yl)-5-(3-(methylsulfonyl)phenyl)-[1,2,4]triazolo[1,5-a]pyridin-2-amine;
N-(4-(4-(2-methoxyethyl)piperazin-1-yl)phenyl)-5-(3-(methylsulfonyl)phenyl)-[1,2,4]triazolo[1,5-a]pyridin-2-amine;
N,N-dimethyl-4-(5-(3-(methylsulfonyl)phenyl)-[1,2,4]triazolo[1,5-a]pyridin-2-ylamino)benzenesulfonamide;
(4-(5-(3-(methylsulfonyl)phenyl)-[1,2,4]triazolo[1,5-a]pyridin-2-ylamino)phenyl)methanol;
N-(4-((dimethylamino)methyl)phenyl)-5-(3-(methylsulfonyl)phenyl)[1,2,4]triazolo[1,5-a]pyridin-2-amine;
N,N-dimethyl-4-(5-(3-(methylsulfonyl)phenyl)-[1,2,4]triazolo[1,5-a]pyridin-2-ylamino)picolinamide;
N,N-dimethyl-3-(5-(3-(methylsulfonyl)phenyl)-[1,2,4]triazolo[1,5-a]pyridin-2-ylamino)benzenesulfonamide;
5-(3-(methylsulfonyl)phenyl)[1,2,4]triazolo[1,5-a]pyridin-2-amine;
N-(4-methoxyphenyl)-5-(3-(methylsulfonyl)phenyl)-[1,2,4]triazolo[1,5-a]pyridin-2-amine;
N-(4-(2-(dimethylamino)ethoxy)phenyl)-5-(3-(methylsulfonyl)phenyl)-[1,2,4]triazolo[1,5-a]pyridin-2-amine;
5-(3-(methylsulfonyl)phenyl)-N-(4-(trifluoromethoxy)phenyl)-[1,2,4]triazolo[1,5-a]pyridin-2-amine;
N-(4-(methoxymethyl)phenyl)-5-(3-(methylsulfonyl)phenyl)[1,2,4]triazolo[1,5-a]pyridin-2-amine;
(3-(5-(3-(methylsulfonyl)phenyl)-[1,2,4]triazolo[1,5-a]pyridin-2-ylamino)phenyl)methanol;
5-(3-(methylsulfonyl)phenyl)-N-(3-(morpholinomethyl)phenyl)-[1,2,4]triazolo[1,5-a]pyridin-2-amine;
N-(3-((4-methylpiperazin-1-yl)methyl)phenyl)-5-(3-(methylsulfonyl)phenyl)-[1,2,4]triazolo[1,5-a]pyridin-2-amine;
N-methyl-3-(5-(3-(methylsulfonyl)phenyl)-[1,2,4]triazolo[1,5-a]pyridin-2-ylamino)benzamide;
N,N-dimethyl-3-(5-(3-(methylsulfonyl)phenyl)-[1,2,4]triazolo[1,5-a]pyridin-2-ylamino)benzamide;
5-(3-(methylsulfonyl)phenyl)-N-(4-(2-morpholinoethoxy)phenyl)-[1,2,4]triazolo[1,5-a]pyridin-2-amine;
4-(5-(3-(methylsulfonyl)phenyl)-[1,2,4]triazolo[1,5-a]pyridin-2-ylamino)benzenesulfonamide;
N-(3-((dimethylamino)methyl)phenyl)-5-(3-(methylsulfonyl)phenyl)-[1,2,4]triazolo[1,5-a]pyridin-2-amine;
3-(5-(3-(methylsulfonyl)phenyl)-[1,2,4]triazolo[1,5-a]pyridin-2-ylamino)benzamide;
N,5-bis(3-(methylsulfonyl)phenyl)-[1,2,4]triazolo[1,5-a]pyridin-2-amine;
5-(3-(methylsulfonyl)phenyl)-N-(3-(methylsulfonylmethyl)phenyl)-[1,2,4]triazolo[1,5-a]pyridin-2-amine;
N-(1-ethyl-1H-pyrazol-4-yl)-5-(3-(methylsulfonyl)phenyl)-[1,2,4]triazolo[1,5-a]pyridin-2-amine;
N-(3-(methoxymethyl)phenyl)-5-(3-(methylsulfonyl)phenyl)-[1,2,4]triazolo[1,5-a]pyridin-2-amine;
N-methyl-4-(5-(3-(methylsulfonyl)phenyl)-[1,2,4]triazolo[1,5-a]pyridin-2-ylamino)benzenesulfonamide;
5-(3-(methylsulfonyl)phenyl)-N-(4-(piperidin-4-yl)phenyl)-[1,2,4]triazolo[1,5-a]pyridin-2-amine;
N-(6-(1-methylpiperidin-4-yl)pyridin-3-yl)-5-(3-(methylsulfonyl)phenyl)-[1,2,4]triazolo[1,5-a]pyridin-2-amine;
5-(3-(methylsulfonyl)phenyl)-N-(6-(piperidin-4-yl)pyridin-3-yl)-[1,2,4]triazolo[1,5-a]pyridin-2-amine;
5-(3-(methylsulfonyl)phenyl)-N-(4-(tetrahydro-2H-pyran-4-yl)phenyl)-[1,2,4]triazolo[1,5-a]pyridin-2-amine;
5-(3-(methylsulfonyl)phenyl)-N-(1-(tetrahydrofuran-3-yl)-1H-pyrazol-4-yl)-[1,2,4]triazolo[1,5-a]pyridin-2-amine;
N-(1-(1-methylpyrrolidin-3-yl)-1H-pyrazol-4-yl)-5-(3-(methylsulfonyl)phenyl)-[1,2,4]triazolo[1,5-a]pyridin-2-amine;
5-(3-(methylsulfonyl)phenyl)-N-(1-((tetrahydrofuran-3-yl)methyl)-1H-pyrazol-4-yl)-[1,2,4]triazolo[1,5-a]pyridin-2-amine;
N-(1-((1-methylpyrrolidin-3-yl)methyl)-1H-pyrazol-4-yl)-5-(3-(methylsulfonyl)phenyl)-[1,2,4]triazolo[1,5-a]pyridin-2-amine;
5-(3-(methylsulfonyl)phenyl)-N-(1-((tetrahydro-2H-pyran-4-yl)methyl)-1H-pyrazol-4-yl)-[1,2,4]triazolo[1,5-a]pyridin-2-amine;
N-(1-((1-methylpiperidin-4-yl)methyl)-1H-pyrazol-4-yl)-5-(3-(methylsulfonyl)phenyl)-[1,2,4]triazolo[1,5-a]pyridin-2-amine; and
N-(1-(1-methylpiperidin-4-yl)-1H-pyrazol-4-yl)-5-(3-(methylsulfonyl)phenyl)-[1,2,4]triazolo[1,5-a]pyridin-2-amine.

\* \* \* \* \*